United States Patent
Bobrowicz et al.

(10) Patent No.: US 8,936,918 B2
(45) Date of Patent: Jan. 20, 2015

(54) YEAST STRAIN FOR THE PRODUCTION OF PROTEINS WITH MODIFIED O-GLYCOSYLATION

(75) Inventors: Piotr Bobrowicz, Hanover, NH (US); William J. Cook, Hanover, NH (US); Stephen Hamilton, Enfield, NH (US); Juergen Nett, Grantham, NH (US); Terrance A. Stadheim, Lyme, NH (US); Stefan Wildt, Somerville, MA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 13/978,714

(22) PCT Filed: Feb. 20, 2012

(86) PCT No.: PCT/US2012/025809
§ 371 (c)(1), (2), (4) Date: Jul. 9, 2013

(87) PCT Pub. No.: WO2012/115903
PCT Pub. Date: Aug. 30, 2012

(65) Prior Publication Data
US 2013/0295608 A1 Nov. 7, 2013

Related U.S. Application Data

(60) Provisional application No. 61/446,846, filed on Feb. 25, 2011.

(51) Int. Cl.
C12P 21/06 (2006.01)
C07K 14/39 (2006.01)
C12P 21/00 (2006.01)
C12N 9/90 (2006.01)

(52) U.S. Cl.
CPC ............. *C07K 14/39* (2013.01); *C12P 21/005* (2013.01); *C12N 9/90* (2013.01)
USPC .......................................................... 435/69.1

(58) Field of Classification Search
None
See application file for complete search history.

(56) References Cited

U.S. PATENT DOCUMENTS

| 5,714,377 | A | 2/1998 | Tanner et al. |
|---|---|---|---|
| 7,029,872 | B2 | 4/2006 | Gerngross |
| 7,198,921 | B2 | 4/2007 | Miura et al. |
| 7,259,001 | B2 | 8/2007 | Cheung |
| 7,449,308 | B2 | 11/2008 | Gerngross et al. |
| 7,598,055 | B2 | 10/2009 | Bobrowicz et al. |
| 7,625,756 | B2 | 12/2009 | Hamilton |
| 2002/0192752 | A1 | 12/2002 | Goddard et al. |
| 2005/0170452 | A1 | 8/2005 | Wildt et al. |
| 2005/0260729 | A1 | 11/2005 | Hamilton |
| 2006/0040353 | A1 | 2/2006 | Davidson et al. |
| 2006/0211085 | A1 | 9/2006 | Bobrowicz |
| 2006/0286637 | A1 | 12/2006 | Hamilton et al. |
| 2007/0037248 | A1 | 2/2007 | Bobrowicz et al. |
| 2010/0331192 | A1* | 12/2010 | Zha et al. .......................... 506/1 |

FOREIGN PATENT DOCUMENTS

| EP | 1313471 | 5/2003 |
|---|---|---|
| WO | 2004074499 | 9/2004 |
| WO | 2007/061631 | 5/2007 |
| WO | 2007/136752 | 11/2007 |
| WO | 2008112092 | 9/2008 |
| WO | 2009/143041 | 11/2009 |
| WO | 2010/099153 | 9/2010 |

OTHER PUBLICATIONS

Gerngross, Nature Biotechnology, 2004, vol. 22, pp. 1409-1414.*
Jenks et al., Mol. Cell. Biol., 2008, vol. 28, pp. 3883-3893.*
Hobson et al., The Journal of Biological Chemistry, 2004, vol. 279, pp. 39628-39635.*
Bobrowicz et al., Glycobiology, 2004, vol. 14, pp. 757-766.*
Grote et al., Nucleic Acids Research, 2005, vol. 33, pp. W526-W531.*
Waterham et al., Gene, 1997, vol. 186, pp. 37-44.*
Zhang et al., Biochem. J., 2006, vol. 394, pp. 115-124.*
POMGnT1, Genbank, 2007, pp. 1-3.*
Lussier et al., Cell Biology and Metabolism, 1996, vol. 271, pp. 11001-11008.*
Hamilton et al., Science, 2006, vol. 313, pp. 1441-1443.*
Choi et al., PNAS, 2003, vol. 100, pp. 5022-5027.*
Willer et al., Current Opinion in Structural Biology, 2003, vol. 13, pp. 621-630.*
PCT—International Search Report—dated May 21, 2012.
Lussier et al., J. Biol. Chem., vol. 272, No. 24, (1997) pp. 15527-15531—Abstract Only.
Uniprot. PMGT1—Human (2011) p. 1 and p. 3.
Ballou, C. E., Methods Enzymol. vol. 185 (1990) pp. 440-470.
Zamze et al., Glycobiology, vol. 9, (1999) pp. 823-831.
Chiba et al., J. Biol. Chem. vol. 272 (1997) p. 2156.
Sasaki et al., Biochem. Biophys. Acta (1998) vol. 1425, p. 599.
Manya et al., J. Biol. Chem. vol. 282 (2007) pp. 20200-20206.
Trimble et al., Glycobiology, vol. 14, No. 3 (2004) pp. 265-274.
Mille et al., J. Biol. Chem. vol. 283 (2008) pp. 9724-9736.
Li et al., Nat. Biotechnol. vol. 24 (2006), pp. 210-215.
Rothstein et al., Methods Enzymol. vol. 194 (1991) pp. 281-301.
Baudin et al., Nucleic Acids Res. vol. 21 (1993) pp. 3329-3330.
Hamilton et al., Science, vol. 303 (2006) pp. 1441-1443.
Choi et al., PNAS, vol. 100 (2003) pp. 5022-5027.
Marks et al., J. Mol. Biol., vol. 222, (1991) pp. 581-585.
Caldas et al., Protein Engineering vol. 13 (2000) pp. 353-360.
Hamilton et al., Science, vol. 301 (2003) pp. 1244-1246.
Bobrowicz et al., Glycobiology, vol. 14 (2004) pp. 757-766.
Gleeson, P. A., Histochem. Cell Biol. vol. 109 (1998) pp. 517-532.
Strahl-Bolsinger et al., Protein O-Mannosylation, Biochim. Biophys Acta vol. 1426 (1999) pp. 297-307.
Harvey, et al., Mass Spectrometry Reviews vol. 18 (1999) pp. 349-451.
Stadheim et al., Nat. Protoc. vol. 3 (2006) pp. 1026-1031.
Laemmli, U. K., Nature vol. 227 (1970) pp. 680-685.

* cited by examiner

*Primary Examiner* — Anne Gussow
*Assistant Examiner* — Mindy G Brown

(57) ABSTRACT

Lower eukaryotic host cells have been recombinantly engineered to produce glycoprotein having human-like O-glycosylation. The glycoproteins are useful for the production of glycoprotein compositions with advantages for the production of human therapeutics.

16 Claims, 11 Drawing Sheets

• manitol-GlcNAc co-
migrates with arabitol
standard

Percentages of O-glycan species from PANEL A.

| man1 | Man2 | Man-GlcNAc | Man-GlcNAc-Gal | Man-GlcNAc-Gal-Sia |
|---|---|---|---|---|
| 11 | 6 | 0 | 27 | 56 |

SEQUENCE LISTING

<160> NUMBER OF SEQ ID NOS: 144

<210> SEQ ID NO 1
<211> LENGTH: 111
<212> TYPE: DNA
<213> ORGANISM: Artificial Sequence
<220> FEATURE:
<223> OTHER INFORMATION: ScGLS1-s ER/Golgi Transmembrane Domain

<400> SEQUENCE: 1
atgcttattt caaaatctaa gatgtttaaa acattttgga tactaaccag catagttctc    60
ctggcatctg ccaccgttga tattagtaaa ctacaagaat tcgggcgcgc c    111

<210> SEQ ID NO 2
<211> LENGTH: 37
<212> TYPE: PRT
<213> ORGANISM: Artificial Sequence
<220> FEATURE:
<223> OTHER INFORMATION: ScGLS1-s ER/Golgi Transmembrane Domain

<400> SEQUENCE: 2

Met Leu Ile Ser Lys Ser Lys Met Phe Lys Thr Phe Trp Ile Leu Thr
1               5                   10                  15

Ser Ile Val Leu Leu Ala Ser Ala Thr Val Asp Ile Ser Lys Leu Gln
            20                  25                  30

Glu Phe Gly Arg Ala
        35

<210> SEQ ID NO 3
<211> LENGTH: 99
<212> TYPE: DNA
<213> ORGANISM: Artificial Sequence
<220> FEATURE:
<223> OTHER INFORMATION: ScMNS1-s ER/Golgi Transmembrane Domain

<400> SEQUENCE: 3
atgaagaact ctgtcggtat ttcaattgca accattgttg ctatcatagc agctatatac    60
tatgtgccat ggtacgaaca ctttgagaga gggcgcgcc    99

<210> SEQ ID NO 4
<211> LENGTH: 33
<212> TYPE: PRT
<213> ORGANISM: Artificial Sequence
<220> FEATURE:
<223> OTHER INFORMATION: ScMNS1-s ER/Golgi Transmembrane Domain

<400> SEQUENCE: 4

Met Lys Asn Ser Val Gly Ile Ser Ile Ala Thr Ile Val Ala Ile Ile
1               5                   10                  15

Ala Ala Ile Tyr Tyr Val Pro Trp Tyr Glu His Phe Glu Arg Gly Arg
            20                  25                  30

Ala

<210> SEQ ID NO 5
<211> LENGTH: 255
<212> TYPE: DNA
<213> ORGANISM: Artificial Sequence
<220> FEATURE:
<223> OTHER INFORMATION: ScMNS1-m ER/Golgi Transmembrane Domain

<400> SEQUENCE: 5
atgaagaact ctgtcggtat ttcaattgca accattgttg ctatcatagc agctatatac    60
tatgtgccat ggtacgaaca ctttgagaga aagtcaccgg gggccggaga atgagagat    120 cggattgaaa gcatgttctt ggaatcgtgg agagactatt ccaagcatgg ctgggatac    180 gatgtgtatg gacctattga gcacacttcc cataatatgc ctcgtggcaa ccagccgtta    240 ggctggggggc gcgcc    255

<210> SEQ ID NO 6
<211> LENGTH: 85
<212> TYPE: PRT
<213> ORGANISM: Artificial Sequence

```
<220> FEATURE:
<223> OTHER INFORMATION: ScMNS1-m ER/Golgi Transmembrane Domain

<400> SEQUENCE: 6

Met Lys Asn Ser Val Gly Ile Ser Ile Ala Thr Ile Val Ala Ile Ile
1               5                   10                  15

Ala Ala Ile Tyr Tyr Val Pro Trp Tyr Glu His Phe Glu Arg Lys Ser
            20                  25                  30

Pro Gly Ala Gly Glu Met Arg Asp Arg Ile Glu Ser Met Phe Leu Glu
        35                  40                  45

Ser Trp Arg Asp Tyr Ser Lys His Gly Trp Gly Tyr Asp Val Tyr Gly
    50                  55                  60

Pro Ile Glu His Thr Ser His Asn Met Pro Arg Gly Asn Gln Pro Leu
65                  70                  75                  80

Gly Trp Gly Arg Ala
            85

<210> SEQ ID NO 7
<211> LENGTH: 318
<212> TYPE: DNA
<213> ORGANISM: Artificial Sequence
<220> FEATURE:
<223> OTHER INFORMATION: ScSEC12-m ER/Golgi Transmembrane Domain

<400> SEQUENCE: 7
atgaacacta tccacataat aaaattaccg cttaactacg ccaactacac ctcaatgaaa      60
caaaaaatct ctaaattttt caccaacttc atccttattg tgctgctttc ttacattta      120 cagttctcct ataagcacaa tttgcattcc atgctttca attacgcgaa ggacaatttt      180
ctaacgaaaa gagacaccat ctcttcgccc tacgtagttg atgaagactt acatcaaaca      240
actttgtttg gcaaccacgg tacaaaaaca tctgtaccta gcgtagattc cataaaagtg      300
catggcgtgg ggcgcgcc                                                    318

<210> SEQ ID NO 8
<211> LENGTH: 106
<212> TYPE: PRT
<213> ORGANISM: Artificial Sequence
<220> FEATURE:
<223> OTHER INFORMATION: ScSEC12-m ER/Golgi Transmembrane Domain

<400> SEQUENCE: 8

Met Asn Thr Ile His Ile Ile Lys Leu Pro Leu Asn Tyr Ala Asn Tyr
1               5                   10                  15

Thr Ser Met Lys Gln Lys Ile Ser Lys Phe Phe Thr Asn Phe Ile Leu
            20                  25                  30

Ile Val Leu Leu Ser Tyr Ile Leu Gln Phe Ser Tyr Lys His Asn Leu
        35                  40                  45

His Ser Met Leu Phe Asn Tyr Ala Lys Asp Asn Phe Leu Thr Lys Arg
    50                  55                  60

Asp Thr Ile Ser Ser Pro Tyr Val Val Asp Glu Asp Leu His Gln Thr
65                  70                  75                  80

Thr Leu Phe Gly Asn His Gly Thr Lys Thr Ser Val Pro Ser Val Asp
            85                  90                  95

Ser Ile Lys Val His Gly Val Gly Arg Ala
            100                 105

<210> SEQ ID NO 9
<211> LENGTH: 99
```

<212> TYPE: DNA
<213> ORGANISM: Artificial Sequence
<220> FEATURE:
<223> OTHER INFORMATION: PpSEC12-s ER/Golgi Transmembrane Domain

<400> SEQUENCE: 9

```
atgcccagaa aaatatttaa ctacttcatt ttgactgtat tcatggcaat tcttgctatt    60
gttttacaat ggtctataga gaatggacat gggcgcgcc                            99
```

<210> SEQ ID NO 10
<211> LENGTH: 33
<212> TYPE: PRT
<213> ORGANISM: Artificial Sequence
<220> FEATURE:
<223> OTHER INFORMATION: PpSEC12-s ER/Golgi Transmembrane Domain

<400> SEQUENCE: 10

Met Pro Arg Lys Ile Phe Asn Tyr Phe Ile Leu Thr Val Phe Met Ala
1               5                   10                  15

Ile Leu Ala Ile Val Leu Gln Trp Ser Ile Glu Asn Gly His Gly Arg
            20                  25                  30

Ala

<210> SEQ ID NO 11
<211> LENGTH: 159
<212> TYPE: DNA
<213> ORGANISM: Artificial Sequence
<220> FEATURE:
<223> OTHER INFORMATION: PpOCH1-s ER/Golgi Transmembrane Domain

<400> SEQUENCE: 11

```
atggcgaagg cagatggcag tttgctctac tataatcctc acaatccacc cagaaggtat    60
tacttctaca tggctatatt cgccgtttct gtcatttgcg ttttgtacgg accctcacaa   120
caattatcat ctccaaaaat agactatgat gggcgcgcc                          159
```

<210> SEQ ID NO 12
<211> LENGTH: 53
<212> TYPE: PRT
<213> ORGANISM: Artificial Sequence
<220> FEATURE:
<223> OTHER INFORMATION: PpOCH1-s ER/Golgi Transmembrane Domain

<400> SEQUENCE: 12

Met Ala Lys Ala Asp Gly Ser Leu Leu Tyr Tyr Asn Pro His Asn Pro
1               5                   10                  15

Pro Arg Arg Tyr Tyr Phe Tyr Met Ala Ile Phe Ala Val Ser Val Ile
            20                  25                  30

Cys Val Leu Tyr Gly Pro Ser Gln Gln Leu Ser Ser Pro Lys Ile Asp
        35                  40                  45

Tyr Asp Gly Arg Ala
    50

<210> SEQ ID NO 13
<211> LENGTH: 129
<212> TYPE: DNA
<213> ORGANISM: Artificial Sequence
<220> FEATURE:
<223> OTHER INFORMATION: ScMNN9-s ER/Golgi Transmembrane Domain

<400> SEQUENCE: 13

```
atgtcacttt ctcttgtatc gtaccgccta agaaagaacc cgtgggttaa cattttctcta   60
```

```
cctgttttgg ccatatttct aatatatata attttttccc agagagatca atctctgttg      120
gggcgcgcc                                                              129
```

<210> SEQ ID NO 14
<211> LENGTH: 43
<212> TYPE: PRT
<213> ORGANISM: Artificial Sequence
<220> FEATURE:
<223> OTHER INFORMATION: ScMNN9-s ER/Golgi Transmembrane Domain

<400> SEQUENCE: 14

Met Ser Leu Ser Leu Val Ser Tyr Arg Leu Arg Lys Asn Pro Trp Val
1               5                   10                  15

Asn Ile Phe Leu Pro Val Leu Ala Ile Phe Leu Ile Tyr Ile Ile Phe
            20                  25                  30

Phe Gln Arg Asp Gln Ser Leu Leu Gly Arg Ala
        35                  40

<210> SEQ ID NO 15
<211> LENGTH: 303
<212> TYPE: DNA
<213> ORGANISM: Artificial Sequence
<220> FEATURE:
<223> OTHER INFORMATION: ScVAN1-m ER/Golgi Transmembrane Domain

<400> SEQUENCE: 15

```
atgggcatgt tttttaattt aaggtcaaat ataagaaga aagccatgga caatggacta       60
agcctgccca tttcaaggaa cggtagctcg aacaacatca aggacaaacg ctcagagcat      120
aactccaact cattaaaggg caaatacagg taccagccgc gctccacacc gtctaaattc      180
cagcttacgg tgagtatcac atctcttatt attatcgccg ttctgtcgtt atatctcttt      240
atatcatttc tctccggaat gggcattggt gtatccacgc aaaatggtag gtcggggcgc      300
gcc                                                                   303
```

<210> SEQ ID NO 16
<211> LENGTH: 101
<212> TYPE: PRT
<213> ORGANISM: Artificial Sequence
<220> FEATURE:
<223> OTHER INFORMATION: ScVAN1-m ER/Golgi Transmembrane Domain

<400> SEQUENCE: 16

Met Gly Met Phe Phe Asn Leu Arg Ser Asn Ile Lys Lys Lys Ala Met
1               5                   10                  15

Asp Asn Gly Leu Ser Leu Pro Ile Ser Arg Asn Gly Ser Ser Asn Asn
            20                  25                  30

Ile Lys Asp Lys Arg Ser Glu His Asn Ser Asn Ser Leu Lys Gly Lys
        35                  40                  45

Tyr Arg Tyr Gln Pro Arg Ser Thr Pro Ser Lys Phe Gln Leu Thr Val
    50                  55                  60

Ser Ile Thr Ser Leu Ile Ile Ile Ala Val Leu Ser Leu Tyr Leu Phe
65                  70                  75                  80

Ile Ser Phe Leu Ser Gly Met Gly Ile Gly Val Ser Thr Gln Asn Gly
                85                  90                  95

Arg Ser Gly Arg Ala
            100

<210> SEQ ID NO 17
<211> LENGTH: 189

-continued

<210> SEQ ID NO 17
<211> LENGTH: 189
<212> TYPE: DNA
<213> ORGANISM: Artificial Sequence
<220> FEATURE:
<223> OTHER INFORMATION: ScANP1-s ER/Golgi Transmembrane Domain

<400> SEQUENCE: 17

```
atgaagtata ataacagaaa actctcgttc aacccctacca cagtaagtat cgctggaacg    60
ttgcttacgg tgttctttct cacaagactc gtgctttcgt tcttctcgat atcgctattc   120
cagctggtaa ctttccaagg aatcttcaag ccctatgttc agattttaa aaatactccc    180
gggcgcgcc                                                            189
```

<210> SEQ ID NO 18
<211> LENGTH: 63
<212> TYPE: PRT
<213> ORGANISM: Artificial Sequence
<220> FEATURE:
<223> OTHER INFORMATION: ScANP1-s ER/Golgi Transmembrane Domain

<400> SEQUENCE: 18

```
Met Lys Tyr Asn Asn Arg Lys Leu Ser Phe Asn Pro Thr Thr Val Ser
  1               5                  10                  15
Ile Ala Gly Thr Leu Leu Thr Val Phe Phe Leu Thr Arg Leu Val Leu
             20                  25                  30
Ser Phe Phe Ser Ile Ser Leu Phe Gln Leu Val Thr Phe Gln Gly Ile
         35                  40                  45
Phe Lys Pro Tyr Val Pro Asp Phe Lys Asn Thr Pro Gly Arg Ala
     50                  55                  60
```

<210> SEQ ID NO 19
<211> LENGTH: 111
<212> TYPE: DNA
<213> ORGANISM: Artificial Sequence
<220> FEATURE:
<223> OTHER INFORMATION: ScHOC-s ER/Golgi Transmembrane Domain

<400> SEQUENCE: 19

```
atggccaaaa caacaaaaag agcctccagt ttcaggaggt tgatgatatt cgccataata    60
gccctcatct cattagcatt tggagttaga tacctatttc acgggcgcgc c            111
```

<210> SEQ ID NO 20
<211> LENGTH: 37
<212> TYPE: PRT
<213> ORGANISM: Artificial Sequence
<220> FEATURE:
<223> OTHER INFORMATION: ScHOC-s ER/Golgi Transmembrane Domain

<400> SEQUENCE: 20

```
Met Ala Lys Thr Thr Lys Arg Ala Ser Ser Phe Arg Arg Leu Met Ile
  1               5                  10                  15
Phe Ala Ile Ile Ala Leu Ile Ser Leu Ala Phe Gly Val Arg Tyr Leu
             20                  25                  30
Phe His Gly Arg Ala
         35
```

<210> SEQ ID NO 21
<211> LENGTH: 228
<212> TYPE: DNA
<213> ORGANISM: Artificial Sequence
<220> FEATURE:
<223> OTHER INFORMATION: ScMNN10-s ER/Golgi Transmembrane Domain

<400> SEQUENCE: 21

```
atgtctagtg taccttataa ttcccaactt cctatatcca accatctaga gtacgatgaa    60
gatgaaaaga gagcagagg ctcaaaacta ggcctgaaat ataaaatgat atactggagg   120
aaaactttat gcagttcgct agcgagatgg agaaagctaa tactattaat atctttagct   180 ttgttttat tcatatggat aagcgattcc accataagcg ggcgcgcc                  228
```

<210> SEQ ID NO 22
<211> LENGTH: 76
<212> TYPE: PRT
<213> ORGANISM: Artificial Sequence
<220> FEATURE:
<223> OTHER INFORMATION: ScMNN10-s ER/Golgi Transmembrane Domain

<400> SEQUENCE: 22

```
Met Ser Ser Val Pro Tyr Asn Ser Gln Leu Pro Ile Ser Asn His Leu
1               5                   10                  15

Glu Tyr Asp Glu Asp Glu Lys Lys Ser Arg Gly Ser Lys Leu Gly Leu
            20                  25                  30

Lys Tyr Lys Met Ile Tyr Trp Arg Lys Thr Leu Cys Ser Ser Leu Ala
        35                  40                  45

Arg Trp Arg Lys Leu Ile Leu Leu Ile Ser Leu Ala Leu Phe Leu Phe
    50                  55                  60

Ile Trp Ile Ser Asp Ser Thr Ile Ser Gly Arg Ala
65                  70                  75
```

<210> SEQ ID NO 23
<211> LENGTH: 165
<212> TYPE: DNA
<213> ORGANISM: Artificial Sequence
<220> FEATURE:
<223> OTHER INFORMATION: ScMNN11-s ER/Golgi Transmembrane Domain

<400> SEQUENCE: 23

```
atggcaatca aaccaagaac gaagggcaaa acgtactcct caagatcggt gggttcgcag    60
tggttcaaca ggcttggttt caagcagaac aagtacggaa cttgtaaatt tttgtcgata   120
ataacggcct tgttttttat cctctatttc ttctccgggc gcgcc                    165
```

<210> SEQ ID NO 24
<211> LENGTH: 55
<212> TYPE: PRT
<213> ORGANISM: Artificial Sequence
<220> FEATURE:
<223> OTHER INFORMATION: ScMNN11-s ER/Golgi Transmembrane Domain

<400> SEQUENCE: 24

```
Met Ala Ile Lys Pro Arg Thr Lys Gly Lys Thr Tyr Ser Ser Arg Ser
1               5                   10                  15

Val Gly Ser Gln Trp Phe Asn Arg Leu Gly Phe Lys Gln Asn Lys Tyr
            20                  25                  30

Gly Thr Cys Lys Phe Leu Ser Ile Ile Thr Ala Phe Val Phe Ile Leu
        35                  40                  45

Tyr Phe Phe Ser Gly Arg Ala
    50                  55
```

<210> SEQ ID NO 25
<211> LENGTH: 183
<212> TYPE: DNA
<213> ORGANISM: Artificial Sequence
<220> FEATURE:
<223> OTHER INFORMATION: ScKRE2-s ER/Golgi Transmembrane Domain

<400> SEQUENCE: 25

```
atggccctct tctcagtaa gagactgttg agatttaccg tcattgcagg tgcggttatt    60
gttctcctcc taacattgaa ttccaacagt agaactcagc aatatattcc gagttccatc   120
tccgctgcat tgattttac ctcaggatct atatcccctg aacaacaagt catcgggcgc    180
gcc                                                                  183
```

<210> SEQ ID NO 26
<211> LENGTH: 61
<212> TYPE: PRT
<213> ORGANISM: Artificial Sequence
<220> FEATURE:
<223> OTHER INFORMATION: ScKRE2-s ER/Golgi Transmembrane Domain

<400> SEQUENCE: 26

```
Met Ala Leu Phe Leu Ser Lys Arg Leu Leu Arg Phe Thr Val Ile Ala
1               5                   10                  15
Gly Ala Val Ile Val Leu Leu Leu Thr Leu Asn Ser Asn Ser Arg Thr
            20                  25                  30
Gln Gln Tyr Ile Pro Ser Ser Ile Ser Ala Ala Phe Asp Phe Thr Ser
        35                  40                  45
Gly Ser Ile Ser Pro Glu Gln Gln Val Ile Gly Arg Ala
    50                  55                  60
```

<210> SEQ ID NO 27
<211> LENGTH: 315
<212> TYPE: DNA
<213> ORGANISM: Artificial Sequence
<220> FEATURE:
<223> OTHER INFORMATION: ScKRE2-l ER/Golgi Transmembrane Domain

<400> SEQUENCE: 27

```
atggccctct tctcagtaa gagactgttg agatttaccg tcattgcagg tgcggttatt    60
gttctcctcc taacattgaa ttccaacagt agaactcagc aatatattcc gagttccatc   120
tccgctgcat tgattttac ctcaggatct atatcccctg aacaacaagt catctctgag    180
gaaaatgatg ctaaaaaatt agagcaaagt gctctgaatt cagaggcaag cgaagactcc   240
gaagccatgg atgaagaatc caaggctctg aaagctgccg ctgaaaaggc agatgccccg   300
atcgacgggc gcgcc                                                    315
```

<210> SEQ ID NO 28
<211> LENGTH: 105
<212> TYPE: PRT
<213> ORGANISM: Artificial Sequence
<220> FEATURE:
<223> OTHER INFORMATION: ScKRE2-l ER/Golgi Transmembrane Domain

<400> SEQUENCE: 28

```
Met Ala Leu Phe Leu Ser Lys Arg Leu Leu Arg Phe Thr Val Ile Ala
1               5                   10                  15
Gly Ala Val Ile Val Leu Leu Leu Thr Leu Asn Ser Asn Ser Arg Thr
            20                  25                  30
Gln Gln Tyr Ile Pro Ser Ser Ile Ser Ala Ala Phe Asp Phe Thr Ser
        35                  40                  45
Gly Ser Ile Ser Pro Glu Gln Gln Val Ile Ser Glu Glu Asn Asp Ala
    50                  55                  60
Lys Lys Leu Glu Gln Ser Ala Leu Asn Ser Glu Ala Ser Glu Asp Ser
65                  70                  75                  80
```

Glu Ala Met Asp Glu Glu Ser Lys Ala Leu Lys Ala Ala Glu Lys
                85                  90                  95

Ala Asp Ala Pro Ile Asp Gly Arg Ala
            100                 105

<210> SEQ ID NO 29
<211> LENGTH: 225
<212> TYPE: DNA
<213> ORGANISM: Artificial Sequence
<220> FEATURE:
<223> OTHER INFORMATION: PpKTR1-s ER/Golgi Transmembrane Domain

<400> SEQUENCE: 29
atggaattag tgcgcctggc caatcttgtc aacgtcaacc acccttttcga gcaaagcaat      60 atatatcgcg ttccactttt cttccttctc tcaactacca gaccagacag gacaacggta     120
caaatggcag gtgcaactag gatcaattca cgagtagttc ggtttgctat tttcgcatca     180
atcctggtac tgttaggatt catcctatca agagggggc gcgcc                      225

<210> SEQ ID NO 30
<211> LENGTH: 75
<212> TYPE: PRT
<213> ORGANISM: Artificial Sequence
<220> FEATURE:
<223> OTHER INFORMATION: PpKTR1-s ER/Golgi Transmembrane Domain

<400> SEQUENCE: 30

Met Glu Leu Val Arg Leu Ala Asn Leu Val Asn Val Asn His Pro Phe
1               5                   10                  15

Glu Gln Ser Asn Ile Tyr Arg Val Pro Leu Phe Phe Leu Leu Ser Thr
                20                  25                  30

Thr Arg Pro Asp Arg Thr Thr Val Gln Met Ala Gly Ala Thr Arg Ile
            35                  40                  45

Asn Ser Arg Val Val Arg Phe Ala Ile Phe Ala Ser Ile Leu Val Leu
        50                  55                  60

Leu Gly Phe Ile Leu Ser Arg Gly Gly Arg Ala
65                  70                  75

<210> SEQ ID NO 31
<211> LENGTH: 102
<212> TYPE: DNA
<213> ORGANISM: Artificial Sequence
<220> FEATURE:
<223> OTHER INFORMATION: PpKTR3-s ER/Golgi Transmembrane Domain

<400> SEQUENCE: 31
atgatgcgag caagattaag ccttgaacga gttaacttga gctttattac gtccgtatttt     60 ttggcttcag ttgcagttct tttcatctct ttggggcgcg cc                        102

<210> SEQ ID NO 32
<211> LENGTH: 34
<212> TYPE: PRT
<213> ORGANISM: Artificial Sequence
<220> FEATURE:
<223> OTHER INFORMATION: PpKTR3-s ER/Golgi Transmembrane Domain

<400> SEQUENCE: 32

Met Met Arg Ala Arg Leu Ser Leu Glu Arg Val Asn Leu Ser Phe Ile
1               5                   10                  15

Thr Ser Val Phe Leu Ala Ser Val Ala Val Leu Phe Ile Ser Leu Gly
                20                  25                  30

Arg Ala

<210> SEQ ID NO 33
<211> LENGTH: 102
<212> TYPE: DNA
<213> ORGANISM: Artificial Sequence
<220> FEATURE:
<223> OTHER INFORMATION: PpKRE2-s ER/Golgi Transmembrane Domain

<400> SEQUENCE: 33

```
atggtacaca tagggttcag aagcttgaaa gcggtgttca ttttggccct ttcgtcattg    60
attctgtacg ggattgtcac gacctttgac ggggggcgcg cc                      102
```

<210> SEQ ID NO 34
<211> LENGTH: 34
<212> TYPE: PRT
<213> ORGANISM: Artificial Sequence
<220> FEATURE:
<223> OTHER INFORMATION: PpKRE2-s ER/Golgi Transmembrane Domain

<400> SEQUENCE: 34

Met Val His Ile Gly Phe Arg Ser Leu Lys Ala Val Phe Ile Leu Ala
1               5                   10                  15

Leu Ser Ser Leu Ile Leu Tyr Gly Ile Val Thr Thr Phe Asp Gly Gly
            20                  25                  30

Arg Ala

<210> SEQ ID NO 35
<211> LENGTH: 126
<212> TYPE: DNA
<213> ORGANISM: Artificial Sequence
<220> FEATURE:
<223> OTHER INFORMATION: ScKTR1-s ER/Golgi Transmembrane Domain

<400> SEQUENCE: 35

```
atggcgaaga ttatgatccc agctagcaag cagcctgttt acaaaaaatt aggacttctt    60
ctggtcgccg tgtttactgt gtatgtgttc tttcatggag ctcagtatgc gagaggcggg   120
cgcgcc                                                              126
```

<210> SEQ ID NO 36
<211> LENGTH: 42
<212> TYPE: PRT
<213> ORGANISM: Artificial Sequence
<220> FEATURE:
<223> OTHER INFORMATION: ScKTR1-s ER/Golgi Transmembrane Domain

<400> SEQUENCE: 36

Met Ala Lys Ile Met Ile Pro Ala Ser Lys Gln Pro Val Tyr Lys Lys
1               5                   10                  15

Leu Gly Leu Leu Leu Val Ala Val Phe Thr Val Tyr Val Phe Phe His
            20                  25                  30

Gly Ala Gln Tyr Ala Arg Gly Gly Arg Ala
        35                  40

<210> SEQ ID NO 37
<211> LENGTH: 129
<212> TYPE: DNA
<213> ORGANISM: Artificial Sequence
<220> FEATURE:
<223> OTHER INFORMATION: ScKTR2-s ER/Golgi Transmembrane Domain

<400> SEQUENCE: 37

```
atgcaaatct gcaaggtatt tcttacacag gttaaaaaac tacttttgt tagtcttcta      60 ttttgcttga tagctcaaac atgttggctt gcacttgtac catatcagag acagctgagc    120
gggcgcgcc                                                             129
```

<210> SEQ ID NO 38
<211> LENGTH: 43
<212> TYPE: PRT
<213> ORGANISM: Artificial Sequence
<220> FEATURE:
<223> OTHER INFORMATION: ScKTR2-s ER/Golgi Transmembrane Domain

<400> SEQUENCE: 38

```
Met Gln Ile Cys Lys Val Phe Leu Thr Gln Val Lys Lys Leu Leu Phe
1               5                   10                  15

Val Ser Leu Leu Phe Cys Leu Ile Ala Gln Thr Cys Trp Leu Ala Leu
            20                  25                  30

Val Pro Tyr Gln Arg Gln Leu Ser Gly Arg Ala
        35                  40
```

<210> SEQ ID NO 39
<211> LENGTH: 102
<212> TYPE: DNA
<213> ORGANISM: Artificial Sequence
<220> FEATURE:
<223> OTHER INFORMATION: KlGNT1-s ER/Golgi Transmembrane Domain

<400> SEQUENCE: 39

```
atggcttttg gatctagaag gaaaatcaag gccattttgg tcgctgcttc tgctatggtc     60
tttatttctc tacttggaac gtttggatcc gacgggcgcg cc                       102
```

<210> SEQ ID NO 40
<211> LENGTH: 34
<212> TYPE: PRT
<213> ORGANISM: Artificial Sequence
<220> FEATURE:
<223> OTHER INFORMATION: KlGNT1-s ER/Golgi Transmembrane Domain

<400> SEQUENCE: 40

```
Met Ala Phe Gly Ser Arg Arg Lys Ile Lys Ala Ile Leu Val Ala Ala
1               5                   10                  15

Ser Ala Met Val Phe Ile Ser Leu Leu Gly Thr Phe Gly Ser Asp Gly
            20                  25                  30

Arg Ala
```

<210> SEQ ID NO 41
<211> LENGTH: 117
<212> TYPE: DNA
<213> ORGANISM: Artificial Sequence
<220> FEATURE:
<223> OTHER INFORMATION: ScMNN2-s ER/Golgi Transmembrane Domain

<400> SEQUENCE: 41

```
atgctgctta ccaaaaggtt ttcaaagctg ttcaagctga cgttcatagt tttgatattg     60
tgcgggctgt tcgtcattac aaacaaatac atggatgaga cacgtcggg gcgcgcc       117
```

<210> SEQ ID NO 42
<211> LENGTH: 39
<212> TYPE: PRT
<213> ORGANISM: Artificial Sequence
<220> FEATURE:
<223> OTHER INFORMATION: ScMNN2-s ER/Golgi Transmembrane Domain

<400> SEQUENCE: 42

Met Leu Leu Thr Lys Arg Phe Ser Lys Leu Phe Lys Leu Thr Phe Ile
1               5                   10                  15

Val Leu Ile Leu Cys Gly Leu Phe Val Ile Thr Asn Lys Tyr Met Asp
            20                  25                  30

Glu Asn Thr Ser Gly Arg Ala
        35

<210> SEQ ID NO 43
<211> LENGTH: 300
<212> TYPE: DNA
<213> ORGANISM: Artificial Sequence
<220> FEATURE:
<223> OTHER INFORMATION: ScMNN2-m ER/Golgi Transmembrane Domain

<400> SEQUENCE: 43
atgctgctta ccaaaaggtt ttcaaagctg ttcaagctga cgttcatagt tttgatattg    60
tgcgggctgt tcgtcattac aaacaaatac atggatgaga cacgtcggt caaggagtac   120
aaggagtact tagacagata tgtccagagt tactccaata gtattcatc ttcctcagac   180
gccgccagcg ctgacgattc aaccccattg agggacaatg atgaggcagg caatgaaaag   240
ttgaaaagct tctacaacaa cgttttcaac tttctaatgg ttgattcgcc cgggcgcgcc   300

<210> SEQ ID NO 44
<211> LENGTH: 100
<212> TYPE: PRT
<213> ORGANISM: Artificial Sequence
<220> FEATURE:
<223> OTHER INFORMATION: ScMNN2-m ER/Golgi Transmembrane Domain

<400> SEQUENCE: 44

Met Leu Leu Thr Lys Arg Phe Ser Lys Leu Phe Lys Leu Thr Phe Ile
1               5                   10                  15

Val Leu Ile Leu Cys Gly Leu Phe Val Ile Thr Asn Lys Tyr Met Asp
            20                  25                  30

Glu Asn Thr Ser Val Lys Glu Tyr Lys Glu Tyr Leu Asp Arg Tyr Val
        35                  40                  45

Gln Ser Tyr Ser Asn Lys Tyr Ser Ser Ser Asp Ala Ala Ser Ala
    50                  55                  60

Asp Asp Ser Thr Pro Leu Arg Asp Asn Asp Glu Ala Gly Asn Glu Lys
65                  70                  75                  80

Leu Lys Ser Phe Tyr Asn Asn Val Phe Asn Phe Leu Met Val Asp Ser
                85                  90                  95

Pro Gly Arg Ala
        100

<210> SEQ ID NO 45
<211> LENGTH: 114
<212> TYPE: DNA
<213> ORGANISM: Artificial Sequence
<220> FEATURE:
<223> OTHER INFORMATION: ScMNN5-s ER/Golgi Transmembrane Domain

<400> SEQUENCE: 45
atgctgatta ggttaaagaa gagaaaaatc ctgcaggtca tcgtgagcgc agtagtgcta    60
atttttatttt ttgttctgt gcataatgat gtgtcttcta gttgggggcg cgcc         114

<210> SEQ ID NO 46

```
<211> LENGTH: 38
<212> TYPE: PRT
<213> ORGANISM: Artificial Sequence
<220> FEATURE:
<223> OTHER INFORMATION: ScMNN5-s ER/Golgi Transmembrane Domain

<400> SEQUENCE: 46

Met Leu Ile Arg Leu Lys Lys Arg Lys Ile Leu Gln Val Ile Val Ser
1               5                   10                  15

Ala Val Val Leu Ile Leu Phe Phe Cys Ser Val His Asn Asp Val Ser
            20                  25                  30

Ser Ser Trp Gly Arg Ala
        35

<210> SEQ ID NO 47
<211> LENGTH: 117
<212> TYPE: DNA
<213> ORGANISM: Artificial Sequence
<220> FEATURE:
<223> OTHER INFORMATION: ScYUR1-s ER/Golgi Transmembrane Domain

<400> SEQUENCE: 47
atggcaaaag gaggctcgct atacatcgtt ggcatattct taccaatatg gacctttatg      60
atctatattt ttggcaaaga gttattcctc atacgaaaat accaaaaggg gcgcgcc        117

<210> SEQ ID NO 48
<211> LENGTH: 39
<212> TYPE: PRT
<213> ORGANISM: Artificial Sequence
<220> FEATURE:
<223> OTHER INFORMATION: ScYUR1-s ER/Golgi Transmembrane Domain

<400> SEQUENCE: 48

Met Ala Lys Gly Gly Ser Leu Tyr Ile Val Gly Ile Phe Leu Pro Ile
1               5                   10                  15

Trp Thr Phe Met Ile Tyr Ile Phe Gly Lys Glu Leu Phe Leu Ile Arg
            20                  25                  30

Lys Tyr Gln Lys Gly Arg Ala
        35

<210> SEQ ID NO 49
<211> LENGTH: 135
<212> TYPE: DNA
<213> ORGANISM: Artificial Sequence
<220> FEATURE:
<223> OTHER INFORMATION: ScMNN1-s ER/Golgi Transmembrane Domain

<400> SEQUENCE: 49
atgttggcac tccggagatt tatattaaac caaaggtctt tgagatcgtg taccataccg      60
attctagtcg gagccttgat cattattctc gtgctattcc aactagttac ccaccgaaat     120 gatgcgggc gcgcc                                                       135

<210> SEQ ID NO 50
<211> LENGTH: 45
<212> TYPE: PRT
<213> ORGANISM: Artificial Sequence
<220> FEATURE:
<223> OTHER INFORMATION: ScMNN1-s ER/Golgi Transmembrane Domain

<400> SEQUENCE: 50

Met Leu Ala Leu Arg Arg Phe Ile Leu Asn Gln Arg Ser Leu Arg Ser
1               5                   10                  15
```

Cys Thr Ile Pro Ile Leu Val Gly Ala Leu Ile Ile Leu Val Leu
            20                  25                  30

Phe Gln Leu Val Thr His Arg Asn Asp Ala Gly Arg Ala
            35                  40              45

<210> SEQ ID NO 51
<211> LENGTH: 99
<212> TYPE: DNA
<213> ORGANISM: Artificial Sequence
<220> FEATURE:
<223> OTHER INFORMATION: ScMNN6-s ER/Golgi Transmembrane Domain

<400> SEQUENCE: 51
atgcacgtac tgctgagcaa aaaatagca cgctttctgt tgatttcgtt tgttttcgtg      60
cttgcgctaa tggtgacaat aaatcatcca gggcgcgcc                          99

<210> SEQ ID NO 52
<211> LENGTH: 32
<212> TYPE: PRT
<213> ORGANISM: Artificial Sequence
<220> FEATURE:
<223> OTHER INFORMATION: ScMNN6-s ER/Golgi Transmembrane Domain

<400> SEQUENCE: 52

Met His Val Leu Leu Ser Lys Lys Ile Ala Arg Phe Leu Leu Ile Ser
1               5                   10                  15

Phe Val Phe Val Leu Ala Leu Met Val Thr Ile Asn His Pro Gly Arg
            20                  25                  30

<210> SEQ ID NO 53
<211> LENGTH: 222
<212> TYPE: DNA
<213> ORGANISM: Artificial Sequence
<220> FEATURE:
<223> OTHER INFORMATION: ScPMT1-s ER/Golgi Transmembrane Domain

<400> SEQUENCE: 53
atgtcggaag agaaaacgta caaacgtgta gagcaggatg atcccgtgcc cgaactggat      60
atcaagcagg gccccgtaag acccttattt gttaccgatc cgagtgccga attggcctcg    120
ttacgaacca tggtcactct taaagagaag ctgttagtgg cctgtcttgc tgtctttaca    180
gcggtcatta gattgcatgg cttggcatgg cctgggcgcg cc                      222

<210> SEQ ID NO 54
<211> LENGTH: 74
<212> TYPE: PRT
<213> ORGANISM: Artificial Sequence
<220> FEATURE:
<223> OTHER INFORMATION: ScPMT1-s ER/Golgi Transmembrane Domain

<400> SEQUENCE: 54

Met Ser Glu Glu Lys Thr Tyr Lys Arg Val Glu Gln Asp Asp Pro Val
1               5                   10                  15

Pro Glu Leu Asp Ile Lys Gln Gly Pro Val Arg Pro Phe Ile Val Thr
            20                  25                  30

Asp Pro Ser Ala Glu Leu Ala Ser Leu Arg Thr Met Val Thr Leu Lys
            35                  40                  45

Glu Lys Leu Leu Val Ala Cys Leu Ala Val Phe Thr Ala Val Ile Arg
        50                  55                  60

Leu His Gly Leu Ala Trp Pro Gly Arg Ala
65                  70

<210> SEQ ID NO 55
<211> LENGTH: 246
<212> TYPE: DNA
<213> ORGANISM: Artificial Sequence
<220> FEATURE:
<223> OTHER INFORMATION: ScPMT2-s ER/Golgi Transmembrane Domain

<400> SEQUENCE: 55

```
atgtcctcgt cttcgtctac cgggtacagc aaaaacaatg ccgcccacat taagcaagag      60
aatacactga gacaaagaga atcgtcttcc atcagcgtca gtgaggaact ttcgagcgct     120
gatgagagag acgcggaaga tttctcgaag gaaaagcccg ctgcacaaag ctcactgtta     180
cgcctggaat ccgttgtaat gccggtgatc tttactgcat tggcgttgtt taccaggggg     240
cgcgcc                                                                246
```

<210> SEQ ID NO 56
<211> LENGTH: 82
<212> TYPE: PRT
<213> ORGANISM: Artificial Sequence
<220> FEATURE:
<223> OTHER INFORMATION: ScPMT2-s ER/Golgi Transmembrane Domain

<400> SEQUENCE: 56

```
Met Ser Ser Ser Ser Thr Gly Tyr Ser Lys Asn Ala Ala His
 1               5                  10                  15

Ile Lys Gln Glu Asn Thr Leu Arg Gln Arg Glu Ser Ser Ile Ser
             20                  25                  30

Val Ser Glu Glu Leu Ser Ser Ala Asp Glu Arg Asp Ala Glu Asp Phe
         35                  40                  45

Ser Lys Glu Lys Pro Ala Ala Gln Ser Ser Leu Leu Arg Leu Glu Ser
     50                  55                  60

Val Val Met Pro Val Ile Phe Thr Ala Leu Ala Leu Phe Thr Arg Gly
 65                  70                  75                  80

Arg Ala
```

<210> SEQ ID NO 57
<211> LENGTH: 222
<212> TYPE: DNA
<213> ORGANISM: Artificial Sequence
<220> FEATURE:
<223> OTHER INFORMATION: ScPMT3-s ER/Golgi Transmembrane Domain

<400> SEQUENCE: 57

```
atgccgtaca gagtggcgac gggctacagt gaaaaaagta ctgacgatga tttgatatgg      60
agaacgccaa tagtaaaaga ggaactcgag gatgctgaca cttttttaaa ggatgatgcc     120
gagttgtatg ataaagtcaa gaacgagagt gcagtatcac acctggatac catagttatg     180
ccgatcattt tcacggtact gggcatgttc actgggcgcg cc                        222
```

<210> SEQ ID NO 58
<211> LENGTH: 74
<212> TYPE: PRT
<213> ORGANISM: Artificial Sequence
<220> FEATURE:
<223> OTHER INFORMATION: ScPMT3-s ER/Golgi Transmembrane Domain

<400> SEQUENCE: 58

```
Met Pro Tyr Arg Val Ala Thr Gly Tyr Ser Glu Lys Ser Thr Asp Asp
 1               5                  10                  15

Asp Leu Ile Trp Arg Thr Pro Ile Val Lys Glu Glu Leu Glu Asp Ala
```

```
                        20                  25                  30

Asp Asn Phe Leu Lys Asp Asp Ala Glu Leu Tyr Asp Lys Val Lys Asn
                35                  40                  45

Glu Ser Ala Val Ser His Leu Asp Thr Ile Val Met Pro Ile Ile Phe
        50                  55                  60

Thr Val Leu Gly Met Phe Thr Gly Arg Ala
65                  70

<210> SEQ ID NO 59
<211> LENGTH: 366
<212> TYPE: DNA
<213> ORGANISM: Artificial Sequence
<220> FEATURE:
<223> OTHER INFORMATION: ScPMT4-s ER/Golgi Transmembrane Domain

<400> SEQUENCE: 59
atgtctgtgc ccaaaaaacg taaccatggg aagttaccac cttccactaa ggacgtagac    60
gatccttcgt tgaagtacac gaaggccgcg cctaaatgtg aacaagttgc tgaacattgg   120
ctcttgcagc cactaccgga accggaatca cgttatagct tttgggtaac aattgttacc   180
ttattagcgt ttgctgctag attttataag atctggtatc caaaagaagt tgttttttgat   240 gaggtacatt tcgggaaatt tgcatcgtat tacttagaaa ggtcttattt ctttgacgtt   300
catccccctt ttgctaagat gatgattgcc ttcattggtt ggttatgtgg ctatgatggg   360
cgcgcc                                                               366

<210> SEQ ID NO 60
<211> LENGTH: 122
<212> TYPE: PRT
<213> ORGANISM: Artificial Sequence
<220> FEATURE:
<223> OTHER INFORMATION: ScPMT4-s ER/Golgi Transmembrane Domain

<400> SEQUENCE: 60

Met Ser Val Pro Lys Lys Arg Asn His Gly Lys Leu Pro Pro Ser Thr
1               5                   10                  15

Lys Asp Val Asp Asp Pro Ser Leu Lys Tyr Thr Lys Ala Ala Pro Lys
                20                  25                  30

Cys Glu Gln Val Ala Glu His Trp Leu Leu Gln Pro Leu Pro Glu Pro
            35                  40                  45

Glu Ser Arg Tyr Ser Phe Trp Val Thr Ile Val Thr Leu Leu Ala Phe
        50                  55                  60

Ala Ala Arg Phe Tyr Lys Ile Trp Tyr Pro Lys Glu Val Val Phe Asp
65                  70                  75                  80

Glu Val His Phe Gly Lys Phe Ala Ser Tyr Tyr Leu Glu Arg Ser Tyr
                85                  90                  95

Phe Phe Asp Val His Pro Pro Phe Ala Lys Met Met Ile Ala Phe Ile
            100                 105                 110

Gly Trp Leu Cys Gly Tyr Asp Gly Arg Ala
        115                 120

<210> SEQ ID NO 61
<211> LENGTH: 204
<212> TYPE: DNA
<213> ORGANISM: Artificial Sequence
<220> FEATURE:
<223> OTHER INFORMATION: ScPMT5-s ER/Golgi Transmembrane Domain

<400> SEQUENCE: 61
```

```
atgaataaag agcatttgct gaaggtggat cccatcccg atgtgactat taaacgcggc    60
cctttgaggt cttttctcat aacaaaaccc tgtgataatt tgagttcatt acgaacagtt   120
acttcatcta aggaaaagct tctagttggc tgtttgctga tatttactgc catcgtaagg   180
ctacacaata tctccgggcg cgcc                                          204
```

```
<210> SEQ ID NO 62
<211> LENGTH: 68
<212> TYPE: PRT
<213> ORGANISM: Artificial Sequence
<220> FEATURE:
<223> OTHER INFORMATION: ScPMT5-s ER/Golgi Transmembrane Domain

<400> SEQUENCE: 62
```

Met Asn Lys Glu His Leu Leu Lys Val Asp Pro Ile Pro Asp Val Thr
1               5                   10                  15

Ile Lys Arg Gly Pro Leu Arg Ser Phe Leu Ile Thr Lys Pro Cys Asp
            20                  25                  30

Asn Leu Ser Ser Leu Arg Thr Val Thr Ser Ser Lys Glu Lys Leu Leu
        35                  40                  45

Val Gly Cys Leu Leu Ile Phe Thr Ala Ile Val Arg Leu His Asn Ile
    50                  55                  60

Ser Gly Arg Ala
65

```
<210> SEQ ID NO 63
<211> LENGTH: 552
<212> TYPE: DNA
<213> ORGANISM: Artificial Sequence
<220> FEATURE:
<223> OTHER INFORMATION: ScPMT6-s ER/Golgi Transmembrane Domain

<400> SEQUENCE: 63
```

```
atgagtaaag ccaagggaac gggattttca tcaattgata ctgaagatga aaacttacgc    60
gaacgttatg ttaatcaacc aaaagctaat gcctccgata ttcaagatga acaattagat   120
tgctttgagc aactagaaga aaaacatagg acaaaaaaaa atgaagaata cactgcgttg   180 aaaatttaa gggatgtcat aggtcccctt ttattaacta taacttcgtt ttatctaaga   240
ttccaacata tagatcagaa caattatgtt gtctgggatg aggctcattt tgggaaattc   300
ggatcatact acatcaaaca tgagtactac cacgatgtcc accctccact tggtaaaatg   360
cttattgcat tgagcgaatg gatggcagga tttgacggtc aatttgactt ttcctctaat   420
aatgcatatc cggaaaacgt aaactttaaa ctaatgagaa aatttaatgc cacatttgga   480
gctctatgta caccagtagc tttctttaca gccaaatgga tggggttcaa ttatttact   540 gttgggcgcg cc                                                       552
```

```
<210> SEQ ID NO 64
<211> LENGTH: 184
<212> TYPE: PRT
<213> ORGANISM: Artificial Sequence
<220> FEATURE:
<223> OTHER INFORMATION: ScPMT6-s ER/Golgi Transmembrane Domain

<400> SEQUENCE: 64
```

Met Ser Lys Ala Lys Gly Thr Gly Phe Ser Ser Ile Asp Thr Glu Asp
1               5                   10                  15

Glu Asn Leu Arg Glu Arg Tyr Val Asn Gln Pro Lys Ala Asn Ala Ser
            20                  25                  30

Asp Ile Gln Asp Glu Gln Leu Asp Cys Phe Gln Leu Glu Lys
    35                  40                  45

His Arg Thr Lys Lys Asn Glu Glu Tyr Thr Ala Leu Lys Ile Leu Arg
 50                  55                  60

Asp Val Ile Gly Pro Leu Leu Leu Thr Ile Thr Ser Phe Tyr Leu Arg
 65                  70                  75                  80

Phe Gln His Ile Asp Gln Asn Asn Tyr Val Val Trp Asp Glu Ala His
                 85                  90                  95

Phe Gly Lys Phe Gly Ser Tyr Tyr Ile Lys His Glu Tyr His Asp
             100                 105                 110

Val His Pro Pro Leu Gly Lys Met Leu Ile Ala Leu Ser Glu Trp Met
         115                 120                 125

Ala Gly Phe Asp Gly Gln Phe Asp Phe Ser Ser Asn Asn Ala Tyr Pro
     130                 135                 140

Glu Asn Val Asn Phe Lys Leu Met Arg Gln Phe Asn Ala Thr Phe Gly
145                 150                 155                 160

Ala Leu Cys Thr Pro Val Ala Phe Phe Thr Ala Lys Trp Met Gly Phe
                165                 170                 175

Asn Tyr Phe Thr Val Gly Arg Ala
            180

<210> SEQ ID NO 65
<211> LENGTH: 339
<212> TYPE: DNA
<213> ORGANISM: Artificial Sequence
<220> FEATURE:
<223> OTHER INFORMATION: ScPMT1-m ER/Golgi Transmembrane Domain

<400> SEQUENCE: 65
atgtcggaag agaaaacgta caaacgtgta gagcaggatg atcccgtgcc cgaactggat       60
atcaagcagg gccccgtaag acccttatt gttaccgatc cgagtgccga attggcctcg      120
ttacgaacca tggtcactct taaagagaag ctgttagtgg cctgtcttgc tgtctttaca      180
gcggtcatta gattgcatgg cttggcatgg cctgacagcg tggtgtttga tgaagtacat      240
ttcggtgggt ttgcctcgca atacattagg gggacttact tcatggatgt gcatcctcct      300
cttgcaaaga tgttgtatgc tggtgtggca gggcgcgcc                             339

<210> SEQ ID NO 66
<211> LENGTH: 113
<212> TYPE: PRT
<213> ORGANISM: Artificial Sequence
<220> FEATURE:
<223> OTHER INFORMATION: ScPMT1-m ER/Golgi Transmembrane Domain

<400> SEQUENCE: 66

Met Ser Glu Glu Lys Thr Tyr Lys Arg Val Glu Gln Asp Asp Pro Val
 1               5                  10                  15

Pro Glu Leu Asp Ile Lys Gln Gly Pro Val Arg Pro Phe Ile Val Thr
             20                  25                  30

Asp Pro Ser Ala Glu Leu Ala Ser Leu Arg Thr Met Val Thr Leu Lys
         35                  40                  45

Glu Lys Leu Leu Val Ala Cys Leu Ala Val Phe Thr Ala Val Ile Arg
     50                  55                  60

Leu His Gly Leu Ala Trp Pro Asp Ser Val Val Phe Asp Glu Val His
 65                  70                  75                  80

Phe Gly Gly Phe Ala Ser Gln Tyr Ile Arg Gly Thr Tyr Phe Met Asp
                 85                  90                  95

Val His Pro Pro Leu Ala Lys Met Leu Tyr Ala Gly Val Ala Gly Arg
            100                 105                 110

Ala

<210> SEQ ID NO 67
<211> LENGTH: 369
<212> TYPE: DNA
<213> ORGANISM: Artificial Sequence
<220> FEATURE:
<223> OTHER INFORMATION: ScPMT2-m ER/Golgi Transmembrane Domain

<400> SEQUENCE: 67
atgtcctcgt cttcgtctac cgggtacagc aaaaacaatg ccgcccacat taagcaagag    60
aatacactga gacaaagaga atcgtcttcc atcagcgtca gtgaggaact ttcgagcgct   120
gatgagagag acgcggaaga tttctcgaag gaaaagcccg ctgcacaaag ctcactgtta   180
cgcctggaat ccgttgtaat gccggtgatc tttactgcat tggcgttgtt taccaggatg   240
tacaaaatcg gcatcaacaa ccatgttgtt tgggatgagg cgcactttgg taaatttggt   300
tcttattact tgagacacga attttaccac gatgtccatc ctcccctagg aaaaatgctg   360
gggcgcgcc                                                           369

<210> SEQ ID NO 68
<211> LENGTH: 123
<212> TYPE: PRT
<213> ORGANISM: Artificial Sequence
<220> FEATURE:
<223> OTHER INFORMATION: ScPMT2-m ER/Golgi Transmembrane Domain

<400> SEQUENCE: 68

Met Ser Ser Ser Ser Ser Thr Gly Tyr Ser Lys Asn Asn Ala Ala His
1               5                   10                  15

Ile Lys Gln Glu Asn Thr Leu Arg Gln Arg Glu Ser Ser Ile Ser
            20                  25                  30

Val Ser Glu Glu Leu Ser Ser Ala Asp Glu Arg Asp Ala Glu Asp Phe
        35                  40                  45

Ser Lys Glu Lys Pro Ala Ala Gln Ser Ser Leu Leu Arg Leu Glu Ser
    50                  55                  60

Val Val Met Pro Val Ile Phe Thr Ala Leu Ala Leu Phe Thr Arg Met
65                  70                  75                  80

Tyr Lys Ile Gly Ile Asn Asn His Val Val Trp Asp Glu Ala His Phe
                85                  90                  95

Gly Lys Phe Gly Ser Tyr Tyr Leu Arg His Glu Phe Tyr His Asp Val
            100                 105                 110

His Pro Pro Leu Gly Lys Met Leu Gly Arg Ala
        115                 120

<210> SEQ ID NO 69
<211> LENGTH: 339
<212> TYPE: DNA
<213> ORGANISM: Artificial Sequence
<220> FEATURE:
<223> OTHER INFORMATION: ScPMT3-m ER/Golgi Transmembrane Domain

<400> SEQUENCE: 69
atgccgtaca gagtggcgac gggctacagt gaaaaaagta ctgacgatga tttgatatgg    60
agaacgccaa tagtaaaaga ggaactcgag gatgctgaca actttttaaa ggatgatgcc   120
gagttgtatg ataaagtcaa gaacgagagt gcagtatcac acctggatac catagttatg   180

```
ccgatcattt tcacggtact gggcatgttc actagaatgt acaagattgg tcgtaataat    240
catgtggtct gggatgaagc tcattttggt aagttcggct cttactatct gagacacgaa    300
ttttaccatg atgttcatcc acctttaggt gggcgcgcc                           339
```

<210> SEQ ID NO 70
<211> LENGTH: 113
<212> TYPE: PRT
<213> ORGANISM: Artificial Sequence
<220> FEATURE:
<223> OTHER INFORMATION: ScPMT3-m ER/Golgi Transmembrane Domain

<400> SEQUENCE: 70

```
Met Pro Tyr Arg Val Ala Thr Gly Tyr Ser Glu Lys Ser Thr Asp Asp
1               5                   10                  15

Asp Leu Ile Trp Arg Thr Pro Ile Val Lys Glu Glu Leu Glu Asp Ala
                20                  25                  30

Asp Asn Phe Leu Lys Asp Ala Glu Leu Tyr Asp Lys Val Lys Asn
            35                  40                  45

Glu Ser Ala Val Ser His Leu Asp Thr Ile Val Met Pro Ile Ile Phe
    50                  55                  60

Thr Val Leu Gly Met Phe Thr Arg Met Tyr Lys Ile Gly Arg Asn Asn
65                  70                  75                  80

His Val Val Trp Asp Glu Ala His Phe Gly Lys Phe Gly Ser Tyr Tyr
                85                  90                  95

Leu Arg His Glu Phe Tyr His Asp Val His Pro Pro Leu Gly Gly Arg
            100                 105                 110

Ala
```

<210> SEQ ID NO 71
<211> LENGTH: 414
<212> TYPE: DNA
<213> ORGANISM: Artificial Sequence
<220> FEATURE:
<223> OTHER INFORMATION: ScPMT4-m ER/Golgi Transmembrane Domain

<400> SEQUENCE: 71

```
atgtctgtgc ccaaaaaacg taaccatggg aagttaccac cttccactaa ggacgtagac    60
gatccttcgt tgaagtacac gaaggccgcg cctaaatgtg aacaagttgc tgaacattgg    120
ctcttgcagc cactaccgga accggaatca cgttatagct tttgggtaac aattgttacc    180
ttattagcgt ttgctgctag attttataag atctggtatc caaaagaagt tgttttttgat   240 gaggtacatt tcgggaaatt tgcatcgtat tacttagaaa ggtcttattt ctttgacgtt    300
catccccctt tgctaagat gatgattgcc ttcattggtt ggttatgtgg ctatgatggt    360
tcctttaagt ttgatgagat tgggtattct tatgaaactc atccagggcg cgcc           414
```

<210> SEQ ID NO 72
<211> LENGTH: 138
<212> TYPE: PRT
<213> ORGANISM: Artificial Sequence
<220> FEATURE:
<223> OTHER INFORMATION: ScPMT4-m ER/Golgi Transmembrane Domain

<400> SEQUENCE: 72

```
Met Ser Val Pro Lys Lys Arg Asn His Gly Lys Leu Pro Pro Ser Thr
1               5                   10                  15

Lys Asp Val Asp Asp Pro Ser Leu Lys Tyr Thr Lys Ala Ala Pro Lys
                20                  25                  30
```

-continued

```
Cys Glu Gln Val Ala Glu His Trp Leu Leu Gln Pro Leu Pro Glu Pro
         35                  40                  45

Glu Ser Arg Tyr Ser Phe Trp Val Thr Ile Val Thr Leu Leu Ala Phe
 50                  55                  60

Ala Ala Arg Phe Tyr Lys Ile Trp Tyr Pro Lys Glu Val Val Phe Asp
 65                  70                  75                  80

Glu Val His Phe Gly Lys Phe Ala Ser Tyr Tyr Leu Glu Arg Ser Tyr
                 85                  90                  95

Phe Phe Asp Val His Pro Pro Phe Ala Lys Met Met Ile Ala Phe Ile
            100                 105                 110

Gly Trp Leu Cys Gly Tyr Asp Gly Ser Phe Lys Phe Asp Glu Ile Gly
        115                 120                 125

Tyr Ser Tyr Glu Thr His Pro Gly Arg Ala
    130                 135
```

<210> SEQ ID NO 73
<211> LENGTH: 264
<212> TYPE: DNA
<213> ORGANISM: Artificial Sequence
<220> FEATURE:
<223> OTHER INFORMATION: ScPMT5-m ER/Golgi Transmembrane Domain

<400> SEQUENCE: 73

```
atgaataaag agcatttgct gaaggtggat cccatccccg atgtgactat taaacgcggc      60
cctttgaggt cttttctcat aacaaaaccc tgtgataatt tgagttcatt acgaacagtt    120
acttcatcta aggaaaagct tctagttggc tgtttgctga tatttactgc catcgtaagg    180
ctacacaata tctccctgcc aaatagtgtt gttttggtg aaaatgaagt tggtacattt     240
gtttctcaat acgtggggcg cgcc                                           264
```

<210> SEQ ID NO 74
<211> LENGTH: 88
<212> TYPE: PRT
<213> ORGANISM: Artificial Sequence
<220> FEATURE:
<223> OTHER INFORMATION: ScPMT5-m ER/Golgi Transmembrane Domain

<400> SEQUENCE: 74

```
Met Asn Lys Glu His Leu Leu Lys Val Asp Pro Ile Pro Asp Val Thr
 1               5                  10                  15

Ile Lys Arg Gly Pro Leu Arg Ser Phe Leu Ile Thr Lys Pro Cys Asp
                20                  25                  30

Asn Leu Ser Ser Leu Arg Thr Val Thr Ser Ser Lys Glu Lys Leu Leu
         35                  40                  45

Val Gly Cys Leu Leu Ile Phe Thr Ala Ile Val Arg Leu His Asn Ile
 50                  55                  60

Ser Leu Pro Asn Ser Val Val Phe Gly Glu Asn Glu Val Gly Thr Phe
 65                  70                  75                  80

Val Ser Gln Tyr Val Gly Arg Ala
                 85
```

<210> SEQ ID NO 75
<211> LENGTH: 594
<212> TYPE: DNA
<213> ORGANISM: Artificial Sequence
<220> FEATURE:
<223> OTHER INFORMATION: ScPMT6-m ER/Golgi Transmembrane Domain

<400> SEQUENCE: 75

```
atgagtaaag ccaagggaac gggattttca tcaattgata ctgaagatga aaacttacgc    60
gaacgttatg ttaatcaacc aaaagctaat gcctccgata ttcaagatga acaattagat   120
tgctttgagc aactagaaga aaaacatagg acaaaaaaaa atgaagaata cactgcgttg   180
aaaattttaa gggatgtcat aggtcccctt ttattaacta taacttcgtt ttatctaaga   240
ttccaacata tagatcagaa caattatgtt gtctgggatg aggctcattt tgggaaattc   300
ggatcatact acatcaaaca tgagtactac cacgatgtcc accctccact tggtaaaatg   360
cttattgcat tgagcgaatg gatggcagga tttgacggtc aatttgactt ttcctctaat   420
aatgcatatc cggaaaacgt aaactttaaa ctaatgagac aatttaatgc cacatttgga   480
gctctatgta caccagtagc tttctttaca gccaaatgga tggggttcaa ttattttact   540
gtttatttga ttgctacgat ggtaacgttg aacattcat atattgggcg cgcc          594

<210> SEQ ID NO 76
<211> LENGTH: 198
<212> TYPE: PRT
<213> ORGANISM: Artificial Sequence
<220> FEATURE:
<223> OTHER INFORMATION: ScPMT6-m ER/Golgi Transmembrane Domain

<400> SEQUENCE: 76

Met Ser Lys Ala Lys Gly Thr Gly Phe Ser Ser Ile Asp Thr Glu Asp
1               5                   10                  15

Glu Asn Leu Arg Glu Arg Tyr Val Asn Gln Pro Lys Ala Asn Ala Ser
            20                  25                  30

Asp Ile Gln Asp Glu Gln Leu Asp Cys Phe Glu Gln Leu Glu Glu Lys
        35                  40                  45

His Arg Thr Lys Lys Asn Glu Glu Tyr Thr Ala Leu Lys Ile Leu Arg
    50                  55                  60

Asp Val Ile Gly Pro Leu Leu Leu Thr Ile Thr Ser Phe Tyr Leu Arg
65                  70                  75                  80

Phe Gln His Ile Asp Gln Asn Asn Tyr Val Val Trp Asp Glu Ala His
                85                  90                  95

Phe Gly Lys Phe Gly Ser Tyr Tyr Ile Lys His Glu Tyr Tyr His Asp
            100                 105                 110

Val His Pro Pro Leu Gly Lys Met Leu Ile Ala Leu Ser Glu Trp Met
        115                 120                 125

Ala Gly Phe Asp Gly Gln Phe Asp Phe Ser Ser Asn Asn Ala Tyr Pro
    130                 135                 140

Glu Asn Val Asn Phe Lys Leu Met Arg Gln Phe Asn Ala Thr Phe Gly
145                 150                 155                 160

Ala Leu Cys Thr Pro Val Ala Phe Phe Thr Ala Lys Trp Met Gly Phe
                165                 170                 175

Asn Tyr Phe Thr Val Tyr Leu Ile Ala Thr Met Val Thr Leu Glu His
            180                 185                 190

Ser Tyr Ile Gly Arg Ala
        195

<210> SEQ ID NO 77
<211> LENGTH: 264
<212> TYPE: DNA
<213> ORGANISM: Artificial Sequence
<220> FEATURE:
<223> OTHER INFORMATION: PpPMT1-s ER/Golgi Transmembrane Domain

<400> SEQUENCE: 77
```

```
atgtgccaga tatttctccc gcaaaacgta acacgttgtt ctgtttccct tttgacaatg    60
agtaaaacaa gtcctcaaga ggtgccagaa acactactg agcttaaaat ctcaaaagga    120
gagctccgtc cttttattgt gacctctcca tctcctcaat tgagcaagtc tcgttctgtg    180
acttcaacca aggagaagct gatattggct agtttgttca tatttgcaat ggtcatcagg    240
ttccacaacg tcgccgggcg cgcc                                            264
```

<210> SEQ ID NO 78
<211> LENGTH: 88
<212> TYPE: PRT
<213> ORGANISM: Artificial Sequence
<220> FEATURE:
<223> OTHER INFORMATION: PpPMT1-s ER/Golgi Transmembrane Domain

<400> SEQUENCE: 78

```
Met Cys Gln Ile Phe Leu Pro Gln Asn Val Thr Arg Cys Ser Val Ser
1               5                   10                  15

Leu Leu Thr Met Ser Lys Thr Ser Pro Gln Glu Val Pro Glu Asn Thr
            20                  25                  30

Thr Glu Leu Lys Ile Ser Lys Gly Glu Leu Arg Pro Phe Ile Val Thr
        35                  40                  45

Ser Pro Ser Pro Gln Leu Ser Lys Ser Arg Ser Val Thr Ser Thr Lys
    50                  55                  60

Glu Lys Leu Ile Leu Ala Ser Leu Phe Ile Phe Ala Met Val Ile Arg
65                  70                  75                  80

Phe His Asn Val Ala Gly Arg Ala
                85
```

<210> SEQ ID NO 79
<211> LENGTH: 603
<212> TYPE: DNA
<213> ORGANISM: Artificial Sequence
<220> FEATURE:
<223> OTHER INFORMATION: PpPMT2-s ER/Golgi Transmembrane Domain

<400> SEQUENCE: 79

```
atgacaggcc gtgtcgacca gaaatctgat cagaaggtga aggaattgat cgaaaagatc    60
gactccgaat ccacttccag agttttcag gaagaaccag tcacttcgat cttgacacgt    120
tacgaaccct atgtcgcccc aattatattc acgttgttgt ccttttcac tcgtatgtac    180 aaaattggga tcaacaacca cgtcgtttgg gatgaagctc acttcggaaa gtttggctcc    240
tactatctca gacacgagtt ctaccacgat gtccaccctc cgttgggtaa gatgttggtc    300
ggtctatctg gctacattgc cggttacaat ggctcctggg atttcccctc cggtcaagag    360
taccctgact atattgatta cgttaaaatg aggttattca atgccacctt cagtgcctta    420
tgtgtgccat tcgcctattt caccatgaag gagattggat ttgatatcaa gacaacttgg    480
ctattcacac tgatggtctt gtgtgaaaca agttattgta cgttaggaaa attcatcttg    540
ctggattcaa tgctgctgct attcactgtg actacggttt tcacctttgt taggggcgc    600 gcc                                                                  603
```

<210> SEQ ID NO 80
<211> LENGTH: 201
<212> TYPE: PRT
<213> ORGANISM: Artificial Sequence
<220> FEATURE:
<223> OTHER INFORMATION: PpPMT2-s ER/Golgi Transmembrane Domain

```
<400> SEQUENCE: 80

Met Thr Gly Arg Val Asp Gln Lys Ser Asp Gln Lys Val Lys Glu Leu
1               5                   10                  15

Ile Glu Lys Ile Asp Ser Glu Ser Thr Ser Arg Val Phe Gln Glu Glu
                20                  25                  30

Pro Val Thr Ser Ile Leu Thr Arg Tyr Glu Pro Tyr Val Ala Pro Ile
            35                  40                  45

Ile Phe Thr Leu Leu Ser Phe Phe Thr Arg Met Tyr Lys Ile Gly Ile
        50                  55                  60

Asn Asn His Val Val Trp Asp Glu Ala His Phe Gly Lys Phe Gly Ser
65                  70                  75                  80

Tyr Tyr Leu Arg His Glu Phe Tyr His Asp Val His Pro Pro Leu Gly
                85                  90                  95

Lys Met Leu Val Gly Leu Ser Gly Tyr Ile Ala Gly Tyr Asn Gly Ser
            100                 105                 110

Trp Asp Phe Pro Ser Gly Gln Glu Tyr Pro Asp Tyr Ile Asp Tyr Val
        115                 120                 125

Lys Met Arg Leu Phe Asn Ala Thr Phe Ser Ala Leu Cys Val Pro Phe
130                 135                 140

Ala Tyr Phe Thr Met Lys Glu Ile Gly Phe Asp Ile Lys Thr Thr Trp
145                 150                 155                 160

Leu Phe Thr Leu Met Val Leu Cys Glu Thr Ser Tyr Cys Thr Leu Gly
                165                 170                 175

Lys Phe Ile Leu Leu Asp Ser Met Leu Leu Leu Phe Thr Val Thr Thr
            180                 185                 190

Val Phe Thr Phe Val Arg Gly Arg Ala
        195                 200

<210> SEQ ID NO 81
<211> LENGTH: 165
<212> TYPE: DNA
<213> ORGANISM: Artificial Sequence
<220> FEATURE:
<223> OTHER INFORMATION: PpPMT4-s ER/Golgi Transmembrane Domain

<400> SEQUENCE: 81
atgataaaat caagaaagag atcgagaaaa gtttctttga acactgaaaa ggagctgaaa      60
aatagccata tttctcttgg agatgaaaga tggtacactg tgggtcttct cttggtgaca     120
atcacagctt tctgtactcg attctatgct atcaacgggc gcgcc                     165

<210> SEQ ID NO 82
<211> LENGTH: 55
<212> TYPE: PRT
<213> ORGANISM: Artificial Sequence
<220> FEATURE:
<223> OTHER INFORMATION: PpPMT4-s ER/Golgi Transmembrane Domain

<400> SEQUENCE: 82

Met Ile Lys Ser Arg Lys Arg Ser Arg Lys Val Ser Leu Asn Thr Glu
1               5                   10                  15

Lys Glu Leu Lys Asn Ser His Ile Ser Leu Gly Asp Glu Arg Trp Tyr
                20                  25                  30

Thr Val Gly Leu Leu Leu Val Thr Ile Thr Ala Phe Cys Thr Arg Phe
            35                  40                  45

Tyr Ala Ile Asn Gly Arg Ala
        50                  55
```

<210> SEQ ID NO 83
<211> LENGTH: 129
<212> TYPE: DNA
<213> ORGANISM: Artificial Sequence
<220> FEATURE:
<223> OTHER INFORMATION: PpPMT5-s ER/Golgi Transmembrane Domain

<400> SEQUENCE: 83

```
atgacattct tcttattaga ctgcctagtt ttgtataatc ttacagaaat tctagctcaa      60
gccctcttac ttgttcttct tctatgtcaa ctgattcctc aatatatgtg gttggtggcc     120
gggcgcgcc                                                             129
```

<210> SEQ ID NO 84
<211> LENGTH: 43
<212> TYPE: PRT
<213> ORGANISM: Artificial Sequence
<220> FEATURE:
<223> OTHER INFORMATION: PpPMT5-s ER/Golgi Transmembrane Domain

<400> SEQUENCE: 84

```
Met Thr Phe Phe Leu Leu Asp Cys Leu Val Leu Tyr Asn Leu Thr Glu
 1               5                  10                  15

Ile Leu Ala Gln Ala Leu Leu Leu Val Leu Leu Leu Cys Gln Leu Ile
            20                  25                  30

Pro Gln Tyr Met Trp Leu Val Ala Gly Arg Ala
        35                  40
```

<210> SEQ ID NO 85
<211> LENGTH: 216
<212> TYPE: DNA
<213> ORGANISM: Artificial Sequence
<220> FEATURE:
<223> OTHER INFORMATION: PpPMT6-s ER/Golgi Transmembrane Domain

<400> SEQUENCE: 85

```
atggcaacag aggaagagag aaatgaactg agaagtcgga tggacgccaa taattcaaaa      60
gtttccacgt tcactacgaa caattcagat gatccttctg ttgatagcca gggtaaggtg     120
aaaattaagt catgggtttg gagccttgaa tctttaattg gccctctggt gatcactgcc     180
ttggcaattt ttcttcgagt ttaccaaggg cgcgcc                               216
```

<210> SEQ ID NO 86
<211> LENGTH: 72
<212> TYPE: PRT
<213> ORGANISM: Artificial Sequence
<220> FEATURE:
<223> OTHER INFORMATION: PpPMT6-s ER/Golgi Transmembrane Domain

<400> SEQUENCE: 86

```
Met Ala Thr Glu Glu Glu Arg Asn Glu Leu Arg Ser Arg Met Asp Ala
 1               5                  10                  15

Asn Asn Ser Lys Val Ser Thr Phe Thr Thr Asn Ser Asp Asp Pro
            20                  25                  30

Ser Val Asp Ser Gln Gly Lys Val Lys Ile Lys Ser Trp Val Trp Ser
        35                  40                  45

Leu Glu Ser Leu Ile Gly Pro Leu Val Ile Thr Ala Leu Ala Ile Phe
    50                  55                  60

Leu Arg Val Tyr Gln Gly Arg Ala
65                  70
```

<210> SEQ ID NO 87
<211> LENGTH: 399
<212> TYPE: DNA
<213> ORGANISM: Artificial Sequence
<220> FEATURE:
<223> OTHER INFORMATION: PpPMT1-m ER/Golgi Transmembrane Domain

<400> SEQUENCE: 87

```
atgtgccaga tatttctccc gcaaaacgta acacgttgtt ctgtttccct tttgacaatg      60
agtaaaacaa gtcctcaaga ggtgccagaa acactactg agcttaaaat ctcaaaagga     120
gagctccgtc cttttattgt gacctctcca tctcctcaat tgagcaagtc tcgttctgtg     180
acttcaacca aggagaagct gatattggct agtttgttca tatttgcaat ggtcatcagg     240
ttccacaacg tcgcccaccc tgacagcgtt gtgtttgatg aagttcactt tggggggttt     300
gccagaaagt acatttttggg aaccttttc atggatgttc atccgccatt ggccaagcta     360
ttatttgctg gtgttggcag tcttggtgga gggcgcgcc                            399
```

<210> SEQ ID NO 88
<211> LENGTH: 133
<212> TYPE: PRT
<213> ORGANISM: Artificial Sequence
<220> FEATURE:
<223> OTHER INFORMATION: PpPMT1-m ER/Golgi Transmembrane Domain

<400> SEQUENCE: 88

```
Met Cys Gln Ile Phe Leu Pro Gln Asn Val Thr Arg Cys Ser Val Ser
1               5                   10                  15
Leu Leu Thr Met Ser Lys Thr Ser Pro Gln Glu Val Pro Glu Asn Thr
            20                  25                  30
Thr Glu Leu Lys Ile Ser Lys Gly Glu Leu Arg Pro Phe Ile Val Thr
        35                  40                  45
Ser Pro Ser Pro Gln Leu Ser Lys Ser Arg Ser Val Thr Ser Thr Lys
    50                  55                  60
Glu Lys Leu Ile Leu Ala Ser Leu Phe Ile Phe Ala Met Val Ile Arg
65                  70                  75                  80
Phe His Asn Val Ala His Pro Asp Ser Val Val Phe Asp Glu Val His
                85                  90                  95
Phe Gly Gly Phe Ala Arg Lys Tyr Ile Leu Gly Thr Phe Phe Met Asp
            100                 105                 110
Val His Pro Pro Leu Ala Lys Leu Leu Phe Ala Gly Val Gly Ser Leu
        115                 120                 125
Gly Gly Gly Arg Ala
    130
```

<210> SEQ ID NO 89
<211> LENGTH: 639
<212> TYPE: DNA
<213> ORGANISM: Artificial Sequence
<220> FEATURE:
<223> OTHER INFORMATION: PpPMT2-m ER/Golgi Transmembrane Domain

<400> SEQUENCE: 89

```
atgacaggcc gtgtcgacca gaaatctgat cagaaggtga aggaattgat cgaaaagatc      60
gactccgaat ccacttccag agttttcag gaagaaccag tcacttcgat cttgacacgt     120
tacgaaccct atgtcgcccc aattatattc acgttgttgt cctttttcac tcgtatgtac     180
aaaattggga tcaacaacca cgtcgtttgg gatgaagctc acttcggaaa gtttggctcc     240
tactatctca gacacgagtt ctaccacgat gtccacccct cgttgggtaa gatgttggtc     300
```

```
ggtctatctg gctacattgc cggttacaat ggctcctggg atttcccctc cggtcaagag      360
taccctgact atattgatta cgttaaaatg aggttattca atgccacctt cagtgcctta      420
tgtgtgccat tcgcctattt caccatgaag gagattggat ttgatatcaa gacaacttgg      480
ctattcacac tgatggtctt gtgtgaaaca agttattgta cgttaggaaa attcatcttg      540
ctggattcaa tgctgctgct attcactgtg actacggttt tcacctttgt taggttccat      600
aacgaaaaca gtaaaccagg aaactcgttt gggcgcgcc                             639

<210> SEQ ID NO 90
<211> LENGTH: 213
<212> TYPE: PRT
<213> ORGANISM: Artificial Sequence
<220> FEATURE:
<223> OTHER INFORMATION: PpPMT2-m ER/Golgi Transmembrane Domain

<400> SEQUENCE: 90

Met Thr Gly Arg Val Asp Gln Lys Ser Asp Gln Lys Val Lys Glu Leu
1               5                   10                  15

Ile Glu Lys Ile Asp Ser Glu Ser Thr Ser Arg Val Phe Gln Glu Glu
            20                  25                  30

Pro Val Thr Ser Ile Leu Thr Arg Tyr Glu Pro Tyr Val Ala Pro Ile
        35                  40                  45

Ile Phe Thr Leu Leu Ser Phe Phe Thr Arg Met Tyr Lys Ile Gly Ile
    50                  55                  60

Asn Asn His Val Val Trp Asp Glu Ala His Phe Gly Lys Phe Gly Ser
65                  70                  75                  80

Tyr Tyr Leu Arg His Glu Phe Tyr His Asp Val His Pro Pro Leu Gly
                85                  90                  95

Lys Met Leu Val Gly Leu Ser Gly Tyr Ile Ala Gly Tyr Asn Gly Ser
            100                 105                 110

Trp Asp Phe Pro Ser Gly Gln Glu Tyr Pro Asp Tyr Ile Asp Tyr Val
        115                 120                 125

Lys Met Arg Leu Phe Asn Ala Thr Phe Ser Ala Leu Cys Val Pro Phe
    130                 135                 140

Ala Tyr Phe Thr Met Lys Glu Ile Gly Phe Asp Ile Lys Thr Thr Trp
145                 150                 155                 160

Leu Phe Thr Leu Met Val Leu Cys Glu Thr Ser Tyr Cys Thr Leu Gly
                165                 170                 175

Lys Phe Ile Leu Leu Asp Ser Met Leu Leu Leu Phe Thr Val Thr Thr
            180                 185                 190

Val Phe Thr Phe Val Arg Phe His Asn Glu Asn Ser Lys Pro Gly Asn
        195                 200                 205

Ser Phe Gly Arg Ala
    210

<210> SEQ ID NO 91
<211> LENGTH: 204
<212> TYPE: DNA
<213> ORGANISM: Artificial Sequence
<220> FEATURE:
<223> OTHER INFORMATION: PpPMT4-m ER/Golgi Transmembrane Domain

<400> SEQUENCE: 91
atgataaaat caagaaagag atcgagaaaa gtttctttga acactgaaaa ggagctgaaa      60
aatagccata tttctcttgg agatgaaaga tggtacactg tgggtcttct cttggtgaca     120
```

```
atcacagctt tctgtactcg attctatgct atcaactatc cagatgaggt tgtttttgac    180
gaagttcatt tcggagggcg cgcc                                           204
```

<210> SEQ ID NO 92
<211> LENGTH: 68
<212> TYPE: PRT
<213> ORGANISM: Artificial Sequence
<220> FEATURE:
<223> OTHER INFORMATION: PpPMT4-m ER/Golgi Transmembrane Domain

<400> SEQUENCE: 92

```
Met Ile Lys Ser Arg Lys Arg Ser Arg Lys Val Ser Leu Asn Thr Glu
1               5                   10                  15

Lys Glu Leu Lys Asn Ser His Ile Ser Leu Gly Asp Glu Arg Trp Tyr
            20                  25                  30

Thr Val Gly Leu Leu Leu Val Thr Ile Thr Ala Phe Cys Thr Arg Phe
        35                  40                  45

Tyr Ala Ile Asn Tyr Pro Asp Glu Val Val Phe Asp Glu Val His Phe
    50                  55                  60

Gly Gly Arg Ala
65
```

<210> SEQ ID NO 93
<211> LENGTH: 249
<212> TYPE: DNA
<213> ORGANISM: Artificial Sequence
<220> FEATURE:
<223> OTHER INFORMATION: PpPMT5-m ER/Golgi Transmembrane Domain

<400> SEQUENCE: 93

```
atgacattct tcttattaga ctgcctagtt ttgtataatc ttacagaaat tctagctcaa    60
gccctcttac ttgttcttct tctatgtcaa ctgattcctc aatatatgtg gttggtggcc   120
cgcgaaatga ctcctgagat atttggtcaa acctaccaaa ggacaccaca ccacagtact   180
atagcacaac aatacatggc cgcctttgag tacaaaaagg gcattcaaag accctatttt   240
gggcgcgcc                                                           249
```

<210> SEQ ID NO 94
<211> LENGTH: 83
<212> TYPE: PRT
<213> ORGANISM: Artificial Sequence
<220> FEATURE:
<223> OTHER INFORMATION: PpPMT5-m ER/Golgi Transmembrane Domain

<400> SEQUENCE: 94

```
Met Thr Phe Phe Leu Leu Asp Cys Leu Val Leu Tyr Asn Leu Thr Glu
1               5                   10                  15

Ile Leu Ala Gln Ala Leu Leu Leu Val Leu Leu Leu Cys Gln Leu Ile
            20                  25                  30

Pro Gln Tyr Met Trp Leu Val Ala Arg Glu Met Thr Pro Glu Ile Phe
        35                  40                  45

Gly Gln Thr Tyr Gln Arg Thr Pro His His Ser Thr Ile Ala Gln Gln
    50                  55                  60

Tyr Met Ala Ala Phe Glu Tyr Lys Lys Gly Ile Gln Arg Pro Tyr Phe
65                  70                  75                  80

Gly Arg Ala
```

<210> SEQ ID NO 95
<211> LENGTH: 339

<210> SEQ ID NO 95
<211> LENGTH: 339
<212> TYPE: DNA
<213> ORGANISM: Artificial Sequence
<220> FEATURE:
<223> OTHER INFORMATION: PpPMT6-m ER/Golgi Transmembrane Domain

<400> SEQUENCE: 95

```
atggcaacag aggaagagag aaatgaactg agaagtcgga tggacgccaa taattcaaaa      60
gtttccacgt tcactacgaa caattcagat gatccttctg ttgatagcca gggtaaggtg     120
aaaattaagt catgggtttg agccttgaa tctttaattg ccctctggt gatcactgcc      180
ttggcaattt ttcttcgagt ttaccaaata ggaaaagctg atagggttgt ttgggatgaa     240
gctcatttcg gaaagtttgg gtcattctac ttgaagcacc agttctattt tgatgtccat     300
cctcccctgg gaaaacttct tacaggtttg gggcgcgcc                            339
```

<210> SEQ ID NO 96
<211> LENGTH: 113
<212> TYPE: PRT
<213> ORGANISM: Artificial Sequence
<220> FEATURE:
<223> OTHER INFORMATION: PpPMT6-m ER/Golgi Transmembrane Domain

<400> SEQUENCE: 96

```
Met Ala Thr Glu Glu Arg Asn Glu Leu Arg Ser Arg Met Asp Ala
1               5                   10                  15

Asn Asn Ser Lys Val Ser Thr Phe Thr Thr Asn Ser Asp Asp Pro
            20                  25                  30

Ser Val Asp Ser Gln Gly Lys Val Lys Ile Lys Ser Trp Val Trp Ser
        35                  40                  45

Leu Glu Ser Leu Ile Gly Pro Leu Val Ile Thr Ala Leu Ala Ile Phe
    50                  55                  60

Leu Arg Val Tyr Gln Ile Gly Lys Ala Asp Arg Val Val Trp Asp Glu
65                  70                  75                  80

Ala His Phe Gly Lys Phe Gly Ser Phe Tyr Leu Lys His Gln Phe Tyr
                85                  90                  95

Phe Asp Val His Pro Pro Leu Gly Lys Leu Leu Thr Gly Leu Gly Arg
                100                 105                 110

Ala
```

<210> SEQ ID NO 97
<211> LENGTH: 99
<212> TYPE: DNA
<213> ORGANISM: Artificial Sequence
<220> FEATURE:
<223> OTHER INFORMATION: ScBOS1-s ER/Golgi Transmembrane Domain

<400> SEQUENCE: 97

```
atgaacgctc tttacaacca tgctgtgaag caaaaaaatc aactacaaca agagttggcc      60
aggtttgaaa agaattctgt gaccgcccct gggcgcgcc                             99
```

<210> SEQ ID NO 98
<211> LENGTH: 33
<212> TYPE: PRT
<213> ORGANISM: Artificial Sequence
<220> FEATURE:
<223> OTHER INFORMATION: ScBOS1-s ER/Golgi Transmembrane Domain

<400> SEQUENCE: 98

```
Met Asn Ala Leu Tyr Asn His Ala Val Lys Gln Lys Asn Gln Leu Gln
1               5                   10                  15
```

Gln Glu Leu Ala Arg Phe Glu Lys Asn Ser Val Thr Ala Pro Gly Arg
            20                  25                  30

Ala

<210> SEQ ID NO 99
<211> LENGTH: 108
<212> TYPE: DNA
<213> ORGANISM: Artificial Sequence
<220> FEATURE:
<223> OTHER INFORMATION: ScBET1-s ER/Golgi Transmembrane Domain

<400> SEQUENCE: 99
atgagttcaa gatttgcagg gggaaacgct tatcaacgtg atactggtag aacacagtta      60
ttcggaccgg ctgatggatc aaatagtctc gatgacaatg ggcgcgcc                  108

<210> SEQ ID NO 100
<211> LENGTH: 36
<212> TYPE: PRT
<213> ORGANISM: Artificial Sequence
<220> FEATURE:
<223> OTHER INFORMATION: ScBET1-s ER/Golgi Transmembrane Domain

<400> SEQUENCE: 100

Met Ser Ser Arg Phe Ala Gly Gly Asn Ala Tyr Gln Arg Asp Thr Gly
1               5                   10                  15

Arg Thr Gln Leu Phe Gly Pro Ala Asp Gly Ser Asn Ser Leu Asp Asp
            20                  25                  30

Asn Gly Arg Ala
        35

<210> SEQ ID NO 101
<211> LENGTH: 114
<212> TYPE: DNA
<213> ORGANISM: Artificial Sequence
<220> FEATURE:
<223> OTHER INFORMATION: ScSEC22-s ER/Golgi Transmembrane Domain

<400> SEQUENCE: 101
atgtccgcgc aaaagatcaa cttcgatctc ttgatcagtc aatatgctcc tattgtcatt      60
gtcgctttct ttttcgtctt tctcttctgg tggatcttcc tcaaagggcg cgcc           114

<210> SEQ ID NO 102
<211> LENGTH: 38
<212> TYPE: PRT
<213> ORGANISM: Artificial Sequence
<220> FEATURE:
<223> OTHER INFORMATION: ScSEC22-s ER/Golgi Transmembrane Domain

<400> SEQUENCE: 102

Met Ser Ala Gln Lys Ile Asn Phe Asp Leu Leu Ile Ser Gln Tyr Ala
1               5                   10                  15

Pro Ile Val Ile Val Ala Phe Phe Phe Val Phe Leu Phe Trp Trp Ile
            20                  25                  30

Phe Leu Lys Gly Arg Ala
        35

<210> SEQ ID NO 103
<211> LENGTH: 96
<212> TYPE: DNA
<213> ORGANISM: Artificial Sequence
<220> FEATURE:
<223> OTHER INFORMATION: PpBOS1-s ER/Golgi Transmembrane Domain

<400> SEQUENCE: 103

```
atgaaggcat tgaagacaa gtggattttt tatggtggcg ctataagtgt ttttgttatt    60
ttctatttgg cggtcaaata tttaagaggg cgcgcc                             96
```

<210> SEQ ID NO 104
<211> LENGTH: 32
<212> TYPE: PRT
<213> ORGANISM: Artificial Sequence
<220> FEATURE:
<223> OTHER INFORMATION: PpBOS1-s ER/Golgi Transmembrane Domain

<400> SEQUENCE: 104

Met Lys Ala Phe Glu Asp Lys Trp Ile Phe Tyr Gly Gly Ala Ile Ser
1               5                   10                  15

Val Phe Val Ile Phe Tyr Leu Ala Val Lys Tyr Leu Arg Gly Arg Ala
            20                  25                  30

<210> SEQ ID NO 105
<211> LENGTH: 111
<212> TYPE: DNA
<213> ORGANISM: Artificial Sequence
<220> FEATURE:
<223> OTHER INFORMATION: PpBET1-s ER/Golgi Transmembrane Domain

<400> SEQUENCE: 105

```
atgaggatga tggtaatggc taagaaaaca ggtatttcat ggaagttatg gctgctgttc    60
ttcttcctcg tctggctttg gttctttttt gtgtggctta gagggcgcgc c           111
```

<210> SEQ ID NO 106
<211> LENGTH: 37
<212> TYPE: PRT
<213> ORGANISM: Artificial Sequence
<220> FEATURE:
<223> OTHER INFORMATION: PpBET1-s ER/Golgi Transmembrane Domain

<400> SEQUENCE: 106

Met Arg Met Met Val Met Ala Lys Lys Thr Gly Ile Ser Trp Lys Leu
1               5                   10                  15

Trp Leu Leu Phe Phe Phe Leu Val Trp Leu Trp Phe Phe Phe Val Trp
            20                  25                  30

Leu Arg Gly Arg Ala
        35

<210> SEQ ID NO 107
<211> LENGTH: 114
<212> TYPE: DNA
<213> ORGANISM: Artificial Sequence
<220> FEATURE:
<223> OTHER INFORMATION: PpSEC22-s ER/Golgi Transmembrane Domain

<400> SEQUENCE: 107

```
atggcagctc gaagaatcaa tttggaggct ctgataaaac agtacgttcc ggttgcaatg    60
gtggggattt tcttcgtatt tataatatgg tggatattct tgcgcgggcg cgcc        114
```

<210> SEQ ID NO 108
<211> LENGTH: 38
<212> TYPE: PRT
<213> ORGANISM: Artificial Sequence
<220> FEATURE:
<223> OTHER INFORMATION: PpSEC22-s ER/Golgi Transmembrane Domain

<400> SEQUENCE: 108

Met Ala Ala Arg Arg Ile Asn Leu Glu Ala Leu Ile Lys Gln Tyr Val
1               5                   10                  15

Pro Val Ala Met Val Gly Ile Phe Phe Val Phe Ile Trp Trp Ile
            20                  25                  30

Phe Leu Arg Gly Arg Ala
            35

<210> SEQ ID NO 109
<211> LENGTH: 1809
<212> TYPE: DNA
<213> ORGANISM: Human

<400> SEQUENCE: 109

```
cgcgccattt ctgaagctaa cgaggaccct gaaccagaac aagattacga cgaggctttg        60
ggaagattgg aaccaccaag aagaagaggt tccggtccaa gaagagtttt ggacgttgag       120
gtttactctt ccagatccaa ggtttacgtt gctgttgacg gtactactgt tttggaggac       180
gaggctagag aacaaggtag aggtatccac gttatcgttt gaaccaggc tactggtcat        240
gttatggcta agagagtttt cgacacttac tctccacacg aagatgaggc tatggttttg       300
ttcttgaaca tggttgctcc agtagagtt ttgatttgta ctgttaagga cgagggatcc        360
ttccatttga aggacactgc taaggctttg ttgagatcct tgggttctca agctggtcca       420
gctttgggat ggagagatac ttgggctttc gttggtagaa agggtggtcc agttttcggt       480
gaaaagcact ctaagtcccc agctttgtcc tcttggggtg acccagtttt gttgaaaact       540
gacgttccat gtcctctgc tgaagaggct gaatgtcact gggctgacac tgagttgaac        600
agaagaagaa gaagattctg ttccaaggtt gagggttacg gttctgtttg ttcctgtaag       660
gacccaactc caattgaatt ctccccagac ccattgccag ataacaaggt tttgaacgtt       720
ccagttgctg ttatcgctgg taacagacca aactacttgt acagaatgtt gagatctttg       780
ttgtccgctc agggagtttc tccacagatg atcactgttt tcatcgacgg ttactacgaa       840
gaaccaatgg acgttgttgc tttgttcgga ttgagaggta ttcagcacac tccaatctcc       900
atcaagaacg ctagagtttc caacactac aaggcttcct tgactgctac tttcaacttg        960
ttcccagagg ctaagttcgc tgttgttttg gaagaggact tggacattgc tgttgatttc      1020
ttctccttct tgtcccaatc catccacttg ttggaagagg atgactcctt gtactgtatc      1080
tctgcttgga acgaccaagg ttacgaacac actgctgagg atccagcttt gttgtacaga      1140
gttgagacta tgccaggatt gggatgggtt ttgagaagat ccttgtacaa gaagagttg       1200
gagccaaagt ggccaactcc agaaaagttg tgggattggg acatgtggat gagaatgcca      1260
gagcagagaa gaggtagaga gtgtatcatc ccagacgttt ccagatctta ccacttcggt      1320
attgttggat tgaacatgaa cggttacttc cacgaggctt acttcaagaa gcacaagttc      1380
aacactgttc caggtgttca gttgagaaac gttgactcct tgaagaaaga ggcttacgag      1440
gttgaggttc acagattgtt gtctgaggct gaggttttgg accattccaa gaacccatgt      1500
gaggactcat tcttgccaga tactgagggt catacttacg ttgctttcat cagaatggaa      1560
aaggacgacg acttcactac ttggactcag ttggctaagt gtttgcacat ttgggacttg      1620
gatgttagag gtaaccacag aggattgtgg agattgttca gaagaagaa ccacttcttg       1680
gttgttggtg ttccagcttc tccatactcc gttaagaagc caccatccgt tactccaatt      1740
ttcttggagc caccaccaaa ggaagaaggt gctcctggtg ctccagagca aacttaatag      1800
ttaattaaa                                                              1809
```

<210> SEQ ID NO 110
<211> LENGTH: 598
<212> TYPE: PRT
<213> ORGANISM: Human

<400> SEQUENCE: 110

Arg Ala Ile Ser Glu Ala Asn Glu Asp Pro Glu Pro Glu Gln Asp Tyr
1               5                   10                  15

Asp Glu Ala Leu Gly Arg Leu Glu Pro Pro Arg Arg Gly Ser Gly
            20                  25                  30

Pro Arg Arg Val Leu Asp Val Glu Val Tyr Ser Ser Arg Ser Lys Val
            35                  40                  45

Tyr Val Ala Val Asp Gly Thr Thr Val Leu Glu Asp Glu Ala Arg Glu
50                  55                  60

Gln Gly Arg Gly Ile His Val Ile Val Leu Asn Gln Ala Thr Gly His
65                  70                  75                  80

Val Met Ala Lys Arg Val Phe Asp Thr Tyr Ser Pro His Glu Asp Glu
                85                  90                  95

Ala Met Val Leu Phe Leu Asn Met Val Ala Pro Gly Arg Val Leu Ile
            100                 105                 110

Cys Thr Val Lys Asp Glu Gly Ser Phe His Leu Lys Asp Thr Ala Lys
            115                 120                 125

Ala Leu Leu Arg Ser Leu Gly Ser Gln Ala Gly Pro Ala Leu Gly Trp
130                 135                 140

Arg Asp Thr Trp Ala Phe Val Gly Arg Lys Gly Gly Pro Val Phe Gly
145                 150                 155                 160

Glu Lys His Ser Lys Ser Pro Ala Leu Ser Ser Trp Gly Asp Pro Val
                165                 170                 175

Leu Leu Lys Thr Asp Val Pro Leu Ser Ser Ala Glu Glu Ala Glu Cys
            180                 185                 190

His Trp Ala Asp Thr Glu Leu Asn Arg Arg Arg Arg Phe Cys Ser
            195                 200                 205

Lys Val Glu Gly Tyr Gly Ser Val Cys Ser Cys Lys Asp Pro Thr Pro
210                 215                 220

Ile Glu Phe Ser Pro Asp Pro Leu Pro Asp Asn Lys Val Leu Asn Val
225                 230                 235                 240

Pro Val Ala Val Ile Ala Gly Asn Arg Pro Asn Tyr Leu Tyr Arg Met
                245                 250                 255

Leu Arg Ser Leu Leu Ser Ala Gln Gly Val Ser Pro Gln Met Ile Thr
            260                 265                 270

Val Phe Ile Asp Gly Tyr Tyr Glu Glu Pro Met Asp Val Val Ala Leu
            275                 280                 285

Phe Gly Leu Arg Gly Ile Gln His Thr Pro Ile Ser Ile Lys Asn Ala
290                 295                 300

Arg Val Ser Gln His Tyr Lys Ala Ser Leu Thr Ala Thr Phe Asn Leu
305                 310                 315                 320

Phe Pro Glu Ala Lys Phe Ala Val Val Leu Glu Glu Asp Leu Asp Ile
                325                 330                 335

Ala Val Asp Phe Phe Ser Phe Leu Ser Gln Ser Ile His Leu Leu Glu
            340                 345                 350

Glu Asp Asp Ser Leu Tyr Cys Ile Ser Ala Trp Asn Asp Gln Gly Tyr
            355                 360                 365

Glu His Thr Ala Glu Asp Pro Ala Leu Leu Tyr Arg Val Glu Thr Met
370                 375                 380

```
Pro Gly Leu Gly Trp Val Leu Arg Arg Ser Leu Tyr Lys Glu Glu Leu
385                 390                 395                 400

Glu Pro Lys Trp Pro Thr Pro Glu Lys Leu Trp Asp Trp Asp Met Trp
            405                 410                 415

Met Arg Met Pro Glu Gln Arg Arg Gly Arg Glu Cys Ile Ile Pro Asp
        420                 425                 430

Val Ser Arg Ser Tyr His Phe Gly Ile Val Gly Leu Asn Met Asn Gly
            435                 440                 445

Tyr Phe His Glu Ala Tyr Phe Lys Lys His Lys Phe Asn Thr Val Pro
        450                 455                 460

Gly Val Gln Leu Arg Asn Val Asp Ser Leu Lys Lys Glu Ala Tyr Glu
465                 470                 475                 480

Val Glu Val His Arg Leu Leu Ser Glu Ala Glu Val Leu Asp His Ser
                485                 490                 495

Lys Asn Pro Cys Glu Asp Ser Phe Leu Pro Asp Thr Glu Gly His Thr
            500                 505                 510

Tyr Val Ala Phe Ile Arg Met Glu Lys Asp Asp Phe Thr Thr Trp
        515                 520                 525

Thr Gln Leu Ala Lys Cys Leu His Ile Trp Asp Leu Asp Val Arg Gly
            530                 535                 540

Asn His Arg Gly Leu Trp Arg Leu Phe Arg Lys Asn His Phe Leu
545                 550                 555                 560

Val Val Gly Val Pro Ala Ser Pro Tyr Ser Val Lys Lys Pro Pro Ser
                565                 570                 575

Val Thr Pro Ile Phe Leu Glu Pro Pro Lys Glu Glu Gly Ala Pro
            580                 585                 590

Gly Ala Pro Glu Gln Thr
        595

<210> SEQ ID NO 111
<211> LENGTH: 1804
<212> TYPE: DNA
<213> ORGANISM: Mouse

<400> SEQUENCE: 111
cgcgccattt ctgaagctaa cgaggaccct gaaccagaac aagattacga cgaggctttg      60
ggaagattgg aatccccaag aagaagagga tcctccccta gaaagttttt ggacgttgag     120
gtttactctt ccagatccaa ggtttacgtt gctgttgacg gtactactgt tttggaggac     180
gaggctagag aacaaggtag aggtatccac gttatcgttt tgaaccaggc tactggtcat     240
gttatggcta agagagtttt cgacacttac tctccacacg aagatgaggc tatggttttg     300
ttcttgaaca tggttgctcc aggtagagtt ttgatttgta ctgttaagga cgagggatcc     360
ttccatttga aggacactgc taaggctttg ttgagatcct ggggttctca agctggtcca     420
gctttgggat ggagagatac ttgggctttc gttggtagaa agggtggtcc agttttgggt     480
gaaaagcact ctaagtcccc agctttgtcc tcttggggtg acccagtttt gttgaaaact     540
gacgttccat tgtcctctgc tgaagaggct gaatgtcact gggctgacac tgagttgaac     600
agaagaagaa gaagattctg ttccaaggtt gagggttacg ttctgtttg ttcctgtaag     660 gacccaactc caattgaatt ctcccccagac ccattgccag ataacaaggt tttgaacgtt     720
ccagttgctg ttatcgctgg taacagacca aactacttgt acagaatgtt gagatctttg     780
ttgtccgctc agggagtttc tccacagatg atcactgttt tcatcgacgg ttactacgaa     840
```

-continued

```
gaaccaatgg acgttgttgc tttgttcgga ttgagaggta ttcagcacac tccaatctcc    900
atcaagaacg ctagagtttc ccaacactac aaggcttcct tgactgctac tttcaacttg    960
ttcccagagg ctaagttcgc tgttgttttg gaagaggact tggacattgc tgttgatttc   1020
ttctccttct tgtcccaatc catccacttg tggaagagg atgactcctt gtactgtatc    1080
tctgcttgga acgaccaagg ttacgaacac actgctgagg atccagcttt gttgtacaga   1140
gttgagacta tgccaggatt gggatgggtt tgagaaagt ccttgtacaa agaggagttg    1200
gagccaaagt ggccaactcc agaaaagttg tgggattggg acatgtggat gagaatgcca   1260
gagcagagaa gaggtagaga gtgtatcatc ccagacgttt ccagatctta ccacttcggt   1320
attgttggat tgaacatgaa cggttacttc cacgaggctt acttcaagaa gcacaagttc   1380
aacactgttc caggtgttca gttgagaaac gttgactcct tgaagaaaga ggcttacgag   1440
gttgagatcc acagattgtt gtctgaggct gaggttttgg atcactccaa ggatccatgt   1500
gaggactcat tcttgccaga tactgagggt catacttacg ttgctttcat cagaatggaa   1560
actgacgacg actttgctac ttggactcag ttggctaagt gtttgcacat ttgggacttg   1620
gatgttagag gtaaccacag aggattgtgg agattgttca gaaagaagaa ccacttcttg   1680
gttgttggtg ttccagcttc tccatactcc gttaagaagc caccatccgt tactccaatt   1740
ttcttggagc caccaccaaa ggaagaaggt gctcctggag ctgctgaaca aacttagtag   1800
ttaa                                                                1804
```

<210> SEQ ID NO 112
<211> LENGTH: 598
<212> TYPE: PRT
<213> ORGANISM: Mouse

<400> SEQUENCE: 112

```
Arg Ala Ile Ser Glu Ala Asn Glu Asp Pro Glu Pro Glu Gln Asp Tyr
1               5                   10                  15

Asp Glu Ala Leu Gly Arg Leu Glu Ser Pro Arg Arg Gly Ser Ser
            20                  25                  30

Pro Arg Arg Val Leu Asp Val Glu Val Tyr Ser Ser Arg Ser Lys Val
        35                  40                  45

Tyr Val Ala Val Asp Gly Thr Thr Val Leu Glu Asp Glu Ala Arg Glu
    50                  55                  60

Gln Gly Arg Gly Ile His Val Ile Val Leu Asn Gln Ala Thr Gly His
65                  70                  75                  80

Val Met Ala Lys Arg Val Phe Asp Thr Tyr Ser Pro His Glu Asp Glu
                85                  90                  95

Ala Met Val Leu Phe Leu Asn Met Val Ala Pro Gly Arg Val Leu Ile
            100                 105                 110

Cys Thr Val Lys Asp Glu Gly Ser Phe His Leu Lys Asp Thr Ala Lys
        115                 120                 125

Ala Leu Leu Arg Ser Leu Gly Ser Gln Ala Gly Pro Ala Leu Gly Trp
    130                 135                 140

Arg Asp Thr Trp Ala Phe Val Gly Arg Lys Gly Gly Pro Val Leu Gly
145                 150                 155                 160

Glu Lys His Ser Lys Ser Pro Ala Leu Ser Ser Trp Gly Asp Pro Val
                165                 170                 175

Leu Leu Lys Thr Asp Val Pro Leu Ser Ser Ala Glu Glu Ala Glu Cys
            180                 185                 190

His Trp Ala Asp Thr Glu Leu Asn Arg Arg Arg Arg Phe Cys Ser
```

```
            195                 200                 205
Lys Val Glu Gly Tyr Gly Ser Val Cys Ser Cys Lys Asp Pro Thr Pro
210                 215                 220

Ile Glu Phe Ser Pro Asp Pro Leu Pro Asp Asn Lys Val Leu Asn Val
225                 230                 235                 240

Pro Val Ala Val Ile Ala Gly Asn Arg Pro Asn Tyr Leu Tyr Arg Met
                245                 250                 255

Leu Arg Ser Leu Leu Ser Ala Gln Gly Val Ser Pro Gln Met Ile Thr
                260                 265                 270

Val Phe Ile Asp Gly Tyr Tyr Glu Glu Pro Met Asp Val Val Ala Leu
            275                 280                 285

Phe Gly Leu Arg Gly Ile Gln His Thr Pro Ile Ser Ile Lys Asn Ala
290                 295                 300

Arg Val Ser Gln His Tyr Lys Ala Ser Leu Thr Ala Thr Phe Asn Leu
305                 310                 315                 320

Phe Pro Glu Ala Lys Phe Ala Val Val Leu Glu Glu Asp Leu Asp Ile
                325                 330                 335

Ala Val Asp Phe Phe Ser Phe Leu Ser Gln Ser Ile His Leu Leu Glu
                340                 345                 350

Glu Asp Asp Ser Leu Tyr Cys Ile Ser Ala Trp Asn Asp Gln Gly Tyr
            355                 360                 365

Glu His Thr Ala Glu Asp Pro Ala Leu Leu Tyr Arg Val Glu Thr Met
370                 375                 380

Pro Gly Leu Gly Trp Val Leu Arg Lys Ser Leu Tyr Lys Glu Glu Leu
385                 390                 395                 400

Glu Pro Lys Trp Pro Thr Pro Glu Lys Leu Trp Asp Trp Asp Met Trp
                405                 410                 415

Met Arg Met Pro Glu Gln Arg Arg Gly Arg Glu Cys Ile Ile Pro Asp
                420                 425                 430

Val Ser Arg Ser Tyr His Phe Gly Ile Val Gly Leu Asn Met Asn Gly
            435                 440                 445

Tyr Phe His Glu Ala Tyr Phe Lys Lys His Lys Phe Asn Thr Val Pro
450                 455                 460

Gly Val Gln Leu Arg Asn Val Asp Ser Leu Lys Lys Glu Ala Tyr Glu
465                 470                 475                 480

Val Glu Ile His Arg Leu Leu Ser Glu Ala Glu Val Leu Asp His Ser
                485                 490                 495

Lys Asp Pro Cys Glu Asp Ser Phe Leu Pro Asp Thr Glu Gly His Thr
                500                 505                 510

Tyr Val Ala Phe Ile Arg Met Glu Thr Asp Asp Phe Ala Thr Trp
            515                 520                 525

Thr Gln Leu Ala Lys Cys Leu His Ile Trp Asp Leu Asp Val Arg Gly
530                 535                 540

Asn His Arg Gly Leu Trp Arg Leu Phe Arg Lys Asn His Phe Leu
545                 550                 555                 560

Val Val Gly Val Pro Ala Ser Pro Tyr Ser Val Lys Lys Pro Pro Ser
                565                 570                 575

Val Thr Pro Ile Phe Leu Glu Pro Pro Lys Glu Glu Gly Ala Pro
                580                 585                 590

Gly Ala Ala Glu Gln Thr
            595

<210> SEQ ID NO 113
```

<211> LENGTH: 1616
<212> TYPE: DNA
<213> ORGANISM: Chicken

<400> SEQUENCE: 113

```
cgcgccgctt atgaagaaga ggaagagtcc gctcaagatt acgacgacga gatgttgaat      60
gttgaggctc caagacaccc agtttccaac aagaaggttt tggacgttga ggtttactct     120
tccagatcca aggtttacgt tgctgttgac ggtactactg ttttggagga cgaggctaga     180
gaacaaggta gaggtatcca cgttatcgtt ttgaaccagg ctactggtca tgttatggct     240
aagagagttt tcgacactta ctctccacac gaagatgagg ctatggtttt gttcttgaac     300
atggttgcta gaggtagaat cttgatcttc actatcaagg acgagggatc cttccacttg     360
aaagagactg ctaagaacgt tttgaagtcc ttgggttccc aagttgctcc attcttgtct     420
tggagagaca tgtggacttt tgttggaaag aagggtggag aagtttacgg tgaaaagcac     480
gctaagtctc cagctttgtc tacttggggt gacccagttt tgttgaaaac tgaggttcac     540
ttgacttccg ttgaggatgc tgaatgtcac tggccagaca ctgagttgaa cagaagaaga     600
agaagattct gttccaaggt tgagggttac ggttctgttt gttcctgtaa ggacccaact     660
ccaatcgaat tcaacccaga cccattgaag acaacaagg ttttcgatgt tccagttgct     720
gttatcgctg gtaacagacc aaactacttg tacagaatgt tgagatcctt gttgtccgct     780
caaggtgtta acccacagat gatcactgtt ttcatcgacg ttactacga agaaccaatg     840
gacgttgttg agttgttcgg tttgtccggt attcaacaca ctccaatctc catcaagaac     900
gctagagttt cccaacacta caaggcttcc ttgactgcta cttttcaactt gttcccagac     960
gctaagttcg ctgttgtttt ggaagaggac ttggacattt ccgttgattt cttctccttc    1020
ttgtcccaat ccatccactt gttggaagag atgagtcct tgtactgtat ctctgcttgg    1080
aacgaccaag gttacgaaca cactgctgag gatccatcct tgttgtacag agttgagact    1140
atgccaggat tgggatgggt tttgagaaag tcattgtata aggacgaatt ggaaccaaag    1200
tggccaactc cagaaaagtt gtgggattgg acatgtgga tgagaatgcc agagcagaga    1260
aagggtagag agtgtatcat tccagacatc tccagatctt accacttcgg tattgttgga    1320
ttgaacatga acgttacttt ccacgaggct tacttcaaga gcacaagtt caacactgtt    1380
ccaaacgttc agttgaagaa cgttgagtcc ttgagaaagg acgcttacga agctgagatc    1440
cacagattgt tgggtgaagc tgaggttttg gaccactcca gaacccatg tgaggattct    1500
ttcgttcctg acactgaggg taaagtttac gttatgttca tcaagatgga acaagaggct    1560
gacttcacta cttggactca gttggctaaa gaattgatgg cttagtagtt aattaa       1616
```

<210> SEQ ID NO 114
<211> LENGTH: 534
<212> TYPE: PRT
<213> ORGANISM: Chicken

<400> SEQUENCE: 114

Arg Ala Ala Tyr Glu Glu Glu Glu Ser Ala Gln Asp Tyr Asp Asp
1               5                   10                  15

Glu Met Leu Asn Val Glu Ala Pro Arg His Pro Val Ser Asn Lys Lys
            20                  25                  30

Val Leu Asp Val Glu Val Tyr Ser Ser Arg Ser Lys Val Tyr Val Ala
        35                  40                  45

Val Asp Gly Thr Thr Val Leu Glu Asp Glu Ala Arg Glu Gln Gly Arg
    50                  55                  60

```
Gly Ile His Val Ile Val Leu Asn Gln Ala Thr Gly His Val Met Ala
 65                  70                  75                  80

Lys Arg Val Phe Asp Thr Tyr Ser Pro His Glu Asp Glu Ala Met Val
                 85                  90                  95

Leu Phe Leu Asn Met Val Ala Arg Gly Arg Ile Leu Ile Phe Thr Ile
                100                 105                 110

Lys Asp Glu Gly Ser Phe His Leu Lys Glu Thr Ala Lys Asn Val Leu
                115                 120                 125

Lys Ser Leu Gly Ser Gln Val Ala Pro Phe Leu Ser Trp Arg Asp Met
            130                 135                 140

Trp Thr Phe Val Gly Lys Lys Gly Glu Val Tyr Gly Glu Lys His
145                 150                 155                 160

Ala Lys Ser Pro Ala Leu Ser Thr Trp Gly Asp Pro Val Leu Leu Lys
                165                 170                 175

Thr Glu Val His Leu Thr Ser Val Glu Asp Ala Glu Cys His Trp Pro
                180                 185                 190

Asp Thr Glu Leu Asn Arg Arg Arg Arg Phe Cys Ser Lys Val Glu
            195                 200                 205

Gly Tyr Gly Ser Val Cys Ser Cys Lys Asp Pro Thr Pro Ile Glu Phe
210                 215                 220

Asn Pro Asp Pro Leu Lys Asp Asn Lys Val Phe Asp Val Pro Val Ala
225                 230                 235                 240

Val Ile Ala Gly Asn Arg Pro Asn Tyr Leu Tyr Arg Met Leu Arg Ser
                245                 250                 255

Leu Leu Ser Ala Gln Gly Val Asn Pro Gln Met Ile Thr Val Phe Ile
                260                 265                 270

Asp Gly Tyr Tyr Glu Glu Pro Met Asp Val Val Glu Leu Phe Gly Leu
            275                 280                 285

Ser Gly Ile Gln His Thr Pro Ile Ser Ile Lys Asn Ala Arg Val Ser
            290                 295                 300

Gln His Tyr Lys Ala Ser Leu Thr Ala Thr Phe Asn Leu Phe Pro Asp
305                 310                 315                 320

Ala Lys Phe Ala Val Val Leu Glu Glu Asp Leu Asp Ile Ser Val Asp
                325                 330                 335

Phe Phe Ser Phe Leu Ser Gln Ser Ile His Leu Leu Glu Glu Asp Glu
                340                 345                 350

Ser Leu Tyr Cys Ile Ser Ala Trp Asn Asp Gln Gly Tyr Glu His Thr
            355                 360                 365

Ala Glu Asp Pro Ser Leu Leu Tyr Arg Val Glu Thr Met Pro Gly Leu
            370                 375                 380

Gly Trp Val Leu Arg Lys Ser Leu Tyr Lys Asp Glu Leu Glu Pro Lys
385                 390                 395                 400

Trp Pro Thr Pro Glu Lys Leu Trp Asp Trp Asp Met Trp Met Arg Met
                405                 410                 415

Pro Glu Gln Arg Lys Gly Arg Glu Cys Ile Ile Pro Asp Ile Ser Arg
                420                 425                 430

Ser Tyr His Phe Gly Ile Val Gly Leu Asn Met Asn Gly Tyr Phe His
                435                 440                 445

Glu Ala Tyr Phe Lys Lys His Lys Phe Asn Thr Val Pro Asn Val Gln
            450                 455                 460

Leu Lys Asn Val Glu Ser Leu Arg Lys Asp Ala Tyr Glu Ala Glu Ile
465                 470                 475                 480
```

His Arg Leu Leu Gly Glu Ala Glu Val Leu Asp His Ser Lys Asn Pro
            485                 490                 495

Cys Glu Asp Ser Phe Val Pro Asp Thr Glu Gly Lys Val Tyr Val Met
        500                 505                 510

Phe Ile Lys Met Glu Gln Glu Ala Asp Phe Thr Thr Trp Thr Gln Leu
    515                 520                 525

Ala Lys Glu Leu Met Ala
    530

<210> SEQ ID NO 115
<211> LENGTH: 1781
<212> TYPE: DNA
<213> ORGANISM: Zebrafish

<400> SEQUENCE: 115

| | | | | | |
|---|---|---|---|---|---|
| cgccgcttct | gaagatgatg | ctgctcaaga | atacgatgac | gctttgccaa | acatggaaac | 60 |
| tccaagaaga | ccagcttccg | gtagaaaggt | tttggacatc | gaggtttact | cttccagatc | 120 |
| caaggtttac | gttgctgttg | acggtactac | tgttttggag | gacgagatta | gagaacaggg | 180 |
| tagaggtatc | cacgttatcg | ttttgaacca | ggctactggt | catgttatgg | ctaagagagt | 240 |
| tttcgacact | tactctccac | acgaagatga | ggctatgatc | ttgttcttga | acatggttac | 300 |
| tagaggtaga | atcttgatct | tcactatcaa | ggacgaggga | actttccatt | gaaggacgc | 360 |
| tgctaagaac | ttgttgaagg | gattgggttc | ccaagttgct | gttactttgg | gatggagaga | 420 |
| catgtggact | ttggttgtta | agaagggtgg | acaggtttac | ggtgaaaagc | actctaagtc | 480 |
| cccagctttg | tctacttggg | gtgacccagt | tttgttgaaa | actgaggttc | agttgactgc | 540 |
| ttctgaagag | gctgaatgtc | actgggctga | cactgagttg | aacagaagaa | gaaagttgtt | 600 |
| ctgttccaag | gttgaaggtt | acggttctat | ctgttcctgt | aaggacccag | ctccaattga | 660 |
| attcaaccca | gatccattgt | ccaacaacaa | cgtttacaac | atccctgttg | ctgttatcgc | 720 |
| tggtaacaga | ccaaactact | tgtacagaat | gttgagatcc | ttgttgtcct | ctcacggtgt | 780 |
| taacccacag | atgatcactg | ttttcatcga | cggttactac | gaagaaccaa | tggacgttgt | 840 |
| tgacttgttc | ggattgaagg | gtgttcaaca | cactccaatc | tccatcaaga | acgctagagt | 900 |
| ttcccaacac | tacaaggctt | ccttgactgc | tactttcaac | ttgcacccag | atgctgactt | 960 |
| cgctatcgtt | ttggaagagg | acttggacat | ttccatcgat | ttcttctcat | tcttgggaca | 1020 |
| gactatccac | ttgttgcacg | aggacgattc | cttgtactgt | atctccgctt | ggaacgacca | 1080 |
| aggttacgaa | cacactgctg | aggatccatc | cttgttgtac | agagttgagt | ccatgccagg | 1140 |
| attgggatgg | gttttgaaga | agtcattgta | taaggacgaa | ttggaaccaa | agtggccaac | 1200 |
| tccagaaaag | ttgtgggatt | gggacatgtg | tgatgagaatg | ccagagcaga | gaaagggaag | 1260 |
| agagtgtgtt | attccagacg | tttccagatc | ttaccacttc | ggtatcatcg | gattgaacat | 1320 |
| gaacggttac | ttccacgagg | tttacttcaa | gaagcacaag | ttcaacacta | tcccaaacgt | 1380 |
| tcagatgaag | aacgttgaga | acttgaagaa | ggacccatac | gagattgaga | tccaaaaactt | 1440 |
| gttgagagag | gctgaagttt | tggaccactc | caagaaccca | tgtgaggatt | ccttcatccc | 1500 |
| agacactgag | ggaaagactt | tcgttatgtt | catcaagatg | gaacaagaga | ctgacactaa | 1560 |
| cacttggact | gagttggcta | agtgtttgca | tgtttgggac | ttggatgtta | gaggttacca | 1620 |
| caagggtttg | tggagattgt | tcagaaagaa | gaaccacatc | ttggttgttg | ctttcccaat | 1680 |
| ttccccatac | tccgttaaga | agccatccaa | cgttactcca | atccacttgg | aaccagctcc | 1740 |
| aaaagaagaa | ggtccaccag | ttgagcagat | gtagtagtta | a | | 1781 |

<210> SEQ ID NO 116
<211> LENGTH: 590
<212> TYPE: PRT
<213> ORGANISM: Zebrafish

<400> SEQUENCE: 116

```
Arg Ala Ala Ser Glu Asp Ala Ala Gln Glu Tyr Asp Asp Ala Leu
1               5                   10                  15

Pro Asn Met Glu Thr Pro Arg Arg Pro Ala Ser Gly Arg Lys Val Leu
            20                  25                  30

Asp Ile Glu Val Tyr Ser Ser Arg Ser Lys Val Tyr Val Ala Val Asp
        35                  40                  45

Gly Thr Thr Val Leu Glu Asp Glu Ile Arg Glu Gln Gly Arg Gly Ile
    50                  55                  60

His Val Ile Val Leu Asn Gln Ala Thr Gly His Val Met Ala Lys Arg
65                  70                  75                  80

Val Phe Asp Thr Tyr Ser Pro His Glu Asp Glu Ala Met Ile Leu Phe
                85                  90                  95

Leu Asn Met Val Thr Arg Gly Arg Ile Leu Ile Phe Thr Ile Lys Asp
            100                 105                 110

Glu Gly Thr Phe His Leu Lys Asp Ala Ala Lys Asn Leu Leu Lys Gly
        115                 120                 125

Leu Gly Ser Gln Val Ala Val Thr Leu Gly Trp Arg Asp Met Trp Thr
    130                 135                 140

Leu Val Val Lys Lys Gly Gly Gln Val Tyr Gly Glu Lys His Ser Lys
145                 150                 155                 160

Ser Pro Ala Leu Ser Thr Trp Gly Asp Pro Val Leu Leu Lys Thr Glu
                165                 170                 175

Val Gln Leu Thr Ala Ser Glu Glu Ala Glu Cys His Trp Ala Asp Thr
            180                 185                 190

Glu Leu Asn Arg Arg Arg Lys Leu Phe Cys Ser Lys Val Glu Gly Tyr
        195                 200                 205

Gly Ser Ile Cys Ser Cys Lys Asp Pro Ala Pro Ile Glu Phe Asn Pro
    210                 215                 220

Asp Pro Leu Ser Asn Asn Asn Val Tyr Asn Ile Pro Val Ala Val Ile
225                 230                 235                 240

Ala Gly Asn Arg Pro Asn Tyr Leu Tyr Arg Met Leu Arg Ser Leu Leu
                245                 250                 255

Ser Ser His Gly Val Asn Pro Gln Met Ile Thr Val Phe Ile Asp Gly
            260                 265                 270

Tyr Tyr Glu Glu Pro Met Asp Val Val Asp Leu Phe Gly Leu Lys Gly
        275                 280                 285

Val Gln His Thr Pro Ile Ser Ile Lys Asn Ala Arg Val Ser Gln His
    290                 295                 300

Tyr Lys Ala Ser Leu Thr Ala Thr Phe Asn Leu His Pro Asp Ala Asp
305                 310                 315                 320

Phe Ala Ile Val Leu Glu Glu Asp Leu Asp Ile Ser Ile Asp Phe Phe
                325                 330                 335

Ser Phe Leu Gly Gln Thr Ile His Leu Leu His Glu Asp Asp Ser Leu
            340                 345                 350

Tyr Cys Ile Ser Ala Trp Asn Asp Gln Gly Tyr Glu His Thr Ala Glu
        355                 360                 365

Asp Pro Ser Leu Leu Tyr Arg Val Glu Ser Met Pro Gly Leu Gly Trp
```

```
                370             375             380
Val Leu Lys Lys Ser Leu Tyr Lys Asp Glu Leu Glu Pro Lys Trp Pro
385             390             395             400

Thr Pro Glu Lys Leu Trp Asp Trp Asp Met Trp Arg Met Pro Glu
            405             410             415

Gln Arg Lys Gly Arg Glu Cys Val Ile Pro Asp Val Ser Arg Ser Tyr
            420             425             430

His Phe Gly Ile Ile Gly Leu Asn Met Asn Gly Tyr Phe His Glu Val
            435             440             445

Tyr Phe Lys Lys His Lys Phe Asn Thr Ile Pro Asn Val Gln Met Lys
450             455             460

Asn Val Glu Asn Leu Lys Lys Asp Pro Tyr Glu Ile Glu Ile Gln Asn
465             470             475             480

Leu Leu Arg Glu Ala Glu Val Leu Asp His Ser Lys Asn Pro Cys Glu
            485             490             495

Asp Ser Phe Ile Pro Asp Thr Glu Gly Lys Thr Phe Val Met Phe Ile
            500             505             510

Lys Met Glu Gln Glu Thr Asp Thr Asn Thr Trp Thr Glu Leu Ala Lys
515             520             525

Cys Leu His Val Trp Asp Leu Asp Val Arg Gly Tyr His Gly Leu Trp
530             535             540

Arg Leu Phe Arg Lys Lys Asn His Ile Leu Val Val Ala Phe Pro Ile
545             550             555             560

Ser Pro Tyr Ser Val Lys Lys Pro Ser Asn Val Thr Pro Ile His Leu
            565             570             575

Glu Pro Ala Pro Lys Glu Glu Gly Pro Pro Val Glu Gln Met
            580             585             590

<210> SEQ ID NO 117
<211> LENGTH: 1789
<212> TYPE: DNA
<213> ORGANISM: Xenopus

<400> SEQUENCE: 117
cgcgccgtta acgaagaaga gatcgaccaa gactacgacg aatccttgca acaagctgac     60
tctccaagaa gaccagctaa ctccaagaag gttttggaca ctgagatcta ctcttccaga    120
tccaaggttt acattgctgt tgacggtact actgttttgg aggacgaggt tcacgaacaa    180
ggtagaggta tccacgttat cgttttgaac caggctactg gtcatgttat ggctaagaga    240
gttttcgaca cttactctcc acacgaagat gaggctatgg ttttgttctt gaacatggtt    300
gctagaggta gaatcttgat cttcactatc aaggacgagg gatcctttca cttgaaggac    360
actgctaaga acttgttgaa gtccttgggt tcccaaattg ctccatcctt gggatggaga    420
gacatgtgga ctttcgttgt taagaagggt ggacaggttt acggtgaaaa gcactctaag    480
tccccagctt tgtctacttg gggtgaccca atcttgttga aaactgacat ccagttggtt    540
ccaccagagg atgctgaatg tcactggcca gacactgagt tgaacagaag aagaaagaga    600
ttctgttcca aggttgaggg ttacggttct gtttgttcct gtaaggaccc aactccaatc    660
gaattcaacc caatgccatt gaaagagaac aaggttacaa ctgttccagt tgctgttatc    720
gctggtaaca gaccaaacta cttgtacaga atgttgagat ccttgttgtc cgctcaggga    780
gtttctccac agatgatcac tgttttcatc gacggttact acgaagaacc aatggacgtt    840
gttgagttgt acggattgaa gggtattcag cacactccaa tctccatcaa gaacgctaga    900
```

-continued

```
gtttcccaac actacaaggc ttccttgact gctactttca acttgcaccc agacgctaag    960
ttcgctatcg ttttggaaga ggacttggac atttccgttg atttcttctc cttcttgtcc   1020
cagactatcc acttgttgga agaggatgag tccttgtact gtatctctgc ttggaacgac   1080
caaggttacg aacacactgc tgaggattct tccttgttgt acagagttga gtccatgcca   1140
ggattgggat gggttttgag aaagaacttg tacaaggacg agttggaacc aaaatggcca   1200
actccagaga agttgtggga ttgggacatg tggatgagaa tgccagagca gagaaaggac   1260
agagagtgtt tgattccaga cgtttccaga tcttaccact tcggtattgt tggattgaac   1320
atgaacggtt acttccacga ggcttacttc aagaagcaca agttcaacac tgttccaaac   1380
gttcagttgt ccaacgttaa gtccttgcag aaggacgctt acgagattga gatccacaga   1440
atcttgtctg aggctgaggt tttggaccat tccaagaacc catgtgagga ttccttcatc   1500
ccagacacag agggaaagac ttacatcatg tacatcaaga tggaacaaga ggctgacttc   1560
actacttgga ctcagttggc taagtgtttg cacatttggg acttggatgt tagaggtaac   1620
cacaagggtt tgtggagatt gttcagaaag aagaaccact tcttggttgt tggtttccca   1680
ttctccccat acgctgttaa gaagccagct tccgttactc caatctactt ggagccacca   1740
ccaaaagaag aagctgctgt tgctggtatt gaccagtcct agtagttaa                1789
```

<210> SEQ ID NO 118
<211> LENGTH: 592
<212> TYPE: PRT
<213> ORGANISM: Xenopus

<400> SEQUENCE: 118

```
Arg Ala Val Asn Glu Glu Ile Asp Gln Asp Tyr Asp Glu Ser Leu
1               5                  10                  15

Gln Gln Ala Asp Ser Pro Arg Arg Pro Ala Asn Ser Lys Lys Val Leu
            20                  25                  30

Asp Thr Glu Ile Tyr Ser Ser Arg Ser Lys Val Tyr Ile Ala Val Asp
        35                  40                  45

Gly Thr Thr Val Leu Glu Asp Glu Val His Glu Gln Gly Arg Gly Ile
    50                  55                  60

His Val Ile Val Leu Asn Gln Ala Thr Gly His Val Met Ala Lys Arg
65                  70                  75                  80

Val Phe Asp Thr Tyr Ser Pro His Glu Asp Glu Ala Met Val Leu Phe
                85                  90                  95

Leu Asn Met Val Ala Arg Gly Arg Ile Leu Ile Phe Thr Ile Lys Asp
            100                 105                 110

Glu Gly Ser Phe His Leu Lys Asp Thr Ala Lys Asn Leu Leu Lys Ser
        115                 120                 125

Leu Gly Ser Gln Ile Ala Pro Ser Leu Gly Trp Arg Asp Met Trp Thr
    130                 135                 140

Phe Val Val Lys Lys Gly Gly Gln Val Tyr Gly Glu Lys His Ser Lys
145                 150                 155                 160

Ser Pro Ala Leu Ser Thr Trp Gly Asp Pro Ile Leu Leu Lys Thr Asp
                165                 170                 175

Ile Gln Leu Val Pro Pro Glu Asp Ala Glu Cys His Trp Pro Asp Thr
            180                 185                 190

Glu Leu Asn Arg Arg Arg Lys Arg Phe Cys Ser Lys Val Glu Gly Tyr
        195                 200                 205

Gly Ser Val Cys Ser Cys Lys Asp Pro Thr Pro Ile Glu Phe Asn Pro
    210                 215                 220
```

Met Pro Leu Lys Glu Asn Lys Val Thr Thr Val Pro Val Ala Val Ile
225                 230                 235                 240

Ala Gly Asn Arg Pro Asn Tyr Leu Tyr Arg Met Leu Arg Ser Leu Leu
            245                 250                 255

Ser Ala Gln Gly Val Ser Pro Gln Met Ile Thr Val Phe Ile Asp Gly
        260                 265                 270

Tyr Tyr Glu Glu Pro Met Asp Val Val Glu Leu Tyr Gly Leu Lys Gly
    275                 280                 285

Ile Gln His Thr Pro Ile Ser Ile Lys Asn Ala Arg Val Ser Gln His
290                 295                 300

Tyr Lys Ala Ser Leu Thr Ala Thr Phe Asn Leu His Pro Asp Ala Lys
305                 310                 315                 320

Phe Ala Ile Val Leu Glu Glu Asp Leu Asp Ile Ser Val Asp Phe Phe
                325                 330                 335

Ser Phe Leu Ser Gln Thr Ile His Leu Leu Glu Glu Asp Glu Ser Leu
            340                 345                 350

Tyr Cys Ile Ser Ala Trp Asn Asp Gln Gly Tyr Glu His Thr Ala Glu
        355                 360                 365

Asp Ser Ser Leu Leu Tyr Arg Val Glu Ser Met Pro Gly Leu Gly Trp
    370                 375                 380

Val Leu Arg Lys Asn Leu Tyr Lys Asp Glu Leu Glu Pro Lys Trp Pro
385                 390                 395                 400

Thr Pro Glu Lys Leu Trp Asp Trp Asp Met Trp Met Arg Met Pro Glu
                405                 410                 415

Gln Arg Lys Asp Arg Glu Cys Leu Ile Pro Asp Val Ser Arg Ser Tyr
            420                 425                 430

His Phe Gly Ile Val Gly Leu Asn Met Asn Gly Tyr Phe His Glu Ala
        435                 440                 445

Tyr Phe Lys Lys His Lys Phe Asn Thr Val Pro Asn Val Gln Leu Ser
    450                 455                 460

Asn Val Lys Ser Leu Gln Lys Asp Ala Tyr Glu Ile Glu Ile His Arg
465                 470                 475                 480

Ile Leu Ser Glu Ala Glu Val Leu Asp His Lys Asn Pro Cys Glu Asp
                485                 490                 495

Ser Phe Ile Pro Asp Thr Glu Gly Lys Thr Tyr Ile Met Tyr Ile Lys
            500                 505                 510

Met Glu Gln Glu Ala Asp Phe Thr Thr Trp Thr Gln Leu Ala Lys Cys
        515                 520                 525

Leu His Ile Trp Asp Leu Asp Val Arg Gly Asn His Lys Gly Leu Trp
    530                 535                 540

Arg Leu Phe Arg Lys Lys Asn His Phe Leu Val Val Gly Phe Pro Phe
545                 550                 555                 560

Ser Pro Tyr Ala Val Lys Lys Pro Ala Ser Val Thr Pro Ile Tyr Leu
                565                 570                 575

Glu Pro Pro Pro Lys Glu Glu Ala Ala Val Ala Gly Ile Asp Gln Ser
            580                 585                 590

<210> SEQ ID NO 119
<211> LENGTH: 33
<212> TYPE: DNA
<213> ORGANISM: Artificial Sequence
<220> FEATURE:
<223> OTHER INFORMATION: PCR primer PpHIS3 1

<400> SEQUENCE: 119

-continued

```
gagctcggcc acggtggccc tgtgagtctg gct                                      33

<210> SEQ ID NO 120
<211> LENGTH: 32
<212> TYPE: DNA
<213> ORGANISM: Artificial Sequence
<220> FEATURE:
<223> OTHER INFORMATION: PCR primer PpHIS3 2

<400> SEQUENCE: 120
ggccggcctc agaaaagaac accttcgta ct                                        32

<210> SEQ ID NO 121
<211> LENGTH: 614
<212> TYPE: DNA
<213> ORGANISM: Artificial Sequence
<220> FEATURE:
<223> OTHER INFORMATION: PpHIS3 ORF (the 5' arm)

<400> SEQUENCE: 121
gagctcggcc acggtggccc tgtgagtctg gctcaatcac ttttcaaaga taaggactat          60
tctgcagaac atgcagccca ggcaacatca tcccagttca tctctgtgaa cacaggaata        120
ggattcctgg accatatgtt acacgcactt gctaagcacg gcggctggtc tgtcattatc        180
gaatgtgtag gtgatttgca cattgatgac catcattcag cagaagatac tggaatcgca        240
ttggggatgg cattcaaaga agccttgggc catgttcgtg gtatcaaaag attcgggtcc        300
ggatttgctc cactagacga agctctcagt cgggctgtta ttgatatgtc taacaggccc        360
tatgctgttg tcgatctggg tttgaaaaga gagaagattg agacctatc gtgtgagatg         420 attccccatg ttttggaaag ttttgcccaa ggagcccatg taaccatgca cgtagattgt        480
ttgcgaggtt caacgacca tcatcgtgcc gagagtgcat tcaaagcttt ggctatagct         540
atcaaagagg ccatttcaag caacggcacg gacgacattc caagtacgaa gggtgttctt       600
ttctgaggcc ggcc                                                          614

<210> SEQ ID NO 122
<211> LENGTH: 33
<212> TYPE: DNA
<213> ORGANISM: Artificial Sequence
<220> FEATURE:
<223> OTHER INFORMATION: PCR Primer PpHIS3 3

<400> SEQUENCE: 122
atttaaatgt ctggaaggtg tctacatctg tga                                      33

<210> SEQ ID NO 123
<211> LENGTH: 34
<212> TYPE: DNA
<213> ORGANISM: Artificial Sequence
<220> FEATURE:
<223> OTHER INFORMATION: PCR Primer PpHIS3 4

<400> SEQUENCE: 123
gtcgacggcc agtctggcca agtaatcatt gtct                                     34

<210> SEQ ID NO 124
<211> LENGTH: 1067
<212> TYPE: DNA
<213> ORGANISM: Artificial Sequence
<220> FEATURE:
<223> OTHER INFORMATION: PpHIS3 ORF (the 3' arm)
```

<400> SEQUENCE: 124

```
atttaaatgt ctggaaggtg tctacatctg tgaaatccgt atttatttaa gtaaaacaat      60
cagtaatata agatcttagt tggtttacca catagtcggt accggtcgtg tgaacaatag     120
ttcaatgcct ccgattgtgc cttattgttg tggtctgcat tttcgcggcg aaatttctac     180
ttcagatcgg ggctgagatg accttagtac tcacatcaac cagctcgttg aaagttccca     240
catgaccact caatgtttaa tagcttggca cccatgaggt tgaagaaact acttaaggtg     300
ttttgtgcct cagtagtgct gttagcggcg acatctgtgg tgttattttt ccactttgga     360
ggtcagatca taatccccat accggaacgc actgtgacct aagtactcc tcccgcaaac      420
gatacttggc agtttcaaca gttcttcaac ggctatttag acgccctgtt agagaataac     480
ctgtcgtatc cgataccaga aaggtggaat catgaagtta caaatgtaag attcttcaat     540
cgcataggtg aattgctctc ggagagtagg ctacaggagc tgattcattt tagtcctgag     600
ttcatagagg ataccagtga caaattcgac aatattgttg aacaaattcc agcaaaatgg     660
ccttacgaaa acatgtacag aggagatgga tacgttattg ttggtggtgg cagacacacc     720
tttttggcac tgctgaatat caacgctttg agaagagcag gcaataaact gccagttgag     780
gtcgtgttgc caacttacga cgactatgag gaagatttct gtgaaaatca ttttccactt     840
ttgaatgcaa gatgcgtaat cttagaagaa cgatttggtg accaagttta tccccggtta     900
caactaggag gctaccagtt taaaatattt gcgatagcag caagttcatt caaaaactgc     960
tttttgttag attcagataa tatacccttg cgaaagatgg ataagatatt ctcaagcgaa    1020
ctatacaaga ataagacaat gattacttgg ccagactggc cgtcgac                  1067
```

<210> SEQ ID NO 125
<211> LENGTH: 32
<212> TYPE: DNA
<213> ORGANISM: Artificial Sequence
<220> FEATURE:
<223> OTHER INFORMATION: PCR primer PpALG3TT-f

<400> SEQUENCE: 125

```
ggccggccat ttacaattag taatattaag gt                                    32
```

<210> SEQ ID NO 126
<211> LENGTH: 30
<212> TYPE: DNA
<213> ORGANISM: Artificial Sequence
<220> FEATURE:
<223> OTHER INFORMATION: PCR primer PpALG3TT-rev

<400> SEQUENCE: 126

```
gtttaaacct actaagcgac gaaaacggga                                       30
```

<210> SEQ ID NO 127
<211> LENGTH: 392
<212> TYPE: DNA
<213> ORGANISM: Artificial Sequence
<220> FEATURE:
<223> OTHER INFORMATION: PpALG3 transcription terminator

<400> SEQUENCE: 127

```
ggccggccat ttacaattag taatattaag gtggtaaaaa cattcgtaga attgaaatga      60
attaatatag tatgacaatg gttcatgtct ataaatctcc ggcttcggta ccttctcccc     120
aattgaatac attgtcaaaa tgaatggttg aactattagg ttcgccagtt tcgttattaa     180
gaaaactgtt aaaatcaaat tccatatcat cggttccagt gggaggacca gttccatcgc     240
```

```
caaaatcctg taagaatcca ttgtcagaac ctgtaaagtc agtttgagat gaaattttc    300 cggtctttgt tgacttggaa gcttcgttaa ggttaggtga acagtttga tcaaccagcg    360 gctcccgttt tcgtcgctta gtaggtttaa ac                                 392
```

```
<210> SEQ ID NO 128
<211> LENGTH: 506
<212> TYPE: DNA
<213> ORGANISM: Artificial Sequence
<220> FEATURE:
<223> OTHER INFORMATION: PpGAP promoter

<400> SEQUENCE: 128
ctcgagagat cttttttgta gaaatgtctt ggtgtcctcg tccaatcagg tagccatctc    60
tgaaatatct ggctccgttg caactccgaa cgacctgctg gcaacgtaaa attctccggg   120
gtaaaactta aatgtggagt aatggaacca gaaacgtctc ttcccttctc tctccttcca   180
ccgcccgtta ccgtccctag gaaattttac tctgctggag agcttcttct acggcccct    240 tgcagcaatg ctcttcccag cattacgttg cgggtaaaac ggaggtcgtg taccccgacct  300 agcagcccag ggatggaaaa gtcccggccg tcgctggcaa taatagcggg cggacgcatg   360
tcatgagatt attggaaacc accagaatcg aatataaaag gcgaacacct ttcccaattt   420
tggtttctcc tgacccaaag actttaaatt taatttattt gtccctattt caatcaattg   480
aacaactatc aaaacacagc ggccgc                                        506
```

```
<210> SEQ ID NO 129
<211> LENGTH: 300
<212> TYPE: DNA
<213> ORGANISM: Artificial Sequence
<220> FEATURE:
<223> OTHER INFORMATION: ScCYC transcription terminator

<400> SEQUENCE: 129
ttaattaaac aggccccttt tcctttgtcg atatcatgta attagttatg tcacgcttac    60
attcacgccc tcctcccaca tccgctctaa ccgaaaagga aggagttaga caacctgaag   120
tctaggtccc tatttatttt ttttaatagt tatgttagta ttaagaacgt tatttatatt   180
tcaaattttt ctttttttc tgtacaaacg cgtgtacgca tgtaacatta tactgaaaac   240
cttgcttgag aaggttttgg gacgctcgaa ggctttaatt tgcaagctgc cggctcttaa   300
```

```
<210> SEQ ID NO 130
<211> LENGTH: 954
<212> TYPE: DNA
<213> ORGANISM: Artificial Sequence
<220> FEATURE:
<223> OTHER INFORMATION: PpAOX1 promoter

<400> SEQUENCE: 130
ctcgagagat ctaacatcca aagacgaaag gttgaatgaa accttttgc catccgacat    60 ccacaggtcc attctcacac ataagtgcca aacgcaacag gaggggatac actagcagca   120
gaccgttgca aacgcaggac ctccactcct cttctcctca acacccactt ttgccatcga   180
aaaaccagcc cagttattgg gcttgattgg agctcgctca ttccaattcc ttctattagg   240
ctactaacac catgacttta ttagcctgtc tatcctggcc ccctggcga ggttcatgtt    300 tgtttatttc cgaatgcaac aagctccgca ttacacccga acatcactcc agatgagggc   360
tttctgagtg tggggtcaaa tagtttcatg ttccccaaat ggcccaaaac tgacagttta   420
```

| | | |
|---|---|---|
| aacgctgtct | tggaacctaa tatgacaaaa gcgtgatctc atccaagatg aactaagttt | 480 |
| ggttcgttga | aatgctaacg gccagttggt caaaagaaa cttccaaaag tcggcatacc | 540 |
| gtttgtcttg | tttggtattg attgacgaat gctcaaaaat aatctcatta atgcttagcg | 600 |
| cagtctctct | atcgcttctg aaccccggtg cacctgtgcc gaaacgcaaa tggggaaaca | 660 |
| cccgcttttt | ggatgattat gcattgtctc acattgtat gcttccaaga ttctggtggg | 720 |
| aatactgctg | atagcctaac gttcatgatc aaaatttaac tgttctaacc cctacttgac | 780 |
| agcaatatat | aaacagaagg aagctgccct gtcttaaacc ttttttttta tcatcattat | 840 |
| tagcttactt | tcataattgc gactggttcc aattgacaag cttttgattt taacgactt | 900 |
| taacgacaac | ttgagaagat caaaaaacaa ctaattattc gaaacggcgg ccgc | 954 |

<210> SEQ ID NO 131
<211> LENGTH: 1415
<212> TYPE: DNA
<213> ORGANISM: Artificial Sequence
<220> FEATURE:
<223> OTHER INFORMATION: TNFR-IgG1

<400> SEQUENCE: 131

| | | |
|---|---|---|
| cagctgccag | ctcaagttgc ttttactcca tacgctccag aaccaggttc tacttgtaga | 60 |
| ttgagagagt | actacgacca aactgctcag atgtgttgtt ccaagtgttc tccaggtcaa | 120 |
| cacgctaagg | ttttctgtac taagacttcc gacactgttt gtgactcttg tgaggactcc | 180 |
| acttacactc | aattgtggaa ctgggttcca gaatgtttgt cctgtggttc cagatgttct | 240 |
| tccgaccaag | ttgagactca ggcttgtact agagagcaga acagaatctg tacttgtaga | 300 |
| cctggttggt | actgtgcttt gtccaagcaa gagggttgta gattgtgtgc tccattgaga | 360 |
| aagtgtagac | aggtttcgg tgttgctaga ccaggtacag aaacttccga cgttgtttgt | 420 |
| aagccatgtg | ctccaggaac tttctccaac actacttcct ccactgacat ctgtagacca | 480 |
| caccaaatct | gtaacgttgt tgctatccca ggtaacgctt ctatggacgc tgtttgtact | 540 |
| tctacttccc | caactagatc catggctcca ggtgctgttc atttgccaca gccagtttcc | 600 |
| actagatccc | aacacactca accaactcca gaaccatcta ctgctccatc cacttccttt | 660 |
| ttgttgccaa | tgggaccatc tccacctgct gaaggttcta ctggtgacga accaaagtcc | 720 |
| tgtgacaaga | ctcatacttg tccaccatgt ccagctccag aattgttggg tggtccatcc | 780 |
| gttttttgt | tcccaccaaa gccaaaggac actttgatga tctccagaac tccagaggtt | 840 |
| acatgtgttg | ttgttgacgt ttctcacgag gacccagagg ttaagttcaa ctggtacgtt | 900 |
| gacggtgttg | aagttcacaa cgctaagact aagccaagag aagagcagta caactccaca | 960 |
| tacagagttg | tttccgtttt gactgttttg caccaggatt ggttgaacgg aaaggactac | 1020 |
| aagtgtaagg | tttccaacaa ggctttgcca gctccaatgc aaaagactat ctccaaggct | 1080 |
| aagggtcaac | caagagagcc acaggttac actttgccac catccagaga tgagttgact | 1140 |
| aagaatcagg | tttccttgac ttgttgggtt aagggattct acccaagaca catcgctgtt | 1200 |
| gaatgggaat | ctaacggaca gccagagaac aactacaaga ctactccacc agttttggac | 1260 |
| tctgacggtt | ccttcttctt gtactccaag ttgactgttg acaagtccag atggcaacag | 1320 |
| ggtaacgttt | tctcctgttc cgttatgcat gaggctttgc acaaccacta cactcaaaag | 1380 |
| tccttgtctt | tgtcccctgg taagtagggc cggcc | 1415 |

<210> SEQ ID NO 132
<211> LENGTH: 1415

<212> TYPE: DNA
<213> ORGANISM: Artificial Sequence
<220> FEATURE:
<223> OTHER INFORMATION: TNFR-Fc

<400> SEQUENCE: 132

| | | | | | |
|---|---|---|---|---|---|
| cagctgccag | ctcaagttgc | ttttactcca | tacgctccag | aaccaggttc | tacttgtaga | 60 |
| ttgagagagt | actacgacca | aactgctcag | atgtgttgtt | ccaagtgttc | tccaggtcaa | 120 |
| cacgctaagg | ttttctgtac | taagacttcc | gacactgttt | gtgactcttg | tgaggactcc | 180 |
| acttacactc | aattgtggaa | ctgggttcca | gaatgtttgt | cctgtggttc | cagatgttct | 240 |
| tccgaccaag | ttgagactca | ggcttgtact | agagagcaga | acagaatctg | tacttgtaga | 300 |
| cctggttggt | actgtgcttt | gtccaagcaa | gagggttgta | gattgtgtgc | tccattgaga | 360 |
| aagtgtagac | aggtttcgg | tgttgctaga | ccaggtacag | aaacttccga | cgttgtttgt | 420 |
| aagccatgtg | ctccaggaac | tttctccaac | actacttcct | ccactgacat | ctgtagacca | 480 |
| caccaaatct | gtaacgttgt | tgctatccca | ggtaacgctt | ctatggacgc | tgtttgtact | 540 |
| tctacttccc | caactagatc | catggctcca | ggtgctgttc | atttgccaca | gccagtttcc | 600 |
| actagatccc | aacacactca | accaactcca | gaaccatcta | ctgctccatc | cacttccttt | 660 |
| ttgttgccaa | tgggaccatc | tccacctgct | gaaggttcta | ctggtgacga | gccaaagtcc | 720 |
| tgtgacaaga | cacatacttg | tccaccatgt | ccagctccag | aattgttggg | tggtccatcc | 780 |
| gttttcttgt | tcccaccaaa | gccaaaggac | actttgatga | tctccagaac | tccagaggtt | 840 |
| acatgtgttg | ttgttgacgt | ttctcacgag | gacccagagg | ttaagttcaa | ctggtacgtt | 900 |
| gacggtgttg | aagttcacaa | cgctaagact | aagccaagag | aagagcagta | caactccact | 960 |
| tacagagttg | tttccgtttt | gactgttttg | caccaggatt | ggttgaacgg | taaagaatac | 1020 |
| aagtgtaagg | tttccaacaa | ggctttgcca | gctccaatcg | aaaagacaat | ctccaaggct | 1080 |
| aagggtcaac | caagagagcc | acaggtttac | actttgccac | catccagaga | agagatgact | 1140 |
| aagaaccagg | tttccttgac | ttgtttggtt | aaaggattct | acccatccga | cattgctgtt | 1200 |
| gaatgggaat | ctaacggtca | accagagaac | aactacaaga | ctactccacc | agttttggat | 1260 |
| tctgacggtt | ccttcttctt | gtactccaag | ttgactgttg | acaagtccag | atggcaacag | 1320 |
| ggtaacgttt | tctcctgttc | cgttatgcat | gaggctttgc | acaaccacta | cactcaaaag | 1380 |
| tccttgtctt | tgtccccagg | taagtagggc | cggcc | | | 1415 |

<210> SEQ ID NO 133
<211> LENGTH: 40
<212> TYPE: DNA
<213> ORGANISM: Artificial Sequence
<220> FEATURE:
<223> OTHER INFORMATION: PCR Primer

<400> SEQUENCE: 133
gggtacccag ctgccagctc aagttgcttt tactccatac  40

<210> SEQ ID NO 134
<211> LENGTH: 57
<212> TYPE: DNA
<213> ORGANISM: Artificial Sequence
<220> FEATURE:
<223> OTHER INFORMATION: PCR Primer

<400> SEQUENCE: 134
gtgtcttgtc acaggacttt ggctcgtcac cagtagaacc ttcagcaggt ggagatg  57

<210> SEQ ID NO 135
<211> LENGTH: 57
<212> TYPE: DNA
<213> ORGANISM: Artificial Sequence
<220> FEATURE:
<223> OTHER INFORMATION: PCR Primer

<400> SEQUENCE: 135
catctccacc tgctgaaggt tctactggtg acgagccaaa gtcctgtgac aagacac    57

<210> SEQ ID NO 136
<211> LENGTH: 48
<212> TYPE: DNA
<213> ORGANISM: Artificial Sequence
<220> FEATURE:
<223> OTHER INFORMATION: PCR Primer

<400> SEQUENCE: 136
ggagctcggc cggccctact tacctgggga caaagacaag gactttttg    48

<210> SEQ ID NO 137
<211> LENGTH: 66
<212> TYPE: DNA
<213> ORGANISM: Artificial Sequence
<220> FEATURE:
<223> OTHER INFORMATION: HSA pre-signal sequence

<400> SEQUENCE: 137
gaattcgaaa cgatgaagtg ggttaccttt atctctttgt tgtttctttt ctcttctgct    60
tactct    66

<210> SEQ ID NO 138
<211> LENGTH: 1478
<212> TYPE: DNA
<213> ORGANISM: Artificial Sequence
<220> FEATURE:
<223> OTHER INFORMATION: HSAss-TNFR-Fc

<400> SEQUENCE: 138
gaattcgaaa cgatgaagtg ggttaccttt atctctttgt tgtttctttt ctcttctgct    60
tactctctgc cagctcaagt tgcttttact ccatacgctc cagaaccagg ttctacttgt    120
agattgagag agtactacga ccaaactgct cagatgtgtt gttccaagtg ttctccaggt    180
caacacgcta aggttttctg tactaagact tccgacactg tttgtgactc ttgtgaggac    240
tccacttaca ctcaattgtg gaactgggtt ccagaatgtt tgtcctgtgg ttccagatgt    300
tcttccgacc aagttgagac tcaggcttgt actagagagc agaacagaat ctgtacttgt    360
agacctggtt ggtactgtgc tttgtccaag caagagggtg tagattgtg tgctccattg    420 agaaagtgta gaccaggttt cggtgttgct agaccaggta cagaaacttc gacgttgtt    480 tgtaagccat gtgctccagg aactttctcc aacactactt cctccactga catctgtaga    540
ccacaccaaa tctgtaacgt tgttgctatc ccaggtaacg cttctatgga cgctgttgt    600 acttctactt ccccaactag atccatggct ccaggtgctg ttcatttgcc acagccagtt    660
tccactagat cccaacacac tcaaccaact ccagaaccat ctactgctcc atccacttcc    720
tttttgttgc aatgggacc atctccacct gctgaaggtt ctactggtga cgagccaaag    780
tcctgtgaca agacacatac ttgtccacca tgtccagctc agaattgtt gggtggtcca    840 tccgtttttct tgttcccacc aaagccaaag gacactttga tgatctccag aactccagag    900
gttacatgtg ttgttgttga cgtttctcac gaggacccag aggttaagtt caactggtac    960

```
gttgacggtg ttgaagttca caacgctaag actaagccaa gagaagagca gtacaactcc    1020
acttacagag ttgtttccgt tttgactgtt ttgcaccagg attggttgaa cggtaaagaa    1080
tacaagtgta aggtttccaa caaggctttg ccagctccaa tcgaaaagac aatctccaag    1140
gctaagggtc aaccaagaga gccacaggtt tacactttgc caccatccag agaagagatg    1200
actaagaacc aggtttcctt gacttgtttg gttaaaggat tctacccatc cgacattgct    1260
gttgaatggg aatctaacgg tcaaccagag aacaactaca agactactcc accagttttg    1320
gattctgacg gttccttctt cttgtactcc aagttgactg ttgacaagtc cagatggcaa    1380
cagggtaacg ttttctcctg ttccgttatg catgaggctt tgcacaacca ctacactcaa    1440
aagtccttgt ctttgtcccc aggtaagtag ggccggcc                            1478
```

<210> SEQ ID NO 139
<211> LENGTH: 485
<212> TYPE: PRT
<213> ORGANISM: Artificial Sequence
<220> FEATURE:
<223> OTHER INFORMATION: HSAss-TNFR-Fc peptide

<400> SEQUENCE: 139

```
Met Lys Trp Val Thr Phe Ile Ser Leu Leu Phe Leu Phe Ser Ser Ala
1               5                   10                  15

Tyr Ser Leu Pro Ala Gln Val Ala Phe Thr Pro Tyr Ala Pro Glu Pro
            20                  25                  30

Gly Ser Thr Cys Arg Leu Arg Glu Tyr Tyr Asp Gln Thr Ala Gln Met
        35                  40                  45

Cys Cys Ser Lys Cys Ser Pro Gly Gln His Ala Lys Val Phe Cys Thr
    50                  55                  60

Lys Thr Ser Asp Thr Val Cys Asp Ser Cys Glu Asp Ser Thr Tyr Thr
65                  70                  75                  80

Gln Leu Trp Asn Trp Val Pro Glu Cys Leu Ser Cys Gly Ser Arg Cys
                85                  90                  95

Ser Ser Asp Gln Val Glu Thr Gln Ala Cys Thr Arg Glu Gln Asn Arg
            100                 105                 110

Ile Cys Thr Cys Arg Pro Gly Trp Tyr Cys Ala Leu Ser Lys Gln Glu
        115                 120                 125

Gly Cys Arg Leu Cys Ala Pro Leu Arg Lys Cys Arg Pro Gly Phe Gly
    130                 135                 140

Val Ala Arg Pro Gly Thr Glu Thr Ser Asp Val Val Cys Lys Pro Cys
145                 150                 155                 160

Ala Pro Gly Thr Phe Ser Asn Thr Thr Ser Ser Thr Asp Ile Cys Arg
                165                 170                 175

Pro His Gln Ile Cys Asn Val Val Ala Ile Pro Gly Asn Ala Ser Met
            180                 185                 190

Asp Ala Val Cys Thr Ser Thr Ser Pro Thr Arg Ser Met Ala Pro Gly
        195                 200                 205

Ala Val His Leu Pro Gln Pro Val Ser Thr Arg Ser Gln His Thr Gln
    210                 215                 220

Pro Thr Pro Glu Pro Ser Thr Ala Pro Ser Thr Ser Phe Leu Leu Pro
225                 230                 235                 240

Met Gly Pro Ser Pro Ala Glu Gly Ser Thr Gly Asp Glu Pro Lys
                245                 250                 255

Ser Cys Asp Lys Thr His Thr Cys Pro Pro Cys Pro Ala Pro Glu Leu
            260                 265                 270
```

Leu Gly Gly Pro Ser Val Phe Leu Phe Pro Pro Lys Pro Lys Asp Thr
            275                 280                 285

Leu Met Ile Ser Arg Thr Pro Glu Val Thr Cys Val Val Val Asp Val
        290                 295                 300

Ser His Glu Asp Pro Glu Val Lys Phe Asn Trp Tyr Val Asp Gly Val
305                 310                 315                 320

Glu Val His Asn Ala Lys Thr Lys Pro Arg Glu Glu Gln Tyr Asn Ser
            325                 330                 335

Thr Tyr Arg Val Val Ser Val Leu Thr Val Leu His Gln Asp Trp Leu
        340                 345                 350

Asn Gly Lys Glu Tyr Lys Cys Lys Val Ser Asn Lys Ala Leu Pro Ala
            355                 360                 365

Pro Ile Glu Lys Thr Ile Ser Lys Ala Lys Gly Gln Pro Arg Glu Pro
        370                 375                 380

Gln Val Tyr Thr Leu Pro Pro Ser Arg Glu Glu Met Thr Lys Asn Gln
385                 390                 395                 400

Val Ser Leu Thr Cys Leu Val Lys Gly Phe Tyr Pro Ser Asp Ile Ala
            405                 410                 415

Val Glu Trp Glu Ser Asn Gly Gln Pro Glu Asn Asn Tyr Lys Thr Thr
        420                 425                 430

Pro Pro Val Leu Asp Ser Asp Gly Ser Phe Phe Leu Tyr Ser Lys Leu
            435                 440                 445

Thr Val Asp Lys Ser Arg Trp Gln Gln Gly Asn Val Phe Ser Cys Ser
        450                 455                 460

Val Met His Glu Ala Leu His Asn His Tyr Thr Gln Lys Ser Leu Ser
465                 470                 475                 480

Leu Ser Pro Gly Lys
            485

<210> SEQ ID NO 140
<211> LENGTH: 467
<212> TYPE: PRT
<213> ORGANISM: Artificial Sequence
<220> FEATURE:
<223> OTHER INFORMATION: Secreted TNFR-Fc peptide

<400> SEQUENCE: 140

Leu Pro Ala Gln Val Ala Phe Thr Pro Tyr Ala Pro Glu Pro Gly Ser
1               5                   10                  15

Thr Cys Arg Leu Arg Glu Tyr Tyr Asp Gln Thr Ala Gln Met Cys Cys
            20                  25                  30

Ser Lys Cys Ser Pro Gly Gln His Ala Lys Val Phe Cys Thr Lys Thr
        35                  40                  45

Ser Asp Thr Val Cys Asp Ser Cys Glu Asp Ser Thr Tyr Thr Gln Leu
    50                  55                  60

Trp Asn Trp Val Pro Glu Cys Leu Ser Cys Gly Ser Arg Cys Ser Ser
65                  70                  75                  80

Asp Gln Val Glu Thr Gln Ala Cys Thr Arg Glu Gln Asn Arg Ile Cys
            85                  90                  95

Thr Cys Arg Pro Gly Trp Tyr Cys Ala Leu Ser Lys Gln Glu Gly Cys
        100                 105                 110

Arg Leu Cys Ala Pro Leu Arg Lys Cys Arg Pro Gly Phe Gly Val Ala
    115                 120                 125

Arg Pro Gly Thr Glu Thr Ser Asp Val Val Cys Lys Pro Cys Ala Pro
130                 135                 140

```
Gly Thr Phe Ser Asn Thr Thr Ser Ser Thr Asp Ile Cys Arg Pro His
145                 150                 155                 160

Gln Ile Cys Asn Val Val Ala Ile Pro Gly Asn Ala Ser Met Asp Ala
            165                 170                 175

Val Cys Thr Ser Thr Ser Pro Thr Arg Ser Met Ala Pro Gly Ala Val
        180                 185                 190

His Leu Pro Gln Pro Val Ser Thr Arg Ser Gln His Thr Gln Pro Thr
    195                 200                 205

Pro Glu Pro Ser Thr Ala Pro Ser Thr Ser Phe Leu Leu Pro Met Gly
210                 215                 220

Pro Ser Pro Pro Ala Glu Gly Ser Thr Gly Asp Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
            325                 330                 335

Lys Glu Tyr Lys Cys Lys Val Ser Asn Lys Ala Leu Pro Ala Pro Ile
        340                 345                 350

Glu Lys Thr Ile Ser Lys Ala Lys Gly Gln Pro Arg Glu Pro Gln Val
    355                 360                 365

Tyr Thr Leu Pro Pro Ser Arg Glu Glu Met Thr Lys Asn Gln Val Ser
370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
            405                 410                 415

Val Leu Asp Ser Asp Gly Ser Phe Phe Leu Tyr Ser Lys Leu Thr Val
        420                 425                 430

Asp Lys Ser Arg Trp Gln Gln Gly Asn Val Phe Ser Cys Ser Val Met
    435                 440                 445

His Glu Ala Leu His Asn His Tyr Thr Gln Lys Ser Leu Ser Leu Ser
450                 455                 460

Pro Gly Lys
465

<210> SEQ ID NO 141
<211> LENGTH: 27
<212> TYPE: DNA
<213> ORGANISM: Artificial Sequence
<220> FEATURE:
<223> OTHER INFORMATION: PCR Primer

<400> SEQUENCE: 141
gggagagttg aaggttgtat tattgcc                                       27

<210> SEQ ID NO 142
<211> LENGTH: 26
```

```
<212> TYPE: DNA
<213> ORGANISM: Artificial Sequence
<220> FEATURE:
<223> OTHER INFORMATION: PCR Primer

<400> SEQUENCE: 142
ctactaagcg acgaaaacgg gagccg                                    26

<210> SEQ ID NO 143
<211> LENGTH: 27
<212> TYPE: DNA
<213> ORGANISM: Artificial Sequence
<220> FEATURE:
<223> OTHER INFORMATION: PCR Primer

<400> SEQUENCE: 143
gttccctcat taagaggatc acaaacg                                   27

<210> SEQ ID NO 144
<211> LENGTH: 25
<212> TYPE: DNA
<213> ORGANISM: Artificial Sequence
<220> FEATURE:
<223> OTHER INFORMATION: PCR Primer

<400> SEQUENCE: 144
gataatagtg cgggctggta cttcg                                     25
```

YEAST STRAIN FOR THE PRODUCTION OF PROTEINS WITH MODIFIED O-GLYCOSYLATION

CROSS REFERENCE TO RELATED APPLICATIONS

This application is the National Stage of International Application No. PCT/US2012/025809 filed on Feb. 20, 2012, which claims the benefit under 35 U.S.C. 119(e) of U.S. Provisional Application No. 61/446,846, filed Feb. 25, 2011.

FIELD OF THE INVENTION

The present invention relates to the field of molecular biology, in particular the invention is concerned with lower eukaryotic cells, such as yeast strains, genetically engineered to produce glycoproteins having humanized O-glycosylation and their production from recombinant expression systems.

BACKGROUND OF THE INVENTION

Significant structural differences exist between the O-glycosylation pathways and patterns of lower eukaryotes (i.e., yeast and filamentous fungi) and mammals (particularly humans). Because the human immune system may recognize the alternative glycosylation of lower eukaryotes as foreign, any protein-based therapeutic products produced in fungal systems have the potential to provoke an immunogenic response when injected into humans. This response may limit the effectiveness of a therapeutic over multiple administrations and, in the most serious cases, may cause adverse effects in the patient.

In fact, the presence of fungal glycosylation is a common signal for clearance by the innate human immune system; see, e.g., Ballou, C. E., 1990 *Methods Enzymol.* 185:440. This raises concern about the potential for rapid clearance or immunogenicity of therapeutic proteins produced in yeast, such as *Pichia pastoris* and injected into humans, including but not limited to proteins having N and O glycans typical of yeast.

Previous attempts at reducing the immunogenicity of therapeutic proteins produced in yeast have largely focused on reducing the immunogenicity of N glycans (see, e.g., Gerngross U.S. Pat. No. 7,029,872). More recent attempts have focused on reducing or eliminating altogether fungal O-glycosylation in order to reduce or eliminate this response; see, e.g., Tanner, U.S. Pat. No. 5,714,377; and Bobrowicz et al., WO2007/061631. By contrast, the present inventors have surprisingly found unexpected advantages in producing a protein with certain O-glycosylation patterns similar to the O-glycosylation observed on native human glycoproteins, or closer to the O-glycosylation observed on recombinant glycoproteins produced in mammalian cells.

SUMMARY OF THE INVENTION

The present invention provides methods and materials for the production of recombinant glycoproteins with improved properties useful in the development of human therapeutics or veterinary therapeutic products. In certain embodiments, the invention comprises lower eukaryotic host cells (including yeast and filamentous fungi) which have been engineered to produce glycoproteins having a predominant human-like O-glycan. In preferred embodiments, the host cells produce glycoproteins having predominantly a human-like O-glycan selected from O-Man-GlcNAc, O-Man-GlcNAc-Gal, or O-Man-GlcNAc-Gal-Sia.

As a first aspect, the present invention provides lower eukaryotic host cells for use in the methods of the present invention which are modified by the knock-out and/or inactivation of one or more genes involved in O-glycosylation, including but not limited to those encoding beta-mannosyltransferases (bmts; see, e.g., US 2006/0211085), phosphomannose transferases, or one or more additional genes involved in O-glycosylation.

As a second aspect, the present invention provides lower eukaryotic host cells such as those described above for use in the methods of the present invention which are modified to express exogenous (non-native) genes involved in the human or mammalian O-linked glycosylation pathways by transfection or transformation with exogenous genes involved in O-glycosylation, and in particular genes encoding protein O-mannose β-1,2-N-acetylglucosaminyltransferase 1 ("PomGnT1") or the catalytic domain thereof as well as one or more additional genes encoding for one or more steps in the human or mammalian O-glycosylation pathways. In particular embodiments, these one or more additional genes encode, without limitation, the following enzymes or catalytic domains thereof: UDP-GlcNAc transporter; α-1,2-mannosidase; β-1,4-galactose transferase ("β1,4GalT"); UDP-galactose transporter (UGT); UDP-Gal epimerase; α-2,6-sialic acid transferase ("α2,6SialT"); α-2,3-sialic acid transferase ("α2,3SialT"); UDP-N-acetylglucosamine-2-epimerase/N-acetylmannosamine kinase("GNE"); N-acetylneuraminate-9-phosphate synthase("SPS"); sialylate-9-P phosphatase ("SPP"); CMP-sialic acid synthase("CSS"); and CMP-sialic acid transporter ("CST").

As a third aspect, the present invention provides lower eukaryotic host cells such as those described above for use in the methods of the present invention which are modified to express a recombinant glycoprotein of interest by the transfection or transformation of the host cell with an exogenous gene encoding the glycoprotein. Thereby, when cultured under appropriate conditions for expression, the host cells as describe herein will express and secrete improved recombinant glycoproteins comprising particular human-like O-glycosylation.

The present invention further comprises methods for producing a recombinant glycoprotein having predominantly a human-like O-glycan, said method comprising a) selecting a lower eukaryotic host cell; b) attenuating one or more endogenous glycosylation enzymes in the host cell (where said host cell of step (a) is not already so attenuated); c) transforming the host cell with nucleic acid sequence encoding an O-linked mannose β1,2-N-acetylglucosaminyltransferase 1 (POMGnT1), a UDP-GlcNAc transporter, an alpha-1,2 mannosidase, and the glycoprotein; and d) culturing the cell under conditions suitable for expression of the nucleic acid sequence to produce the recombinant glycoprotein having predominantly a human-like O-glycan. In particular embodiments, the host cell is further transformed with nucleic acid encoding, without limitation, the following enzymes or catalytic domains thereof: β-1,4-galactose transferase ("β1,4GalT"); UDP-galactose transporter (UGT); UDP-Gal epimerase; α-2,6-sialic acid transferase ("α2,6SialT"); α-2,3-sialic acid transferase ("α2,3SialT"); UDP-N-acetylglucosamine-2-epimerase/N-acetylmannosamine kinase("GNE"); N-acetylneuraminate-9-phosphate synthase ("SPS"); sialylate-9-P phosphatase ("SPP"); CMP-sialic acid synthase("CSS"); and CMP-sialic acid transporter ("CST").

In other embodiments, the present invention comprises recombinant glycoprotein compositions produced from the lower eukaryotic host cells of the invention.

The lower eukaryotic host cells of the present invention may optionally be engineered to produce glycoproteins having a predominant human-like N-glycan. In preferred embodiments, the host cells produce glycoproteins having a predominant N-glycan selected from: Man5GlcNAc2, GlcNAcMan5GlcNAc2, GalGlcNAcMan5GlcNAc2, SiaGalGlcNAcMan5GlcNAc2, Man3GlcNAc2, GlcNAcMan3GlcNAc2, GalGlcNAcMan3GlcNAc2, SiaGalGlcNAcMan3GlcNAc2, GlcNAc2Man3GlcNAc2, GalGlcNAc2Man3GlcNAc2, Gal2GlcNAc2Man3GlcNAc2, SiaGal2GlcNAc2Man3GlcNAc2, or Sia2Gal2GlcNAc2Man3GlcNAc2.

In particular embodiments, the glycoprotein compositions provided herein comprise glycoproteins having fucosylated and non-fucosylated hybrid and complex N-glycans, including bisected and multiantennary species, including but not limited to N-glycans such as $GlcNAc_{(1-4)}Man_3GlcNAc_2$; $Gal_{(1-4)}GlcNAc_{(1-4)}Man_3GlcNAc_2$; $NANA_{(1-4)}Gal_{(1-4)}GlcNAc_{(1-4)}Man_3GlcNAc_2$.

In particular embodiments, the glycoprotein compositions provided herein comprise glycoproteins having at least one hybrid N-glycan selected from the group consisting of $GlcNAcMan_3GlcNAc_2$; $GalGlcNAcMan_3GlcNAc_2$; $NANAGalGlcNAcMan_3GlcNAc_2$; $GlcNAcMan_5GlcNAc_2$; $GalGlcNAcMan_5GlcNAc_2$; and $NANAGalGlcNAcMan_5GlcNAc_2$. In particular aspects, the hybrid N-glycan is the predominant N-glycan species in the composition. In further aspects, the hybrid N-glycan is a particular N-glycan species that comprises about 30%, 40%, 50%, 60%, 70%, 80%, 90%, 95%, 97%, 98%, 99%, or 100% of the hybrid N-glycans in the composition.

In particular embodiments, the glycoprotein compositions provided herein comprise glycoproteins having at least one complex N-glycan selected from the group consisting of $GlcNAc_2Man_3GlcNAc_2$; $GalGlcNAc_2Man_3GlcNAc_2$; $Gal_2GlcNAc_2Man_3GlcNAc_2$; $NANAGal_2GlcNAc_2Man_3GlcNAc_2$; and $NANA_2Gal_2GlcNAc_2Man_3GlcNAc_2$. In particular aspects, the complex N-glycan is the predominant N-glycan species in the composition. In further aspects, the complex N-glycan is a particular N-glycan species that comprises about 30%, 40%, 50%, 60%, 70%, 80%, 90%, 95%, 97%, 98%, 99%, or 100% of the complex N-glycans in the composition.

In particular embodiments, the N-glycan is fusosylated. In general, the fucose is in an α1,3-linkage with the GlcNAc at the reducing end of the N-glycan, an α1,6-linkage with the GlcNAc at the reducing end of the N-glycan, an α1,2-linkage with the Gal at the non-reducing end of the N-glycan, an α1,3-linkage with the GlcNac at the non-reducing end of the N-glycan, or an α1,4-linkage with a GlcNAc at the non-reducing end of the N-glycan.

Therefore, in particular aspects of the above the glycoprotein compositions, the glycoform is in an α1,3-linkage or α1,6-linkage fucose to produce a glycoform selected from the group consisting of $GlcNAcMan_5GlcNAc_2(Fuc)$, $GlcNAcMan_3GlcNAc_2(Fuc)$, $GlcNAc_2Man_3GlcNAc_2(Fuc)$, $GalGlcNAc_2Man_3GlcNAc_2(Fuc)$, $Gal_2GlcNAc_2Man_3GlcNAc_2(Fuc)$, $NANAGal_2GlcNAc_2Man_3GlcNAc_2(Fuc)$, and $NANA_2Gal_2GlcNAc_2Man_3GlcNAc_2(Fuc)$; in an α1,3-linkage or α1,4-linkage fucose to produce a glycoform selected from the group consisting of $GlcNAc(Fuc)Man_5GlcNAc_2$, $GlcNAc(Fuc)Man_3GlcNAc_2$, $GlcNAc_2(Fuc_{1-2})Man_3GlcNAc_2$, $GalGlcNAc_2(Fuc_{1-2})Man_3GlcNAc_2$, $Gal_2GlcNAc_2(Fuc1-2)Man3GlcNAc2$, $NANAGal2GlcNAc2(Fuc_{1-2})Man_3GlcNAc_2$, and $NANA_2Gal_2GlcNAc_2(Fuc_{1-2})Man_3GlcNAc_2$; or in an α1,2-linkage fucose to produce a glycoform selected from the group consisting of $Gal(Fuc)GlcNAc_2Man_3GlcNAc_2$, $Gal_2(Fuc_{1-2})GlcNAc_2Man_3GlcNAc_2$, $NANAGal_2(Fuc_{1-2})GlcNAc_2Man_3GlcNAc_2$, and $NANA_2Gal_2(Fuc_{1-2})GlcNAc_2Man_3GlcNAc_2$.

In further aspects of the above, the complex N-glycans further include fucosylated and non-fucosylated bisected and multiantennary species.

In further aspects, the glycoproteins comprise high mannose N-glycans, including but not limited to, $Man_5GlcNAc_2$, or N-glycans that consist of the $Man_3GlcNAc_2$ N-glycan structure.

BRIEF DESCRIPTION OF THE SEQUENCES

SEQUENCE ID NOs: 1-108 illustrate various ER and/or Golgi localization leader sequences.

SEQUENCE ID NOs: 109-118 illustrate POMGnT1 sequences.

SEQUENCE ID NOs: 119-120, 122-123, 125-126, 133-134, 135-136 and 141-148 illustrate PCR primers utilized in Examples.

SEQUENCE ID NOs: 121 and 124 illustrate PpHI3 ORF and 3' untranslated fragments, respectively.

SEQUENCE ID NO: 127 illustrates a DNA fragment encompassing the PpALG3 transcriptional termination sequence.

SEQUENCE ID NO: 128 illustrates a PpGAP promoter sequence.

SEQUENCE ID NO: 129 illustrates a ScCYC1 transcriptional terminator sequence.

SEQUENCE ID NO: 130 illustrates a PpAOX1 promoter sequence.

SEQUENCE ID NOs: 131-132 and 138-140 illustrate sequences comprising TNFR-IgG1 sequence.

SEQUENCE ID NO: 137 illustrates sequence encoding the HSA pre-signal peptide.

DETAILED DESCRIPTION OF THE INVENTION

The present invention relates to methods and materials for generating glycoproteins having human O-glycosylation in lower eukaryotes, e.g., yeast (including but not limited to *Pichia pastoris*), or filamentous fungi which do not inherently have human O-glycosylation synthesis and transfer machinery. Recombinant glycoproteins produced using the disclosed methods and materials bear glycosylation patterns common with human or mammalian-produced proteins and, as such, are able to be injected into humans with greatly reduced or eliminated potential for an immunogenic response.

Applicants have found, moreover, that humanizing the O-glycans can enhance the bioactivity (such as bioavailability and serum half-life) of therapeutic proteins particularly sialylated O-glycans, for example, by improving pharmacokinetic properties, hence facilitating better control over in vivo drug activity.

Accordingly, the present invention relates to the development of protein expression systems for yeasts and filamentous fungi, such as *Pichia pastoris*, based on improved vectors, novel nucleic acids, host cell lines, and methods for using the foregoing in the production of recombinant glycoproteins with decreased immunogenicity and/or better pharmacokinetic properties.

Figure 9:
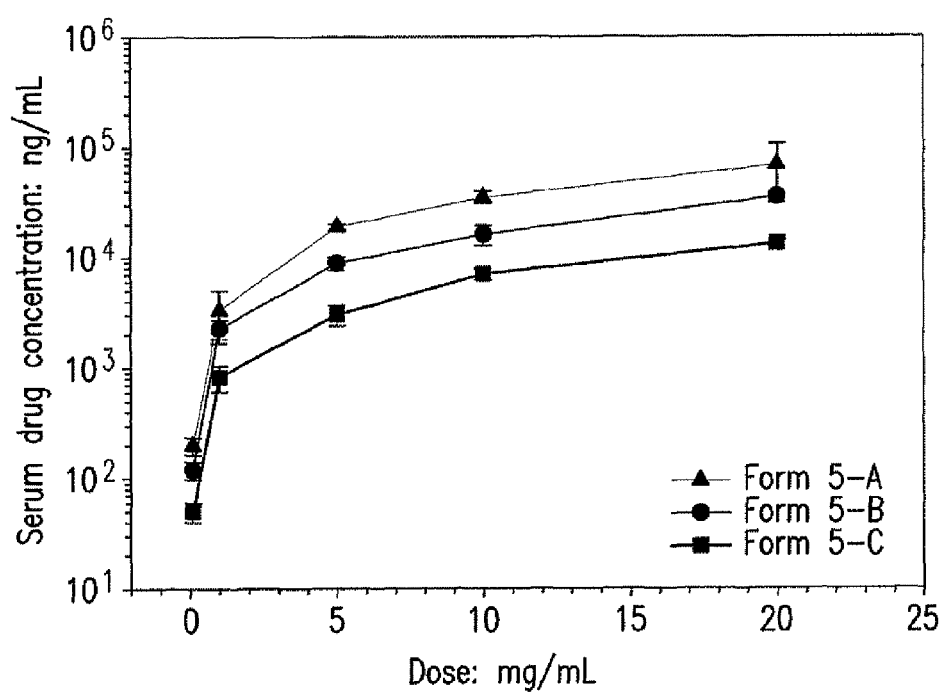
FIG. 9 illustrates how increased O-sialylation of a glycoprotein results in increased bioavailability in B6 mice. Serum concentrations of mice 48 hours after subcutaneous administration of different doses of TNFRII-Fc are shown. Total sialic acid content (mol/mol) was as follows: Form 5-A: 21; Form 5-B: 16; and Form 5-C: 11.

The present inventors have found that improved glycoprotein therapeutics can be obtained in recombinant lower eukaryotic host cells by modifying the glycosylation machinery present in the lower eukaryotic cells. The cells as will be described herein are or have been genetically modified (e.g., through particular deletions and insertions) so as to specifically produce recombinant glycoproteins having certain human like O-glycosylation. More specifically, Applicants found that, through the steps of (i) attenuating the lower eukaryotic host cell's endogenous O-glycosylation pathway (or, alternatively, exploiting host cells so attenuated) and (ii) expressing heterologous genes encoding particular O-glycosylation enzymes, the host cell was able to produce proteins having particular human-like O-glycans instead of the native, lower eukaryotic immunogenic O-glycans. Following the changes described and transfection with an exogenous gene of interest, Applicants found that the modified lower eukaryotic host cells were able to produce glycoproteins (including therapeutic glycoproteins) with particular human-like O-glycosylation (and, in particular embodiments human-like N-glycosylation as well). FIGS. 9 and 10 illustrate how increased O-sialylation of a glycoprotein as disclosed in the present invention results in increased bioavailability in B6 mice and both increased bioavailability and serum half-life in rats. In addition, the lower eukaryotic host cells, such as *Pichia pastoris*, are able to produce therapeutic glycoproteins in high titers, with the predominant species of glycoprotein having human O-glycans (and optionally N-glycans) which exhibit improved efficacy compared to therapeutic glycoprotein produced in mammalian cells or in lower eukaryotic host cells retaining the endogenous glycosylation machinery.

Although a previous invention from Bobrowicz et al., WO2007/061631, has described methods for reducing fungal O-glycans to a single O-linked mannose, it may be advantageous to produce a protein that has similar or identical O-glycosylation to certain O-glycoforms observed from mammalian cell culture or of human origins. For purposes of the present invention, such proteins with similar or identical O-glycosylation to certain O-glycoforms observed from mammalian cell culture or of human origin ("human-like" O-glycans for purposes herein) are proteins having as the predominant O-glycan species, glycans comprising (1) a terminal GlcNAc linked to a single mannose residue which is linked to a serine or threonine residue on the protein (i.e., O-Man-GlcNAc); (2) a terminal GlcNAc-Gal (i.e., galactose linked to the terminal GlcNAc referred to above) linked to a single mannose residue which is linked to a serine or threonine residue on the protein (i.e., O-Man-GlcNAc-Gal); or (3) terminal GlcNAc-Gal-Sia (i.e., sialic acid linked to the terminal GlcNAc-Gal referred to in (2)) linked to a single mannose residue which is linked to a serine or threonine residue on the protein (i.e., O-Man-GlcNAc-Gal-Sia). These structures are closely related to O-glycan structures typically observed on nerve cells and other brain-related or neural-related cells (See, Zamze et al., *Glycobiology;* 9:823-831 (1999). The most well studied example of the mammalian sialylated O-mannose glycan is on alpha-dystroglycan ("Alpha-DG"); Chiba et al., 1997 *J Biol. Chem* 272:2156; Sasaki et al., 1998 *Biochem. Biophys. Acta* 1425:599. Alpha-DG contains the O-glycan (sialic acid-alpha-2,3-Gal-beta-1,4-GlcNAc-beta-1,2-mannose) in "high abundance" on Ser/Thr within a mucin-like domain located at the N-terminal end of mature alpha-DG. Manya et al., 2007 *J Biol Chem* 282:20200, identified at least some of the O-mannosylated residues.

The present invention provides methods and materials useful for producing recombinant glycoproteins bearing predominantly human-like O-glycan structures (as defined herein) in lower eukaryotic expression systems. Lower eukaryotes such as yeast are preferred for expression of glycoproteins because they can be economically cultured, give high yields, and when appropriately modified are capable of suitable glycosylation. Various yeasts, such as *Kluyveromyces lactis*, *Pichia pastoris*, *Pichia methanolica*, and *Hansenula polymorpha* are preferred for cell culture because they are able to grow to high cell densities and secrete large quantities of recombinant protein. In specific embodiments, the lower eukaryote is *Pichia finlandica, Pichia trehalophila, Pichia koclamae, Pichia membranaefaciens, Pichia minuta (Ogataea minuta, Pichia lindneri), Pichia opuntiae, Pichia thermotolerans, Pichia salictaria, Pichia guercuum, Pichia pijperi* or *Pichia stiptis*. Likewise, filamentous fungi, such as *Aspergillus niger, Fusarium* sp, *Neurospora crassa* and others can be used to produce glycoproteins of the invention at an industrial scale.

As a first aspect, the present invention provides lower eukaryotic host cells for use in the methods of the present invention which are modified by the knock-out and/or inactivation of one or more genes involved in O-glycosylation, including but not limited to those encoding beta-mannosyltransferases (bmts; see, e.g., US 2006/0211085 and Trimble R B et al., 2003 *Glycobiology* 14:265-274), phosphomannose transferase (see, e.g., Trimble R B et al., 2003 *Glycobiology* 14:265-274), or one or more additional genes involved in O-glycosylation. In particular embodiments, the one or more genes involved in O-glycosylation which are knocked out and/or inactivated encode enzymes selected from: beta-mannosyl transferases (e.g., BMT 1, 2, 3 and 4 genes; see, e.g., Mille et al., 2008 *J. Biol. Chem.* 283:9724-9736; US 2006/0211085) or phospho-mannose transferases (e.g., MNN4A [also known as MNN4], MNN4B [also known as MNN4L1 or MNNS; see, e.g., U.S. Pat. No. 7,259,001] and PNO1 [see, e.g., U.S. Pat. No. 7,198,921] genes; Li et al., 2006 *Nat. Biotechnol.* 24:210-215). In specific embodiments, genes encoding Ktr and Kre2/Mnt1 mannosyltransferases, including Ktr1 and Ktr3 (KTR1 and KTR3 genes) and alpha1,2-mannosyltransferase Kre2 (KRE2 gene, see, e.g., U.S. Pat. No. 7,217,548) are left intact or in a state that enables them to produce functional protein. In alternative embodiments, the gene encoding Ktr1 is deleted or inactivated while the other MNT genes are left in a state that enables them to produce functional protein. It has been found that inactivation of KTR1 increases level of O-Man1 2-fold. In specific embodiments, at least one of the genes encoding Mnn4a, Mnn4b and Pno1 are deleted. In alternative embodiments, genes encoding Ktr1, Ktr3 and Kre2 are deleted or inactivated.

Disruption of genes can be done by any method suitable in the art to disrupt the gene and/or translation into the encoded protein; and includes but is not limited to disrupting the open reading frame of the gene, disrupting expression of the open reading frame or abrogating translation of RNAs encoding the intended protein and using interfering RNA, antisense RNA, or the like. Suitable methods include, for example, the procedure of Rothstein, 1991 *Methods Enzymol.* 194:281-301, or the PCR-mediated approach of Baudin et al., 1993 *Nucleic Acids Res.* 21:3329-3330. In specific embodiments, alternative genes in the above families not specifically mentioned above are left intact (i.e., not disrupted).

As a second aspect, the present invention provides host cells (in particular, those described above in the first aspect) for use in the methods of the present invention which are modified to express recombinant, exogenous (non-native) genes involved in the human or mammalian O-linked glycosylation pathways. In specific embodiments, the host cells express an extra copy of each of the exogenous genes involved in the human or mammalian O-linked glycosylation pathways. The cells may be obtained through transfection or transformation of cells with exogenous genes involved in O-glycosylation, and in particular genes encoding protein O-mannose β-1,2-N-acetylglucosaminyltransferase 1 ("PomGnT1"), or the catalytic domain thereof, as well as one or more additional genes encoding for enzymes responsible for one or more steps in the human or mammalian O-glycosylation pathways, including but not limited to the following enzymes or the catalytic domains thereof: UDP-GlcNAc transporter; α-1,2-mannosidase (see, e.g., WO 2007/061631); β-1,4-galactose transferase ("β1,4GalT"); UDP-galactose transporter (UGT); UDP-Gal epimerase; α-2,6-sialic acid transferase ("α2,6SialT"); α-2,3-sialic acid transferase ("α2,3SialT"); UDP-N-acetylglucosamine-2-epimerase/N-acetylmannosamine kinase ("GNE"); N-acetylneuraminate-9-phosphate synthase ("SPS"); sialylate-9-P phosphatase ("SPP"); CMP-sialic acid synthase ("CSS"); and CMP-sialic acid transporter ("CST"). In additional embodiments, nucleic acid encoding genes for O-fucosylation may be added. O-fucose glycans may, in specific embodiments, range from the monosaccharide Fuc-O-Ser/Thr to the tetrasaccharide NeuAcα2, 3/6 Galβ1,3 Fuc-O-Ser/Thr and the di- and tri-intermediates. In specific embodiments, the host cell is transformed with nucleic acid encoding genes for adding fucose, NeuAcα2, 3/6 Galβ1, or Fuc-O-Ser/Thr (GDP-fucose protein O-fucosyltransferase; POFUT1); and/or one or more genes for adding GlcNAc-linked β1,3 to Fuc-O-Ser/Thr: Manic, Radical and/or Lunatic Fringe. Nucleic acid introduced may be operatively linked to a fungal-derived promoter and transcription terminator as well as a fungal-derived leader sequence having a signal sequence and an endoplasmic reticulum ("ER")- or Golgi-localizing transmembrane domain. The genes encoding PomGnT1, β1,4GalT, α2,6SialT and α2,3SialT, in particular embodiments, are operatively linked to a fungal-derived (in particular embodiments, that derived from *Saccharomyces cerevisiae, Pichia pastoris*, or *Kluyveromyces lactis*) promoter and transcription terminator as well as a fungal-derived leader sequence having a signal sequence and an endoplasmic reticulum ("ER")- or Golgi-localizing transmembrane domain. The signal sequence serves to direct the nascent protein to the ER. The transmembrane domain is utilized to localize and anchor the protein to an ER or Golgi membrane. The gene encoding α-1,2-mannosidase is operatively linked to a fungal-based (in particular embodiments, *Pichia*-derived) promoter and transcription terminator as well as a fungus-derived signal sequence (in specific embodiments wherein the signal sequence is the *Saccharomyces* alphaMAT pre-signal sequence). The genes encoding UDP-GlcNAc transporter, UDP-galactose transporter, UDP-Gal epimerase, ONE, SPS, SPP, CSS and CST are operatively linked to a fungal-based (in particular embodiments, *Pichia*-derived) promoter and transcription terminator. In particular embodiments, the promoter utilized is the *Pichia* AOX1 promoter or the GAP promoter. In other embodiments, the promoter utilized is the *Pichia* TEF promoter or the PMA promoter; see, e.g., Hamilton et al., 2006 *Science* 303:1441-1443. In specific embodiments, the α2,6SialT gene is operatively linked to the *Pichia* TEF promoter. In specific embodiments, the CST gene is operatively linked to the PMA promoter.

In specific embodiments, the POMGnT1 enzyme or catalytic domain encoded is that of, or derived from that of, human, mouse or frog.

In specific embodiments, the POMGnT1 enzyme comprises sequence SEQ ID NO: 110, SEQ ID NO: 112, or SEQ ID NO: 118. In specific embodiments, the POMGnT sequence is selected from: SEQ ID NO: 109, SEQ ID NO: 111, or SEQ ID NO: 117. SEQ ID NOs: 109, 111 and 117, codon-optimized sequences encoding the POMGnT1 enzyme form specific embodiments of the present invention.

In specific embodiments, the UDP-GlcNAc transporter is that of, or derived from that of, *Kluyveromyces lactis* or mouse UDP-GlcNAc transporter.

The alpha 1,2-mannosidase of the cell lines and methods of the present invention must be active on O-linked alpha 1,2-mannose. In specific embodiments, the alpha 1,2-mannosidase is a fungal alpha 1,2-mannosidase and in specific embodiments is that of, or derived from that of, *Trichoderma reesei* alpha-1,2-mannosidase, *Saccharomyces* sp., *Coccidiodes* species (e.g., *C. immitis* such as that described in accession no. EAS32290, or *C. posadasii* mannosidase such as that described in accession no. ABA54911; see, e.g., U.S. application Ser. No. 61/369,157, filed Jul. 30, 2010) or *Aspergillus* sp. (see, e.g., Bobrowicz et. al., WO2007/061631) alpha-1,2-mannosidase. In specific embodiments, the alpha-1,2-mannosidase is under the control of the *Pichia* AOX1 promoter. Thus, upon switching the methanol media, the mannosidase is expressed generating single mannose structures.

Cells in accordance with the present invention may be generated utilizing procedures available in the art, within publications referenced herein, and as described herein; see, e.g., Hamilton et al., 2006 *Science* 313: 1441-1443; and WO 07/136752.

Expression of exogenous genes in a host requires the use of regulatory regions functional in such hosts, whether native or non-native, or introduced or present in cell line utilized. A wide variety of transcriptional, translational, localization and other regulatory sequences can be employed. In specific embodiments, the regulatory sequences are those of other yeast or filamentous fungi. In specific embodiments, the regulatory sequences are vertebrate, including but not limited to frog, murine or human sequences.

In particular instances, as described above, the exogenous genes are operatively linked to an endoplasmic reticulum ("ER") or Golgi localization sequence, see, e.g., Choi et al., 2003 PNAS 100:5022, and U.S. Pat. No. 7,449,308. The ER or Golgi leader/localization sequence utilized targets the sequence operatively linked therewith to the endoplasmic reticulum or the early Golgi. In specific embodiments, the ER/Golgi leader sequence is a membrane targeting region from an ER and/or Golgi residing membrane protein of *S. cerevisiae, P. pastoris*, or *K. lactis*. In specific embodiments, the ER/Golgi leader sequence comprises a signal sequence to direct the nascent protein to the ER and a localization signal consisting essentially of: (i) the cytoplasmic tail and a segment of the transmembrane domain capable of retaining the operatively linked protein in the ER and/or Golgi for a period of time to permit the desired function; (ii) part or all of the entire stem region; or (iii) the entire stem region and optionally parts of the catalytic domain. In specific embodiments, the ER and/or Golgi leader sequence is an ER and/or Golgi leader sequence, or derived from an ER and/or Golgi leader sequence of a protein selected from: ScMNS1-s, ScSEC12-m, ScMNN9-s, ScKRE2-s, ScMNN2-s or ScMNN6-s. In specific embodiments, the ER and/or Golgi leader sequence is derived from an ER and/or Golgi leader sequence of a protein selected from: ScMNS1-s, ScMNN9-s, PpKRE2-s, K1GNT1-s, ScMNN2-s, ScMNN2-m, ScMNN5-s, ScMNN6-s, ScPMT5-m, PpPMT1-m or PpBET1-s. Certain leaders falling into this category are disclosed in the prior art, see, e.g., Choi et al., 2003 PNAS 100:5022 and U.S. Pat. No. 7,449,308. The disclosed leaders and combinations thereof comprising the leader and exogenous gene as described herein, optionally containing a transcription terminator sequence, form specific embodiments hereof. Specific embodiments relate to the PMT, BET1, BOS1 and SEC22 leaders and leader combinations as described herein. In particular, the present invention relates to leaders and their corresponding SEQ ID NOs disclosed in Table 1, in specific embodiments, Leader #s 33-34, 27-32 and 35-54, as well as combinations comprising the foregoing leaders and exogenous genes.

In specific embodiments, the ER and/or Golgi leader sequence is that of, or derived from that of, the leader sequence of a protein selected from: *S. cerevisiae* alpha-glucosidase I encoded by GLS1, *S. cerevisiae* alpha-1,2-mannosidase encoded by MNS1, *S. cerevisiae* and *P. pastoris* nucleotide exchange factor encoded by SEC12 which cycles between the ER and Golgi, *S. cerevisiae* and *P. pastoris* protein O-mannosyltransferases encoded by PMT 1, 2, 3, 4, 5 & 6 that encode integral ER membrane spanning domains, or SNARE proteins encoded by BOS1, BET1, and SEC22 from *S. cerevisiae* and *P. pastoris*. The region typically is an amino-terminal signal sequence followed by a transmembrane or other anchoring domain. In specific embodiments, the sequences listed immediately above are used as ER localization sequences.

In specific embodiments, the ER and/or Golgi leader sequence is that of, or derived from that of, the leader sequence of a protein selected from: *P. pastoris* Och1p, *S. cerevisiae* Mnn9p, Van1p, Anp1p, Hoc1p, Mnn10p or Mnn11p (and in particular embodiments is an amino-terminal fragment thereof). In specific embodiments, the sequences listed immediately above are used as early or cis-Golgi localization sequences.

In specific embodiments, the ER and/or Golgi leader sequence is that of, or derived from that of, the leader sequence of a protein selected from: *S. cerevisiae* Mnn1p or Mnn6p (and in particular embodiments is an amino-terminal fragment thereof). In specific embodiments, the sequences listed immediately above are used as late Golgi localization sequences.

Table 1 provides specific embodiments of ER and/or Golgi leader sequences contemplated herein. Additional sequences (with SEQ ID NOs) are also provided herein. Use of any of SEQ ID NOs: 1-108 is contemplated herein, Table 2 provides results achieved upon fusing particular disclosed leader sequences to human "Hs", murine "Mm" or frog "Xen" POMGnT1 catalytic domain sequences and expressing them from the methanol-inducible AOX1 promoter. The present invention contemplates the use of human, murine, or frog POMGnT1 sequences (inclusive but not limited to the catalytic domain sequences) and expressing them from a suitable promoter, including but not limited to the methanol-inducible AOX1 promoter or the GAP promoter.

In specific embodiments, the ER and/or Golgi leader sequence is one selected from: Tables 1 or 2, SEQ ID NOs: 1-108, or is derived from the leader sequence of ScMNN6-s, ScPMT1-s, ScPMT2-s, ScPMT3-s, ScPMT4-s, ScPMT5-s or ScPMT6-s.

In particular embodiments, human POMGnT1 sequence or a catalytic domain sequence thereof is fused to a leader sequence which is that of, or derived from that of, a protein selected from: PpSEC12-s, ScMNN9-s, K1GNT1-s, ScMNN2-s, ScMNN2-m, ScPMT5-m, PpPMT1-m or PpBET1-S. In specific embodiments, human POMGnT1 sequence or a catalytic domain sequence thereof is fused to a leader sequence selected from: SEQ ID NO 3 (or sequence encoding SEQ ID NO 4); SEQ ID NO 13 (or sequence encoding SEQ ID NO 14); SEQ ID NO 39 (or sequence encoding SEQ ID NO 40); SEQ ID NO 41 (or sequence encoding SEQ ID NO 42); SEQ ID NO 43 (or sequence encoding SEQ ID NO 44); SEQ ID NO 73 (or sequence encoding SEQ ID NO 74); SEQ ID NO 87 (or sequence encoding SEQ ID NO 88) or SEQ ID NO 105 (or sequence encoding SEQ ID NO 106).

In particular embodiments, murine POMGnT1 sequence or catalytic domain sequence thereof is fused to a leader sequence which is that of, or derived from that of, a protein selected from: ScMNN9-s, PpKRE2-s, ScKTR2-s, K1GNT1-s, ScMNN2-s, ScMNN2-m, ScMNN5-s, ScMNN6-s, ScPMT5-m, ScPMT6-m, PpPMT1-s, PpPMT2-s, PpPMT4-s, or PpBET1-s. In specific embodiments, murine POMGnT1 sequence or a catalytic domain sequence thereof is fused to a leader sequence selected from: SEQ ID NO 13 (or sequence encoding SEQ ID NO 14); SEQ ID NO 33 (or sequence encoding SEQ ID NO 34); SEQ ID NO 37 (or sequence encoding SEQ ID NO 38); SEQ ID NO 39 (or sequence encoding SEQ ID NO 40); SEQ ID NO 41 (or sequence encoding SEQ ID NO 42); SEQ ID NO 43 (or sequence encoding SEQ ID NO 44); SEQ ID NO 45 (or sequence encoding SEQ ID NO 46); SEQ ID NO 51 (or sequence encoding SEQ ID NO 52); SEQ ID NO 73 (or sequence encoding SEQ ID NO: 74); SEQ ID NO 75 (or sequence encoding SEQ ID NO 76); SEQ ID NO 77 (or sequence encoding SEQ ID NO 78); SEQ ID NO 79 (or sequence encoding SEQ ID NO 80); SEQ ID NO 81 (or sequence encoding. SEQ ID NO 82); or SEQ ID NO 105 (or sequence encoding SEQ ID NO 106).

In particular embodiments frog POMGnT1 sequence or catalytic domain sequence thereof is fused to a leader sequence which is that of, or derived from that of, a protein selected from: ScMNS1-s, ScSEC12-m, PpSEC12-s, ScMNN9-s, ScANP1-s, ScHOC1-s, ScMNN10-s, ScMNN11-s, PpKRE2-s, ScKTR2-s, K1GNT1-s, ScMNN2-s, ScMNN2-m, ScMNN1-s, ScMNN6-s, ScPMT5-m, PpPMT1-m, or PpBET1-s. In specific embodiments, frog POMGnT1 sequence or a catalytic domain sequence thereof is fused to a leader sequence selected from: SEQ ID NO 3 (or sequence encoding SEQ ID NO 4); SEQ ID NO 7 (or sequence encoding SEQ ID NO 8); SEQ ID NO 9 (or sequence encoding SEQ ID NO 10); SEQ ID NO 13 (or sequence encoding SEQ ID NO 14); SEQ ID NO 17 (or sequence encoding SEQ ID NO 18); SEQ ID NO 19 (or sequence encoding SEQ ID NO 20); SEQ ID NO 21 (or sequence encoding SEQ ID NO 22); SEQ ID NO 23 (or sequence encoding SEQ ID NO 24); SEQ ID NO 33 (or sequence encoding SEQ ID NO 34); SEQ ID NO 37 (or sequence encoding SEQ ID NO 38); SEQ ID NO 39 (or sequence encoding SEQ ID NO 40); SEQ ID NO 41 (or sequence encoding SEQ ID NO 42); SEQ ID NO 43 (or sequence encoding SEQ ID NO 44); SEQ ID NO 49 (or sequence encoding SEQ ID NO 50); SEQ ID NO 51 (or sequence encoding SEQ ID NO 52); SEQ ID NO 73 (or sequence encoding SEQ ID NO 74); SEQ ID NO 87 (or sequence encoding SEQ ID NO 88); or SEQ ID NO 105 (or sequence encoding SEQ ID NO 106).

In specific embodiments, the ER and/or Golgi leader sequence is that of, or derived from that of a protein selected from: ScMNN1-s, ScMNN9-s, PpKre2-s, ScMNN2-s, ScMNN2-m, ScMNN5-s, ScMNN6-s, ScPMT5-m, PpPMT1-m or PpBET1-s. In specific embodiments, the ER and/or Golgi leader sequence is selected from: SEQ ID NO 49 (or sequence encoding SEQ ID NO 50); SEQ ID NO 13 (or sequence encoding SEQ ID NO 14); SEQ ID NO 33 (or sequence encoding SEQ ID NO 34); SEQ ID NO 39 (or sequence encoding SEQ ID NO 40); SEQ ID NO 41 (or sequence encoding SEQ ID NO 42); SEQ ID NO 43 (or sequence encoding SEQ ID NO 44); SEQ ID NO 45 (or sequence encoding SEQ ID NO 46); SEQ ID NO 51 (or sequence encoding SEQ ID NO 52); SEQ ID NO 93 (or sequence encoding SEQ ID NO 94); SEQ ID NO 87 (or sequence encoding SEQ ID NO 88); or SEQ ID NO 105 (or sequence encoding SEQ ID NO 106).

In specific embodiments, the ER and/or Golgi leader sequence is that of, or derived from that of, a protein selected from: PpSEC12, ScMNN9, PpKRE2, ScKTR2, K1GNT1, ScMNN2, ScMNN6, ScPMT5, PpPMT1 or PpBET1.

In specific embodiments, the ER and/or Golgi leader sequence is that of, or derived from that of, a protein selected from: ScMNN9; K1GNT1, ScMNN2, ScPMT5 or PpBET1.

The exogenous gene fused to the ER and/or Golgi leader sequence is operatively linked to a promoter. The promoter may be any promoter element which drives expression of the exogenous gene to which it is fused including, but not limited to, the *Pichia* AOX1 promoter or the GAP promoter. In particular preferred embodiments, where the leader is ScMNN2-s, ScMNN2-m, ScPMT5-m, or PpPMT1-m, the promoter is AOX1.

Particular embodiments comprise the following promoter-leader-POMGnT1 sequence combinations: AOX1-PpKRE2s-mouse POMGnT1; GAP-K1GNT1s-mouse POMGnT1; AOX1-K1GNT1s-mouse POMGnT1; GAP-K1GNT1s-frog POMGnT1; AOX1-ScMNN2s-mouse POMGnT1; GAP-ScMNN5s-mouse POMGnT1; AOX1-ScMNN5s-mouse POMGnT1; GAP-ScMNN6s-mouse POMGnT1; or AOX1-ScPMT5m-mouse POMGnT1.

Particular embodiments comprise the GAP-ScMNN6s-human POMGnT1 promoter-leader-POMGnT1 sequence combination.

The exogenous genes may also be operatively linked to a transcription termination sequence including but not limited to that of ScCYC1 and PpAOX1.

The exogenous gene may optionally be operatively linked to additional regulatory sequences, including but not limited to signal sequences.

These leaders performed well in assays designed to measure GlcNAc transfer onto O-Man1, for example by lectin staining (lectin GS-II) and Dionex-HPLC (HPAEC-PAD) analysis of released O-glycans.

As a third aspect, the present invention provides host cells (in particular, those described in the first and second aspects) for use in the methods of the present invention which are modified to express the recombinant glycoprotein of interest by the transfection or transformation of the host cell with an exogenous gene encoding the glycoprotein. Thereby, when cultured under appropriate conditions for expression, the host cell will express and secrete improved recombinant glycoproteins comprising particular human-like O-glycosylation.

The lower eukaryotic host cells of the present invention may be transformed with a recombinant vector comprising a nucleic acid encoding a desired human glycoprotein, such as a human therapeutic drug or a veterinary drug. The nucleic acids can be DNA or RNA, typically DNA. The nucleic acid encoding the glycoprotein is operably linked to regulatory sequences that allow expression and secretion of the glycoprotein. Such regulatory sequences include a promoter and optionally an enhancer upstream, or 5', to the nucleic acid encoding the fusion protein and a transcription termination site 3' or downstream from the nucleic acid encoding the glycoprotein. For secreted glycoproteins, the nucleic acid typically includes a signal peptide. The signal peptide is responsible for targeting the protein to the secretory pathway for glycosylation and secretion, typically the endoplasmic reticulum. The nucleic acid also typically encodes a 5' untranslated region having a ribosome binding site and a 3' untranslated region. The nucleic acid is often a component of a vector replicable in cells in which the glycoprotein is expressed. The vector can also contain a marker to allow recognition of transformed cells. However, some cell types, particularly yeast, can be successfully transformed with a nucleic acid lacking extraneous vector sequences.

Nucleic acids encoding desired glycoproteins can be obtained from several sources. cDNA sequences can be amplified from cell lines known to express the glycoprotein using primers to conserved regions (see, e.g., Marks et al., *J. Mol. Biol.* 581-596 (1991)). Nucleic acids can also be synthesized de novo based on sequences in the scientific literature. Nucleic acids can also be synthesized by extension of overlapping oligonucleotides spanning a desired sequence (see, e.g., Caldas et al., Protein Engineering, 13, 353-360 (2000)). Using known techniques, the nucleic acid sequences used in the present invention can be codon-optimized for better expression in the host cells of the invention. Preferably, using the degeneracy of the genetic code, the primary amino acid sequence encoded by any DNA sequences encoding the therapeutic glycoprotein will be unchanged by such codon-optimization. If desired, one can add and/or remove one or more N-glycosylation sites by altering the chimeric DNA sequence used to express the primary amino acid sequence of the recombinant glycoprotein. In preferred embodiments, the host cells are transformed with a vector comprising nucleic acid encoding a soluble TNF-receptor fusion molecule (TNFRII-Fc); human granulocyte-colony stimulating factor (hG-CSF;) human granulocyte-macrophage colony-stimulating factor (hGM-CSF); or human erythropoietin (hEPO).

The recombinant glycoproteins produced in the present invention preferably comprise human therapeutic glycoproteins, including, but not limited to, granulocyte colony-stimulating factor (G-CSF), granulocyte-macrophage colony-stimulating factor (GM-CSF), erythropoietin (EPO) and TNF-receptors; or soluble TNF-receptor fusion molecules, such as Enbrel (Amgen). For human therapeutics, the recombinant glycoprotein preferably originates from humans or closely related species. Recombinant glycoproteins may also be produced for veterinary indications, in which case the recombinant glycoprotein sequence preferably originates from the same or a closely relates species to that of the intended veterinary subject.

Figure 1:
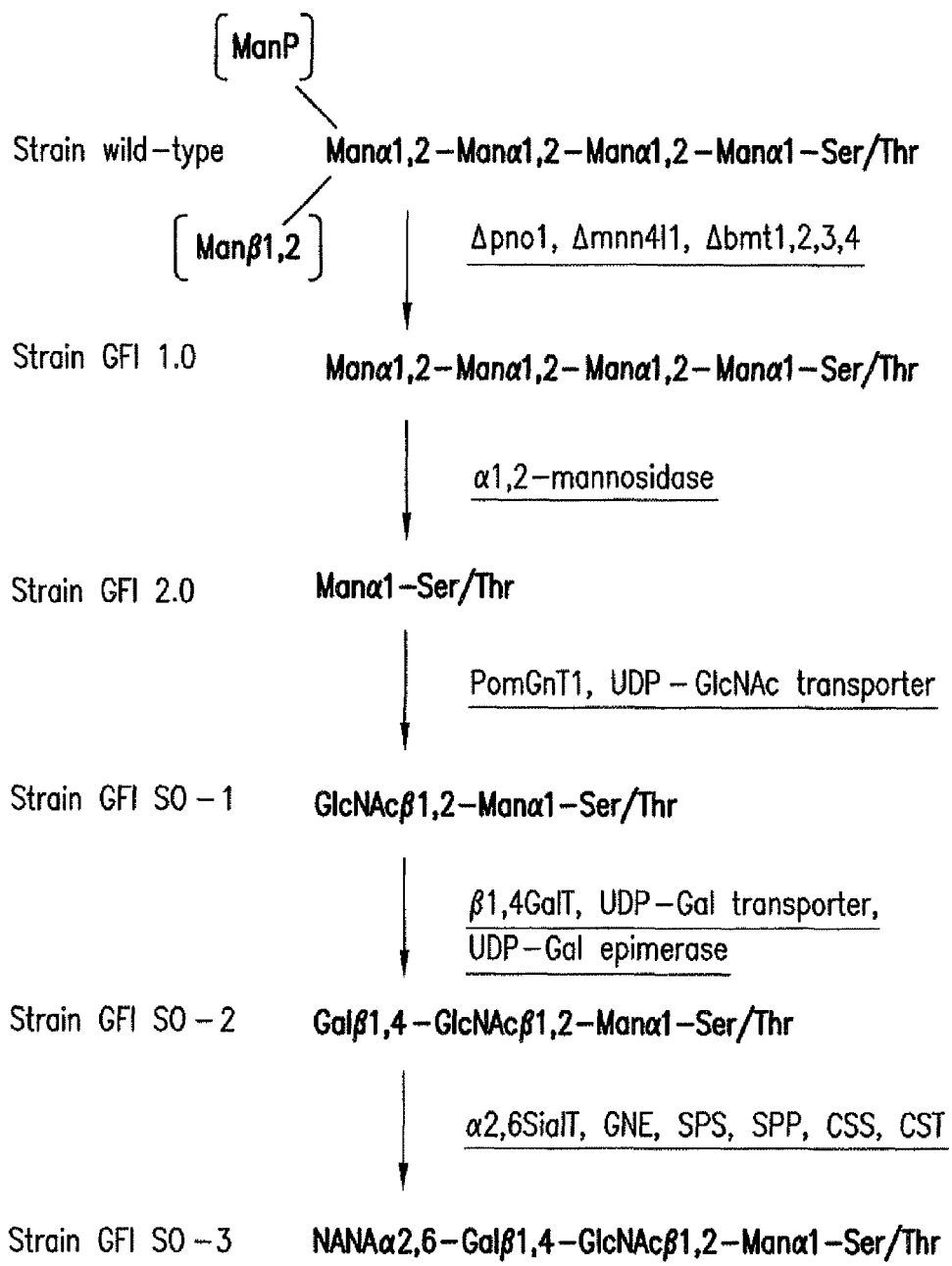
FIG. 1 illustrates an overview of a process for generating sialylated O-mannosyl glycans in Pichia pastoris.

A particular embodiment of the present invention is generally illustrated in FIG. 1.

In other embodiments, the present invention further comprises a method for producing a recombinant glycoprotein having predominantly a human-like O-glycan, said method comprising a) selecting a lower eukaryotic host cell; b) attenuating the activity of one or more endogenous O-glycosylation enzymes in the host cell (where said host cell of step (a) is not already so attenuated); c) transforming the host cell with nucleic acid sequence encoding an O-linked mannose β1,2-N-acetylglucosaminyltransferase 1 (POMGnT1), a UDP-GlcNAc transporter, an alpha-1,2 mannosidase; and the glycoprotein; and d) culturing the cell under conditions suitable for expression of the nucleic acid sequence to produce the recombinant glycoprotein having predominantly a human-like O-glycan. In particular embodiments, the host cell is further transformed with nucleic acid encoding, without limitation, the following enzymes or catalytic domains thereof: β-1,4-galactose transferase ("β1,4GalT"); UDP-galactose transporter (UGT); UDP-Gal epimerase; α-2,6-sialic acid transferase ("α2,6SialT"); α-2,3-sialic acid transferase ("α2,3SialT"); UDP-N-acetylglucosamine-2-epimerase/N-acetylmannosamine kinase("GNE"); N-acetylneuraminate-9-phosphate synthase("SPS"); sialylate-9-P phosphatase ("SPP"); CMP-sialic acid synthase("CSS"); and CMP-sialic acid transporter ("CST"). In specific embodiments, the host cell is further transformed with nucleic acid encoding the following enzymes or catalytic domains thereof: β1,4GalT, UDP-galactose transporter and UDP-Gal epimerase. In other embodiments, the host cell is further transformed with nucleic acid encoding the following enzymes or catalytic domains thereof: β1,4GalT; UDP-galactose transporter; UDP-Gal epimerase; α2,6SialT; GNE; SPS; SPP; CSS; and CST. In other embodiments, the host cell is further transformed with nucleic acid encoding the following enzymes or catalytic domains thereof: β1,4GalT; UDP-galactose transporter; UDP-Gal epimerase; α2,3SialT; GNE; SPS; SPP; CSS; and CST. In particular embodiments, the host cell is transformed with an extra copy of nucleic acid encoding at least one of the five genes required for sialylation: α2,3SialT (or α2,6SialT); GNE; SPS; SPP; CSS; and/or CST. In incorporating these five genes into a different loci in the genome, Applicants found that providing the extra copy results in a higher percentage of desired sialylated O-glycans. Further embodiments are wherein any of the cells above cells further do not express KTR1. The recombinant glycoprotein can be isolated, purified and formulated with pharmaceutically acceptable excipients to produce a therapeutic glycoprotein composition. In particular embodiments, the predominant O-glycan is O-Man-GlcNAc; O-Man-GlcNAc-Gal; or O-Man-GlcNAc-Gal-Sia.

Specific embodiments of the present invention relate to a method for producing a recombinant glycoprotein having human or mammalian O-like glycosylation in lower eukaryotic host cells which comprise: (1) providing lower eukaryotic host cells which (a) do not express functional: (i) beta-mannosyltransferase enzymes BMT 1, 2, 3 and 4, and (ii) phospho-mannose transferase enzymes Mnn4a, Mnn4b and Pno1; and (b) do express functional (i) POMGnT1; (ii) UDP-GlcNAc transporter; and (iii) α-1,2-mannosidase enzymes; (2) transfecting or transforming the lower eukaryotic host cells with exogenous nucleic acid encoding the glycoprotein of interest, and (3) culturing the host cells under conditions permitting the exogenous nucleic acid to be expressed and the recombinant glycoprotein to be produced. In specific embodiments, the cells of the above method comprise exogenous nucleic acid encoding the enzymes of step (1)(b). In specific embodiments, the cells further express nucleic acid encoding β1,4GalT, UDP-galactose transporter and UDP-Gal epimerase. These additional genes enable the production of terminal GlcNAc-Gal. In other specific embodiments, the cells further express nucleic acid encoding (i) β1,4GalT, (ii) UDP-galactose transporter, (iii) UDP-Gal epimerase, (iv) α2,6SialT, (v) GNE, (vi) SPS, (vii) SPP, (viii) CSS and (ix) CST. These additional genes enable the production of terminal GlcNAc-Gal-Sia. In other specific embodiments, the cells further express nucleic acid encoding (i) β1,4GalT, (ii) UDP-galactose transporter, (iii) UDP-Gal epimerase, (iv) α2,3SialT, (v) GNE, (vi) SPS, (vii) SPP, (viii) CSS and (ix) CST. Further embodiments are wherein any of the cells above cells further do not express Ktr1.

The determination of whether a cell expresses 'functional' enzyme is based upon whether the enzyme is carrying out its expected function at levels capable of affecting the desired O-glycosylation step. Where the activity is not detectable, the cell is understood herein to not express functional enzyme. In particular embodiments of step (1)(a) above, the cell does not express the enzymes or enzymatic activity at all. In particular embodiments of step (1)(b) where the cell expresses functional enzyme, the cells express native or expected activity of the enzyme. In specific embodiments of (1)(b), the cells are transfected with nucleic acid encoding the entire enzyme, or nucleic acid encoding the catalytic domain of the enzyme sufficient to enable the activity.

The methods, in specific embodiments, employ the cell lines, nucleic acid and vectors disclosed herein. Accordingly, in specific embodiments, the cell of step (a) is transfected with nucleic acid encoding the enzymes. In these embodiments, nucleic acid encoding POMOnT1, β1,4GalT, α2,6SialT and α2,3SialT should be operatively linked to a fungal-derived (in particular embodiments, that derived from *S. cerevisiae*, *Pichia pastoris*, or *Kluyveromyces lactis*) promoter and transcription terminator as well as a fungal-derived leader sequence having a signal sequence and an endoplasmic reticulum ("ER")- or Golgi-localizing transmembrane domain. The signal sequence serves to direct the nascent protein to the ER. The transmembrane domain localizes and anchors the protein to an ER or Golgi membrane. Nucleic acid encoding α-1,2-mannosidase should be operatively linked to a fungal-based (in particular embodiments, *Pichia*-derived) promoter and transcription terminator as well as a fungus-derived signal sequence (in specific embodiments wherein the signal sequence is the *Saccharomyces* alphaMAT pre-signal sequence). Nucleic acid encoding UDP-Gal epimerase, UDP-galactose transporter, GNE, SPS, SPP, CSS and CST should be operatively linked to a fungal-based (in particular embodiments, *Pichia*-derived) promoter and transcription terminator. In particular embodiments, the promoter utilized is the *Pichia* AOX1 promoter or the GAP promoter. In other embodiments, the promoter utilized is the *Pichia* TEF promoter or the PMA promoter; see, e.g., Hamilton et al., 2006 *Science* 303:1441-1443. In specific embodiments, the α2,6SialT gene is operatively linked to the *Pichia* TEF promoter. In specific embodiments, the CST gene is operatively linked to the PMA promoter. Particular embodiments utilize a cell line as described within the present disclosure. The specific cell lines described herein form particular embodiments of the present invention.

Glycosylation in the resultant cells lines may, where desired, be regulated (e.g., reduced or eliminated) by treatment with one or more chemical inhibitors of fungal O-glycosylation, including but not limited to: 5-[[3,4-bis(phenylmethoxy) phenyl]methylene]-4-oxo-2-thioxo-3-thiazolidineacetic acid; 5-[[3-(1-phenylethoxy)-4-(2-phenylethoxy)]phenyl]methylene]-4-oxo-2-thioxo-3-thiazolidineacetic acid; 3-Hydroxy-4-(2-phenylethoxy) benzaldehyde; 3-(1-Phenylethoxy)-4-(2-phenylethoxy)-benzaldehyde; 5-[[3-(1-Phenyl-2-hydroxy)ethoxy)-4-(2-phenylethoxy)]phenyl]methylene]-4-oxo-2-thioxo-3-thiazolidineacetic acid (See WO 2007/061631; incorporated by reference in its entirety). In specific embodiments, the inhibitor is an inhibitor of protein O-mannosyltransferase ("Pmt"); see Orchard et al., EP 1313471. In specific embodiments, the inhibitor is PMTi-3, WO 2007/061631. In specific embodiments, the Pmt inhibitors are those described within WO 09/143041 or U.S. application Ser. No. 61/369,157, filed Jul. 30, 2010. In specific embodiments, Pmt inhibitors are employed in the disclosed processes and provided to the disclosed cells (e.g., in the media) in order to control the overall levels of sialylated O-glycans and/or alter the percentage of different O-glycan species to favor the production of sialylated O-glycans. In particular embodiments, Pmt inhibitor is added in the induction phase as described, for example, in Bobrowicz et al., WO 07/061631. In specific embodiments, Pmt inhibitor is added to the growing yeast with the highest doses added during the methanol induction phase. Administration of Pmt inhibitors can be used to impact the pharmacodynamic properties of the glycoprotein composition by bringing about certain levels of O-sialylation. The particular level desired depends on the specific glycoprotein, as the skilled artisan will appreciate. For instance, with certain therapeutic glycoproteins, too many sialylated O-glycans might interfere with activity. In this situation, lowering the overall numbers of sialylated O-glycans might improve activity. For particular glycoproteins, O-glycans with terminal GlcNAc or galactose reduce protein activity and/or serum half-life. In this latter situation, effectuating a very high percentage of sialylated O-glycans may be required. Alternatively, the maximum number of sialylated O-glycans might be desired for optimal half-life, thus we might add little or no Pmt inhibitor. The skilled artisan can employ these teachings as appropriate in the desired situation.

The present invention additionally encompasses methods for preparing the above modified lower eukaryotic cells and use of same for preparing recombinant glycoproteins, disclosed nucleic acid, and vectors and host cells comprising same.

In other embodiments, the present invention comprises recombinant glycoprotein compositions produced from the lower eukaryotic host cells of the invention. These recombinant glycoprotein compositions comprise predominantly a human-like O-glycan, which may preferably be selected from: O-Man-GlcNAc; O-Man-GlcNAc-Gal; or O-Man-GlcNAc-Gal-Sia. In specific embodiments, the present invention produces recombinant glycoprotein compositions comprising greater than 50% (and, preferably, greater than 60%, 70%, 80%, 85%, 90%, 95% and 97%, respectively) human-like O-glycans as described above and less than 15% (and preferably, less than 10%, and less than 5%) O-Man2 glycans, which are glycans possessing two mannose residues attached to the O-glycosylated serine/threonine residue. In particular embodiments, the present invention produces recombinant glycoprotein compositions comprising greater than 30% (and, preferably, greater than 40%, 50%, 60%, 70%, 80% and 83%, respectively) O-Man-GlcNAc-Gal. In particular embodiments, the present invention produces recombinant glycoprotein compositions comprising greater than 30% (and, preferably, greater than 40%, 50% or 55%©, respectively) O-Man-GlcNAc-Gal-Sia. In specific embodiments, the present invention relates to the above compositions as described and, in addition, those embodiments that comprise less than 30%, 20%, or 15% (and, preferably, less than 10% and less than 5%) O-Man2 glycans, as well as methods of making the compositions as disclosed herein. O-glycan determination can be performed using methods readily available in the art, including but not limited to methods using a Dionex-HPLC (HPAEC-PAD) or other appropriate methods depending on the protein of interest. Recombinant glycoproteins and compositions comprising the glycoproteins produced using the methods and materials (vectors, host cells, etc.) disclosed herein can be formulated with other pharmaceutically acceptable active agents and/or inactive excipients to form glycoprotein compositions.

The present invention further relates to cell lines as described herein and as utilized in the methods disclosed herein.

The present invention can also be used in combination with recent developments allowing the production of therapeutic glycoproteins with human-like N-glycosylation in lower eukaryotic host organisms, yeast and filamentous fungi, such as *Pichia pastoris*; see, e.g., Gerngross, U.S. Pat. No. 7,029,872, the disclosure of which is hereby incorporated by reference. Lower eukaryotes, particularly yeast, can be genetically modified so that they express glycoproteins in which the N-glycosylation pattern is human-like or humanized. Such can be achieved by eliminating selected endogenous glycosylation enzymes and/or supplying exogenous enzymes as described by Gerngross et al., U.S. Pat. No. 7,449,308, the disclosure of which is hereby incorporated herein by reference. If desired, additional genetic engineering of the glycosylation can be performed, such that the glycoprotein can be produced with or without core fucosylation. Use of lower eukaryotic host cells such as yeast are further advantageous in that these cells are able to produce relatively homogenous compositions of glycoprotein, such that the predominant glycoform of the glycoprotein may be present as greater than thirty mole percent of the glycoprotein in the composition. In particular aspects, the predominant glycoform may be present in greater than forty mole percent, fifty mole percent, sixty mole percent, seventy mole percent and, most preferably, greater than eighty mole percent of the glycoprotein present in the composition. Such can be achieved by eliminating selected endogenous glycosylation enzymes and/or supplying exogenous enzymes as described by Gerngross et al., U.S. Pat. Nos. 7,029,872 and 7,449,308, the disclosures of which are incorporated herein by reference. For example, a host cell can be selected or engineered to be depleted in 1,6-mannosyl transferase activities, which would otherwise add mannose residues onto the N-glycan on a glycoprotein.

In specific embodiments, the host cells described herein includes an N-acetylglucosaminyltransferase I (GlcNAc transferase I or GnT I) catalytic domain fused to a cellular targeting signal peptide not normally associated with the catalytic domain and selected to target GlcNAc transferase I activity to the ER or Golgi apparatus of the host cell. Passage of the recombinant glycoprotein through the ER or Golgi apparatus of the host cell produces a recombinant glycoprotein comprising a GlcNAcMan$_5$GlcNAc$_2$ glycoform, for example a recombinant glycoprotein composition comprising predominantly a GlcNAcMan$_5$GlcNAc$_2$ glycoform. U.S. Pat. Nos. 7,029,872, 7,449,308, and U.S. Published Patent Application No. 2005/0170452, the disclosures of which are all incorporated herein by reference, disclose lower eukaryote host cells capable of producing a glycoprotein comprising a GlcNAcMan$_5$GlcNAc$_2$ glycoform. The glycoprotein produced in the above cells can be treated in vitro with a hexaminidase to produce a recombinant glycoprotein comprising a Man$_5$GlcNAc$_2$ glycoform.

In a further embodiment, the immediately preceding host cell further includes a mannosidase II catalytic domain fused to a cellular targeting signal peptide not normally associated with the catalytic domain and selected to target mannosidase II activity to the ER or Golgi apparatus of the host cell. Passage of the recombinant glycoprotein through the ER or Golgi apparatus of the host cell produces a recombinant glycoprotein comprising a GlcNAcMan$_3$GlcNAc$_2$ glycoform, for example a recombinant glycoprotein composition comprising predominantly a GlcNAcMan$_3$GlcNAc$_2$ glycoform. U.S. Pat. Nos. 7,029,872 and 7,625,756, the disclosures of which are all incorporated herein by reference, discloses lower eukaryote host cells that express mannosidase II enzymes and are capable of producing glycoproteins having predominantly a GlcNAc$_2$Man$_3$GlcNAc$_2$ glycoform.

The glycoprotein produced in the above cells can be treated in vitro with a hexaminidase to produce a recombinant glycoprotein comprising a Man$_3$GlcNAc$_2$ glycoform.

In a further embodiment, the immediately preceding host cell further includes N-acetylglucosaminyltransferase II (GlcNAc transferase II or GnT II) catalytic domain fused to a cellular targeting signal peptide not normally associated with the catalytic domain and selected to target GlcNAc transferase II activity to the ER or Golgi apparatus of the host cell. Passage of the recombinant glycoprotein through the ER or Golgi apparatus of the host cell produces a recombinant glycoprotein comprising a GlcNAc$_2$Man$_3$GlcNAc$_2$ glycoform, for example a recombinant glycoprotein composition comprising predominantly a GlcNAc$_2$Man$_3$GlcNAc$_2$ glycoform. U.S. Pat. Nos. 7,029,872 and 7,449,308 and U.S. Published Patent Application No. 2005/0170452, the disclosures of which are all incorporated herein by reference, disclose lower eukaryote host cells capable of producing a glycoprotein comprising a GlcNAc$_2$Man$_3$GlcNAc$_2$ glycoform. The glycoprotein produced in the above cells can be treated in vitro with a hexaminidase to produce a recombinant glycoprotein comprising a Man$_3$GlcNAc$_2$ glycoform.

In a further embodiment, the immediately preceding host cell further includes a galactosyltransferase catalytic domain fused to a cellular targeting signal peptide not normally associated with the catalytic domain and selected to target galactosyltransferase activity to the ER or Golgi apparatus of the host cell. Passage of the recombinant glycoprotein through the ER or Golgi apparatus of the host cell produces a recombinant glycoprotein comprising a GalGlcNAc$_2$Man$_3$GlcNAc$_2$ or Gal$_2$GlcNAc$_2$Man$_3$GlcNAc$_2$ glycoform, or mixture thereof for example a recombinant glycoprotein composition comprising predominantly a GalGlcNAc$_2$Man$_3$GlcNAc$_2$ glycoform or Gal$_2$GlcNAc$_2$Man$_3$GlcNAc$_2$ glycoform or mixture thereof. U.S. Pat. No. 7,029,872 and U.S. Published Patent Application No. 2006/0040353, the disclosures of which are incorporated herein by reference, discloses lower eukaryote host cells capable of producing a glycoprotein comprising a Gal$_2$GlcNAc$_2$Man$_3$GlcNAc$_2$ glycoform. The glycoprotein produced in the above cells can be treated in vitro with a galactosidase to produce a recombinant glycoprotein comprising a GlcNAc$_2$Man$_3$GlcNAc$_2$ glycoform, for example a recombinant glycoprotein composition comprising predominantly a GlcNAc$_2$Man$_3$GlcNAc$_2$ glycoform.

In a further embodiment, the immediately preceding host cell further includes a sialyltransferase catalytic domain fused to a cellular targeting signal peptide not normally associated with the catalytic domain and selected to target sialyltransferase activity to the ER or Golgi apparatus of the host cell. Passage of the recombinant glycoprotein through the ER or Golgi apparatus of the host cell produces a recombinant glycoprotein comprising predominantly a NANA$_2$Gal$_2$GlcNAc$_2$Man$_3$GlcNAc$_2$ glycoform or NANAGal$_2$GlcNAc$_2$Man$_3$GlcNAc$_2$ glycoform or mixture thereof. For lower eukaryote host cells such as yeast and filamentous fungi, it is useful that the host cell further include a means for providing CMP-sialic acid for transfer to the N-glycan. U.S. Published Patent Application No. 2005/0260729, the disclosure of which is incorporated herein by reference, discloses a method for genetically engineering lower eukaryotes to have a CMP-sialic acid synthesis pathway and U.S. Published Patent Application No. 2006/0286637, the disclosure of which is incorporated herein by reference, discloses a method for genetically engineering lower eukaryotes to produce sialylated glycoproteins. The glycoprotein produced in the above cells can be treated in vitro with a neuraminidase to produce a recombinant glycoprotein comprising predominantly a Gal$_2$GlcNAc$_2$Man$_3$GlcNAc$_2$ glycoform or GalGlcNAc$_2$Man$_3$GlcNAc$_2$ glycoform or mixture thereof.

Any one of the preceding host cells can include one or more GlcNAc transferase selected from the group consisting of GnT III, GnT IV, GnT V, GnT VI, and GnT IX to produce glycoproteins having bisected (GnT III) and/or multiantennary (GnT IV, V, VI, and IX) N-glycan structures such as disclosed in U.S. Pat. No. 7,598,055 and U.S. Published Patent Application No. 2007/0037248, the disclosures of which are all incorporated herein by reference.

In further embodiments, the host cell that produces glycoproteins that have predominantly GlcNAcMan$_5$GlcNAc$_2$ N-glycans further includes a galactosyltransferase catalytic domain fused to a cellular targeting signal peptide not normally associated with the catalytic domain and selected to target galactosyltransferase activity to the ER or Golgi apparatus of the host cell. Passage of the recombinant glycoprotein through the ER or Golgi apparatus of the host cell produces a recombinant glycoprotein comprising predominantly the GalGlcNAcMan$_5$GlcNAc$_2$ glycoform.

In a further embodiment, the immediately preceding host cell that produced glycoproteins that have predominantly the GalGlcNAcMan$_5$GlcNAc$_2$ N-glycans further includes a sialyltransferase catalytic domain fused to a cellular targeting signal peptide not normally associated with the catalytic domain and selected to target sialyltransferase activity to the ER or Golgi apparatus of the host cell. Passage of the recombinant glycoprotein through the ER or Golgi apparatus of the host cell produces a recombinant glycoprotein comprising a NANAGalGlcNAcMan$_5$GlcNAc$_2$ glycoform.

In further aspects, any one of the aforementioned host cells, the host cell is further modified to include a fucosyltransferase and a pathway for producing fucose and transporting fucose into the ER or Golgi. Examples of methods for modifying *Pichia pastoris* to render it capable of producing glycoproteins in which one or more of the N-glycans thereon are fucosylated are disclosed in Published International Application No. WO 2008112092, the disclosure of which is incorporated herein by reference. In particular aspects of the invention, the *Pichia pastoris* host cell is further modified to include a fucosylation pathway comprising a GDP-mannose-4,6-dehydratase, GDP-keto-deoxy-mannose-epimerase/GDP-keto-deoxy-galactose-reductase, GDP-fucose transporter, and a fucosyltransferase. In particular aspects, the fucosyltransferase is selected from the group consisting of α1,2-fucosyltransferase, α1,3-fucosyltransferase, α1,4-fucosyltransferase, and α1,6-fucosyltransferase.

Various of the preceding host cells further include one or more sugar transporters such as UDP-GlcNAc transporters (for example, *Kluyveromyces lactis* and *Mus musculus* UDP-GlcNAc transporters), UDP-galactose transporters (for example, *Drosophila melanogaster* UDP-galactose transporter), and CMP-sialic acid transporter (for example, human sialic acid transporter). Because lower eukaryote host cells such as yeast and filamentous fungi lack the above transporters, it is preferable that lower eukaryote host cells such as yeast and filamentous fungi be genetically engineered to include the above transporters.

In a specific embodiment, a host cell can be selected or engineered to be depleted in 1,6-mannosyl transferase activities, which would otherwise add mannose residues onto the N-glycan on a glycoprotein. For example, a glycoengineered *P. pastoris* yeast strain may be generated in which the typical yeast-type N-glycosylation is modified to instead produce fully sialylated human-like N-glycans. First, deletion of the yeast gene OCH1 eliminates the enzyme activity responsible for 'outer chain' glycosylation (Choi et al, Proc Natl Acad Sci US; 100:5022-7 (2003)). A mannosidase I (MNSI) gene and GlcNAc transferase I (GnTI) gene may then be engineered into the strain and properly localized to the secretory pathway to efficiently generate mammalian hybrid-type N-glycans (Choi et al, 2003). In a further step, a mannosidase II (MNSII) gene and GlcNAc transferase II (GnTII) genes may then be engineered into the strain and properly localized to the secretory pathway to efficiently generate mammalian complex-type N-glycans (Hamilton et al, Science; 301:1244-6. (2003)). Furthermore, by engineering into this strain enzymes to generate a pool of UDP-galactose, appropriate Golgi membrane transporters and a gene encoding galactosyltransferase (GalT), a yeast strain can be generated that is capable of transferring a complex-type human N-glycan with terminal β-1,4-galactose (Bobrowicz et al., Glycobiology; 14:757-66 (2004)). Finally, by introducing the enzymes required for in vivo synthesis and transfer of sialic acid (Hamilton et al, Science, 313(5792):1441-3 (2006)), sialylated glycans can be obtained. The disclosure of each of the references cited above is hereby incorporated herein by reference. Where no N-glycosylation is present on the recombinant protein, it is not necessary to engineer the lower eukaryotic host cells' glycosylation machinery in this manner. Moreover, one of skill in the art can add and/or eliminate one or more N-glycosylation sites from the sequence encoding the recombinant glycoprotein. In such embodiments, the glycoprotein compositions of the present invention comprise a predominantly mammalian-like N-glycan or human-like N-glycan. The lower eukaryotic host cells of the present invention may optionally be engineered to produce glycoproteins having a predominantly human-like N-glycan. In preferred embodiments, the host cells produce glycoproteins having a predominant N-glycan selected from: Man5GlcNAc2; GlcNAcMan5GlcNAc2; GalGlcNAcMan5GlcNAc2; SiaGalGlcNAcMan5GlcNAc2; Man3GlcNAc2; GlcNAcMan3GlcNAc2; GalGlcNAcMan3GlcNAc2; SiaGalGlcNAcMan3GlcNAc2; GlcNAc2Man3GlcNAc2; GalGlcNAc2Man3GlcNAc2; Gal2GlcNAc2Man3GlcNAc2; SiaGal2GlcNAc2Man3GlcNAc2; or Sia2Gal2GlcNAc2Man3GlcNAc2. In a preferred embodiment, the predominant N-glycan comprises at least 30 mole percent, preferably at least 40 mole percent and more preferably at least 50 mole percent of the N-glycans stated above present on the glycoprotein in the composition.

Therefore, the methods disclose herein can use any host cell that has been genetically modified to produce glycoproteins wherein the predominant N-glycan is selected from the group consisting of complex N-glycans, hybrid N-glycans, and high mannose N-glycans wherein complex N-glycans may be selected from the group consisting of $GlcNAc_{(2-4)}Man_3GlcNAc_2$, $Gal_{(1-4)}GlcNAc_{(2-4)}Man_3GlcNAc_2$, and $NANA_{(1-4)}Gal_{(1-4)}GlcNAc_{(2-4)}Man_3GlcNAc_2$; hybrid N-glycans maybe selected from the group consisting of $GlcNAcMan_3GlcNAc_2$; $GalGlcNAcMan_3GlcNAc_2$; $NANAGalGlcNAcMan_3GlcNAc_2$ $GlcNAcMan_5GlcNAc_2$, $GalGlcNAcMan_5GlcNAc_2$, and $NANAGalGlcNAcMan_5GlcNAc_2$; and high Mannose N-glycans maybe selected from the group consisting of $Man_5GlcNAc_2$, $Man_6GlcNAc_2$, $Man_7GlcNAc_2$, $Man_8GlcNAc_2$, and $Man_9GlcNAc_2$. Further included are glycoproteins having N-glycans consisting of the N-glycan structure $Man_3GlcNAc_2$, for example, as shown in U.S. Published Application No. 20050170452.

The present invention, as that of the previously described N-glycosylation in lower eukaryotic host organisms, can be used for commercial scale production of recombinant glycoprotein compositions. In addition, the methods and materials of the present invention can be used for veterinary application as well.

As described herein, there are many attributes of the methods and materials of the present invention which provide unobvious advantages for the disclosed recombinantly produced glycoproteins, host cells, nucleic acids, vectors and expression processes over prior known expression processes.

Most notably, the present invention can be used to improve the current state of the art of recombinantly produced glycoprotein therapeutic products. A glycosylated protein produced according to the present invention can be expected to be less immunogenic to humans than glycoproteins produced from wild type yeast or other lower eukaryotic host cells. The glycosylation of recombinant glycoproteins produced according to the present invention can be expected to be much more uniform than glycosylation of glycoprotein compositions produced from mammalian cells. Furthermore, as stated above, humanizing the O-glycans can enhance the bioactivity of therapeutic proteins by improving pharmacokinetic properties, hence, facilitating better control over in vivo drug activity.

Unless otherwise defined herein, scientific and technical terms and phrases used in connection with the present invention shall have the meanings that are commonly understood by those of ordinary skill in the art. Further, unless otherwise required by context, singular terms shall include the plural and plural terms shall include the singular. Generally, nomenclatures used in connection with, and techniques of biochemistry, enzymology, molecular and cellular biology, microbiology, genetics and protein and nucleic acid chemistry and hybridization are those well known and commonly used in the art. The methods and techniques of the present invention are generally performed according to conventional methods well known in the art and as described in various general and more specific references that are cited and discussed throughout the present specification unless otherwise indicated. See, e.g., Sambrook et al. *Molecular Cloning: A Laboratory Manual*, 2d ed., Cold Spring Harbor Laboratory Press, Cold Spring Harbor, N.Y. (1989); Ausubel et al., *Current Protocols in Molecular Biology*, Greene Publishing Associates (1992, and Supplements to 2002); Harlow and Lane, *Antibodies: A Laboratory Manual*, Cold Spring Harbor Laboratory Press, Cold Spring Harbor, N.Y. (1990); Taylor and Drickamer, *Introduction to Glycobiology*, Oxford Univ. Press (2003); *Worthington Enzyme Manual*, Worthington Biochemical Corp., Freehold, N.J.; *Handbook of Biochemistry: Section A Proteins*, Vol I, CRC Press (1976); *Handbook of Biochemistry: Section A Proteins*, Vol II, CRC Press (1976); *Essentials of Glycobiology*, Cold Spring Harbor Laboratory Press (1999).

All publications, patents and other references mentioned herein are hereby incorporated by reference in their entireties.

The following terms, unless otherwise indicated, shall be understood to have the following meanings:

As used herein, the terms "O-glycan" and "O-glycoform" are used interchangeably and refer to an O-linked oligosaccharide, e.g., a glycan that is attached to a peptide chain via the hydroxyl group of either a serine or threonine residue. In fungal cells, native O-glycosylation occurs through attachment of a first mannosyl residue transferred from a dolichol monophosphate mannose (Dol-P-Man) to the protein in the endoplasmic reticulum, and additional mannosyl residues may be attached via transfer from GDP-Man in the Golgi apparatus. Higher eukaryotic cells, such as human or mammalian cells, undergo O-glycosylation through covalent attachment of N-acetyl-galactosamine (GalNAc) to the serine or threonine residue, to form mucin-type glycans. This is in addition to α-dystroglycan-type glycans described above.

As used herein, the terms "N-glycan" and "N glycoform" are used interchangeably and refer to an N-linked oligosaccharide, e.g., one that is attached by an asparagine-N-acetylglucosamine linkage to an asparagine residue of a polypeptide. N-linked glycoproteins contain an N-acetylglucosamine residue linked to the amide nitrogen of an asparagine residue in the protein. The predominant sugars found on glycoproteins are glucose, galactose, mannose, fucose, N-acetylgalactosamine (GalNAc), N-acetylglucosamine (GlcNAc) and sialic acid (e.g., N-acetyl-neuraminic acid (NANA)). The processing of the sugar groups occurs cotranslationally in the lumen of the ER and continues in the Golgi apparatus for N-linked glycoproteins.

N-glycans have a common pentasaccharide core of $Man_3GlcNAc_2$ ("Man" refers to mannose; "Glc" refers to glucose; and "NAc" refers to N-acetyl; GlcNAc refers to N-acetylglucosamine). N-glycans differ with respect to the number of branches (antennae) comprising peripheral sugars (e.g., GlcNAc, galactose, fucose and sialic acid) that are added to the $Man_3GlcNAc_2$ ("Man3") core structure which is also referred to as the "trimannose core", the "pentasaccharide core" or the "paucimannose core". N-glycans are classified according to their branched constituents (e.g., high mannose, complex or hybrid). A "high mannose" type N-glycan has five or more mannose residues. A "complex" type N-glycan typically has at least one GlcNAc attached to the 1,3 mannose arm and at least one GlcNAc attached to the 1,6 mannose arm of a "trimannose" core. Complex N-glycans may also have galactose ("Gal") or N-acetylgalactosamine ("GalNAc") residues that are optionally modified with sialic acid or derivatives (e.g., "NANA" or "NeuAc", where "Neu" refers to neuraminic acid and "Ac" refers to acetyl). Complex N-glycans may also have intrachain substitutions comprising "bisecting" GlcNAc and core fucose ("Fuc"). Complex N-glycans may also have multiple antennae on the "trimannose core," often referred to as "multiple antennary glycans." A "hybrid" N-glycan has at least one GlcNAc on the terminal of the 1,3 mannose arm of the trimannose core and zero or more mannoses on the 1,6 mannose arm of the trimannose core. The various N-glycans are also referred to as "glycoforms."

As used herein, the term "human-like O-glycosylation" will be understood to mean that fungal-specific phosphorylated and beta-linked mannose structures are reduced or eliminated, resulting in reduction or elimination of charge and beta-mannose structures, or that the predominant O-glycan species present on a glycoprotein or in a composition of glycoprotein comprises a glycan which capped with a terminal residue selected from GlcNAc; Gal or Sia. In this manner, the recombinant glycoprotein bearing predominantly human-like O-glycosylation may be recognized by a human or mammalian cell as if it were a natively produced glycoprotein, resulting in improved therapeutic properties of the recombinant glycoprotein.

Abbreviations used herein are of common usage in the art, see, e.g., abbreviations of sugars, above. Other common abbreviations include "PNGase", or "glycanase" or "glucosidase" which all refer to peptide N-glycosidase F (EC 3.2.2.18).

An "isolated" or "substantially pure" nucleic acid or polynucleotide (e.g., an RNA, DNA, various derivatives thereof (e.g., cDNA) or a mixed polymer) is one which is substantially separated from other cellular components that naturally accompany the native polynucleotide in its natural host cell, e.g., ribosomes, polymerases and genomic sequences with which it is naturally associated. The term embraces a nucleic acid or polynucleotide that (1) has been removed from its naturally occurring environment, (2) is not associated with all or a portion of a polynucleotide in which the "isolated polynucleotide" is found in nature, (3) is operatively linked to a polynucleotide which it is not linked to in nature, or (4) does not occur in nature. The term "isolated" or "substantially pure" also can be used in reference to recombinant or cloned DNA isolates, chemically synthesized polynucleotide analogs, or polynucleotide analogs that are biologically synthesized by heterologous systems.

However, "isolated" does not necessarily require that the nucleic acid or polynucleotide so described has itself been physically removed from its native environment. For instance, an endogenous nucleic acid sequence in the genome of an organism is deemed "isolated" herein if a heterologous sequence is placed adjacent to the endogenous nucleic acid sequence, such that the expression of this endogenous nucleic acid sequence is altered. In this context, a heterologous sequence is a sequence that is not naturally adjacent to the endogenous nucleic acid sequence, whether or not the heterologous sequence is itself endogenous (originating from the same host cell or progeny thereof) or exogenous (originating from a different host cell or progeny thereof). By way of example, a promoter sequence can be substituted (e.g., by homologous recombination) for the native promoter of a gene in the genome of a host cell, such that this gene has an altered expression pattern. This gene would now become "isolated" because it is separated from at least some of the sequences that naturally flank it.

A nucleic acid is also considered "isolated" if it contains any modifications that do not naturally occur to the corresponding nucleic acid in a genome. For instance, an endogenous coding sequence is considered "isolated" if it contains an insertion, deletion or a point mutation introduced artificially, e.g., by human intervention. An "isolated nucleic acid" also includes a nucleic acid integrated into a host cell chromosome at a heterologous site and a nucleic acid construct present as an episome. Moreover, an "isolated nucleic acid" can be substantially free of other cellular material, or substantially free of culture medium when produced by recombinant techniques, or substantially free of chemical precursors or other chemicals when chemically synthesized.

The term "vector" as used herein is intended to refer to a nucleic acid molecule capable of transporting another nucleic acid to which it has been linked. One type of vector is a "plasmid", which refers to a circular double stranded DNA loop into which additional DNA segments may be ligated. Other vectors include cosmids, bacterial artificial chromosomes (BAC) and yeast artificial chromosomes (YAC). Another type of vector is a viral vector, wherein additional DNA segments may be ligated into the viral genome (discussed in more detail below). Certain vectors are capable of autonomous replication in a host cell into which they are introduced (e.g., vectors having an origin of replication which functions in the host cell). Other vectors can be integrated into the genome of a host cell upon introduction into the host cell, and are thereby replicated along with the host genome. Moreover, certain preferred vectors are capable of directing the expression of genes to which they are operatively linked. Such vectors are referred to herein as "recombinant expression vectors" (or simply, "expression vectors").

As used herein, the term "sequence of interest" or "gene of interest" refers to a nucleic acid sequence, typically encoding a protein, that is not normally produced in the host cell. The methods disclosed herein allow efficient expression of one or more sequences of interest or genes of interest stably integrated into a host cell genome. Non-limiting examples of sequences of interest include sequences encoding one or more polypeptides having an enzymatic activity, e.g., an enzyme which affects N-glycan synthesis in a host such as mannosyltransferases, N-acetyl-glucosaminyltransferases, UDP-N-acetylglucosamine transporters, galactosyltransferases, UDP-N-acetyl-galactosyltransferase, sialyltransferases and fucosyltransferases. The protein so produced is referred to as a "recombinant" protein.

The term "derived" means the sequence or protein is the same as that from which it was derived ("the reference sequence or protein"), or it has minor differences which do not negatively impact the function thereof as compared to the reference sequence or protein.

The term "marker sequence" or "marker gene" refers to a nucleic acid sequence capable of expressing an activity that allows either positive or negative selection for the presence or absence of the sequence within a host cell. For example, the P. pastoris URA5 gene is a marker gene because its presence can be selected for by the ability of cells containing the gene to grow in the absence of uracil. Its presence can also be selected against by the inability of cells containing the gene to grow in the presence of 5-FOA. Marker sequences or genes do not necessarily need to display both positive and negative selectability. Non-limiting examples of marker sequences or genes from *P. pastoris* include ADE1, ARG4, HIS4 and URA3. For antibiotic resistance marker genes, kanamycin, neomycin, geneticin (or G418), paromomycin and hygromycin resistance genes are commonly used to allow for growth in the presence of these antibiotics.

"Operatively linked" expression control sequences refers to a linkage in which the expression control sequence is contiguous with the gene of interest to control the gene of interest, as well as expression control sequences that act in trans or at a distance to control the gene of interest.

The term "expression control sequence" or "regulatory sequences" are used interchangeably and as used herein refer to polynucleotide sequences which are necessary to affect the expression of coding sequences to which they are operatively linked. Expression control sequences are sequences which control the transcription, post-transcriptional events and translation of nucleic acid sequences. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (e.g., ribosome binding sites); sequences that enhance protein stability; and when desired, sequences that enhance protein secretion. The nature of such control sequences differs depending upon the host organism; in prokaryotes, such control sequences generally include promoter, ribosomal binding site, and transcription termination sequence. The term "control sequences" is intended to include, at a minimum, all components whose presence is essential for expression, and can also include additional components whose presence is advantageous, for example, leader sequences and fusion partner sequences.

The term "recombinant host cell" ("expression host cell", "expression host system", "expression system" or simply "host cell"), as used herein, is intended to refer to a cell into which a recombinant vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. A recombinant host cell may be an isolated cell or cell line grown in culture or may be a cell which resides in a living tissue or organism.

The term "eukaryotic" refers to a nucleated cell or organism, and includes insect cells, plant cells, mammalian cells, animal cells and lower eukaryotic cells.

The term "lower eukaryotic cells" includes yeast, fungi, collar-flagellates, microsporidia, alveolates (e.g., dinoflagellates), stramenopiles (e.g, brown algae, protozoa), rhodophyta (e.g., red algae), plants (e.g., green algae, plant cells, moss) and other protists. Yeast and filamentous fungi include, but are not limited to: *Pichia pastoris, Pichia finlandica, Pichia trehalophila, Pichia koclamae, Pichia membranaefaciens, Pichia minuta (Ogataea minuta, Pichia lindneri), Pichia opuntiae, Pichia thermotolerans, Pichia salictaria, Pichia guercuum, Pichia pijperi, Pichia stiptis, Pichia methanolica, Pichia* sp., *Saccharomyces cerevisiae, Saccharomyces* sp., *Hansenula polymorpha, Kluyveromyces* sp., *Kluyveromyces lactic, Candida albicans, Aspergillus nidulans, Aspergillus niger, Aspergillus oryzae, Trichoderma reesei, Chrysosporium lucknowense, Fusarium* sp., *Fusarium gramineum, Fusarium venenatum, Physcomitrella patens* and *Neurospora crassa*.

The term "peptide" as used herein refers to a short polypeptide, e.g., one that is typically less than about 50 amino acids long and more typically less than about 30 amino acids long. The term as used herein encompasses analogs and mimetics that mimic structural and thus biological function.

The term "polypeptide" encompasses both naturally-occurring and non-naturally-occurring proteins, and fragments, mutants, derivatives and analogs thereof. A polypeptide, may be monomeric or polymeric. Further, a polypeptide may comprise a number of different domains each of which has one or more distinct activities.

The term "isolated protein" or "isolated polypeptide" is a protein or polypeptide that by virtue of its origin or source of derivation (1) is not associated with naturally associated components that accompany it in its native state, (2) exists in a purity not found in nature, where purity can be adjudged with respect to the presence of other cellular material (e.g., is free of other proteins from the same species), (3) is expressed by a cell from a different species, or (4) does not occur in nature (e.g., it is a fragment of a polypeptide found in nature or it includes amino acid analogs or derivatives not found in nature or linkages other than standard peptide bonds). Thus, a polypeptide that is chemically synthesized or synthesized in a cellular system different from the cell from which it naturally originates will be "isolated" from its naturally associated components. A polypeptide or protein may also be rendered substantially free of naturally associated components by isolation, using protein purification techniques well known in the art. As thus defined, "isolated" does not necessarily require that the protein, polypeptide, peptide or oligopeptide so described has been physically removed from its native environment.

As used herein, the term "predominantly" or variations such as "the predominant" or "which is predominant" will, depending on the context used, be understood to mean the glycan species that has the highest mole percent (%) of total O-glycans or N-glycans after the glycoprotein has been treated with enzymes and released glycans analyzed by mass spectroscopy, for example, MALDI-TOF MS. In other words, the phrase "predominantly" is defined as an individual entity, such that a specific "predominant" glycoform is present in greater mole percent than any other individual entity. For example, if a composition consists of species A in 40 mole percent, species B in 35 mole percent and species C in 25 mole percent, the composition comprises predominantly species A.

Unless otherwise defined, all technical and scientific terms used herein have the same meaning as commonly understood by one of ordinary skill in the art to which this invention pertains. Exemplary methods and materials are described below, although methods and materials similar or equivalent to those described herein can also be used in the practice of the present invention and will be apparent to those of skill in the art. All publications and other references mentioned herein are incorporated by reference in their entirety. In case of conflict, the present specification, including definitions, will control. The materials, methods, and examples are illustrative only and not intended to be limiting in any manner.

The following examples illustrate the operation of the invention with respect to certain preferred embodiments, and are in no way limiting of the scope of the invention described in the specification and claims. As will be readily apparent to the skilled artisan, having read the specification, numerous modifications to the methods and materials described herein are possible without deviating from the scope of the invention described and claimed herein.

EXAMPLES

In the following examples, recombinant glycoproteins are expressed in host cells of the species *Pichia pastoris*. The host cells have been genetically engineered to produce glycoproteins with human-like O-glycosylation, as well as human-like N-glycosylation. These examples demonstrate the invention with respect to specific preferred embodiments of the invention, and are not limiting in any manner.

As will be apparent to the skilled practitioner, having read the disclosure and examples herein, numerous modifications, substitutions, adaptations and improvements within the skill of the art can be made without deviating from the scope of the specification and the appended claims. Accordingly, the examples are non-limiting and, with appropriate modifications, the methods and materials described herein may be used for the practice of the invention in other lower eukaryotic organisms.

Example 1

Cloning of ER and Golgi Targeting Sequences

Most of the glycosyltransferases in the ER and Golgi of mammals and yeast are type II membrane proteins (Gleeson, P. A. Targeting of proteins to the Golgi apparatus. Histochem. Cell. Biol. 109, 517-532 (1998)) that consist of a short amino-terminal cytoplasmic tail followed by a transmembrane domain [TMD], a short stem region and a large carboxy-terminal catalytic domain in the lumen of the ER or the Golgi. Another group of glycosyltransferases represented by the Pmts (protein O-mannosyltransferases; Strahl-Bolsinger et al., Protein O-mannosylation, Biochim Biophys Acta 1426: 297 (1999); Tanner et al., U.S. Pat. No. 5,714,377) contain multiple membrane-spanning domains. Because we wanted to test a large variety of targeting sequences, we amplified DNA fragments encoding membrane targeting regions of varying length of ER and Golgi residing membrane proteins of *S. cerevisiae, P. pastoris* and *K. lactis*. For type II membrane proteins, the shortest fragments (designated '-s') contained only the cytoplasmic tail and the TMD. The medium length fragments (designated '-m') also contained parts of, or the entire stem region. The longest fragments (designated '-l') contained the entire stem region and also parts of the catalytic domain. A detailed description of targeting domains (TD) from type II membrane proteins can be found in Gerngross et al., U.S. Pat. No. 7,449,308 (e.g., TABLE 5) and Choi et al., 2003 *PNAS* 100:5022. For other integral membrane proteins, we took either the shortest membrane spanning region (designated '-s') or a region encompassing multiple membrane spanning domains (designated '-m').

In the present example, the ER targeting domains utilized were fragments of the *S. cerevisiae* alpha-glucosidase 1 encoded by GLS1, the *S. cerevisiae* alpha 1,2-mannosidase encoded by MNS1, the *S. cerevisiae* nucleotide exchange factor SEC12 which cycles between the ER and Golgi, fragments from the *S. cerevisiae* and *P. pastoris* PMT1, 2, 3, 4, 5 and 6 that encode integral ER membrane spanning domains, and domains from the SNARE proteins encoded by BOS1, BET1, and SEC22 from *S. cerevisiae* and *P. pastoris*.

As targeting domains for the early or cis-Golgi we chose amino-terminal fragments of the *P. pastoris* Och1p, and of the proteins that make up the *S. cerevisiae* mannan polymerases M-Pol I and M-Pol II, namely Mnn9p, Van1p, Anp1p, Hoc1p, Mnn10p and Mnn11p. Targeting signals for the medial Golgi were derived from *S. cerevisiae* Kre2p, Ktr1p, Mnn2p, Mnn5p, and Yur1p, from *K. lactis* Gnt1p and from *P. pastoris* proteins with homology to Ktr1p, Ktr3p and Kre2p (unpublished results).

As targeting domains for the late Golgi we included amino-terminal regions of *S. cerevisiae* Mnn1p and Mnn6p. The complete list of targeting domains is given in Table 1, and DNA and protein sequences provided (SEQ IDs).

TABLE 1

ER/Golgi leaders fused to POMGnT1

| Leader# | Gene | Size [Nuc] |
|---|---|---|
| 1 | SeGLS1-s | 102 |
| 2 | ScMNS1-s | 90 |
| 3 | ScMNS1-m | 246 |
| 4 | ScSEC12-m | 309 |
| 5 | PpSEC12-s | 87 |
| 6 | PpOCH1-s | 150 |
| 7 | ScMNN9-s | 120 |
| 8 | SeVAN1-m | 294 |
| 9 | ScANP1-s | 180 |
| 10 | ScHOC1-s | 102 |
| 11 | ScMNN10-s | 219 |
| 12 | ScMNN11-s | 156 |
| 13 | ScKRE2-s | 174 |
| 14 | ScKRE2-l | 306 |
| 15 | PpKTR1-s | 216 |
| 16 | PpKTR3-s | 93 |
| 17 | PpKRE2-s | 93 |
| 18 | ScKTR1-s | 117 |
| 19 | ScKTR2-s | 120 |
| 20 | KlGNT1-s | 93 |
| 21 | ScMNN2-s | 108 |
| 22 | ScMNN2-m | 291 |
| 23 | ScMNN5-s | 105 |
| 24 | ScYUR1-s | 108 |
| 25 | ScMNN1-s | 126 |
| 26 | ScMNN6-s | 90 |
| 27 | ScPMT1-s | 213 |
| 28 | ScPMT2-s | 237 |
| 29 | ScPMT3-s | 213 |
| 30 | ScPMT4-s | 357 |
| 31 | ScPMT5-s | 195 |
| 32 | ScPMT6-s | 543 |
| 33 | ScPMT1-m | 330 |
| 34 | ScPMT2-m | 360 |
| 35 | ScPMT3-m | 330 |
| 36 | ScPMT4-m | 405 |
| 37 | ScPMT5-m | 255 |
| 38 | ScPMT6-m | 585 |
| 39 | PpPMT1-s | 255 |
| 40 | PpPMT2-s | 594 |
| 41 | PpPMT4-s | 156 |
| 42 | PpPMT5-s | 120 |
| 43 | PpPMT6-s | 207 |
| 44 | PpPMT1-m | 390 |
| 45 | PpPMT2-m | 630 |
| 46 | PpPMT4-m | 195 |
| 47 | PpPMT5-m | 240 |
| 48 | PpPMT6-m | 330 |
| 49 | ScBOS1-s | 90 |
| 50 | ScBET1-s | 99 |
| 51 | ScSEC22-s | 105 |
| 52 | PpBOS1-s | 87 |
| 53 | PpBET1-s | 102 |
| 54 | PpSEC22-s | 105 |

Sequences of ER/Golgi Transmembrane Domains (Leaders) DNA Followed by Amino Acid Sequences ScGLS1-s
[SEQ ID NO: 1]
ATGCTTATTTCAAAATCTAAGATGTTTAAAACATTTTGGATACTAACCA
GCATAGTTCTCCTGGCATCTGCCACCGTTGATATTAGTAAACTACAAGA
ATTCGGGCGCGCC

[SEQ ID NO: 2]
MLISKSKMFKTFWILTSIVLLASATVDISKLQEFGRA

ScMNS1-s
[SEQ ID NO: 3]
ATGAAGAACTCTGTCGGTATTTCAATTGCAACCATTGTTGCTATCATAG
CAGCTATATACTATGTGCCATGGTACGAACACTTTGAGAGAGGGCGCGC
C

[SEQ ID NO: 4]
MKNSVGISIATIVAIIAAIYYVPWYEHFERGRA

SeMNS1-m
[SEQ ID NO: 5]
ATGAAGAACTCTGTCGGTATTTCAATTGCAACCATTGTTGCTATCATAG
CAGCTATATACTATGTGCCATGGTACGAACACTTTGAGAGAAAGTCACC
GGGGGCCGGAGAAATGAGAGATCGGATTGAAAGCATGTTCTTGGAATCG
TGGAGAGACTATTCCAAGCATGGCTGGGGATACGATGTGTATGGACCTA
TTGAGCACACTTCCCATAATATGCCTCGTGGCAACCAGCCGTTAGGCTG
GGGGCGCGCC

[SEQ ID NO: 6]
MKNSVGISIATIVAIIAAIYYVPWYEHFERKSPGAGEMRDRIESMFLES
WRDYSKHGWGYDVYGPIEHTSHNMPRGNQPLGWGRA

ScSEC12-m
[SEQ ID NO: 7]
ATGAACACTATCCACATAATAAAATTACCGCTTAACTACGCCAACTACA
CCTCAATGAAACAAAAAATCTCTAAATTTTTTCACCAACTTCATCCTTAT
TGTGCTGCTTTCTTACATTTTACAGTTCTCCTATAAGCACAATTTGCAT
TCCATGCTTTTCAATTACGCGAAGGACAATTTTCTAACGAAAAGAGACA
CCATCTCTTCGCCCTACGTAGTTGATGAAGACTTACATCAAACAACTTT
GTTTGGCAACCACGGTACAAAAACATCTGTACCTAGCGTAGATTCCATA
AAAGTGCATGGCGTGGGGCGCGCC

[SEQ ID NO: 8]
MNTIHIIKLPLNYANYTSMKQKISKFFTNFILIVLLSYILQFSYKHNLH
SMLFNYAKDNFLTKRDTISSPYVVDEDLHQTTLFGNHGTKTSVPSVDSI
KVHGVGRA

PpSEC12-s
[SEQ ID NO: 9]
ATGCCCAGAAAAATATTTAACTACTTCATTTTGACTGTATTCATGGCAA
TTCTTGCTATTGTTTTACAATGGTCTATAGAGAATGGACATGGGCGCGC
C

[SEQ ID NO: 10]
MPRKIFNYFILTVFMAILAIVLQWSIENGHGRA

PpOCH1-s
[SEQ ID NO: 11]
ATGGCGAAGGCAGATGGCAGTTTGCTCTACTATAATCCTCACAATCCAC
CCAGAAGGTATTACTTCTACATGGCTATATTCGCCGTTTCTGTCATTTG
CGTTTTGTACGGACCCTCACAACAATTATCATCTCCAAAAATAGACTAT
GATGGGCGCGCC

[SEQ ID NO: 12]
MAKADGSLLYYNPHNPPRRYYFYMAIFAVSVICVLYGPSQQLSSPKIDY
DGRA

ScMNN9-s
[SEQ ID NO: 13]
ATGTCACTTTCTCTTGTATCGTACCGCCTAAGAAAGAACCCGTGGGTTA
ACATTTTTCTACCTGTTTTGGCCATATTTCTAATATATATAATTTTTTT
CCAGAGAGATCAATCTCTGTTGGGCGCGCC

[SEQ ID NO: 14]
MSLSLVSYRLRKNPWVNIFLPVLAIFLIYIIFFQRDQSLLGRA

ScVAN1-m
[SEQ ID NO: 15]
ATGGGCATGTTTTTTAATTTAAGGTCAAATATAAAGAAGAAAGCCATGG
ACAATGGACTAAGCCTGCCCATTTCAAGGAACGGTAGCTCGAACAACAT
CAAGGACAAACGCTCAGAGCATAACTCCAACTCATTAAAGGGCAAATAC
AGGTACCAGCCGCGCTCCACACCGTCTAAATTCCAGCTTACGGTGAGTA
TCACATCTCTTATTATTATCGCCGTTCTGTCGTTATATCTCTTTATATC
ATTTCTCTCCGGAATGGGCATTGGTGTATCCACGCAAAATGGTAGGTCG
GGGCGCGCC

[SEQ ID NO: 16]
MGMFFNLRSNIKKKAMDNGLSLPISRNGSSNNIKDKRSEHNSNSLKGKY
RYQPRSTPSKFQLTVSITSLIIIAVLSLYLFISFLSGMGIGVSTQNGRS
GRA

ScANP1-s
[SEQ ID NO: 17]
ATGAAGTATAATAACAGAAAACTCTCGTTCAACCCTACCACAGTAAGTA
TCGCTGGAACGTTGCTTACGGTGTTCTTTCTCACAAGACTCGTGCTTTC
GTTCTTCTCGATATCGCTATTCCAGCTGGTAACTTTCCAAGGAATCTTC
AAGCCCTATGTTCCAGATTTTAAAAATACTCCCGGGCGCGCC

[SEQ ID NO: 18]
MKYNNRKLSFNPTTVSIAGTLLTVFFLTRLVLSFFSISLFQLVTFQGIF
KPYVPDFKNTPGRA

ScHOC-s
[SEQ ID NO: 19]
ATGGCCAAAACAACAAAAAGAGCCTCCAGTTTCAGGAGGTTGATGATAT
TCGCCATAATAGCCCTCATCTCATTAGCATTTGGAGTTAGATACCTATT
TCACGGGCGCGCC

[SEQ ID NO: 20]
MAKTTKRASSFRRLMIFAIIALISLAFGVRYLFHGRA

ScMNN10-s
[SEQ ID NO: 21]
ATGTCTAGTGTACCTTATAATTCCCAACTTCCTATATCCAACCATCTAG
AGTACGATGAAGATGAAAAGAAGAGCAGAGGCTCAAAACTAGGCCTGAA

```
ATATAAAATGATATACTGGAGGAAAACTTTATGCAGTTCGCTAGCGAGA

TGGAGAAAGCTAATACTATTAATATCTTTAGCTTTGTTTTTATTCATAT

GGATAAGCGATTCCACCATAAGCGGGCGCGCC
```

[SEQ ID NO: 22]
MSSVPYNSQLPISNHLEYDEDEKKSRGSKLGLKYKMIYWRKTLCSSLAR

WRKLILLISLALFLFIWISDSTISGRA

ScMNN11-s

[SEQ ID NO: 23]
```
ATGGCAATCAAACCAAGAACGAAGGGCAAAACGTACTCCTCAAGATCGG

TGGGTTCGCAGTGGTTCAACAGGCTTGGTTTCAAGCAGAACAAGTACGG

AACTTGTAAATTTTTGTCGATAATAACGGCCTTTGTTTTTATCCTCTAT

TTCTTCTCCGGGCGCGCC
```

[SEQ ID NO: 24]
MAIKPRTKGKTYSSRSVGSQWFNRLGFKQNKYGTCKFLSIITAFVFILY

FFSGRA

ScKRE2-s

[SEQ ID NO: 25]
```
ATGGCCCTCTTTCTCAGTAAGAGACTGTTGAGATTTACCGTCATTGCAG

GTGCGGTTATTGTTCTCCTCCTAACATTGAATTCCAACAGTAGAACTCA

GCAATATATTCCGAGTTCCATCTCCGCTGCATTTGATTTTACCTCAGGA

TCTATATCCCCTGAACAACAAGTCATCGGGCGCGCC
```

[SEQ ID NO: 26]
MALFLSKRLLRFTVIAGAVIVLLLTLNSNSRTQQYIPSSISAAFDFTSG

SISPEQQVIGRA

ScKRE2-l

[SEQ ID NO: 27]
```
ATGGCCCTCTTTCTCAGTAAGAGACTGTTGAGATTTACCGTCATTGCAG

GTGCGGTTATTGTTCTCCTCCTAACATTGAATTCCAACAGTAGAACTCA

GCAATATATTCCGAGTTCCATCTCCGCTGCATTTGATTTTACCTCAGGA

TCTATATCCCCTGAACAACAAGTCATCTCTGAGGAAAATGATGCTAAAA

AATTAGAGCAAAGTGCTCTGAATTCAGAGGCAAGCGAAGACTCCGAAGC

CATGGATGAAGAATCCAAGGCTCTGAAAGCTGCCGCTGAAAAGGCAGAT

GCCCCGATCGACGGGCGCGCC
```

[SEQ ID NO: 28]
MALFLSKRLLRFTVIAGAVIVLLLTLNSNSRTQQYIPSSISAAFDFTSG

SISPEQQVISEENDAKKLEQSALNSEASEDSEAMDEESKALKAAAEKAD

APIDGRA

PpKTR1-s

[SEQ ID NO: 29]
```
ATGGAATTAGTGCGCCTGGCCAATCTTGTCAACGTCAACCACCCTTTCG

AGCAAAGCAATATATATCGCGTTCCACTTTTCTTCCTTCTCTCAACTAC

CAGACCAGACAGGACAACGGTACAAATGGCAGGTGCAACTAGGATCAAT

TCACGAGTAGTTCGGTTTGCTATTTTCGCATCAATCCTGGTACTGTTAG

GATTCATCCTATCAAGAGGGGGGCGCGCC
```

[SEQ ID NO: 30]
MELVRLANLVNVNHPFEQSNIYRVPLFFLLSTTRPDRTTVQMAGATRIN

SRVVRFAIFASILVLLGFILSRGGRA

PpKTR3-s

[SEQ ID NO: 31]
```
ATGATGCGAGCAAGATTAAGCCTTGAACGAGTTAACTTGAGCTTTATTA

CGTCCGTATTTTTGGCTTCAGTTGCAGTTCTTTTCATCTCTTTGGGGCG

CGCC
```

[SEQ ID NO: 32]
MMRARLSLERVNLSFITSVFLASVAVLFISLGRA

PpKRE2-s

[SEQ ID NO: 33]
```
ATGGTACACATAGGGTTCAGAAGCTTGAAAGCGGTGTTCATTTTGGCCC

TTTCGTCATTGATTCTGTACGGGATTGTCACGACCTTTGACGGGGGCG

CGCC
```

[SEQ ID NO: 34]
MVHIGFRSLKAVFILALSSLILYGIVTTFDGGRA

ScKTR1-s

[SEQ ID NO: 35]
```
ATGGCGAAGATTATGATCCCAGCTAGCAAGCAGCCTGTTTACAAAAAAT

TAGGACTTCTTCTGGTCGCCGTGTTTACTGTGTATGTGTTCTTTCATGG

AGCTCAGTATGCGAGAGGCGGGCGCGCC
```

[SEQ ID NO: 36]
MAKIMIPASKQPVYKKLGLLLVAVFTVYVFFHGAQYARGGRA

ScKTR2-s

[SEQ ID NO: 37]
```
ATGCAAATCTGCAAGGTATTTCTTACACAGGTTAAAAAACTACTTTTTG

TTAGTCTTCTATTTTGCTTGATAGCTCAAACATGTTGGCTTGCACTTGT

ACCATATCAGAGACAGCTGAGCGGGCGCGCC
```

[SEQ ID NO: 38]
MQICKVFLTQVKKLLFVSLLFCLIAQTCWLALVPYQRQLSGRA

KlGNT1-s

[SEQ ID NO: 39]
```
ATGGCTTTGGATCTAGAAGGAAAATCAAGGCCATTTTGGTCGCTGCTT

CTGCTATGGTCTTTATTTCTCTACTTGGAACGTTTGGATCCGACGGGCG

CGCC
```

[SEQ ID NO: 40]
MAFGSRRKIKAILVAASAMVFISLLGTFGSDGRA

ScMNN2-s

[SEQ ID NO: 41]
```
ATGCTGCTTACCAAAAGGTTTTCAAAGCTGTTCAAGCTGACGTTCATAG

TTTTGATATTGTGCGGGCTGTTCGTCATTACAAACAAATACATGGATGA

GAACACGTCGGGGCGCGCC
```

[SEQ ID NO: 42]
MLLTKRFSKLFKLTFIVLILCGLFVITNKYMDENTSGRA

ScMNN2-m

[SEQ ID NO: 43]
```
ATGCTGCTTACCAAAAGGTTTTCAAAGCTGTTCAAGCTGACGTTCATAG

TTTTGATATTGTGCGGGCTGTTCGTCATTACAAACAAATACATGGATGA

GAACACGTCGGTCAAGGAGTACAAGGAGTACTTAGACAGATATGTCCAG

AGTTACTCCAATAAGTATTCATCTTCCTCAGACGCCGCCAGCGCTGACG
```

-continued

ATTCAACCCCATTGAGGGACAATGATGAGGCAGGCAATGAAAAGTTGAA
AAGCTTCTACAACAACGTTTTCAACTTTCTAATGGTTGATTCGCCCGGG
CGCGCC

[SEQ ID NO: 44]
MLLTKRFSKLFKLTFIVLILCGLFVITNKYMDENTSVKEYKEYLDRYVQ
SYSNKYSSSSDAASADDSTPLRDNDEAGNEKLKSFYNNVFNFLMVDSPG
RA

ScMNN5-s
[SEQ ID NO: 45]
ATGCTGATTAGGTTAAAGAAGAGAAAAATCCTGCAGGTCATCGTGAGCG
CAGTAGTGCTAATTTTATTTTTTTGTTCTGTGCATAATGATGTGTCTTC
TAGTTGGGGGCGCGCC

[SEQ ID NO: 46]
MLIRLKKRKILQVIVSAVVLILFFCSVHNDVSSSWGRA

ScYUR1-s
[SEQ ID NO: 47]
ATGGCAAAAGGAGGCTCGCTATACATCGTTGGCATATTCTTACCAATAT
GGACCTTTATGATCTATATTTTTGGCAAAGAGTTATTCCTCATACGAAA
ATACCAAAAGGGGCGCGCC

[SEQ ID NO: 48]
MAKGGSLYIVGIFLPIWTFMIYIFGKELFLIRKYQKGRA

ScMNN1-s
[SEQ ID NO: 49]
ATGTTGGCACTCCGGAGATTTATATTAAACCAAAGGTCTTTGAGATCGT
GTACCATACCGATTCTAGTCGGAGCCTTGATCATTATTCTCGTGCTATT
CCAACTAGTTACCCACCGAAATGATGCGGGGCGCGCC

[SEQ ID NO: 50]
MLALRRFILNQRSLRSCTIPILVGALIIILVLFQLVTHRNDAGRA

ScMNN6-s
[SEQ ID NO: 51]
ATGCACGTACTGCTGAGCAAAAAAATAGCACGCTTTCTGTTGATTTCGT
TTGTTTTCGTGCTTGCGCTAATGGTGACAATAAATCATCCAGGGCGCGC
C

[SEQ ID NO: 52]
MHVLLSKKIARFLLISFVFVLALMVTINHPGR

ScPMT1-s
[SEQ ID NO: 53]
ATGTCGGAAGAGAAAACGTACAAACGTGTAGAGCAGGATGATCCCGTGC
CCGAACTGGATATCAAGCAGGGCCCCGTAAGACCCTTTATTGTTACCGA
TCCGAGTGCCGAATTGGCCTCGTTACGAACCATGGTCACTCTTAAAGAG
AAGCTGTTAGTGGCCTGTCTTGCTGTCTTTACAGCGGTCATTAGATTGC
ATGGCTTGGCATGGCCTGGGCGCGCC

[SEQ ID NO: 54]
MSEEKTYKRVEQDDPVPELDIKQGPVRPFIVTDPSAELASLRTMVTLKE
KLLVACLAVFTAVIRLHGLAWPGRA

ScPMT2-s
[SEQ ID NO: 55]
ATGTCCTCGTCTTCGTCTACCGGGTACAGCAAAAACAATGCCGCCCACA
ATTAGCAAGAGAATACACTGAGACAAAGAGAATCGTCTTCCATCAGCGT

-continued

CAGTGAGGAACTTTCGAGCGCTGATGAGAGAGACGCGGAAGATTTCTCG
AAGGAAAAGCCCGCTGCACAAAGCTCACTGTTACGCCTGGAATCCGTTG
TAATGCCGGTGATCTTTACTGCATTGGCGTTGTTTACCAGGGGGCGCGC
C

[SEQ ID NO: 56]
MSSSSSTGYSKNNAAHIKQENTLRQRESSSISVSEELSSADERDAEDFS
KEKPAAQSSLLRLESVVMPVIFTALALFTRGRA

ScPMT3-s
[SEQ ID NO: 57]
ATGCCGTACAGAGTGGCGACGGGCTACAGTGAAAAAAGTACTGACGATG
ATTTGATATGGAGAACGCCAATAGTAAAAGAGGAACTCGAGGATGCTGA
CAACTTTTTAAAGGATGATGCCGAGTTGTATGATAAAGTCAAGAACGAG
AGTGCAGTATCACACCTGGATACCATAGTTATGCCGATCATTTTCACGG
TACTGGGCATGTTCACTGGGCGCGCC

[SEQ ID NO: 58]
MPYRVATGYSEKSTDDDLIWRTPIVKEELEDADNFLKDDAELYDKVKNE
SAVSHLDTIVMPIIFTVLGMFTGRA

ScPMT4-s
[SEQ ID NO: 59]
ATGTCTGTGCCCAAAAAACGTAACCATGGGAAGTTACCACCTTCCACTA
AGGACGTAGACGATCCTTCGTTGAAGTACACGAAGGCCGCGCCTAAATG
TGAACAAGTTGCTGAACATTGGCTCTTGCAGCCACTACCGGAACCGGAA
TCACGTTATAGCTTTTGGGTAACAATTGTTACCTTATTAGCGTTTGCTG
CTAGATTTTATAAGATCTGGTATCCAAAAGAAGTTGTTTTTGATGAGGT
ACATTTCGGGAAATTTGCATCGTATTACTTAGAAAGGTCTTATTTCTTT
GACGTTCATCCCCCTTTTGCTAAGATGATGATTGCCTTCATTGGTTGGT
TATGTGGCTATGATGGGCGCGCC

[SEQ ID NO: 60]
MSVPKKRNTIGKLPPSTKDVDDPSLKYTKAAPKCEQVAEHWLLQPLPEP
ESRYSFWVTIVTLLAFAARFYKIWYPKEVVFDEVHFGKFASYYLERSYF
FDVHPPFAKMMIAFIGWLCGYDGRA

ScPMT5-s
[SEQ ID NO: 61]
ATGAATAAAGAGCATTTGCTGAAGGTGGATCCCATCCCCGATGTGACTA
TTAAACGCGGCCCTTTGAGGTCTTTTCTCATAACAAAACCCTGTGATAA
TTTGAGTTCATTACGAACAGTTACTTCATCTAAGGAAAAGCTTCTAGTT
GGCTGTTTGCTGATATTTACTGCCATCGTAAGGCTACACAATATCTCCG
GGCGCGCC

[SEQ ID NO: 62]
MNKEHLLKVDPIPDVTIKRGPLRSFLITKPCDNLSSLRTVTSSKEKLLV
GCLLIFTAIVRLHNISGRA

ScPMT6-s
[SEQ ID NO: 63]
ATGAGTAAAGCCAAGGGAACGGGATTTTCATCAATTGATACTGAAGATG
AAAACTTACGCGAACGTTATGTTAATCAACCAAAAGCTAATGCCTCCGA
TATTCAAGATGAACAATTAGATTGCTTTGAGCAACTAGAAGAAAACAT
AGGACAAAAAAAAATGAAGAATACACTGCGTTGAAAATTTTAAGGGATG

TCATAGGTCCCCTTTTATTAACTATAACTTCGTTTTATCTAAGATTCCA
GACATATAATCAGAACAATTATGTTGTCTGGGATGAGGCTCATTTTGGG
AAATTCGGATCATACTACATCAAACATGAGTACTACCACGATGTCCACC
CTCCACTTGGTAAAATGCTTATTGCATTGAGCGAATGGATGGCAGGATT
TGACGGTCAATTTGACTTTTCCTCTAATAATGCATATCCGGAAAACGTA
AACTTTAAACTAATGAGACAATTTAATGCCACATTTGGAGCTCTATGTA
CACCAGTAGCTTTCTTTACAGCCAAATGGATGGGGTTCAATTATTTTAC
TGTTGGGCGCGCC

[SEQ ID NO: 64]
MSKAKGTGFSSIDTEDENLRERYVNQPKANASDIQDEQLDCFEQLEEKH
RTKKNEEYTALKILRDVIGPLLLTITSFYLRFQHMQNNYVVWDEAHFGK
FGSYYIKHEYYHDVHPPLGKMLIALSEWMAGFDGQFDFSSNNAYPENVN
FKLMRQFNATFGALCTPVAFFTAKWMGFNYFTVGRA

ScPMT1-m
[SEQ ID NO: 65]
ATGTCGGAAGAGAAAACGTACAAACGTGTAGAGCAGGATGATCCCGTGC
CCGAACTGGATATCAAGCAGGGCCCCGTAAGACCCTTTATTGTTACCGA
TCCGAGTGCCGAATTGGCCTCGTTACGAACCATGGTCACTCTTAAAGAG
AAGCTGTTAGTGGCCTGTCTTGCTGTCTTTACAGCGGTCATTAGATTGC
ATGGCTTGGCATGGCCTGACAGCGTGGTGTTTGATGAAGTACATTTCGG
TGGGTTTGCCTCGCAATACATTAGGGGGACTTACTTCATGGATGTGCAT
CCTCCTCTTGCAAAGATGTTGTATGCTGGTGTGGCAGGGCGCGCC

[SEQ ID NO: 66]
MSEEKTYKRVEQDDPVPELDIKQGPVRPFIVTDPSAELASLRTMVTLKE
AKLLVCLAVFTAVIRLHGLAWPDSVVFDEVHFGGFASQYIRGTYFMDVH
PPLAKMLYAGVAGRA

ScPMT2-m
[SEQ ID NO: 67]
ATGTCCTCGTCTTCGTCTACCGGGTACAGCAAAAACAATGCCGCCCACA
TTAAGCAAGAGAATACACTGAGACAAAGAGAATCGTCTTCCATCAGCGT
CAGTGAGGAACTTTCGAGCGCTGATGAGAGAGACGCGGAAGATTTCTCG
AAGGAAAAGCCCGCTGCACAAAGCTCACTGTTACGCCTGGAATCCGTTG
TAATGCCGGTGATCTTTACTGCATTGGCGTTGTTTACCAGGATGTACAA
AATCGGCATCAACAACCATGTTGTTTGGGATGAGGCGCACTTTGGTAAA
TTTGGTTCTTATTACTTGAGACACGAATTTTACCACGATGTCCATCCTC
CCCTAGGAAAAATGCTGGGGCGCGCC

[SEQ ID NO: 68]
MSSSSSTGYSKNNAAHIKQENTLRQRESSSISVSEELSSADERDAEDFS
KEKPAAQSSLLRLESVVMPVIFTALALFTRMYKIGINNHVVWDEAHFGK
FGSYYLRHEFYHDVHPPLGKMLGRA

ScPMT3-m
[SEQ ID NO: 69]
ATGCCGTACAGAGTGGCGACGGGCTACAGTGAAAAAAGTACTGACGATG
ATTTGATATGGAGAACGCCAATAGTAAAAGAGGAACTCGAGGATGCTGA
CAACTTTTTAAAGGATGATGCCGAGTTGTATGATAAAGTCAAGAACGAG
AGTGCAGTATCACACCTGGATACCATAGTTATGCCGATCATTTTCACGG
TACTGGGCATGTTCACTAGAATGTACAAGATTGGTCGTAATAATCATGT
GGTCTGGGATGAAGCTCATTTTGGTAAGTTCGGCTCTTACTATCTGAGA
CACGAATTTTACCATGATGTTCATCCACCTTTAGGTGGGCGCGCC

[SEQ ID NO: 70]
MPYRVATGYSEKSTDDDLIWRTPTVKEELEDADNFLKDDAELYDKVKNE
SAVSHLDTIVMPTIFTVLGMFTRMYKIGRNNHVVWDEAHFGKFGSYYLR
HEFYHDVHPPLGGRA

ScPMT4-m
[SEQ ID NO: 71]
ATGTCTGTGCCCAAAAAACGTAACCATGGGAAGTTACCACCTTCCACTA
AGGACGTAGACGATCCTTCGTTGAAGTACACGAAGGCCGCGCCTAAATG
TGAACAAGTTGCTGAACATTGGCTCTTGCAGCCACTACCGGAACCGGAA
TCACGTTATAGCTTTTGGGTAACAATTGTTACCTTATTAGCGTTTGCTG
CTAGATTTTATAAGATCTGGTATCCAAAAGAAGTTGTTTTTGATGAGGT
ACATTTCGGGAAATTTGCATCGTATTACTTAGAAAGGTCTTATTTCTTT
GACGTTCATCCCCCTTTTGCTAAGATGATGATTGCCTTCATTGGTTGGT
TATGTGGCTATGATGGTTCCTTTAAGTTTGATGAGATTGGGTATTCTTA
TGAAACTCATCCAGGGCGCGCC

[SEQ ID NO: 72]
MSVPKKRNHGKLPPSTKDVDDPSLKYTKAAPKCEQVAEHWLLQPLPEPE
SRYSFWVTIVTLLAFAARFYKIWYPKEVVFDEVHFGKFASYYLERSYFF
DVHPPFAKMMIAFIGWLCGYDGSFKFDEIGYSYETHPGRA

ScPMT5-m
[SEQ ID NO: 73]
ATGAATAAAGAGCATTTGCTGAAGGTGGATCCCATCCCCGATGTGACTA
TTAAACGCGGCCCTTTGAGGTCTTTTCTCATAACAAAACCCTGTGATAA
TTTGAGTTCATTACGAACAGTTACTTCATCTAAGGAAAAGCTTCTAGTT
GGCTGTTTGCTGATATTTACTGCCATCGTAAGGCTACACAATATCTCCC
TGCCAAATAGTGTTGTTTTTGGTGAAAATGAAGTTGGTACATTTGTTTC
TCAATACGTGGGGCGCGCC

[SEQ ID NO: 74]
MNKEHLLKVDPIPDVTIKRGPLRSFLITKPCDNLSSLRTVTSSKEKLLV
GCLLIFTAIVRLHNISLPNSVVFGENEVGTFVSQYVGRA

ScPMT6-m
[SEQ ID NO: 75]
ATGAGTAAAGCCAAGGGAACGGGATTTTCATCAATTGATACTGAAGATG
AAAACTTACGCGAACGTTATGTTAATCAACCAAAAGCTAATGCCTCCGA
TATTCAAGATGAACAATTAGATTGCTTTGAGCAACTAGAAGAAAAACAT
AGGACAAAAAAAATGAAGAATACACTGCGTTGAAAATTTAAGGGATG
TCATAGGTCCCCTTTTATTAACTATAACTTCGTTTTATCTAAGATTCCA
ACATATAGATCAGAACAATTATGTTGTCTGGGATGAGGCTCATTTTGGG
AAATTCGGATCATACTACATCAAACATGAGTACTACCACGATGTCCACC
CTCCACTTGGTAAAATGCTTATTGCATTGAGCGAATGGATGGCAGGATT
TGACGGTCAATTTGACTTTTCCTCTAATAATGCATATCCGGAAAACGTA

```
AACTTTAAACTAATGAGACAATTTAATGCCACATTTGGAGCTCTATGTA

CACCAGTAGCTTTCTTTACAGCCAAATGGATGGGGTTCAATTATTTTAC

TGTTTATTTGATTGCTACGATGGTAACGTTGGAACATTCATATATTGGG

CGCGCC
```

[SEQ ID NO: 76]
MSKAKGTGFSSTDTEDENLRERYVNQPKANASDIQDEQLDCFEQLEEKH

RTKKNEEYTALKILRDVIGPLLLTITSFYLRFQHIDQNNYVVWDEAHFG

KFGSYYIKHEYYHDVHPPLGKMLIALSEWMAGFDGQFDFSSNNAYPENV

NFKLMRQFNATFGALCTPVAFFTAKWMGFNYFTVYLIATMVTLEHSYIG

RA

PpPMT1-s

[SEQ ID NO: 77]
```
ATGTGCCAGATATTTCTCCCGCAAAACGTAACACGTTGTTCTGTTTCCC

TTTTGACAATGAGTAAAACAAGTCCTCAAGAGGTGCCAGAAAACACTAC

TGAGCTTAAAATCTCAAAAGGAGAGCTCCGTCCTTTTATTGTGACCTCT

CCATCTCCTCAATTGAGCAAGTCTCGTTCTGTGACTTCAACCAAGGAGA

AGCTGATATTGGCTAGTTTGTTCATATTTGCAATGGTCATCAGGTTCCA

CAACGTCGCCGGGCGCGCC
```

[SEQ ID NO: 78]
MCQIFLPQNVTRCSVSLLTMSKTSPQEVPENTTELKISKGELRPFIVTS

PSPQLSKSRSVTSTKEKLILASLFIFAMVIRFITNVAGRA

PpPMT2-s

[SEQ ID NO: 79]
```
ATGACAGGCCGTGTCGACCAGAAATCTGATCAGAAGGTGAAGGAATTGA

TCGAAAAGATCGACTCCGAATCCACTTCCAGAGTTTTTCAGGAAGAACC

AGTCACTTCGATCTTGACACGTTACGAACCCTATGTCGCCCCAATTATA

TTCACGTTGTTGTCCTTTTTCACTCGTATGTACAAAATTGGGATCAACA

ACCACGTCGTTTGGGATGAAGCTCACTTCGGAAAGTTTGGCTCCTACTA

TCTCAGACACGAGTTCTACCACGATGTCCACCCTCCGTTGGGTAAGATG

TTGGTCGGTCTATCTGGCTACATTGCCGGTTACAATGGCTCCTGGGATT

TCCCCTCCGGTCAAGAGTACCCTGACTATATTGATTACGTTAAAATGAG

GTTATTCAATGCCACCTTCAGTGCCTTATGTGTGCCATTCGCCTATTTC

ACCATGAAGGAGATTGGATTTGATATCAAGACAACTTGGCTATTCACAC

TGATGGTCTTGTGTGAAACAAGTTATTGTACGTTAGGAAAATTCATCTT

GCTGGATTCAATGCTGCTGCTATTCACTGTGACTACGGTTTTCACCTTT

GTTAGGGGGCGCGCC
```

[SEQ ID NO: 80]
MTGRVDQKSDQKVKELIEKIDSESTSRVFQEEPVTSILTRYEPYVAPII

FTLLSFFTRMYKIGINNFIVVWDEAFIFGKEGSYYLRFIEFYHDVHPPL

GKMLVGLSGYIAGYNGSWDFPSGQEYPDYIDYVKMRLFNATFSALCVPF

AYFTMKEIGFDIKTTWLFTLMVLCETSYCTLGKFILLDSMLLLFTVTTV

FTFVRGRA

PpPMT4-s

[SEQ ID NO: 81]
```
ATGATAAAATCAAGAAAGAGATCGAGAAAAGTTTCTTTGAACACTGAAA

AGGAGCTGAAAAATAGCCATATTTCTCTTGGAGATGAAAGATGGTACAC

TGTGGGTCTTCTCTTGGTGACAATCACAGCTTTCTGTACTCGATTCTAT

GCTATCAACGGGCGCGCC
```

[SEQ ID NO: 82]
MIKSRKRSRKVSLNTEKELKNSHISLGDERWYTVGLLLVTITAFCTRFY

AINGRA

PpPMT5-s

[SEQ ID NO: 83]
```
ATGACATTCTTCTTATTAGACTGCCTAGTTTTGTATAATCTTACAGAAA

TTCTAGCTCAAGCCCTCTTACTTGTTCTTCTTCTATGTCAACTGATTCC

TCAATATATGTGGTTGGTGGCCGGGCGCGCC
```

[SEQ ID NO: 84]
MTFFLLDCLVLYNLTEILAQALLLVLLLCQLIPQYMWLVAGRA

PpPMT6-s

[SEQ ID NO: 85]
```
ATGGCAACAGAGGAAGAGAGAAATGAACTGAGAAGTCGGATGGACGCCA

ATAATTCAAAAGTTTCCACGTTCACTACGAACAATTCAGATGATCCTTC

TGTTGATAGCCAGGGTAAGGTGAAAATTAAGTCATGGGTTTGGAGCCTT

GAATCTTTAATTGGCCCTCTGGTGATCACTGCCTTGGCAATTTTTCTTC

GAGTTTACCAAGGGCGCGCC
```

[SEQ ID NO: 86]
MATEEERNELRSRMDANNSKVSTFTTNNSDDPSVDSQGKVKIKSWVWSL

ESLIGPLVITALAIFLRVYQGRA

PpPMT1-m

[SEQ ID NO: 87]
```
ATGTGCCAGATATTTCTCCCGCAAAACGTAACACGTTGTTCTGTTTCCC

TTTTGACAATGAGTAAAACAAGTCCTCAAGAGGTGCCAGAAAACACTAC

TGAGCTTAAAATCTCAAAAGGAGAGCTCCGTCCTTTTATTGTGACCTCT

CCATCTCCTCAATTGAGCAAGTCTCGTTCTGTGACTTCAACCAAGGAGA

AGCTGATATTGGCTAGTTTGTTCATATTTGCAATGGTCATCAGGTTCCA

CAACGTCGCCCACCCTGACAGCGTTGTGTTTGATGAAGTTCACTTTGGG

GGGTTTGCCAGAAAGTACATTTTGGGAACCTTTTTCATGGATGTTCATC

CGCCATTGGCCAAGCTATTATTTGCTGGTGTTGGCAGTCTTGGTGGAGG

GCGCGCC
```

[SEQ ID NO: 88]
MCQIFLPQNVTRCSVSLLTMSKTSPQEVPENTTELKISKGELRPFIVTS

PSPQLSKSRSVTSTKEKLILASLFIFAMVIRFFINVAHPDSVVFDEVHF

GGFARKYILGTFFMDVHPPLAKLLFAGVGSLGGGRA

PpPMT2-m

[SEQ ID NO: 89]
```
ATGACAGGCCGTGTCGACCAGAAATCTGATCAGAAGGTGAAGGAATTGA

TCGAAAAGATCGACTCCGAATCCACTTCCAGAGTTTTTCAGGAAGAACC

AGTCACTTCGATCTTGACACGTTACGAACCCTATGTCGCCCCAATTATA

TTCACGTTGTTGTCCTTTTTCACTCGTATGTACAAAATTGGGATCAACA
```

ACCACGTCGTTTGGGATGAAGCTCACTTCGGAAAGTTTGGCTCCTACTA
TCTCAGACACGAGTTCTACCACGATGTCCACCCTCCGTTGGGTAAGATG
TTGGTCGGTCTATCTGGCTACATTGCCGGTTACAATGGCTCCTGGGATT
TCCCCTCCGGTCAAGAGTACCCTGACTATATTGATTACGTTAAAATGAG
GTTATTCAATGCCACCTTCAGTGCCTTATGTGTGCCATTCGCCTATTTC
ACCATGAAGGAGATTGGATTTGATATCAAGACAACTTGGCTATTCACAC
TGATGGTCTTGTGTGAAACAAGTTATTGTACGTTAGGAAAATTCATCTT
GCTGGATTCAATGCTGCTGCTATTCACTGTGACTACGGTTTTCACCTTT
GTTAGGTTCCATAACGAAAACAGTAAACCAGGAAACTCGTTTGGGCGCG
CC

[SEQ ID NO: 90]
MTGRVDQKSDQKVKELIEKIDSESTSRVFQEEPVTSILTRYEPYVAPII
FTLLSFFTRMYKIGINNHVVWDEAHFGKFGSYYLRHEFYHDVHPPLGKM
LVGLSGYIAGYNGSWDFFSGQEYPDYIDYVKMRLFNATFSALCVPFAYF
TMKEIGFDIKTTWLFTLMVLCETSYCTLGKFILLDSMLLLFTVTTVFTF
VRFHNENSKPGNSFGRA

PpPMT4-m
[SEQ ID NO: 91]
ATGATAAAATCAAGAAAGAGATCGAGAAAAGTTTCTTTGAACACTGAAA
AGGAGCTGAAAAATAGCCATATTTCTCTTGGAGATGAAAGATGGTACAC
TGTGGGTCTTCTCTTGGTGACAATCACAGCTTTCTGTACTCGATTCTAT
GCTATCAACTATCCAGATGAGGTTGTTTTTGACGAAGTTCATTTCGGAG
GGCGCGCC

[SEQ ID NO: 92]
MIKSRKRSRKVSLNTEKELKNSHISLGDERWYTVGLLLVTITAFCTRFY
AINYPDEVVFDEVHFGGRA

PpPMT5-m
[SEQ ID NO: 93]
ATGACATTCTTCTTATTAGACTGCCTAGTTTTGTATAATCTTACAGAAA
TTCTAGCTCAAGCCCTCTTACTTGTTCTTCTTCTATGTCAACTGATTCC
TCAATATATGTGGTTGGTGGCCCGCGAAATGACTCCTGAGATATTTGGT
CAAACCTACCAAAGGACACCACACCACAGTACTATAGCACAACAATACA
TGGCCGCCTTTGAGTACAAAAAGGGCATTCAAAGACCCTATTTTGGGCG
CGCC

[SEQ ID NO: 94]
MTFFLLDCLVLYNLTEILAQALLLVLLLCQLIPQYMWLVAREMTPEIFG
QTYQRTPHHSTIAQQYMAAFEYKKGIQRPYFGRA

PpPMT6-m
[SEQ ID NO: 95]
ATGGCAACAGAGGAAGAGAGAAATGAACTGAGAAGTCGGATGGACGCCA
ATAATTCAAAAGMCCACGTTCACTACGAACAATTCAGATGATCCTTCTG
TTGATAGCCAGGGTAAGGTGAAAATTAAGTCATGGGTTTGGAGCCTTGA
ATCTTTAATTGGCCCTCTGGTGATCACTGCCTTGGCAATTTTCTTCGA
GTTTACCAAATAGGAAAAGCTGATAGGGTTGTTTGGGATGAAGCTCATT

TCGGAAAGTTTGGGTCATTCTACTTGAAGCACCAGTTCTATTTTGATGT
CCATCCTCCCCTGGGAAAACTTCTTACAGGTTTGGGGCGCGCC

[SEQ ID NO: 96]
MATEEERNELRSRMDANNSKVSTFTTNNSDDPSVDSQGKVKIKSWVWSL
ESLIGPLVITALAIFLRVYQIGKADRVVWDEAHFGKFGSFYLKHQFYFD
VHPPLGKLLTGLGRA

ScBOS1-s
[SEQ ID NO: 97]
ATGAACGCTCTTTACAACCATGCTGTGAAGCAAAAAAATCAACTACAAC
AAGAGTTGGCCAGGTTTGAAAAGAATTCTGTGACCGCCCCTGGGCGCGC
C

[SEQ ID NO: 98]
MNALYNHAVKQKNQLQQELARFEKNSVTAPGRA

ScBET1-s
[SEQ ID NO: 99]
ATGAGTTCAAGATTTGCAGGGGGAAACGCTTATCAACGTGATACTGGTA
GAACACAGTTATTCGGACCGGCTGATGGATCAAATAGTCTCGATGACAA
TGGGCGCGCC

[SEQ ID NO: 100]
MSSRFAGGNAYQRDTGRTQLFGPADGSNSLDDNGRA

ScSEC22-s
[SEQ ID NO: 101]
ATGTCCGCGCAAAAGATCAACTTCGATCTCTTGATCAGTCAATATGCTC
CTATTGTCATTGTCGCTTTCTTTTTCGTCTTTCTCTTCTGGTGGATCTT
CCTCAAAGGGCGCGCC

[SEQ ID NO: 102]
MSAQKINFDLLISQYAPIVIVAFFFVFLFWWIFLKGRA

PpBOS1-s
[SEQ ID NO: 103]
ATGAAGGCATTTGAAGACAAGTGGATTTTTTATGGTGGCGCTATAAGTG
TTTTTGTTATTTTCTATTTGGCGGTCAAATATTTAAGAGGGCGCGCC

[SEQ ID NO: 104]
KAFEDKWIFYGGAISVFVIFYLAVKYLRGRA

PpBET1-s
[SEQ ID NO: 105]
ATGAGGATGATGGTAATGGCTAAGAAAACAGGTATTTCATGGAAGTTAT
GGCTGCTGTTCTTCTTCCTCGTCTGGCTTTGGTTCTTTTTTGTGTGGCT
TAGAGGGCGCGCC

[SEQ ID NO: 106]
MRMMVAKKTGISWKLWLLFFFLVWLWFFFVWLRGRA

PpSEC22-s
[SEQ ID NO: 107]
ATGGCAGCTCGAAGAATCAATTTGGAGGCTCTGATAAAACAGTACGTTC
CGGTTGCAATGGTGGGATTTTCTTCGTATTTATAATATGGTGGATATT
CTTGCGCGGGCGCGCC

[SEQ ID NO: 108]
MAARRINLEALIKQYVPVAMVGIFFVFIIWWIFLRGRA

Example 2

Construction of Targeting Domain ("TD") Libraries

All TDs were amplified by PCR using ExTaq (Takara) and the respective fungal genomic DNA as template, cloned into plasmids pCR2.1 (Invitrogen) and sequenced. The 5'-oligo introduced a NotI site and the CACC Kozak consensus sequence just upstream of the native ATG. In the case of the leaders derived from PpSEC12 or ScSEC12 the codon for the first amino acid of the TD was changed to ATG. The 3'-oligo introduced an AscI site and an additional C, which resulted in a fusion linker encoding GlyArgAla. After amplification of the targeting domain containing plasmids, 36 µg of each was digested with 50 units AscI for 4 hr. The linearized DNA was then ethanol precipitated, digested with 60 units NotI for 15 hr and the resulting inserts were purified by two consecutive rounds of separation on agarose gels. For fragments ranging from 87 to 219 nucleotides we used 2% agarose, for fragments from 240 to 426 nucleotides 1.5% agarose, and for fragments from 435 to 1098 nucleotides 1.0% agarose. 1.2 pmole of each was diluted to 100 µl, arranged in a 96 well plate and stored at −80° C.

Example 3

Generation of POMGnT1 Expression Vectors

Nucleic acids (codon-optimized for *P. pastoris*) encoding the catalytic domains of the human, mouse, chicken, fish, and frog POMGnT1 proteins were synthesized by GeneArt AG (Regensburg, Germany) using amino acid sequences taken from GenBank deposits listed below. Non-codon optimized sequences for human, mouse, chicken, zebrafish and xenopus POMGnT1 are disclosed in the prior art; see, e.g., Q8WZA1 for human; NP_080927 for mouse; XP_426653 for chicken; NP_001036152 for zebrafish; and AAH84747 for xenopus. Nucleotide and amino acid sequences (SEQ ID NOs: 109-118) encoding C-terminal catalytic domains of POMGnT1 are provided. The sequences lack the native N-terminal signal sequence and transmembrane anchoring regions. The nucleic acid sequences are codon-optimized for expression in *Pichia pastoris*. In all cases, an in-frame Asc1 site was added to the 5' end, and a Pac1 site added just 3' to the STOP codon.

```
human POMGnT1
                                         [SEQ ID NO: 109]
CGCGCCATTTCTGAAGCTAACGAGGACCCTGAACCAGAACAAGATTACGA

CGAGGCTTTGGGAAGATTGGAACCACCAAGAAGAAGAGGTTCCGGTCCA

AGAAGAGTTTTGGACGTTGAGGTTTACTCTTCCAGATCCAAGGTTTACGT

TGCTGTTGACGGTACTACTGTTTTGGAGGACGAGGCTAGAGAACAAGGTA

GAGGTATCCACGTTATCGTTTTGAACCAGGCTACTGGTCATGTTATGGCT

AAGAGAGTTTTCGACACTTACTCTCCACACGAAGATGAGGCTATGGTTTT

GTTCTTGAACATGGTTGCTCCAGGTAGAGTTTTGATTTGTACTGTTAAGG

ACGAGGGATCCTTCCATTTGAAGGACACTGCTAAGGCTTTGTTGAGATCC

TTGGGTTCTCAAGCTGGTCCAGCTTTGGGATGGAGAGATACTTGGGCTTT

CGTTGGTAGAAAGGGTGGTCCAGTTTTCGGTGAAAAGCACTCTAAGTCCC

CAGCTTTGTCCTCTTGGGGTGACCCAGTTTTGTTGAAAACTGACGTTCCA

TTGTCCTCTGCTGAAGAGGCTGAATGTCACTGGGCTGACACTGAGTTGAA

CAGAAGAAGAAGAAGATTCTGTTCCAAGGTTGAGGGTTACGGTTCTGTTT

GTTCCTGTAAGGACCCAACTCCAATTGAATTCTCCCCAGACCCATTGCCA

GATAACAAGGTTTTGAACGTTCCAGTTGCTGTTATCGCTGGTAACAGACC

AAACTACTTGTACAGAATGTTGAGATCTTTGTTGTCCGCTCAGGGAGTTT

CTCCACAGATGATCACTGTTTTCATCGACGGTTACTACGAAGAACCAATG

GACGTTGTTGCTTTGTTCGGATTGAGAGGTATTCAGCACACTCCAATCTC

CATCAAGAACGCTAGAGTTTCCCAACACTACAAGGCTTCCTTGACTGCTA

CTTTCAACTTGTTCCCAGAGGCTAAGTTCGCTGTTGTTTTGGAAGAGGAC

TTGGACATTGCTGTTGATTTCTTCTCCTTCTTGTCCCAATCCATCCACTT

GTTGGAAGAGGATGACTCCTTGTACTGTATCTCTGCTTGGAACGACCAAG

GTTACGAACACACTGCTGAGGATCCAGCTTTGTTGTACAGAGTTGAGACT

ATGCCAGGATTGGGATGGGTTTTGAGAAGATCCTTGTACAAAGAAGAGTT

GGAGCCAAAGTGGCCAACTCCAGAAAAGTTGTGGGATTGGGACATGTGGA

TGAGAATGCCAGAGCAGAGAAGAGGTAGAGAGTGTATCATCCCAGACGTT

TCCAGATCTTACCACTTCGGTATTGTTGGATTGAACATGAACGGTTACTT

CCACGAGGCTTACTTCAAGAAGCACAAGTTCAACACTGTTCCAGGTGTTC

AGTTGAGAAACGTTGACTCCTTGAAGAAAGAGGCTTACGAGGTTGAGGTT

CACAGATTGTTGTCTGAGGCTGAGGTTTTGGACCATTCCAAGAACCCATG

TGAGGACTCATTCTTGCCAGATACTGAGGGTCATACTTACGTTGCTTTCA

TCAGAATGGAAAAGGACGACGACTTCACTACTTGGACTCAGTTGGCTAAG

TGTTTGCACATTTGGGACTTGGATGTTAGAGGTAACCACAGAGGATTGTG

GAGATTGTTCAGAAAGAAGAACCACTTCTTGGTTGTTGGTGTTCCAGCTT

CTCCATACTCCGTTAAGAAGCCACCATCCGTTACTCCAATTTTCTTGGAG

CCACCACCAAAGGAAGAAGGTGCTCCTGGTGCTCCAGAGCAAACTTAATA

GTTAATTAAA

[SEQ ID NO: 110]
RAISEANEDPEPEQDYDEALGRLEPPRRRGSGPRRVLDVEVYSSRSKVYV

AVDGTTVLEDEAREQGRGIHVIVLNQATGHVMAKRVFDTYSPHEDEAMVL

FLNMVAPGRVLICTVKDEGSFHLKDTAKALLRSLGSQAGPALGWRDTWAF

VGRKGGPVFGEKHSKSPALSSWGDPVLLKTDVPLSSAEEAECHWADTELN

RRRRRFCSKVEGYGSVCSCKDPTPIEFSPDPLPDNKVLNVPVAVIAGNRP

NYLYRMLRSLLSAQGVSPQMITVFIDGYYEEPMDVVALFGLRGIQHTPIS

IKNARVSQHYKASLTATFNLFPEAKFAVVLEEDLDIAVDFFSFLSQSIHL

LEEDDSLYCISAWNDQGYEHTAEDPALLYRVETMPGLGWVLRRSLYKEEL

EPKWPTPEKLWDWDMWMRMPEQRRGRECIIPDVSRSYHFGIVGLNMNGYF

HEAYFKKHKFNTVPGVQLRNVDSLKKEAYEVEVHRLLSEAEVLDHSKNPC

EDSFLPDTEGHTYVAFIRMEKDDDFTTWTQLAKCLHIWDLDVRGNHRGLW

RLFRKKNHFLVVGVPASPYSVKKPPSVTPIFLEPPPKEEGAPGAPEQT

Mouse POMGnT1
                                         [SEQ ID NO: 111]
CGCGCCATTTCTGAAGCTAACGAGGACCCTGAACCAGAACAAGATTACGA

CGAGGCTTTGGGAAGATTGGAATCCCCAAGAAGAAGAGGATCCTCCCCTA
```

-continued

GAAGAGTTTTGGACGTTGAGGTTTACTCTTCCAGATCCAAGGTTTACGTT
GCTGTTGACGGTACTACTGTTTTGGAGGACGAGGCTAGAGAACAAGGTAG
AGGTATCCACGTTATCGTTTTGAACCAGGCTACTGGTCATGTTATGGCTA
AGAGAGTTTTCGACACTTACTCTCCACACGAAGATGAGGCTATGGTTTTG
TTCTTGAACATGGTTGCTCCAGGTAGAGTTTTGATTTGTACTGTTAAGGA
CGAGGGATCCTTCCATTTGAAGGACACTGCTAAGGCTTTGTTGAGATCCT
TGGGTTCTCAAGCTGGTCCAGCTTTGGGATGGAGAGATACTTGGGCTTTC
GTTGGTAGAAAGGGTGGTCCAGTTTTGGGTGAAAAGCACTCTAAGTCCCC
AGCTTTGTCCTCTTGGGGTGACCCAGTTTTGTTGAAAACTGACGTTCCAT
TGTCCTCTGCTGAAGAGGCTGAATGTCACTGGGCTGACACTGAGTTGAAC
AGAAGAAGAAGAAGATTCTGTTCCAAGGTTGAGGGTTACGGTTCTGTTTG
TTCCTGTAAGGACCCAACTCCAATTGAATTCTCCCCAGACCCATTGCCAG
ATAACAAGGTTTTGAACGTTCCAGTTGCTGTTATCGCTGGTAACAGACCA
AACTACTTGTACAGAATGTTGAGATCTTTGTTGTCCGCTCAGGGAGTTTC
TCCACAGATGATCACTGTTTTCATCGACGGTTACTACGAAGAACCAATGG
ACGTTGTTGCTTTGTTCGGATTGAGAGGTATTCAGCACACTCCAATCTCC
ATCAAGAACGCTAGAGTTTCCCAACACTACAAGGCTTCCTTGACTGCTAC
TTTCAACTTGTTCCCAGAGGCTAAGTTCGCTGTTGTTTTGGAAGAGGACT
TGGACATTGCTGTTGATTTCTTCTCCTTCTTGTCCCAATCCATCCACTTG
TTGGAAGAGGATGACTCCTTGTACTGTATCTCTGCTTGGAACGACCAAGG
TTACGAACACACTGCTGAGGATCCAGCTTTGTTGTACAGAGTTGAGACTA
TGCCAGGATTGGGATGGGTTTTGAGAAAGTCCTTGTACAAAGAGGAGTTG
GAGCCAAAGTGGCCAACTCCAGAAAAGTTGTGGGATTGGACATGTGGAT
GAGAATGCCAGAGCAGAGAAGAGGTAGAGAGTGTATCATCCCAGACGTTT
CCAGATCTTACCACTTCGGTATTGTTGGATTGAACATGAACGGTTACTTC
CACGAGGCTTACTTCAAGAAGCACAAGTTCAACACTGTTCCAGGTGTTCA
GTTGAGAAACGTTGACTCCTTGAAGAAAGAGGCTTACGAGGTTGAGATCC
ACAGATTGTTGTCTGAGGCTGAGGTTTTGGATCACTCCAAGGATCCATGT
GAGGACTCATTCTTGCCAGATACTGAGGGTCATACTTACGTTGCTTTCAT
CAGAATGGAAACTGACGACGACTTTGCTACTTGGACTCAGTTGGCTAAGT
GTTTGCACATTTGGGACTTGGATGTTAGAGGTAACCACAGAGGATTGTGG
AGATTGTTCAGAAAGAAGAACCACTTCTTGGTTGTTGGTGTTCCAGCTTC
TCCATACTCCGTTAAGAAGCCACCATCCGTTACTCCAATTTTCTTGGAGC
CACCACCAAAGGAAGAAGGTGCTCCTGGAGCTGCTGAACAAACTTAGTAG
TTAA

[SEQ ID NO: 112]
RAISEANEDPEPEQDYDEALGRLESPRRRGSSPRRVLDVEVYSSRSKVYV
AVDGTTVLEDEAREQGRGIHVIVLNQATGHVMAKRVFDTYSPHEDEAMVL
FLNMVAPGRVLICTVKDEGSFHLKDTAKALLRSLGSQAGPALGWRDTWAF
VGRKGGPVLGEKHSKSPALSSWGDPVLLKTDVPLSSAEEAECHWADTELN
RRRRRFCSKVEGYGSVCSCKDPTPIEFSPDPLPDNKVLNVPVAVIAGNRP

-continued

NYLYRMLRSLLSAQGVSPQMITVFIDGYYEEPMDVVALFGLRGIQHTPIS
IKNARVSQHYKASLTATFNLFPEAKFAVVLEEDLDIAVDFFSFLSQSIHL
LEEDDSLYCISAWNDQGYEHTAEDPALLYRVETMPGLGWVLRKSLYKEEL
EPKWPTPEKLWDWDMWMRMPEQRRGRECIIPDVSRSYHFGIVGLNMNGYF
HEAYFKKHKFNTVPGVQLRNVDSLKKEAYEVEIHRLLSEAEVLDHSKDPC
EDSFLPDTEGHTYVAFIRMETDDDFATWTQLAKCLHIWDLDVRGNHRGLW
RLFRKKNHFLVVGVPASPYSVKKPPSVTPIFLEPPPKEEGAPGAAEQT

Chicken POMGnT1

[SEQ ID NO: 113]
CGCGCCGCTTATGAAGAAGAGGAAGAGTCCGCTCAAGATTACGACGACG
AGATGTTGAATGTTGAGGCTCCAAGACACCCAGTTTCCAACAAGAAGGTT
TTGGACGTTGAGGTTTACTCTTCCAGATCCAAGGTTTACGTTGCTGTTGA
CGGTACTACTGTTTTGGAGGACGAGGCTAGAGAACAAGGTAGAGGTATCC
ACGTTATCGTTTTGAACCAGGCTACTGGTCATGTTATGGCTAAGAGAGTT
TTCGACACTTACTCTCCACACGAAGATGAGGCTATGGTTTTGTTCTTGAA
CATGGTTGCTAGAGGTAGAATCTTGATCTTCACTATCAAGGACGAGGGAT
CCTTCCACTTGAAAGAGACTGCTAAGAACGTTTTGAAGTCCTTGGGTTCC
CAAGTTGCTCCATTCTTGTCTTGGAGAGACATGTGGACTTTTGTTGGAAA
GAAGGGTGGAGAAGTTTACGGTGAAAAGCACGCTAAGTCTCCAGCTTTGT
CTACTTGGGGTGACCCAGTTTTGTTGAAAACTGAGGTTCACTTGACTTCC
GTTGAGGATGCTGAATGTCACTGGCCAGACACTGAGTTGAACAGAAGAAG
AAGAAGATTCTGTTCCAAGGTTGAGGGTTACGGTTCTGTTTGTTCCTGTA
AGGACCCAACTCCAATCGAATTCAACCCAGACCCATTGAAGGACAACAAG
GTTTTCGATGTTCCAGTTGCTGTTATCGCTGGTAACAGACCAAACTACTT
GTACAGAATGTTGAGATCCTTGTTGTCCGCTCAAGGTGTTAACCCACAGA
TGATCACTGTTTTCATCGACGGTTACTACGAAGAACCAATGGACGTTGTT
GAGTTGTTCGGTTTGTCCGGTATTAACACACTCCAATCTCCATCAAGAA
CGCTAGAGTTTCCCAACACTACAAGGCTTCCTTGACTGCTACTTTCAACT
TGTTCCCAGACGCTAAGTTCGCTGTTGTTTTGGAAGAGGACTTGGACATT
TCCGTTGATTTCTTCTCCTTCTTGTCCCAATCCATCCACTTGTTGGAAGA
GGATGAGTCCTTGTACTGTATCTCTGCTTGGAACGACCAAGGTTACGAAC
ACACTGCTGAGGATCCATCCTTGTTGTACAGAGTTGAGACTATGCCAGGA
TTGGGATGGGTTTTGAGAAAGTCATTGTATAAGGACGAATTGGAACCAAA
GTGGCCAACTCCAGAAAAGTTGTGGGATTGGACATGTGGATGAGAATGC
CAGAGCAGAGAAAGGGTAGAGAGTGTATCATTCCAGACATCTCCAGATCT
TACCACTTCGGTATTGTTGGATTGAACATGAACGGTTACTTCCACGAGGC
TTACTTCAAGAAGCACAAGTTCAACACTGTTCCAAACGTTCAGTTGAAGA
ACGTTGAGTCCTTGAAGAAGGACGCTTACGAAGCTGAGATCCACAGATTG
TTGGGTGAAGCTGAGGTTTTGGACCACTCCAAGAACCCATGTGAGGATTC
TTTCGTTCCTGACACTGAGGGTAAAGTTTACGTTATGTTCATCAAGATGG

-continued

AACAAGAGGCTGACTTCACTACTTGGACTCAGTTGGCTAAAGAATTGATG

GCTTAGTAGTTAATTAA

[SEQ ID NO: 114]
RAAYEEEEESAQDYDDEMLNVEAPRHPVSNKKVLDVEVYSSRSKVYVAVD

GTTVLEDEAREQGRGIHVIVLNQATGHVMAKRVFDTYSPHEDEAMVLFLN

MVARGRILIFTIKDEGSFHLKETAKNVLKSLGSQVAPFLSWRDMWTFVGK

KGGEVYGEKHAKSPALSTWGDPVLLKTEVHLTSVEDAECHWPDTELNRRR

RRFCSKVEGYGSVCSCKDPTPIEFNPDPLKDNKVFDVPVAVIAGNRPNYL

YRMLRSLLSAQGVNPQMITVFIDGYYEEPMDVVELFGLSGIQHTPISIKN

ARVSQHYKASLTATFNLFPDAKFAVVLEEDLDISVDFFSFLSQSIHLLEE

DESLYCISAWNDQGYEHTAEDPSLLYRVETMPGLGWVLRKSLYKDELEPK

WPTPEKLWDWDMWMRMPEQRKGRECIIPDISRSYHFGIVGLNMMGYFHEA

YFKKHKFNTVPNVQLKNVESLRKDAYEAEIHRLLGEAEVLDHSKNPCEDS

FVPDTEGKVYVMFIKMEQEADFTTWTQLAKELMA

Zebrafish POMGnT1

[SEQ ID NO: 115]
CGCCGCTTCTGAAGATGATGCTGCTCAAGAATACGATGACGCTTTGCCAA

ACATGGAAACTCCAAGAAGACCAGCTTCCGGTAGAAAGGTTTTGGACATC

GAGGTTTACTCTTCCAGATCCAAGGTTTACGTTGCTGTTGACGGTACTAC

TGTTTTGGAGGACGAGATTAGAGAACAGGGTAGAGGTATCCACGTTATCG

TTTTGAACCAGGCTACTGGTCATGTTATGGCTAAGAGAGTTTTCGACACT

TACTCTCCACACGAAGATGAGGCTATGATCTTGTTCTTGAACATGGTTAC

TAGAGGTAGAATCTTGATCTTCACTATCAAGGACGAGGGAACTTTCCATT

TGAAGGACGCTGCTAAGAACTTGTTGAAGGGATTGGGTTCCCAAGTTGCT

GTTACTTTGGGATGGAGAGACATGTGGACTTTGGTTGTTAAGAAGGGTGG

ACAGGTTTACGGTGAAAAGCACTCTAAGTCCCCAGCTTTGTCTACTTGGG

GTGACCCAGTTTTGTTGAAAACTGAGGTTCAGTTGACTGCTTCTGAAGAG

GCTGAATGTCACTGGGCTGACACTGAGTTGAACAGAAGAAGAAAGTTGTT

CTGTTCCAAGGTTGAAGGTTACGGTTCTATCTGTTCCTGTAAGGACCCAG

CTCCAATTGAATTCAACCCAGATCCATTGTCCAACAACAACGTTTACAAC

ATCCCTGTTGCTGTTATCGCTGGTAACAGACCAAACTACTTGTACAGAAT

GTTGAGATCCTTGTTGTCCTCTCACGGTGTTAACCCACAGATGATCACTG

TTTTCATCGACGGTTACTACGAAGAACCAATGGACGTTGTTGACTTGTTC

GGATTGAAGGGTGTTCAACACACTCCAATCTCCATCAAGAACGCTAGAGT

TTCCCAACACTACAAGGCTTCCTTGACTGCTACTTTCAACTTGCACCCAG

ATGCTGACTTCGCTATCGTTTTGGAAGAGGACTTGGACATTTCCATCGAT

TTCTTCTCATTCTTGGGACAGACTATCCACTTGTTGCACGAGGACGATTC

AGGATCCATCCTCTTGTACTGTATCTCCGCTTGGAACGACCAAGGTTACG

AACACACTGCTGTGTTGTACAGAGTTGAGTCCATGCCAGGATTGGGATGG

GTTTTGAAGAAGTCATTGTATAAGGACGAATTGGAACCAAAGTGGCCAAC

TCCAGAAAAGTTGTGGGATTGGACATGTGGATGAGAATGCCAGAGCAGA

GAAAGGGAAGAGAGTGTGTTATTCCAGACGTTTCCAGATCTTACCACTTC

GGTATCATCGGATTGAACATGAACGGTTACTTCCACGAGGTTTACTTCAA

GAAGCACAAGTTCAACACTATCCCAAACGTTCAGATGAAGAACGTTGAGA

ACTTGAAGAAGGACCCATACGAGATTGAGATCCAAAACTTGTTGAGAGAG

GCTGAAGTTTTGGACCACTCCAAGAACCCATGTGAGGATTCCTTCATCCC

AGACACTGAGGGAAAGACTTTCGTTATGTTCATCAAGATGGAACAAGAGA

CTGACACTAACACTTGGACTGAGTTGGCTAAGTGTTTGCATGTTTGGGAC

TTGGATGTTAGAGGTTACCACAAGGGTTTGTGGAGATTGTTCAGAAAGAA

GAACCACATCTTGGTTGTTGCTTTCCCAATTTCCCCATACTCCGTTAAGA

AGCCATCCAACGTTACTCCAATCCACTTGGAACCAGCTCCAAAAGAAGAA

GGTCCACCAGTTGAGCAGATGTAGTAGTTAA

[SEQ ID NO: 116]
RAASEDDAAQEYDDALPNMETPRRPASGRKVLDIEVYSSRSKVYVAVDGT

TVLEDEIREQGRGIHVIVLNQATGHVMAKRVFDTYSPHEDEAMILFLNMV

TRGRILIFTIKDEGTFHLKDAAKNLLKGLGSQVAVTLGWRDMWTLVVKKG

GQVYGEKHSKSPALSTWGDPVLLKTEVQLTASEEAECHWADTELNRRRKL

FCSKVEGYGSICSCKDPAPIEFNPDPLSNNNVYNIPVAVIAGNRPNYLYR

MLRSLLSSHGVNPQMITVFIDGYYEEPMDVVDLFGLKGVQHTPISIKNAR

VSQHYKASLTATFNLHPDADFAIVLEEDLDISIDFFSFLGQIIHLLHEDD

SLYCISAWNDQGYEHTAEDPSLLYRVESMPGLGWVLKKSLYKDELEPKWP

TPEKLWDWDMWMRMPEQRKGRECVIPDVSRSYHFGIIGLNMNGYFHEVYF

KKHKFNTIPNVQMKNVENLKKDPYEIEIQNLLREAEVLDHSKNPCEDSFI

PDTEGKTFVMFIKMEQETDTNTWTELAKCLHVWDLDVRGYHGLWRLFRKK

NHILVVAFPISPYSVKKPSNVTPIHLEPAPKEEGPPVEQM

Xenopus POMGnT1

[SEQ ID NO: 117]
CGCGCCGTTAACGAAGAAGAGATCGACCAAGACTACGACGAATCCTTGCA

ACAAGCTGACTCTCCAAGAAGACCAGCTAACTCCAAGAAGGTTTTGGACA

CTGAGATCTACTCTTCCAGATCCAAGGTTTACATTGCTGTTGACGGTACT

ACTGTTTTGGAGGACGAGGTTCACGAACAAGGTAGAGGTATCCACGTTAT

CGTTTTGAACCAGGCTACTGGTCATGTTATGGCTAAGAGAGTTTTCGACA

CTTACTCTCCACACGAAGATGAGGCTATGGTTTTGTTCTTGAACATGGTT

GCTAGAGGTAGAATCTTGATCTTCACTATCAAGGACGAGGGATCCTTTCA

CTTGAAGGACACTGCTAAGAACTTGTTGAAGTCCTTGGGTTCCCAAATTG

CTCCATCCTTGGGATGAGAGACATGTGGACTTTCGTTGTTAAGAAGGGT

GGACAGGTTTACGGTGAAAAGCACTCTAAGTCCCCAGCTTTGTCTACTTG

GGGTGACCCAATCTTGTTGAAAACTGACATCCAGTTGGTTCCACCAGAGG

ATGCTGAATGTCACTGGCCAGACACTGAGTTGAACAGAAGAAGAAAGAGA

TTCTGTTCCAAGGTTGAGGGTTACGGTTCTGTTTGTTCCTGTAAGGACCC

AACTCCAATCGAATTCAACCCAATGCCATTGAAAGAGAACAAGGTTACAA

CTGTTCCAGTTGCTGTTATCGCTGGTAACAGACCAAACTACTTGTACAGA

ATGTTGAGATCCTTGTTGTCCGCTCAGGGAGTTTCTCCACAGATGATCAC

TGTTTTCATCGACGGTTACTACGAAGAACCAATGGACGTTGTTGAGTTGT

-continued

```
ACGGATTGAAGGGTATTCAGCACACTCCAATCTCCATCAAGAACGCTAGA

GTTTCCCAACACTACAAGGCTTCCTTGACTGCTACTTTCAACTTGCACCC

AGACGCTAAGTTCGCTATCGTTTTGGAAGAGGACTTGGACATTTCCGTTG

ATTTCTTCTCCTTCTTGTCCCAGACTATCCACTTGTTGGAAGAGGATGAG

TCCTTGTACTGTATCTCTGCTTGGAACGACCAAGGTTACGAACACACTGC

TGAGGATTCTTCCTTGTTGTACAGAGTTGAGTCCATGCCAGGATTGGGAT

GGGTTTTGAGAAAGAACTTGTACAAGGACGAGTTGGAACCAAAATGGCCA

ACTCCAGAGAAGTTGTGGGATTGGGACATGTGGATGAGAATGCCAGAGCA

GAGAAAGGACAGAGAGTGTTTGATTCCAGACGTTTCCAGATCTTACCACT

TCGGTATTGTTGGATTGAACATGAACGGTTACTTCCACGAGGCTTACTTC

AAGAAGCACAAGTTCAACACTGTTCCAAACGTTCAGTTGTCCAACGTTAA

GTCCTTGCAGAAGGACGCTTACAGAGATTGAGATCCACAGAATCTTGTCTG

AGGCTGAGGTTTTGGACCATTCCAAGAACCCATGTGAGGATTCCTTCATC

CCAGACACAGAGGGAAAGACTTACATCATGTACATCAAGATGGAACAAGA

GGCTGACTTCACTACTTGGACTCAGTTGGCTAAGTGTTTGCACATTTGGG

ACTTGGATGTTAGAGGTAACCACAAGGGTTTGTGGAGATTGTTCAGAAAG

AAGAACCACTTCTTGGTTGTTGGTTTCCCATTCTCCCCATACGCTGTTAA

GAAGCCAGCTTCCGTTACTCCAATCTACTTGGAGCCACCACCAAAAGAAG

AAGCTGCTGTTGCTGGTATTGACCAGTCCTAGTAGTTAA
                                        [SEQ ID NO: 118]
RAVNEEEIDQDYDESLQQADSPRRPANSKKVLDTEIYSSRSKVYIAVDGT

TVLEDEVHEQGRGIHVIVLNQATGHVMAKRVFDTYSPHEDEAMVLFLNMV

ARGRILIFTIKDEGSFHLKDTAKNLLKSLGSQIAPSLGWRDMWTFVVKKG

GQVYGEKHSKSPALSTWGDPILLKTDIQLVPPEDAECHWPDTELNRRRKR

FCSKVEGYGSVCSCKDPTPIEFNPMPLKENKVTTVPVAVIAGNRPNYLYR

MLRSLLSAQGVSPQMITVFIDGYYEEPMDVVELYGLKGIQHTPISIKNAR

VSQHYKASLTATFNLHPDAKFAIVLEEDLDISVDFFSFLSQTIHLLEEDE

SLYCISAWNDQGYEHTAEDSSLLYRVESMPGLGWVLRKNLYKDELEPKWP

TPEKLWDWDMWMRMPEQRKDRECLIPDVSRSYHFGIVGLNMNGYFHEAYF

KKHKFNTVPNVQLSNVKSLQKDAYEIEIHRILSEAEVLDHKNPCEDSFIP

DTEGKTYIMYIKMEQEADFTTWTQLAKCLHIWDLDVRGNHKGLWRLFRKK

NHFLVVGFPFSPYAVKKPASVTPIYLEPPPKEEAAVAGIDQS
```

Example 4

Generation of pGLY579 and pGLY4863

The vectors that received the TD-POMGnT1 fusions were pGLY579 (places the TD-POMGnT1 fusion under the *P. pastoris* GAP promoter (Cereghino and Cregg, FEMS Microbiol Rev. 24:45-66 (2000)) and pGLY4863 (under the *P. pastoris* AOX1 promoter (Cereghino and Cregg, FEMS Microbiol Rev. 24:45-66 (2000)). pGLY579 is a double-crossover integration vector which contains a PpHIS3 ORF and, separately, nucleotides located immediately 3' to the PpHIS3 ORF. The PpHIS3 ORF (the 5' arm) was generated by PCR using primers PpHIS3 1 (SEQ ID NO:119) and PpHIS3 2 (SEQ ID NO: 120); the resulting DNA is shown (SEQ ID NO: 121). The PpHIS3 3' fragment (3' arm) was generated by PCR using primers PpHIS3 3 (SEQ ID NO: 122) and PpHIS3 4 (SEQ ID NO: 123); the resulting DNA is shown (SEQ ID NO: 124). The template was *P. pastoris* genomic DNA from wild-type strain NRRL-Y11430 (from Northern Regional Research Center, Peoria, Ill.). The PCR fragments were first cloned into pCR2.1 (Invitrogen) and sequenced. The PpHIS3 integration arms were then sub-cloned successively into pGLY566 using enzymes Fse1 and SacI for the 5' arm, and SwaI and SalI for the 3' arm to generate pGLY579; see, e.g., WO 07/136865. Situated just downstream of the PpHIS3 5' arm is a DNA fragment encompassing the PpALG3 transcriptional terminator (TT) sequence, which was cloned by PCR using primers PpALG3TT-f (SEQ ID NO: 125) and PpALG3TT-rev (SEQ ID NO: 126) resulting in the DNA fragment shown (SEQ ID NO: 127). The PpALG3TT was sub-cloned using flanking Fse1 and Pme1 restriction sites. Situated between the PpHIS3 fragments in pGLY579 are the URA5 marker (Nett and Gerngross, Yeast 20:1279 (2003), and an expression cassette consisting of the PpGAP promoter and ScCYC1 transcriptional terminator separated by Not1 and Pac1 restriction sites. The PpGAP promoter sequence (SEQ ID NO: 128) and the ScCYC1 transcriptional terminator sequence (SEQ ID NO: 129) are shown. The PpGAP promoter was replaced with the methanol-inducible PpAOX1 promoter using XhoI and Not1 sites to generate pGLY4863. The PpAOX1 promoter sequence is shown (SEQ ID NO: 130).

PpHIS3 1
[SEQ ID NO: 119]
GAGCTCGGCCACGGTGGCCCTGTGAGTCTGGCT

PpHIS3 2
[SEQ ID NO: 120]
GGCCGGCCTCAGAAAAGAACACCCTTCGTACT

PpHIS3 5' arm
[SEQ ID NO: 121]
GAGCTCGGCCACGGTGGCCCTGTGAGTCTGGCTCAATCACTTTTCAAAGA

TAAGGACTATTCTGCAGAACATGCAGCCCAGGCAACATCATCCCAGTTCA

TCTCTGTGAACACAGGAATAGGATTCCTGGACCATATGTTACACGCACTT

GCTAAGCACGGCGGCTGGTCTGTCATTATCGAATGTGTAGGTGATTTGCA

CATTGATGACCATCATTCAGCAGAAGATACTGGAATCGCATTGGGGATGG

CATTCAAAGAAGCCTTGGGCCATGTTCGTGGTATCAAAAGATTCGGGTCC

GGATTTGCTCCACTAGACGAAGCTCTCAGTCGGGCTGTTATTGATATGTC

TAACAGGCCCTATGCTGTTGTCGATCTGGGTTTGAAAAGAGAGAAGATTG

GAGACCTATCGTGTGAGATGATTCCCCATGTTTTGGAAAGTTTTGCCCAA

GGAGCCCATGTAACCATGCACGTAGATTGTTTGCGAGGTTTCAACGACCA

TCATCGTGCCGAGAGTGCATTCAAAGCTTTGGCTATAGCTATCAAAGAGG

CCATTTCAAGCAACGGCACGGACGACATTCCAAGTACGAAGGGTGTTCTT

TTCTGAGGCCGGCC

PpHIS3 3
[SEQ ID NO: 122]
ATTTAAATGTCTGGAAGGTGTCTACATCTGTGA

PpHIS3 4
[SEQ ID NO: 123]
GTCGACGGCCAGTCTGGCCAAGTAATCATTGTCT

PpHIS3 3' arm

[SEQ ID NO: 124]
ATTTAAATGTCTGGAAGGTGTCTACATCTGTGAAATCCGTATTTATTTAAGTAAAACAATCAGTAATATAAGATCTTAGTTGGTTTACCACATAGTCGGTACCGGTCGTGTGAACAATAGTTCAATGCCTCCGATTGTGCCTTATTGTTGTGGTCTGCATTTTCGCGGCGAAATTTCTACTTCAGATCGGGGCTGAGATGACCTTAGTACTCACATCAACCAGCTCGTTGAAAGTTCCCACATGACCACTCAATGTTTAATAGCTTGGCACCCATGAGGTTGAAGAAACTACTTAAGGTGTTTTGTGCCTCAGTAGTGCTGTTAGCGGCGACATCTGTGGTGTTATTTTTCCACTTTGGAGGTCAGATCATAATCCCCATACCGGAACGCACTGTGACCTTAAGTACTCCTCCCGCAAACGATACTTGGCAGTTTCAACAGTTCTTCAACGGCTATTTAGACGCCCTGTTAGAGAATAACCTGTCGTATCCGATACCAGAAAGGTGGAATCATGAAGTTACAAATGTAAGATTCTTCAATCGCATAGGTGAATTGCTCTCGGAGAGTAGGCTACAGGAGCTGATTCATTTTAGTCCTGAGTTCATAGAGGATACCAGTGACAAATTCGACAATATTGTTGAACAAATTCCAGCAAAATGGCCTTACGAAAACATGTACAGAGGAGATGGATACGTTATTGTTGGTGGTGGCAGACACACCTTTTTGGCACTGCTGAATATCAACGCTTTGAGAAGAGCAGGCAATAAACTGCCAGTTGAGGTCGTGTTGCCAACTTACGACGACTATGAGGAAGATTTCTGTGAAAATCATTTTCCACTTTTGAATGCAAGATGCGTAATCTTAGAAGAACGATTTGGTGACCAAGTTTATCCCCGGTTACAACTAGGAGGCTACCAGTTTAAAATATTTGCGATAGCAGCAAGTTCATTCAAAAACTGCTTTTTGTTAGATTCAGATAATATACCCTTGCGAAAGATGGATAAGATATTCTCAAGCGAACTATACAAGAATAAGACAATGATTACTTGGCCAGACTGGCCGTCGAC

PpALG3TT-f

[SEQ ID NO: 125]
GGCCGGCCATTTACAATTAGTAATATTAAGGT

PpALG3TT-rev

[SEQ ID NO: 126]
GTTTAAACCTACTAAGCGACGAAAACGGGA

PpALG3 transcription terminator

[SEQ ID NO: 127]
GGCCGGCCATTTACAATTAGTAATATTAAGGTGGTAAAAACATTCGTAGAATTGAAATGAATTAATATAGTATGACAATGGTTCATGTCTATAAATCTCCGGCTTCGGTACCTTCTCCCCAATTGAATACATTGTCAAAATGAATGGTTGAACTATTAGGTTCGCCAGTTTCGTTATTAAGAAAACTGTTAAAATCAAATTCCATATCATCGGTTCCAGTGGGAGGACCAGTTCCATCGCCAAAATCCTGTAAGAATCCATTGTCAGAACCTGTAAAGTCAGTTTGAGATGAAATTTTTCCGGTCTTTGTTGACTTGGAAGCTTCGTTAAGGTTAGGTGAAACAGTTTGATCAACCAGCGGCTCCCGTTTTCGTCGCTTAGTAGGTTTAAAC

PpGAP promoter

[SEQ ID NO: 128]
CTCGAGAGATCTTTTTTGTAGAAATGTCTTGGTGTCCTCGTCCAATCAGGTAGCCATCTCTGAAATATCTGGCTCCGTTGCAACTCCGAACGACCTGCTGGCAACGTAAAATTCTCCGGGGTAAAACTTAAATGTGGAGTAATGGAACCA GAAACGTCTCTTCCCTTCTCTCTCCTTCCACCGCCCGTTACCGTCCCTAGGAAATTTTACTCTGCTGGAGAGCTTCTTCTACGGCCCCCTTGCAGCAATGCTCTTCCCAGCATTACGTTGCGGGTAAAACGGAGGTCGTGTACCCGACCTAGCAGCCCAGGGATGGAAAAGTCCCGGCCGTCGCTGGCAATAATAGCGGGCGGACGCATGTCATGAGATTATTGGAAACCACCAGAATCGAATATAAAGGCGAACACCTTTCCCAATTTTGGTTTCTCCTGACCCAAAGACTTTAAATTTAATTTATTTGTCCCTATTTCAATCAATTGAACAACTATCAAAACACAGCGGCCGC

ScCYC transcription terminator

[SEQ ID NO: 129]
TTAATTAAACAGGCCCCTTTTCCTTTGTCGATATCATGTAATTAGTTATGTCACGCTTACATTCACGCCCTCCTCCCACATCCGCTCTAACCGAAAAGGAAGGAGTTAGACAACCTGAAGTCTAGGTCCCTATTTATTTTTTTAATAGTTATGTTAGTATTAAGAACGTTATTTATATTTCAAATTTTTCTTTTTTTCTGTACAAACGCGTGTACGCATGTAACATTATACTGAAAACCTTGCTTGAGAAGGTTTTGGGACGCTCGAAGGCTTTAATTTGCAAGCTGCCGGCTCTTAA

PpAOX1 promoter

[SEQ ID NO: 130]
CTCGAGAGATCTAACATCCAAAGACGAAAGGTTGAATGAAACCTTTTTGCCATCCGACATCCACAGGTCCATTCTCACACATAAGTGCCAAACGCAACAGGAGGGGATACACTAGCAGCAGACCGTTGCAAACGCAGGACCTCCACTCCTCTTCTCCTCAACACCCACTTTTGCCATCGAAAAACCAGCCCAGTTATTGGGCTTGATTGGAGCTCGCTCATTCCAATTCCTTCTATTAGGCTACTAACACCATGACTTTATTAGCCTGTCTATCCTGGCCCCCCTGGCGAGGTTCATGTTTGTTTATTTCCGAATGCAACAAGCTCCGCATTACACCCGAACATCACTCCAGATGAGGGCTTTCTGAGTGTGGGGTCAAATAGTTTCATGTTCCCCAAATGGCCCAAAACTGACAGTTTAAACGCTGTCTTGGAACCTAATATGACAAAAGCGTGATCTCATCCAAGATGAACTAAGTTTGGTTCGTTGAAATGCTAACGGCCAGTTGGTCAAAAGAAACTTCCAAAAGTCGGCATACCGTTTGTCTTGTTTGGTATTGATTGACGAATGCTCAAAAATAATCTCATTAATGCTTAGCGCAGTCTCTCTATCGCTTCTGAACCCCGGTGCACCTGTGCCGAAACGCAAATGGGGAAACACCCGCTTTTTGGATGATTATGCATTGTCTCCACATTGTATGCTTCCAAGATTCTGGTGGGAATACTGCTGATAGCCTAACGTTCATGATCAAAATTTAACTGTTCTAACCCCTACTTGACAGCAATATATAAACAGAAGGAAGCTGCCCTGTCTTAAACCTTTTTTTTTATCATCATTATTAGCTTACTTTCATAATTGCGACTGGTTCCAATTGACAAGCTTTTGATTTTAACGACTTTTAACGACAACTTGAGAAGATCAAAAAACAACTAATTATTCGAAACGGCGGCCGC

Example 5

Generation of TD-POMGnT1 Library

Figure 11:
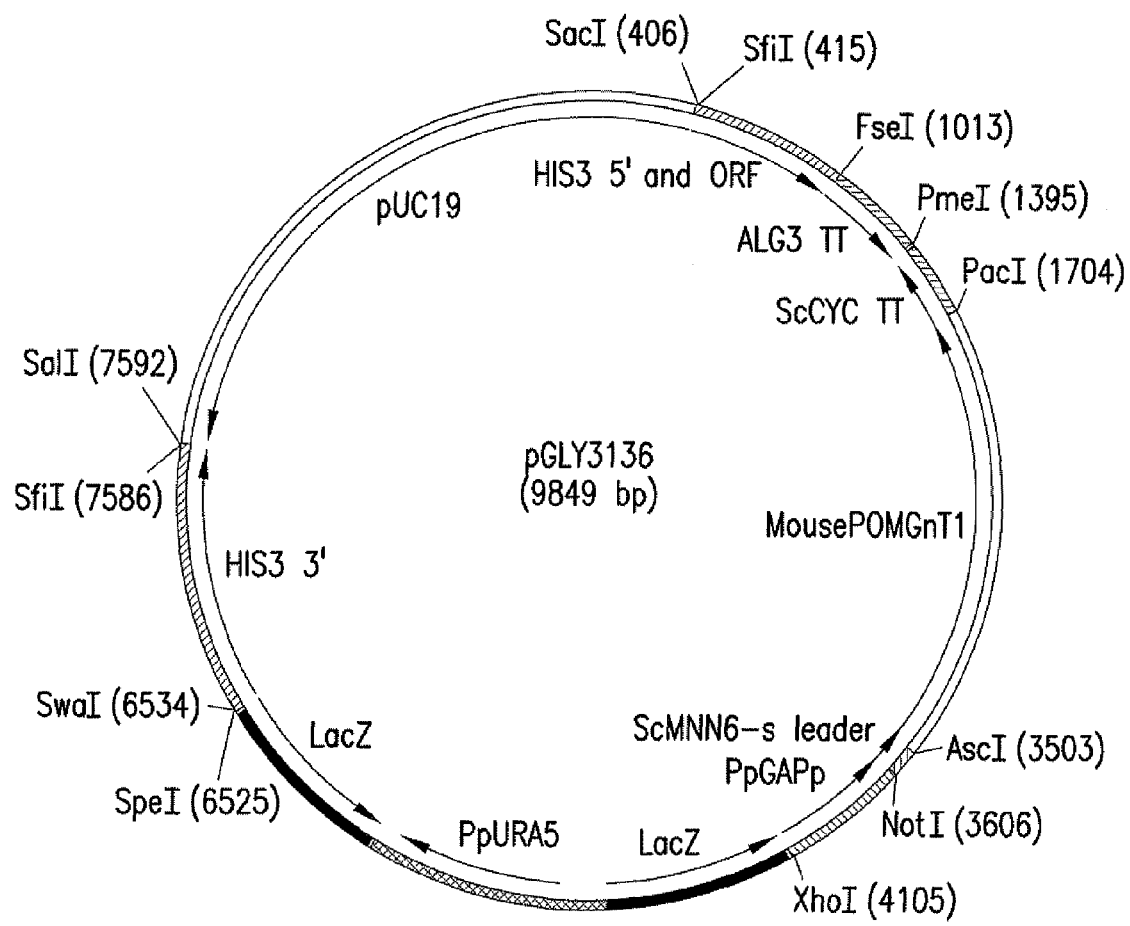
FIG. 11 illustrates the TD-POMGnT1 expression/integration vector pGLY3136.

Construction of TD-POMGnT1 expression/integration vectors were carried out as described below. The POMGnT1 catalytic domains were isolated from GeneArt vectors following digestion with AscI and PacI and cloned into integration plasmids pGLY579 (for GAPp-driven expression) and pGLY4863 (for AOX1p-driven expression). The agarose gel purified targeting domain (TD) fragments were then in a high throughput format ligated in frame into these plasmids to create the fusion libraries. Thirty μg of each POMGnT1 catalytic domain-containing vector was digested with 10 units AscI overnight. In the morning another 10 units were added and the incubation was continued for another 1 hr. The linearized DNA was ethanol precipitated and incubated with 50 units NotI for 4 hr. Then 20 units calf intestinal alkaline phosphatase were added and the incubation was continued for another 1 hr. After purification by agarose gel extraction, the DNA was diluted to 3 nM and 2.5 μl was loaded into a 96 well PCR plate. Then 2.5 μl of a 12 nM solution of the isolated targeting domain NotI/AscI fragments (see above) was added. After addition of 5 μl 2× ligation buffer and 0.5 μl Quick ligase (NEB) the ligation was allowed to proceed for 5 min at room temperature ("RT"), and 2 μl of the ligation mix was added to 50 μl E. coli strain DH5α made competent according to the method of Hanahan et al. (Methods Enzymol 204: 63-113 (1991)) that were arranged in a 96 well plate. The mixture was incubated for 20 min on ice, heat shocked at 42° C. for 1 min, 200 μl Super Optimal broth with catabolite repression ("SOC") were added to each well of the 96 well plate and the cells were allowed to recover at 37° C. for 1 hr. Of each transformation mix 200 μl were then plated on a single LB Amp plate and incubated overnight. We routinely obtained 10 to 1000 colonies per plate as compared to 0 to 10 colonies on the no insert controls. To assess whether the ligation reaction had resulted in in-frame fusions, plasmid DNA was isolated and an AscI restriction digest was performed. This was based on the fact that only if the AscI site had been recreated a genuine in-frame fusion had occurred. This proved to be true in over 99% of all cases. An example of a TD-POMGnT1 expression/integration vector, pGLY3136, is shown in FIG. 11.

Before transformation into yeast strains, the plasmids were digested with SfiI which cuts at sites flanking the HIS3 sequences, thus freeing a DNA fragment containing the promoter-TD-POMGnT1-transcriptional terminator plus URA5 marker flanked by HIS3 5' and 3' integration sequences.

Example 6

Generation of Strain GFI 2.0

The TD-POMGnT1 library was transformed by electroporation (method below) into strain YGLY7877 (GFI 2.0, FIG. 1) which was derived from strain yGLY14 (och1Δ::lacZ, bmt2Δ::lacZ/KlMNN2-2, mnn4bΔ::lacZ/MmSLC35A3, pno1Δmnn4aΔ::lacZ) and constructed using methods described earlier (Nett and Gerngross, Yeast 20:1279 (2003); Choi et al., PNAS USA 100:5022 (2003); Hamilton et al., Science 301:1244 (2003), and WO 07/136752). Briefly, genes encoding the phosphomannose transferases Pno1, Mnn4a and Mnn4b (Li et al., Nat Biotechnol. 24:210-5 (2006)) and the beta-mannose transferase BMT2 (Mille et al., Biol Chem. 283:9724-36 (2008)) were deleted in wild-type strain NRRL-Y11430 to generate YGLY-14 (Strain GFI 1.0, FIG. 1). In order to minimize the number of downstream steps in our glyco-engineering process, we included two UDP-GlcNAc transporters into the knock-out vectors. The K. lactis UDP-GlcNAc transporter was inserted into the BMT2 deletion vector and the mouse UDP-GlcNAc transporter inserted into the MNN4B deletion vector. This allowed for the stable integration of UDP-GlcNAc transporter genes at sites of gene deletions. In the initial step, YGLY14 was counterselected using 5-Fluoroorotic Acid (5-FOA) (Nett and Gerngross, Yeast 20:1279 (2003) to generate the uracil-auxotrophic strain YGLY-16, which was the recipient of the Trichoderma reesei alpha 1,2-mannosidase (Bobrowicz et al., WO 2007/061631) expression vector pGLY1896. The resulting strain YGLY6361 was counterselected again with 5-FOA to generate the uracil-auxotroph YGLY2004. Genes encoding the beta-mannose transferases BMT1, 3, 4 (Mille et al., J Biol Chem. 283:9724-36 (2008)) were then deleted using the recyclable URA5 marker (see Nett and Gerngross, Yeast 20:1279 (2003) to generate YGLY7827 (GFI 2.0, FIG. 1). YGLY7827 was then transformed with expression vector pGLY3465 (method below), which encodes the TNFRII-Fc reporter protein, to generate YGLY7877. For the above transformation and also those with the TD-POMGnT1 library, transformants were selected on minimal media lacking uracil to select for incorporation of the URA5 marker.

Example 7

Generation of TNFRII-Fc Expression Vector pGLY3465

Expression plasmid vector pGLY3465 contains an expression cassette under the control of the methanol-inducible P. pastoris AOX1 promoter that encodes the TNFR-IgG1 fusion protein. The TNFR-IgG1 fragment was codon-optimized by GeneArt with 5' PvuII and 3' FseI cloning sites (SEQ ID NO: 131), and the GeneArt vector designated pGLY3431. The TNFR domain from pGLY3431 was fused to an alternative IgG1 Fc domain from pGLY1477 (also synthesized by GeneArt) by PCR to give a DNA sequence (SEQ ID NO: 132). Specifically primers with SEQ ID NOs: 133 & 134 were used to amplify the TNFR domain from pGLY3431, while primers with SEQ ID NOs: 135 & 136 were used to amplify the IgG1 Fc domain from pGLY1477. Both of these fragments were then fused together by PCR using primers with SEQ ID NOs: 133 & 136. The TNFR-IgG1 was fused at the N-terminus to a DNA sequence (SEQ ID NO: 137) encoding the human serum albumin ("HSA") pre signal peptide. The DNA encoding the HSA signal sequence (ss) was generated using oligonucleotides purchased from Integrated DNA Technologies (Coralville, Iowa). The fusion of TNFR-IgG1 to HSAss created a DNA fragment (SEQ ID NO: 138, encoding a protein with SEQ ID NO: 139) with unique 5' EcoR1 and 3' Fse1 sites. The nucleic acid fragment encoding the HSAss-TNFR-IgG1 fusion protein was subcloned using the 5' EcoR1 and 3' Fse1 unique sites into an expression plasmid vector pGLY2198, which contains the P. pastoris TRP2 targeting nucleic acid and the Zeocin-resistance marker and generates expression cassettes under the control of the AOX1 promoter and Saccharomyces cerevisiae CYC terminator, to form plasmid pGLY3465. Following transformation of pGLY3465 into Pichia pastoris, methanol induction results in the secretion of TNFR-IgG 1 with the protein sequence of SEQ ID NO: 140. Transformants were selected on rich media containing Zeocin.

[TNFR-IgG1]

SEQ ID NO: 131
CAGCTGCCAGCTCAAGTTGCTTTTACTCCATACGCTCCAGAACCAGGTTCT

```
ACTTGTAGATTGAGAGAGTACTACGACCAAACTGCTCAGATGTGTTGTTCC
AAGTGTTCTCCAGGTCAACACGCTAAGGTTTTCTGTACTAAGACTTCCGAC
ACTGTTTGTGACTCTTGTGAGGACTCCACTTACACTCAATTGTGGAACTGG
GTTCCAGAATGTTTGTCCTGTGGTTCCAGATGTTCTTCCGACCAAGTTGAG
ACTCAGGCTTGTACTAGAGAGCAGAACAGAATCTGTACTTGTAGACCTGG
TTGGTACTGTGCTTTGTCCAAGCAAGAGGGTTGTAGATTGTGTGCTCCATT
GAGAAAGTGTAGACCAGGTTTCGGTGTTGCTAGACCAGGTACAGAAACTT
CCGACGTTGTTTGTAAGCCATGTGCTCCAGGAACTTTCTCCAACACTACTT
CCTCCACTGACATCTGTAGACCACACCAAATCTGTAACGTTGTTGCTATCC
CAGGTAACGCTTCTATGGACGCTGTTTGTACTTCTACTTCCCCAACTAGAT
CCATGGCTCCAGGTGCTGTTCATTTGCCACAGCCAGTTTCCACTAGATCCC
AACACACTCAACCAACTCCAGAACCATCTACTGCTCCATCCACTTCCTTTT
TGTTGCCAATGGGACCATCTCCACCTGCTGAAGGTTCTACTGGTGACGAAC
CAAAGTCCTGTGACAAGACTCATACTTGTCCACCATGTCCAGCTCCAGAAT
TGTTGGGTGGTCCATCCGTTTTTTTGTTCCCACCAAAGCCAAAGGACACTT
TGATGATCTCCAGAACTCCAGAGGTTACATGTGTTGTTGTTGACGTTTCTC
ACGAGGACCCAGAGGTTAAGTTCAACTGGTACGTTGACGGTGTTGAAGTT
CACAACGCTAAGACTAAGCCAAGAGAAGAGCAGTACAACTCCACATACA
GAGTTGTTTCCGTTTTGACTGTTTTGCACCAGGATTGGTTGAACGGAAAGG
ACTACAAGTGTAAGGTTTCCAACAAGGCTTTGCCAGCTCCAATGCAAAAG
ACTATCTCCAAGGCTAAGGGTCAACCAAGAGAGCCACAGGTTTACACTTT
GCCACCATCCAGAGATGAGTTGACTAAGAATCAGGTTTCCTTGACTTGTTT
GGTTAAGGGATTCTACCCAAGACACATCGCTGTTGAATGGGAATCTAACG
GACAGCCAGAGAACAACTACAAGACTACTCCACCAGTTTTGGACTCTGAC
GGTTCCTTCTTCTTGTACTCCAAGTTGACTGTTGACAAGTCCAGATGGCAA
CAGGGTAACGTTTTCTCCTGTTCCGTTATGCATGAGGCTTTGCACAACCAC
TACACTCAAAAGTCCTTGTCTTTGTCCCCTGGTAAGTAGGGCCGGCC
```
[TNFR-Fc]
SEQ ID NO: 132
```
CAGCTGCCAGCTCAAGTTGCTTTTACTCCATACGCTCCAGAACCAGGTTCT
ACTTGTAGATTGAGAGAGTACTACGACCAAACTGCTCAGATGTGTTGTTCC
AAGTGTTCTCCAGGTCAACACGCTAAGGTTTTCTGTACTAAGACTTCCGAC
ACTGTTTGTGACTCTTGTGAGGACTCCACTTACACTCAATTGTGGAACTGG
GTTCCAGAATGTTTGTCCTGTGGTTCCAGATGTTCTTCCGACCAAGTTGAG
ACTCAGGCTTGTACTAGAGAGCAGAACAGAATCTGTACTTGTAGACCTGG
TTGGTACTGTGCTTTGTCCAAGCAAGAGGGTTGTAGATTGTGTGCTCCATT
GAGAAAGTGTAGACCAGGTTTCGGTGTTGCTAGACCAGGTACAGAAACTT
CCGACGTTGTTTGTAAGCCATGTGCTCCAGGAACTTTCTCCAACACTACTT
CCTCCACTGACATCTGTAGACCACACCAAATCTGTAACGTTGTTGCTATCC
CAGGTAACGCTTCTATGGACGCTGTTTGTACTTCTACTTCCCCAACTAGAT
CCATGGCTCCAGGTGCTGTTCATTTGCCACAGCCAGTTTCCACTAGATCCC
```

-continued

AACACACTCAACCAACTCCAGAACCATCTACTGCTCCATCCACTTCCTTTT

TGTTGCCAATGGGACCATCTCCACCTGCTGAAGGTTCTACTGGTGACGAGC

CAAAGTCCTGTGACAAGACACATACTTGTCCACCATGTCCAGCTCCAGAA

TTGTTGGGTGGTCCATCCGTTTTCTTGTTCCCACCAAAGCCAAAGGACACT

TTGATGATCTCCAGAACTCCAGAGGTTACATGTGTTGTTGTTGACGTTTCT

CACGAGGACCCAGAGGTTAAGTTCAACTGGTACGTTGACGGTGTTGAAGT

TCACAACGCTAAGACTAAGCCAAGAGAAGAGCAGTACAACTCCACTTACA

GAGTTGTTTCCGTTTTGACTGTTTTGCACCAGGATTGGTTGAACGGTAAAG

AATACAAGTGTAAGGTTTCCAACAAGGCTTTGCCAGCTCCAATCGAAAAG

ACAATCTCCAAGGCTAAGGGTCAACCAAGAGAGCCACAGGTTTACACTTT

GCCACCATCCAGAGAAGAGATGACTAAGAACCAGGTTTCCTTGACTTGTT

TGGTTAAAGGATTCTACCCATCCGACATTGCTGTTGAATGGGAATCTAACG

GTCAACCAGAGAACAACTACAAGACTACTCCACCAGTTTTGGATTCTGAC

GGTTCCTTCTTCTTGTACTCCAAGTTGACTGTTGACAAGTCCAGATGGCAA

CAGGGTAACGTTTTCTCCTGTTCCGTTATGCATGAGGCTTTGCACAACCAC

TACACTCAAAAGTCCTTGTCTTTGTCCCCAGGTAAGTAGGGCCGGCC

SEQ ID NO: 133
GGGTACCCAGCTGCCAGCTCAAGTTGCTTTTACTCCATAC

SEQ ID NO: 134
GTGTCTTGTCACAGGACTTTGGCTCGTCACCAGTAGAACCTTCAGCAGGTG

GAGATG

SEQ ID NO: 135
CATCTCCACCTGCTGAAGGTTCTACTGGTGACGAGCCAAAGTCCTGTGAC

AAGACAC

SEQ ID NO: 136
GGAGCTCGGCCGGCCCTACTTACCTGGGGACAAAGACAAGGACTTTTG

[HSA pre-signal sequence]
SEQ ID NO: 137
GAATTCGAAACGATGAAGTGGGTTACCTTTATCTCTTTGTTGTTTCTTTTCT

CTTCTGCTTACTCT

[HSAss-TNFR-Fc DNA sequence]
SEQ ID NO: 138
GAATTCGAAACGATGAAGTGGGTTACCTTTATCTCTTTGTTGTTTCTTTTCT

CTTCTGCTTACTCTCTGCCAGCTCAAGTTGCTTTTACTCCATACGCTCCAGA

ACCAGGTTCTACTTGTAGATTGAGAGAGTACTACGACCAAACTGCTCAGA

TGTGTTGTTCCAAGTGTTCTCCAGGTCAACACGCTAAGGTTTTCTGTACTA

AGACTTCCGACACTGTTTGTGACTCTTGTGAGGACTCCACTTACACTCAAT

TGTGGAACTGGGTTCCAGAATGTTTGTCCTGTGGTTCCAGATGTTCTTCCG

ACCAAGTTGAGACTCAGGCTTGTACTAGAGAGCAGAACAGAATCTGTACT

TGTAGACCTGGTTGGTACTGTGCTTTGTCCAAGCAAGAGGGTTGTAGATTG

TGTGCTCCATTGAGAAAGTGTAGACCAGGTTTCGGTGTTGCTAGACCAGG

TACAGAAACTTCCGACGTTGTTTGTAAGCCATGTGCTCCAGGAACTTTCTC

CAACACTACTTCCTCCACTGACATCTGTAGACCACACCAAATCTGTAACGT

TGTTGCTATCCCAGGTAACGCTTCTATGGACGCTGTTTGTACTTCTACTTCC

CCAACTAGATCCATGGCTCCAGGTGCTGTTCATTTGCCACAGCCAGTTTCC

-continued

```
ACTAGATCCCAACACACTCAACCAACTCCAGAACCATCTACTGCTCCATCC
ACTTCCTTTTTGTTGCCAATGGGACCATCTCCACCTGCTGAAGGTTCTACT
GGTGACGAGCCAAAGTCCTGTGACAAGACACATACTTGTCCACCATGTCC
AGCTCCAGAATTGTTGGGTGGTCCATCCGTTTTCTTGTTCCACCAAAGCC
AAAGGACACTTTGATGATCTCCAGAACTCCAGAGGTTACATGTGTTGTTGT
TGACGTTTCTCACGAGGACCCAGAGGTTAAGTTCAACTGGTACGTTGACG
GTGTTGAAGTTCACAACGCTAAGACTAAGCCAAGAGAAGAGCAGTACAA
CTCCACTTACAGAGTTGTTTCCGTTTTGACTGTTTTGCACCAGGATTGGTTG
AACGGTAAAGAATACAAGTGTAAGGTTTCCAACAAGGCTTTGCCAGCTCC
AATCGAAAAGACAATCTCCAAGGCTAAGGGTCAACCAAGAGAGCCACAG
GTTTACACTTTGCCACCATCCAGAGAAGAGATGACTAAGAACCAGGTTTC
CTTGACTTGTTTGGTTAAAGGATTCTACCCATCCGACATTGCTGTTGAATG
GGAATCTAACGGTCAACCAGAGAACAACTACAAGACTACTCCACCAGTTT
TGGATTCTGACGGTTCCTTCTTCTTGTACTCCAAGTTGACTGTTGACAAGT
CCAGATGGCAACAGGGTAACGTTTTCTCCTGTTCCGTTATGCATGAGGCTT
TGCACAACCACTACACTCAAAAGTCCTTGTCTTTGTCCCCAGGTAAGTAGG
GCCGGCC
```

[HSAss-TNFR-Fc peptide sequence]
SEQ ID NO: 139

M K W V T F I S L L F L F S S A Y S L P A Q V A F T P Y A P
E P G S T C R L R E Y Y D Q T A Q M C C S K C S P G Q H A K
V F C T K T S D T V C D S C E D S T Y T Q L W N W V P E C L
S C G S R C S S D Q V E T Q A C T R E Q N R I C T C R P G W
Y C A L S K Q E G C R L C A P L R K C R P G F G V A R P G T
E T S D V V C K P C A P G T F S N T T S S T D I C R P H Q I C
N V V A I P G N A S M D A V C T S T S P T R S M A P G A V H
L P Q P V S T R S Q H T Q P T P E P S T A P S T S F L L P M G
P S P P A E G S T G D E P K S C D K T H T C P P C P A P E L L
G G P S V F L F P P K P K D T L M I S R T P E V T C V V V D
V S H E D P E V K F N W Y V D G V E V H N A K T K P R E E
Q Y N S T Y R V V S V L T V L H Q D W L N G K E Y K C K V
S N K A L P A P I E K T I S K A K G Q P R E P Q V Y T L P P S
R E E M T K N Q V S L T C L V K G F Y P S D I A V E W E S N
G Q P E N N Y K T T P P V L D S D G S F F L Y S K L T V D K
S R W Q Q G N V F S C S V M H E A L H N H Y T Q K S L S L
S P G K

[secreted TNFR-Fc peptide]
SEQ ID NO: 140

L P A Q V A F T P Y A P E P G S T C R L R E Y Y D Q T A Q M
C C S K C S P G Q H A K V F C T K T S D T V C D S C E D S T
Y T Q L W N W V P E C L S C G S R C S S D Q V E T Q A C T
R E Q N R I C T C R P G W Y C A L S K Q E G C R L C A P L R

```
KCRPGFGVARPGTETSDVVCKPCAPGTFSN

TTSSTDICRPHQICNVVAIPGNASMDAVCT

STSPTRSMAPGAVHLPQPVSTRSQHTQPTP

EPSTAPSTSFLLPMGPSPPAEGSTGDEPKSC

DKTHTCPPCPAPELLGGPSVFLFPPKPKDTL

MISRTPEVTCVVVDVSHEDPEVKFNWYVD

GVEVHNAKTKPREEQYNSTYRVVSVLTVL

HQDWLNGKEYKCKVSNKALPAPIEKTISKA

KGQPREPQVYTLPPSREEMTKNQVSLTCLV

KGFYPSDIAVEWESNGQPENNYKTTPPVLD

SDGSFFLYSKLTVDKSRWQQGNVFSCSVMH

EALHNHYTQKSLSLSPGK
```

Example 8

Yeast Transformation

All yeast transformations were as follows. *Pichia pastoris* strains were grown in 50 mL YPD media (yeast extract (1%), peptone (2%), dextrose (2%)) overnight to an optical density ("OD") of between about 0.2 to 6. After incubation on ice for 30 minutes, cells were pelleted by centrifugation at 2500-3000 rpm for 5 minutes. Media was removed and the cells washed three times with ice cold sterile 1M sorbitol before resuspension in 0.5 ml ice cold sterile 1M sorbitol. Ten µL linearized DNA (5-20 µg) and 100 µL cell suspension was combined in an electroporation cuvette and incubated for 5 minutes on ice. Electroporation was in a Bio-Rad GenePulser Xcell following the preset *Pichia pastoris* protocol (2 kV, 25 µF, 200Ω), immediately followed by the addition of 1 mL YPDS recovery media (YPD media plus 1 M sorbitol). The transformed cells were allowed to recover for four hours to overnight at room temperature (26° C.) before plating the cells on selective media.

Example 9

Isolation of Positive Transformants

PCR was used to confirm the double crossover integration of TD-POMGnT1 fusions using PCR primers matching URA5 (SEQ ID NO: 141), PpALG3TT (SEQ ID NO: 142), and PpHIS3 sequences 5' (SEQ ID NO: 143) and 3' (SEQ ID NO:144) to the integration arms. The PCR conditions were one cycle of 98° C. for 2 minutes, 30 cycles of 98° C. for 10 seconds, 50° C. for 30 seconds, and 72° C. for 1 minute, and followed by one cycle of 72° C. for 7 minutes. The PCR products were analyzed by agarose gel electrophoresis following standard methods.

```
SEQ ID NO: 141:
GGGAGAGTTGAAGGTTGTATTATTGCC

SEQ ID NO: 142:
CTACTAAGCGACGAAAACGGGAGCCG

SEQ ID NO: 143:
GTTCCCTCATTAAGAGGATCACAAACG

SEQ ID NO: 144:
GATAATAGTGCGGGCTGGTACTTCG
```

Example 10

Screening of TD-POMGnT1 Fusions by Lectin GS-II Staining

The TD-POMGnT1 fusions were screened in a 96-well format using staining by the alkaline phosphate conjugated GS-II lectin (from *Griffonia simplicifolia*, EY Labs) which binds terminal GlcNAc residues on glycans. Transformants of the TD-POMGnT1 library in strain YGLY 7877 (GFI 2.0) were grown in 0.6 mL BMGY media (1% yeast extract, 2% peptone, 100 mM potassium phosphate buffer pH 6.0, 1.34% yeast nitrogen base, 4×10-5% biotin, and 1% glycerol) for 48 h with strong shaking, pelleted and washed 1× in BMMY media (same as BMGY except 1% methanol replaced the glycerol), and then grown for 48 h in 0.2 mL BMMY. Supernatants were then harvested by centrifugation, and tested for levels of terminal GlcNAc on the TNFRII-Fc reporter protein by GS-II staining in an ELISA format.

Example 11

96-Well Lectin Staining Assay 96-well plates were coated with 100 µl per well of 1 µg/ml monoclonal Ab (anti-hs TNF RII from R& D Systems: MAB726) in coating buffer (Virolabs: RE-COAT-7-100 pH7.2). After incubation at room temperature for one hour, plates were washed 3× using 100µl of wash buffer (Virolabs: RE-WASH-T-100) per well. Wells were blocked using 100µl per well of 1× Tris ELISA Diluent/Blocking buffer (Virolabs: RE-DILU-T-100) followed by incubation at room temperature for one hour, and then washing as before. 100 µl of sample diluted 1:10 were added to each well, followed by incubation at room temperature for one hour, then plates washed as before. GS-II lectin (from *Griffonia Simplicifolia*, EY Laboratories Inc., LA-2402) solution was prepared in 1× Tris ELISA diluent/blocking buffer at a dilution of 1:1000, 100 µl of this lectin solution were added to each well of the plate, followed by incubation at room temperature for one hour. Plates were washed as before. 100 µl of SuperPhos™

4-MUP Solution (Virolabs: X-PHOS-100) were added to each well, followed by incubation at room temperature in the dark for 45 minutes. Plates were read using 360 nm excitation and 450 mm emission wavelengths on a Tecan (Mannedorf, Switzerland) Genius Pro plate reader with Magellan software.

Data from the library where TD-POMGnT1 expression was driven by the PpAOX1 promoter did not necessarily correlate with that of the library having PpGAP promoter-driven expression. Some of the AOX1p-driven TD-POMGnT1 fusions that gave strong GS-II binding gave weak binding with the PpGAP promoter. Additionally, the most active TD-POMGnT1 fusions, when linked to the PpGAP promoter, were toxic to the cells and/or inhibited protein secretion. These included human, mouse, or frog POMGnT1 fused to ScMNN2-s and -m, ScPMT5-m and PpPMT1-m. Similar findings have been made with other enzymes, e.g., MNS1 [Choi et al., PNAS 100:5022 (2003)]. The skilled artisan, with the benefit of the present disclosure, will be able to assess the best combination for the desired outcome and employ same as described herein. As in the present application, the outcome to be assessed is the level of O-linked GlcNAc (as determined by lectin GS-II staining), expression levels of the particular protein of interest and/or cell growth of the production cell. Where the glycoform is O-linked GlcNAc-Gal or O-linked GlcNAc-Gal-Sia, ECA or SNA1, respectively, should be used in the place of lectin GS-II in the above lectin-based assay We used the data obtained for the AOX1p-TD-POMGnT1 library for the initial analysis. We determined that the chicken POMGnT1 catalytic domains were inactive and zebrafish POMGnT1 displayed very weak activity. Results for the AOXp-TD-POMGnT1 library screening are shown in Table 2. The data indicated that the most active POMGnT1 catalytic domains were from human, mouse and frog, and the most active TDs were ScMNS1-s, ScMNN9-s, PpKre2-s, K1Gnt1-s, ScMNN2-s, ScMNN2-m, ScMNN5-s, ScMNN6-s, ScPMT5-m, PpPMT1-m, and PpBET1-s.

TABLE 2

Lectin staining of POMGnT1-leader fusions.

| | | Hs | Mm | Xen |
|---|---|---|---|---|
| 1 | ScGLS1-s | 2 | 3 | 3 |
| 2 | ScMNS1-s | 2 | 3 | 5 |
| 3 | ScMNS1-m | 2 | 0 | 0 |
| 4 | ScSEC12-m | 3 | 3 | 4 |
| 5 | PpSEC12-s | 4 | 3 | 4 |
| 6 | PpOCH1-s | 1 | 2 | 1 |
| 7 | ScMNN9-s | 4 | 4 | 5 |
| 8 | ScVAN1-m | 1 | 0 | 3 |
| 9 | ScANP1-s | 1 | 3 | 4 |
| 10 | ScHOC1-s | 2 | 1 | 4 |
| 11 | ScMNN10-s | 3 | 2 | 4 |
| 12 | ScMNN11-s | 2 | 0 | 4 |
| 13 | ScKRE2-s | 2 | 0 | 3 |
| 14 | ScKRE2-1 | 2 | 2 | 3 |
| 15 | PpKTR1-s | 2 | 1 | 2 |
| 16 | PpKTR3-s | 2 | 1 | 2 |
| 17 | PpKRE2-s | 3 | 4 | 5 |
| 18 | ScKTR1-s | 2 | 3 | 3 |
| 19 | ScKTR2-s | 2 | 4 | 4 |
| 20 | K1GNT1-s | 4 | 4 | 5 |
| 21 | ScMNN2-s | 5 | 4 | 5 |
| 22 | ScMNN2-m | 5 | 5 | 4 |
| 23 | ScMNN5-s | 2 | 5 | 2 |
| 24 | ScYUR1-s | 1 | 1 | 1 |
| 25 | ScMNN1-s | 2 | 1 | 4 |
| 26 | ScMNN6-s | 3 | 5 | 4 |
| 27 | ScPMT1-s | 1 | 1 | 1 |

TABLE 2-continued

Lectin staining of POMGnT1-leader fusions.

| | | Hs | Mm | Xen |
|---|---|---|---|---|
| 28 | ScPMT2-s | 1 | 1 | 1 |
| 29 | ScPMT3-s | 1 | 1 | 1 |
| 30 | ScPMT4-s | 1 | 1 | 1 |
| 31 | ScPMT5-s | 1 | 1 | 1 |
| 32 | ScPMT6-s | 1 | 1 | 1 |
| 33 | ScPMT1-m | 1 | 0 | 0 |
| 34 | ScPMT2-m | 1 | 1 | 1 |
| 35 | ScPMT3-m | 2 | 3 | 1 |
| 36 | ScPMT4-m | 3 | 3 | 1 |
| 37 | ScPMT5-m | 5 | 4 | 4 |
| 38 | ScPMT6-m | 3 | 4 | 2 |
| 39 | PpPMT1-s | 2 | 4 | 2 |
| 40 | PpPMT2-s | 2 | 4 | 2 |
| 41 | PpPMT4-s | 2 | 4 | 2 |
| 42 | PpPMT5-s | 2 | 2 | 2 |
| 43 | PpPMT6-s | 2 | 2 | 2 |
| 44 | PpPMT1-m | 5 | 2 | 4 |
| 45 | PpPMT2-m | 2 | 2 | 2 |
| 46 | PpPMT4-m | 2 | 0 | 2 |
| 47 | PpPMT5-m | 2 | 0 | 2 |
| 48 | PpPMT6-m | 2 | 0 | N/A |
| 49 | ScBOS1-s | 2 | 0 | 1 |
| 50 | ScBET1-s | 2 | 1 | 1 |
| 51 | ScSEC22-s | 2 | 0 | N/A |
| 52 | PpBOS1-s | 2 | 1 | 2 |
| 53 | PpBET1-s | 5 | 5 | 5 |
| 54 | PpSEC22-s | 2 | N/A | 1 |

Example 12

O-Glycan Analysis by HPAEC-PAD

We next analyzed the O-glycans in GFI SO-1 strains (GFI 2.0 strains further expressing POMGnT1; see, e.g., WO 07/136752) expressing the most active TD-POMGnT1 fusions. Strains showing strong GS-II staining were grown in shake flasks containing 100 mL of BMGY for 48 h, pelleted and washed 1× with BMMY, and then grown an additional 48 h in 50 mL BMMY prior to harvest by centrifugation. Secreted TNFRII-Fc was purified from cleared supernatants using protein A chromatography (Li et al. Nat. Biotechnol. 24(2):210-5 (2006)), and the O-glycans released from and separated from protein by alkaline elimination (beta-elimination) (Harvey, Mass Spectrometry Reviews 18: 349-451 (1999), Stadheim et al., Nat. Protoc. 3:1026-31 (2006)). This process also reduces the newly formed reducing terminus of the released O-glycan (either oligomannose or mannose) to mannitol. The mannitol group thus serves as a unique indicator of each O-glycan. 0.5 nmole or more of protein, contained within a volume of 100 μL PBS buffer, was required for beta elimination. The sample was treated with 25 μL alkaline borohydride reagent and incubated at 50° C. for 16 hours. About 20 μL arabitol internal standard was added, followed by 10 μL glacial acetic acid. The sample was then centrifuged through a Millipore filter containing both SEPABEADS and AG 50W-X8 resin and washed with water. The samples, including wash, were transferred to plastic autosampler vials and evaporated to dryness in a centrifugal evaporator. 150 μL 1% AcOH/MeOH was added to the samples and the samples evaporated to dryness in a centrifugal evaporator. This last step was repeated five more times. 200 μL of water was added and 100 μL of the sample was analyzed by high pH anion-exchange chromatography coupled with pulsed electrochemical detection-HPLC (HPAEC-PAD) according to the manufacturer (Dionex, Sunnyvale, Calif.).

Figure 2A:
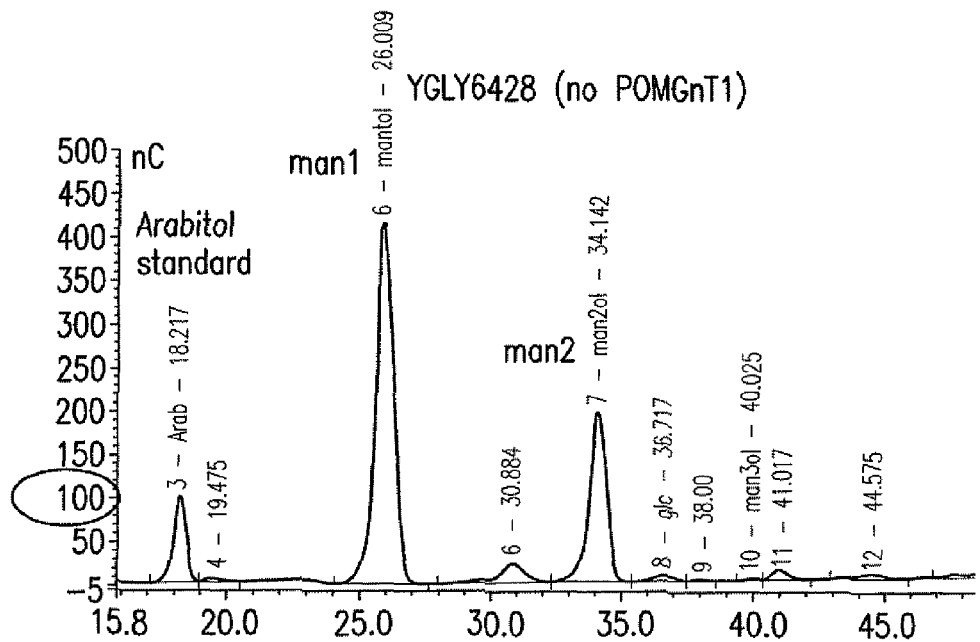
FIGS. 2A-B illustrate TNFRII-Fc O-glycans from Strain GFI SO-1 (see FIG. 1) compared to that from Strain GFI 2.0. Shown are traces from HPAEC-PAD (see below for method) for O-glycans on a reporter protein (TNFRII-Fc) expressed in strain YGLY6428 (Panel A) which has no POMGnT1, and strain YGLY7879 (Panel B) which harbors the mouse POMGnT1-ScMNN6-s fusion. Results indicate a POMGnT1-dependent O-glycan in YGLY7879 that co-migrates with the arabitol standard. Arabitol is added to the samples at a concentration that typically gives a maximum reading of ~100 nano coulombs (nC) in strains lacking POMGnT1. However, with co-elution of both arabitol and Man-GlcNAc, which have an additive effect, the magnitude is increased to approximately 450 nC in strains harboring POMGnT1. This increase in magnitude is highlighted by the circles positioned on the Y-axis.
Figure 2B:
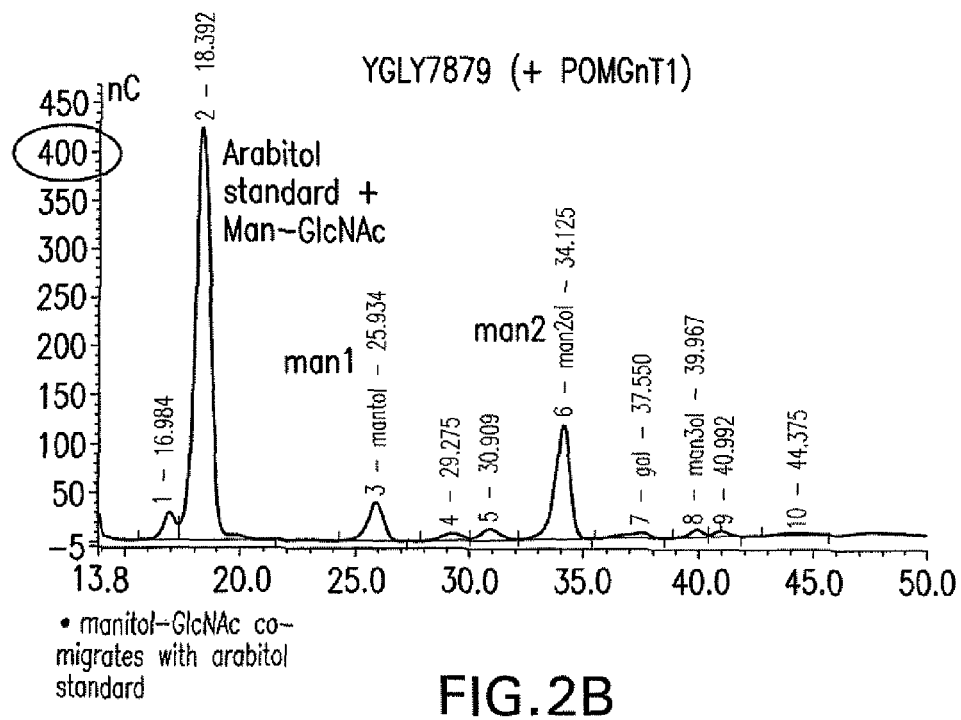
Figure 3A:
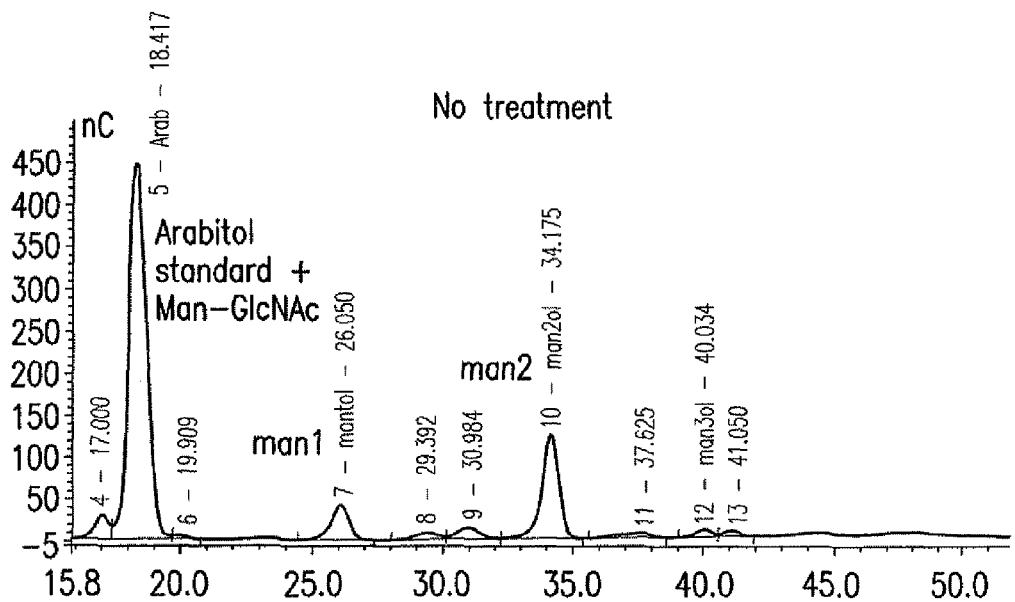
FIGS. 3A-B illustrate TNFRII-Fc O-glycans from Strain GFI SO-1 (YGLY7879 [mouse POMGnT1-ScMNN6-s]) following hexosaminidase treatment to remove GlcNAc. Shown are HPAEC-PAD traces of glycans from strain YGLY7879 without (PANEL A) and with (PANEL B) hexosaminidase treatment to remove terminal GlcNAc. The treatment results in the reduction of the putative arabitol+Man-GlcNAc peak, appearance of a new peak at T=23.909 which is free GlcNAc, and an increase in the manitol (man1) peak. This verifies that the sugar co-migrating with arabitol in POMGnT1-containing GFI SO-1 strains is Man-GlcNAc.
Figure 3B:
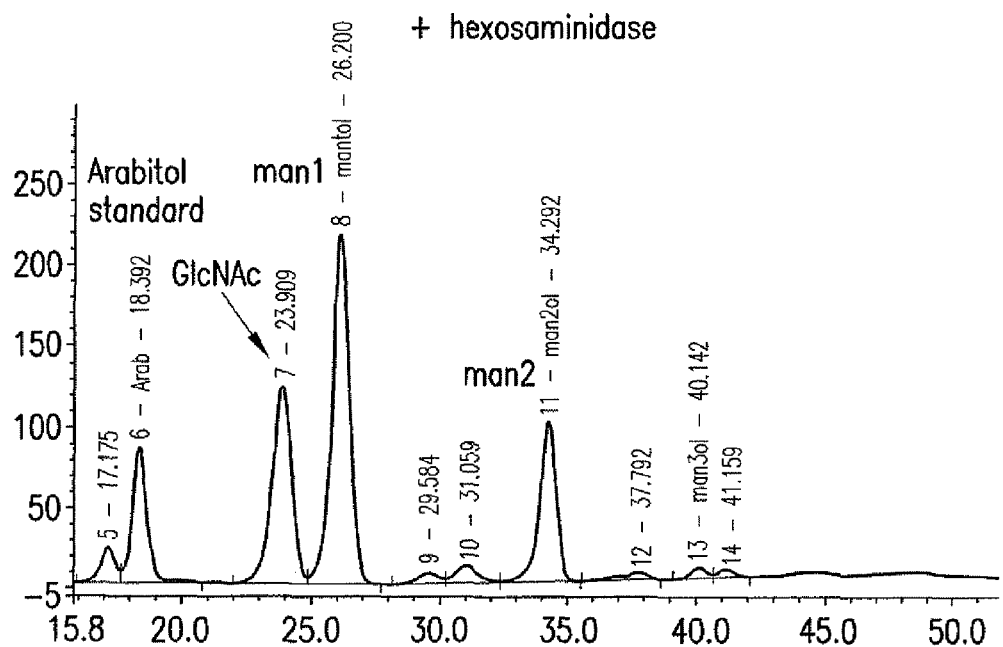

Results: HPAEC-PAD traces for TNFRII-Fc glycans from strain YGLY7879 which harbors PpGAPp-driven ScMNN6s-mousePOMGnT1 fusion is shown in FIG. 2, PANEL B. Comparison is to GFI 2.0 Strain YGLY6428 (PANEL A) which lacks POMGnT1. Results indicated a POMGnT1-dependent O-glycan in YGLY7879 that co-migrated with the arabitol standard. Arabitol was added to the samples at a concentration that typically gave a maximum reading of ~100 nano coulombs (nC) in strains lacking POMGnT1, but up to 450 nC in GFI SO-1 strains that harbor POMGnT1. Shown in FIG. 3 are HPAEC-PAD traces of glycans from strain YGLY7879 without (PANEL A) and with (PANEL B) hexosaminidase treatment that removes terminal GlcNAc residues. Hexosaminidase (β-N-acetyl-hexosaminidase, NE Biolabs, Ipswich, Mass.) treatment was as described by the manufacturer. Briefly, O-glycans released by beta-elimination were buffer-exchanged into 50 mM NaCitrate, pH 6.0, and incubated at 37 C overnight. The treatment results in the reduction of the putative arabitol+Man-GlcNAc peak, appearance of a new peak at T=23.909 which is free GlcNAc, and an increase in the manitol (man1) peak. This verifies that the sugar co-migrating with arabitol in POMGnT1-containing strains is Man-GlcNAc.

Figure 4A:
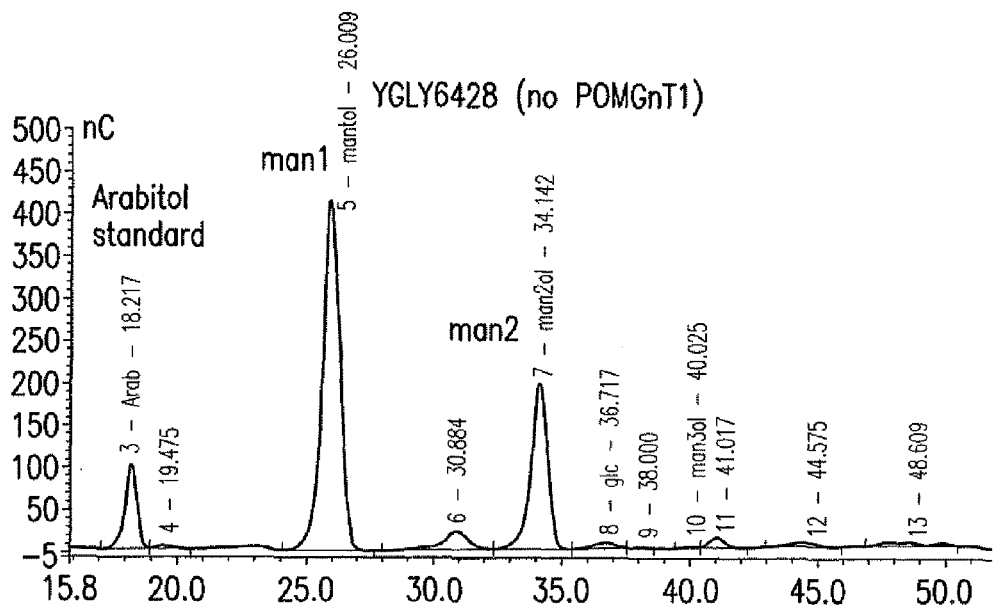
FIGS. 4A-B illustrate TNFRII-Fc O-glycans from Strain GFI SO-2 compared to that from Strain GFI 2.0. Shown are HPAEC-PAD traces of TNFRII-Fc O-glycans from GFI 2.0 strain YGLY6428 (PANEL A) which has no POMGnT1, and GFI SO-2 strain YGLY7880 (PANEL B) which harbors galactose transfer genes and human POMGnT1-ScMNN2-s. Results indicate a novel POMGnT1-dependent O-glycan in YGLY7880 migrating at ~T=21.38 that is Man-GlcNAc-Gal. Note, the peak eluting at T=21.38 has been described as a sorbitol peak by the instrument, as this peak elutes within the range of the sorbitol standard peak, which has been defined during calibration. It is obvious from FIG. 5 that this peak is Man-GlcNAc-Gal, due to its hydrolysis with galactosidase and hexosaminidase treatments.
Figure 4B:
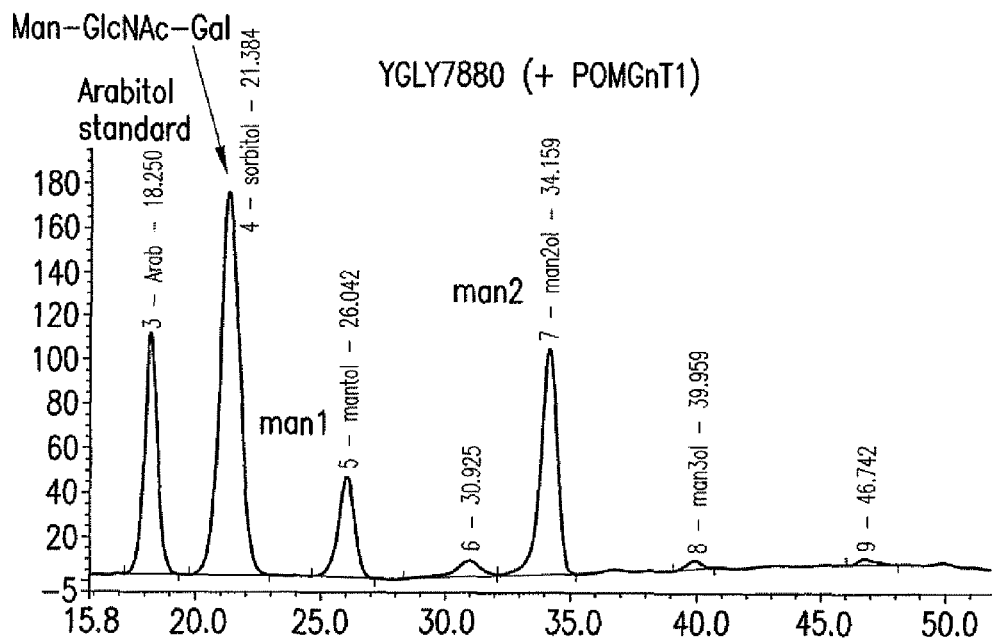
Figure 5A:
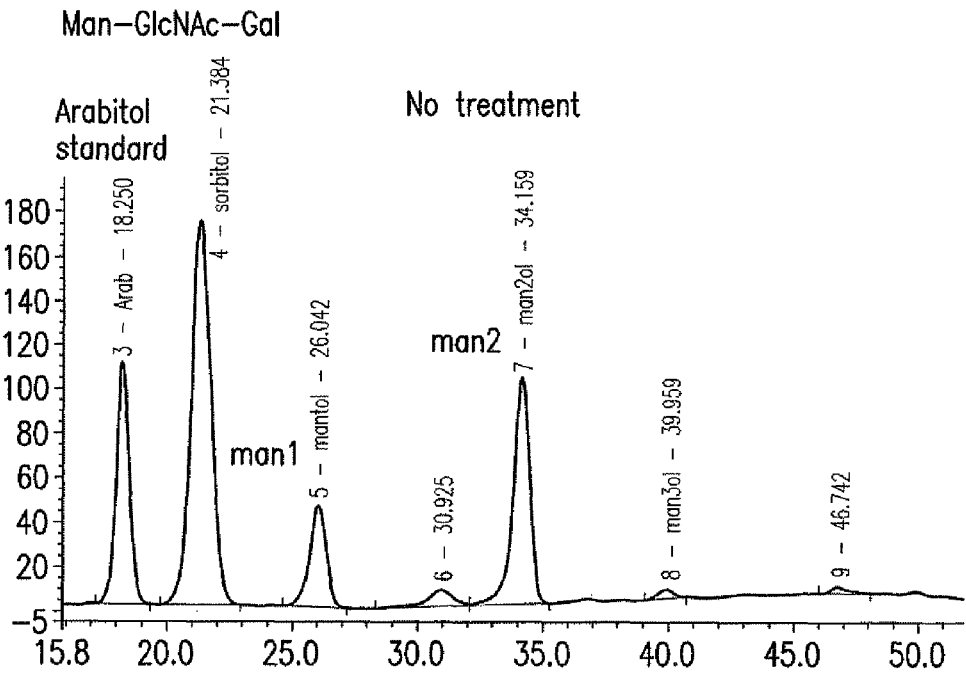
FIGS. 5A-B illustrate TNFRII-Fc O-glycans from GFI SO-2 strain YGLY7880 treated with galactosidase and hexosaminidase. Shown are HPAEC-PAD traces of TNFRII-Fc β-glycans from GFI SO-2 strain YGLY7880 untreated (PANEL A), or treated with galactosidase to remove terminal galactose plus hexosaminidase to remove terminal GlcNAc (PANEL B). The treatment results in the elimination of the putative Man-GlcNAc-Gal peak, appearance of a peak for free GlcNAc at T=23.909, an increase in the manitol (man1) peak, and the appearance of a galactose peak at T=38.35. These results indicate that the POMGnT1-dependent O-glycan in GFI SO-2 strains that migrates at ~T=21.38 is Man-GlcNAc-Gal. Note, the peak eluting at T=21.38 has been labeled as a sorbitol peak by the instrument, see FIG. 4.
Figure 5B:
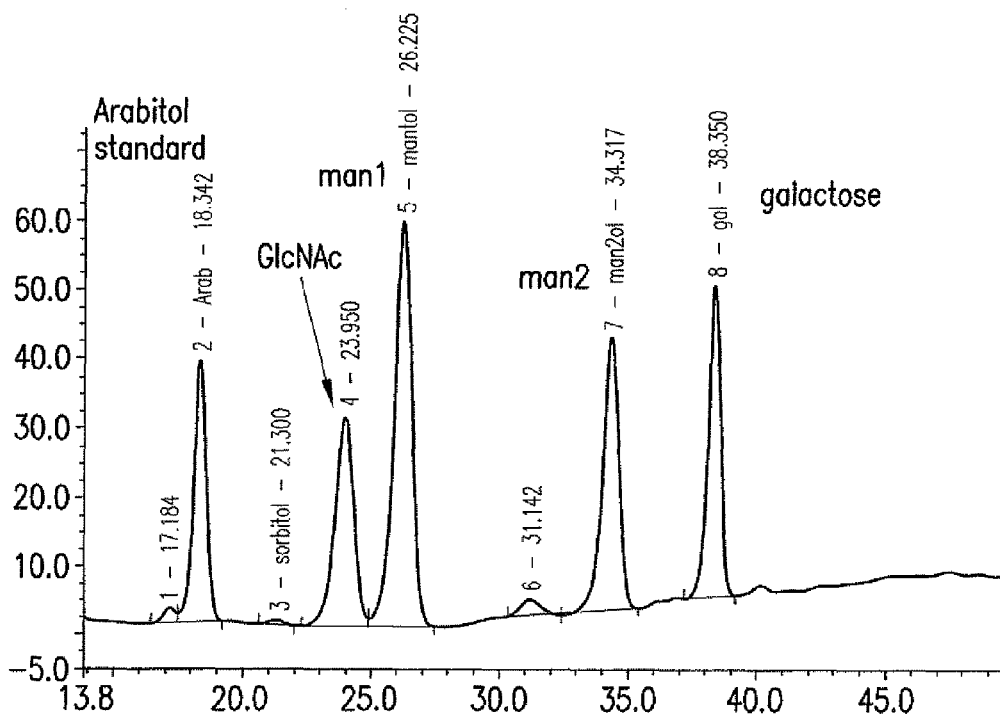

FIGS. 4 and 5 show generation of strains that efficiently transfer galactose to the O-linked Man-GlcNAc. The most active TD-POMGnT1 fusions were screened in a 96-well format using staining by the alkaline phosphate conjugated ECA lectin (from *Erythina cristagalli*, EY Labs LA-5901) which binds terminal galactose residues on glycans. The screening was done exactly as described above for lectin GS-II, except that the TD-POMGnT1 vectors were transformed into strain YGLY7875 which contains enzymes required for galactose synthesis and transfer. YGLY7875 was constructed by transforming YGLY5858 with the TNFRII-Fc expression vector pGLY3465 as described above. Generation of YGLY5858 was as described for YGLY1703 (see, e.g., WO 07/136752) except that it is a uracil auxotroph altered above (see Bobrowicz et al., 2004. *Glycobiology* 14:757-66. Li et al., 2006 *Nat. Biotech* 24:210-215, Gerngross et al. WO 04/074499, and WO 07/136752). One of the most active strains identified by lectin screening was YGLY7880 which harbors the GAPp-ScMNN2s-humanPOMGnT1 fusion. YGLY7880 was cultured in shakeflasks and supernatant subjected to protein A purification as described for FIGS. 2 and 3. FIG. 4 shows HPAEC-PAD traces of TNFRII-Fc O-glycans from GFI 2.0 strain YGLY6428 (PANEL A) which has no POMGnT1, and GFI SO-2 strain YGLY7880 (+POMGnT1) (PANEL B). Results indicate a novel POMGnT1-dependent O-glycan in YGLY7880 migrating at ~T=21.38 that is Man-GlcNAc-Gal. FIG. 5 shows HPAEC-PAD traces of TNFRII-Fc O-glycans from GFI SO-2 strain YGLY7880 untreated (PANEL A), or treated with galactosidase to remove terminal galactose plus hexosaminidase to remove terminal GlcNAc (PANEL B). Hexosamindase (described above) and galactosidase (β1,4-galactosidase, Calbiochem/EMD Biosciences, La Jolla, Calif.) treatment was as described above for hexosaminidase. The treatment results in the elimination of the putative Man-GlcNAc-Gal peak, appearance of a peak for free GlcNAc at T=23.909, an increase in the manitol (man1) peak, and the appearance of a galactose peak at T=38.35. These results indicate that the POMGnT1-dependent O-glycan in GFI 5.0 strains that migrates at ~T=21.38 is Man-GlcNAc-Gal.

Figure 6A:
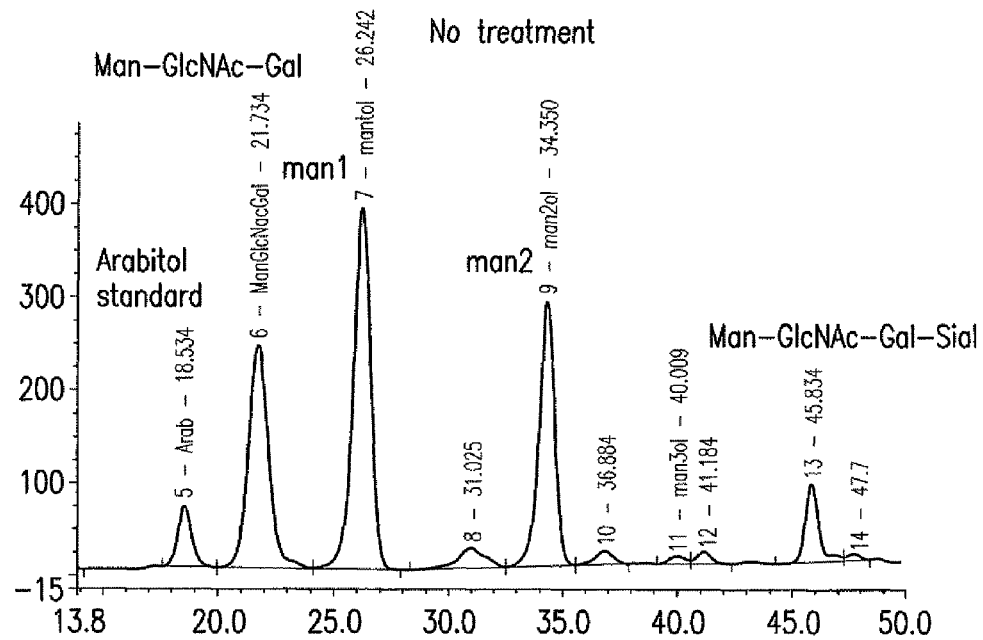
FIGS. 6A-B illustrate TNFRII-Fc O-glycans from GFI SO-3 strain YGLY8750 (musPOMGnT1-ScMNN6-s), treated with neuraminidase, galactosidase and hexosaminidase. Shown are HPAEC-PAD traces of TNFRII-Fc O-glycans from YGLY8750 untreated (PANEL A), or treated with neuraminidase to remove terminal sialic acid, galactosidase to remove terminal galactose, plus hexosaminidase to remove terminal GlcNAc (PANEL B). A sub-optimal dose of enzymes was added in order to generate all possible species. The treatment results in the reduction of the putative Man-GlcNAc-Gal-Sialic acid peak at T=45.8, the reduction of the Man-GlcNAc-Gal peak at T=21.7, appearance of a peak for free GlcNAc at T=23.5, an increase in the manitol (man1) peak, and the appearance of a galactose peak at T=37.9. These results indicate that the POMGnT1-dependent O-glycan in GFI SO-3 strains that migrates at ~T=45.8 is Man-GlcNAc-Gal-sialic acid.
Figure 6B:
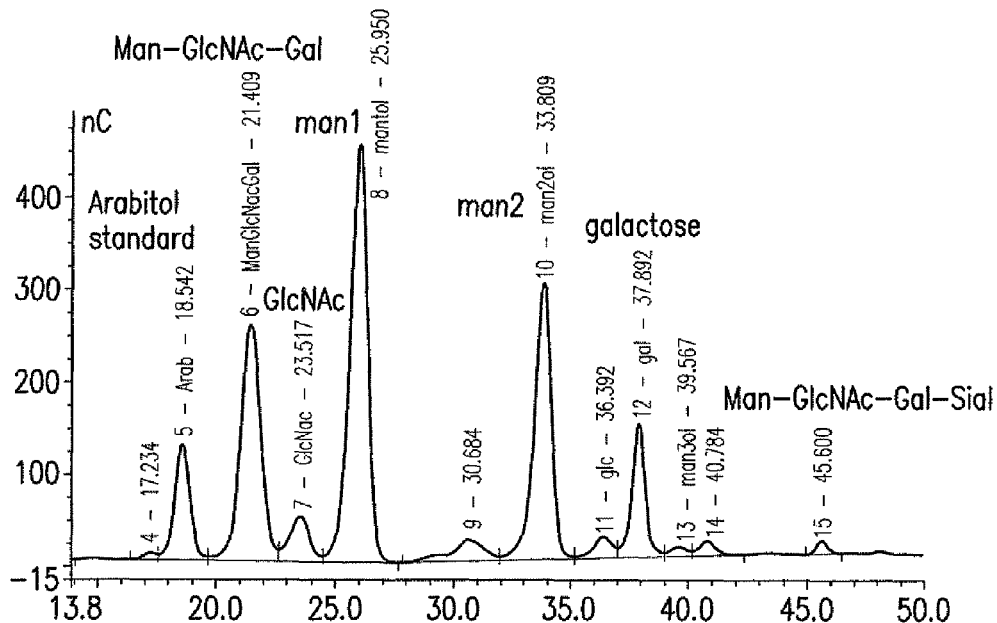

FIG. 6 shows TNFRII-Fc O-glycans in GFI SO-3 strain YGLY8750 which is GFI SO-2 strain YGLY7880 transformed with vector pGLY1758 that harbors the five genes (FIG. 1) required for generating sialylated glycans (Hamilton et al., Science 213:1441 (2006)). Shown are HPAEC-PAD traces of TNFRII-Fc O-glycans from YGLY8750 untreated (PANEL A), or treated with neuraminidase to remove terminal sialic acid, galactosidase to remove terminal galactose, plus hexosaminidase to remove terminal GlcNAc (PANEL B). Hexosaminidase (described above), galactosidase (described above) and neuraminidase (NE Biolabs, Ipswich, Mass.) treatment was as described above for hexosaminidase. Sub-optimal doses of enzymes were added in order to generate all possible species. The treatment results in the reduction of the putative Man-GlcNAc-Gal-Sialic acid peak at T=45.8, the reduction of the Man-GlcNAc-Gal peak at T=21.7, appearance of a peak for free GlcNAc at T=23.5, an increase in the manitol (man1) peak, and the appearance of a galactose peak at T=37.9. These results indicate that the POMGnT1-dependent β-glycan in GFI SO-3 strains that migrates at ~T=45.8 is Man-GlcNAc-Gal-sialic acid.

Figure 7:
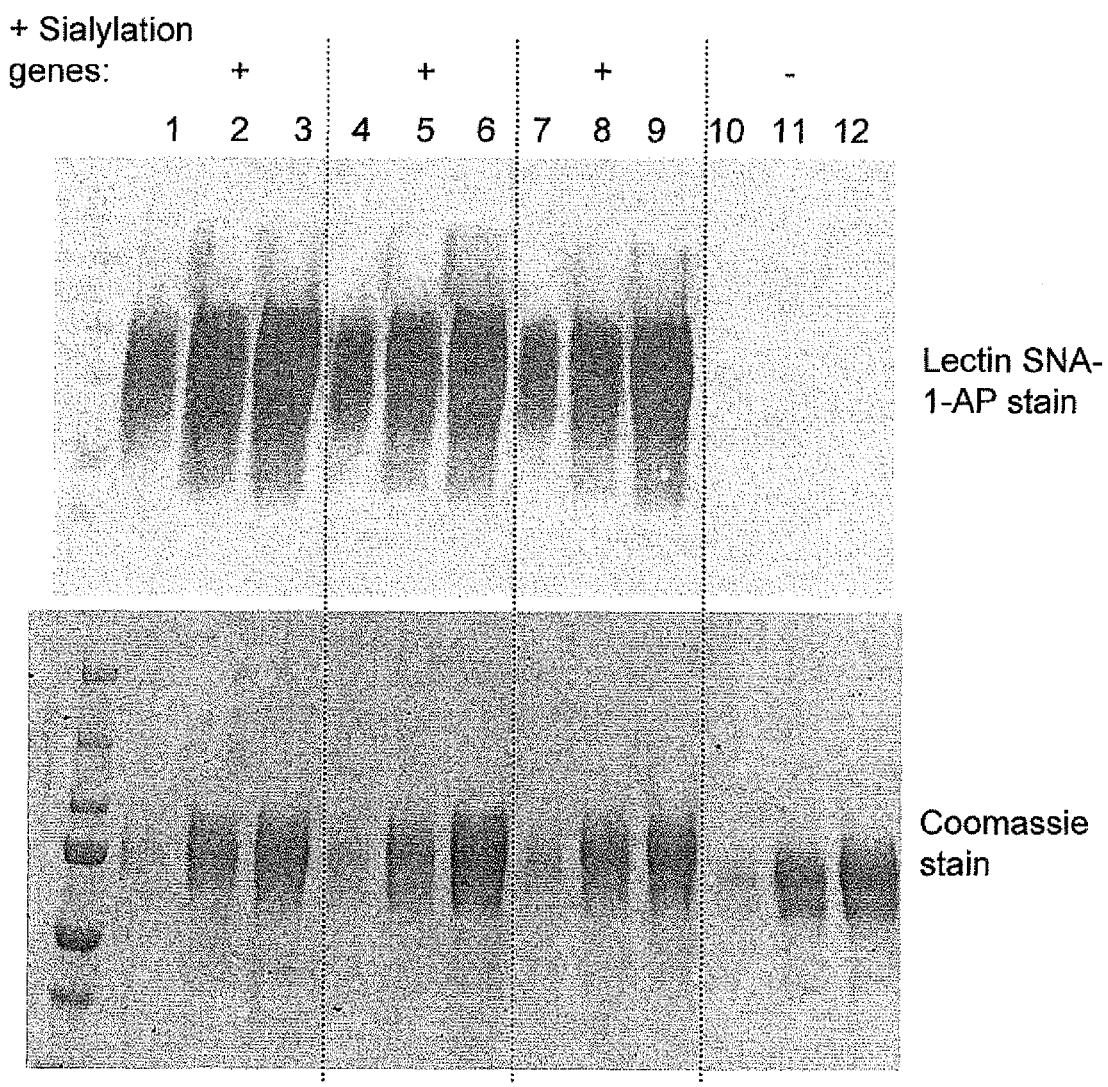
FIG. 7 illustrates Western blotting with lectin SNA-1-AP to detect terminal sialic acid. Shown is a coomassie stained SDS-PAGE gel (bottom) showing TNFRII-Fc protein levels in samples 1-12, and a Western blot (top) using detection by alkaline phosphatase-conjugated lectin SNA-1. Lanes 1-9 are supernatants (2, 6, and 10 uL per strain) from three separate colonies of GFI SO-2 strain YGLY7880 transformed with sialylation vector pGLY1758; lanes 10-12 are from non-transformed YGLY7880. Lectin SNA-1 binds to terminal sialic acid, and thus will detect terminal sialic acid on O-glycans in Strain GFI SO-3 that harbors genes for sialic acid synthesis and transfer. Results indicate strong lectin binding to TNFRII-Fc from samples 1-9 which are from GFI SO-3 strains, but no binding to TNFRII-Fc from samples 10-12 which are from GFI SO-2 strains that lack the ability to transfer sialic acid.

FIG. 7 shows Western blotting with alkaline phosphatase conjugated lectin SNA-1 to visualize high levels of terminal sialic acid on TNFRII-Fc. Shown is a coomassie stained SDS-PAGE gel (bottom) showing TNFRII-Fc protein levels in samples 1-12, and a Western blot (top) using detection by alkaline phosphatase-conjugated lectin SNA-1. Lectin SNA-1 binds to terminal sialic acid, and thus will detect terminal sialic acid on O-glycans in Strain GFI SO-3 that harbors genes for sialic acid synthesis and transfer. Results indicate strong lectin binding to TNFRII-Fc from samples 1-9 which are from GFI SO-3 strains, but no binding to TNFRII-Fc from samples 10-12 which are from GFI SO-2 strains which lack the ability to transfer sialic acid.

Example 13

Western Blotting with Alkaline Phosphatase Conjugated Lectin SNA-1

Three separate colonies of YGLY7880 transformed with sialylation vector pGLY1758 were grown in BMGY and induced in BMMY as described above. Two, six, and ten μL of supernatants were separated by reducing polyacrylamide gel electrophoresis (SDS-PAGE) according to Laemmli, U. K. (1970) Nature 227, 680-685 and then electroblotted onto nitrocellulose membranes (Schleicher & Schuell, now Whatman, Inc., Florham Park, N.J.). The membrane was incubated at room temperature for 30 min. in blocking solution (Roche DIG Glycan Differentiation Kit 1-210-238) that was diluted in TBS (0.05 M Tris-HCl pH 7.5, 0.15 M NaCl), followed by three 5 min. washes in Lectin Binding Buffer (50 mM Tris-HCl pH 7.5, 0.15 M NaCl, 0.1 mM CaCl2, 0.1% Tween-20). Twenty micrograms/mL of lectin SNA-1 (from *Sambucus Nigra*, EY Labs. LA-6802) was diluted in Lectin Binding Buffer (total volume 2.5 mL) and added to the membrane at room temperature for 1 h. Following three 10 min. washes in Lectin Binding Buffer, NBT/BLIP (Roche DIG Glycan Differentiation Kit 1-210-238) in 10 mM Tris pH 9.5 was added until bands were visible.

Figures 8A, 8B:
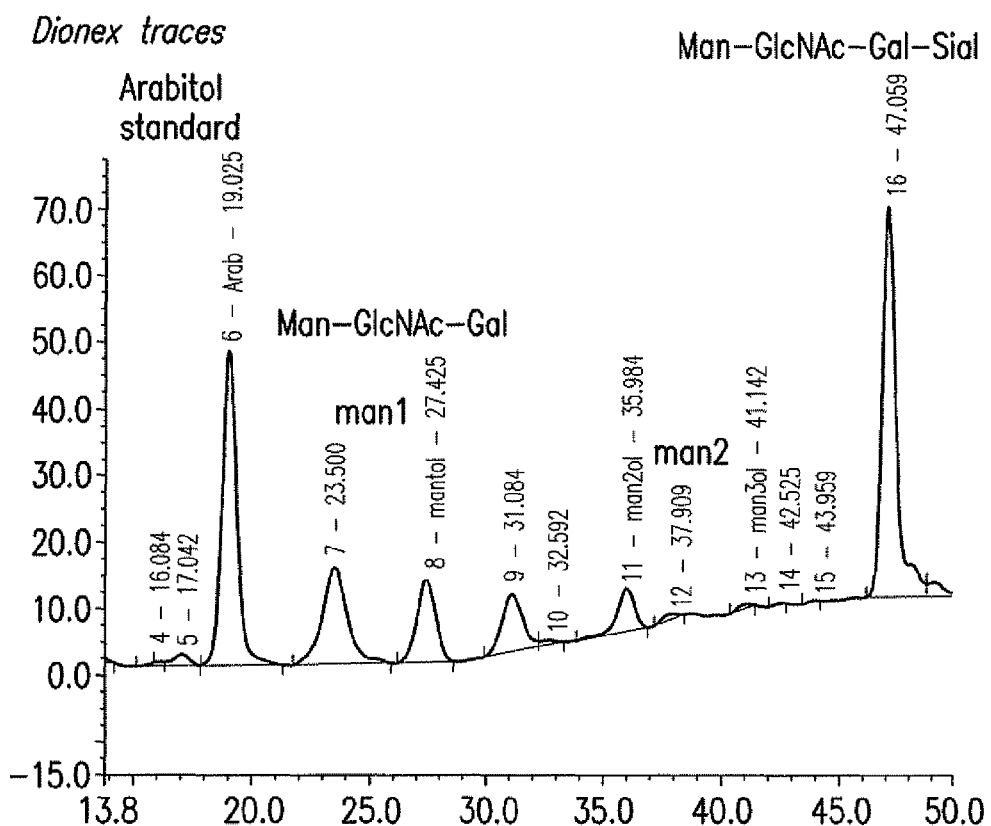
FIGS. 8A-B illustrate TNFRII-Fc O-glycans from GFI SO-3 strain YGLY11603 (musPOMGnT1-ScMNN6-s) which has been optimized for O-sialylation as described in the text. PANEL A shows HPAEC-PAD traces of TNFRII-Fc O-glycans; PANEL B lists percentages of each major O-glycan species.

FIG. 8 shows results of efforts to optimize generation of O-sialylated glycans. We transformed our set of most active TD-POMGnT1 strains into TNFRII-Fc expressing strain YGLY11731 which contains all genes needed for sialylation but lacks POMGnT1. In addition, YGLY11731 contains a plasmid encoding an extra copy of each of the five genes required for sialylation (Hamilton et al., Science 213:1441 (2006)). POMGnT1 transformants were screened using lectin SNA-1 in the 96-well lectin staining assay described above. Colonies that generated the strongest SNA-1 staining were selected for shake flask expression studies. Growth and methanol induction was as described above, except that a synthetic inhibitor of protein O-mannosyltransferase (Pmt) (Orchard et al, EP 1 313 471 B 1) was added during the induction phase as described (Bobrowicz et al., WO2007/061631). Briefly, inhibitor PMTi-3 (Bobrowicz et al., WO2007/061631) was added to a final concentration of 2 μM with BMMY at the start of the induction phase. The Pmt inhibitor reduces the transfer of mannose to serines and threonines, and thus reduces the overall levels of O-linked mannosylation. For TNFRII-Fc, the Pmt inhibitor lowers the number of serines and threonines with O-mannose glycans from ~80 to ~20 per protein molecule. Thus the overall level of O-linked glycans is significantly lowered by the drug. Importantly, this results in a higher percentage of the desired sialylated O-glycan compared to more undesired O-Man-Man (O-Man2) or asialylated O-man-GlcNAc or O-Man-GlcNAc-Gal. Shown in FIG. 8 is the HPAEC-PAD trace (PANEL A) for TNFRII-Fc β-glycans from optimized GFI SO-3 strain YGLY11603 (GAPp-ScMNN6s-mouse POMGnT1). PANEL B lists percentages of each major O-glycan species which were quantified from the HPAEC-PAD trace as described by the manufacturer (Dionex, Sunnyvale, Calif.). Results show that the predominant O-glycan is Man-GlcNAc-Gal-Sialic acid, which makes up 56% of the TNFRII-Fc O-glycans.

Example 14

Total Sialic Acid Determination

We next used an assay that detects total sialic acid content on glycoproteins as a ratio of moles sialic acid/mole protein. Sialic acid was released from glycoprotein samples by acid hydrolysis and analyzed by HPAEC-PAD using the following method: 10-15 μg of protein sample were buffer-exchanged into phosphate buffered saline, Four hundred μL of 0.1M hydrochloric acid was added, and the sample heated at 80° C. for 1 h. After drying in a SpeedVac, the samples were reconstituted with 500 μL of water. One hundred uL was then subjected to HPAEC-PAD analysis. Total sialic content of TNFRII-Fc protein from GFI SO-3 strain YGLY11603 was compared to that from Chinese hamster ovary (CHO) cell produced TNFRII-Fc and also to that from the parent stain YGLY 11731 which lacks POMGnT1. The total sialic acid on TNFRII-Fc is from both N- and O-glycans, and thus TNFRII-Fc sialic acid for CHO-produced and strain YGLY11603 comes from both N- and O-glycans, while that from strain YGLY11731 comes completely from N-glycans. TNFRII-Fc has six potential N-glycan sites per dimer. Results are shown in Table 3. The data indicate that roughly similar levels of sialylated O-glycans were generated as that produced in CHO cells.

TABLE 3

Total sialic acid content.

| Sample | Sialic acid (mol Sial/mol protein) |
| --- | --- |
| MK-TNFR from CHO | 29 |
| MK-TNFR from *P. pastoris* YGLY11731 | 4 |
| MK-TNFR from *P. pastoris* YGLY11603 | 22 |

Example 15

Bioavailability & Serum Half-Life of Modified Glycoproteins

TNFRII-Fc from strain YGLY14252. YGLY14252 was constructed as described above for YGLY11603, except that it was selected for higher TNFRII-Fc expression. This was accomplished by extensive screening of strains using the 96-well lectin SNA-1 staining assay described above. The strains identified by strong SNA-1 staining were further screened by HPAEC-PAD analysis following growth in 50 mL shakeflasks. YGLY14252 was chosen based on having the highest percentage of sialylated O-glycans and highest total sialic acid levels measured as described above. Partially purified TNFRII-Fc from YGLY 14252 was separated by hydroxyapatite chromatography. Wash and bound fractions were collected and total sialic acid content ("TSA") as mol sialic acid/mol TNFRII-Fc was determined. For pooled wash fractions (Form 5-A), TSA=21, and for eluted bound fractions (Form 5-C), TSA=11. In addition, Forms 5-A and 5-C were mixed in equal ratios to generate Form 5-B which had an intermediate TSA=16.

For the bioavailability studies, B6 mice were dosed subcutaneously with glycovariants. Serum samples were collected 48 hours later. TNFRII-Fc concentration was determined with a Gyro-based Immunoassay (anti-TNFRII capture and anti-hFc detection). FIG. 9 illustrates how increased O-sialylation of a glycoprotein results in increased bioavailability in B6 mice. Serum concentrations of mice 48 hours after subcutaneous administration of different doses of TNFRII-Fc are shown. Total sialic acid content (mol/mol) was as follows: Form 5-A: 21; Form 5-B: 16; and Form 5-C: 11.

Figure 10A:
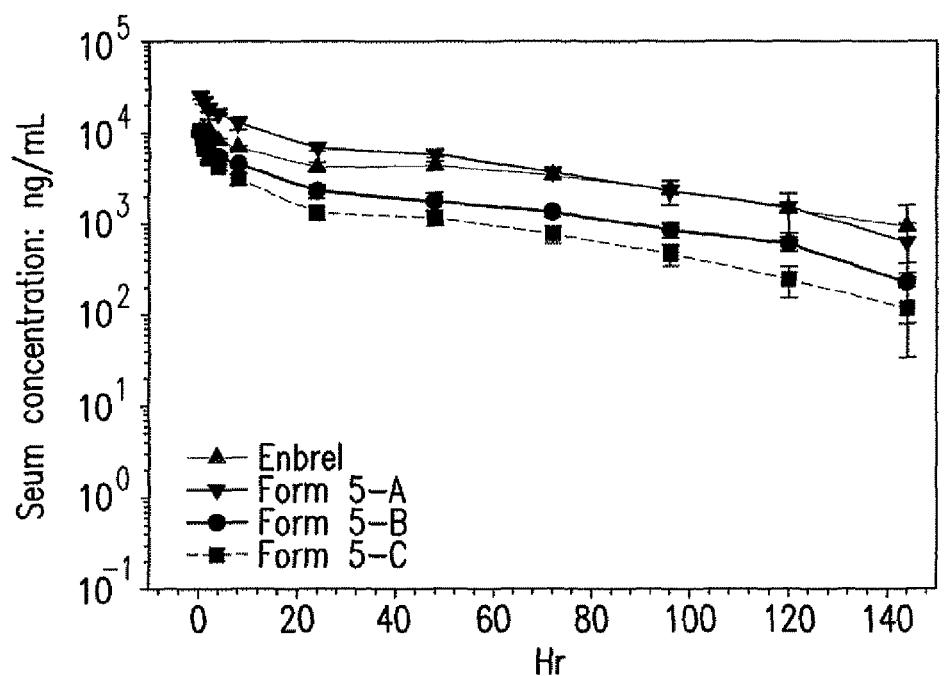
FIGS. 10A-B illustrate how increased O-sialylation of a glycoprotein results in increased serum half-life in rats. Serum time-concentration curves following intravenous ("IV") [FIG. 10A] and subcutaneous ("SC") [FIG. 10B] administrations at 1 mg/kg are shown. Total sialic acid content (mol/mol) was as follows: Form 5-A: 21; Form 5-B: 16; and Form 5-C: 11.
Figure 10B:
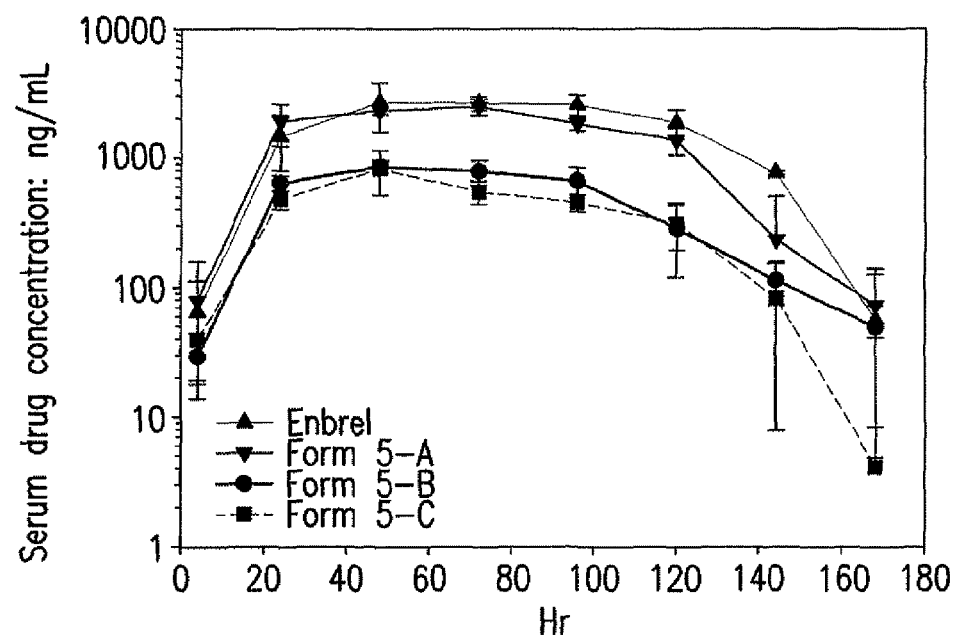

For the serum half-life studies, rats were dosed subcutaneously or intravenously with glycovariants. Serum samples were collected at time intervals post-injection. TNFRII-Fc concentration was determined with a Gyro-based Immunoassay (anti-TNFRII capture and anti-hFc detection). FIGS. 10A-B illustrate how increased O-sialylation of a glycoprotein results in increased serum half-life in rats. Serum time-concentration curves following intravenous ("IV") [FIG. 10A] and subcutaneous ("SC") [FIG. 10B] administrations at 1 mg/kg are shown. Total sialic acid content (mol/mol) was as follows: Form 5-A: 21; Form 5-8: 16; and Form 5-C: 11.

Forms A-C were generated by separating TNFRII-Fc by hydroxyapatite (HA) chromatography. Form A represents fractions eluting from the HA column with the wash, and Form C represents the bound fractions. Form B is a 1:1 mix of Forms A and C.

The invention claimed is:

1. A method of producing a recombinant glycoprotein having O-Man-GlcNAc; O-Man-GlcNAc-Gal; or O-Man-GlcNAc-Gal-Sia as the predominant O-glycan thereof in *Pichia pastoris* host cell which comprises:
   (a) providing *Pichia pastoris* host cells which
      (i) do not express functional beta-mannosyltransferase enzymes Bmt 1, 2, 3 and 4, and phospho-mannose transferase enzymes Mnn4a, Mnn4b and Pno1; and
      (ii) do express functional protein O-linked mannose β-1,2-N-linked acetylglucosaminyltransferase 1 ("POMGnT1"), UDP-GlcNAc transporter and α-1,2-mannosidase enzymes;
   (b) transfecting or transforming the *Pichia pastoris* host cells with nucleic acid encoding the glycoprotein of interest; and
   (c) culturing the *Pichia pastoris* host cells so that the recombinant glycoprotein is produced.

2. The method of claim 1 wherein the cells of step (a) further do not express Ktr1.

3. The method of claim 1 wherein the enzymes of step (a)(ii) further include one of the following combinations of enzymes:
   (a) β1,4GalT, UDP-Gal transporter and UDP-Gal epimerase;
   (b) β1,4GalT, UDP-Gal transporter, UDP-Gal epimerase; α2,6SialT; GNE; SPS; SPP; CSS; and CST; or
   (c) β1,4GalT, UDP-Gal transporter, UDP-Gal epimerase; α2,3SialT; GNE; SPS; SPP; CSS; and CST.

4. The method of claim 1 wherein the UDP-GlcNAc transporter of step (a)(ii) is a *Kluyveromyces lactis* UDP-GlcNAc transporter, or a murine UDP-GlcNAc transporter.

5. The method of claim 1 wherein the α-1,2-mannosidase is derived from *Trichoderma reesei, Saccharomyces* sp., *Coccidiodes* sp., or *Aspergillus* sp.

6. The method of claim 1 wherein the POMGnT1 enzyme of step (a)(ii) comprises SEQ ID NO: 110, SEQ ID NO: 112 or SEQ ID NO: 118.

7. The method of claim 1 wherein the POMGnT1 enzyme from step (a)(ii) is derived from human, murine, or frog POMGnT1 sequences.

8. The method of claim 1 wherein nucleic acid encoding the POMGnT1 enzyme from step (a)(ii) is codon-optimized for expression in the lower eukaryotic host cell.

9. The method of claim 1 wherein the POMGnT1 of step (a)(ii) is encoded by nucleic acid sequence encoding POMGnT1 operatively linked to an ER and/or Golgi leader sequence which is that of or derived from a leader sequence of *S. cerevisiae, Pichia pastoris*, or *Kluyveromyces lactis*.

10. The method of claim 9 wherein the ER and/or Golgi leader sequence is derived from sequence of one of the following proteins: ScMNS1-s, ScMNN9-s, PpKre-2s; K1Gnt1-s, ScMNN2-s, ScMNN2-m, ScMNN5-s, ScMNN6-s, ScPMT5-m, PpPMT1-m or PpBET1-s.

11. The method of claim 9 wherein the nucleic acid sequence encoding POMGnT1 is operatively linked to a sequence selected from: SEQ ID NOs: 1-108.

12. The method of claim 9 wherein the nucleic acid sequence encoding POMGnT1 is operatively linked to a sequence selected from: SEQ ID NO 3 (or sequence encoding SEQ ID NO 4); SEQ ID NO 13 (or sequence encoding SEQ ID NO 14); SEQ ID NO 33 (or sequence encoding SEQ ID NO 34); SEQ ID NO 39 (or sequence encoding SEQ ID NO 40); SEQ ID NO 41 (or sequence encoding SEQ ID NO 42); SEQ ID NO 43 (or sequence encoding SEQ ID NO 44); SEQ ID NO 45 (or sequence encoding SEQ ID NO 46); SEQ ID NO 51 (or sequence encoding SEQ ID NO 52); SEQ ID NO 93 (or sequence encoding SEQ ID NO 94); SEQ ID NO 87 (or sequence encoding SEQ ID NO 88) or SEQ ID NO 105 (or sequence encoding SEQ ID NO 106).

13. The method of claim 9 wherein the nucleic acid sequence encoding POMGnT1 is operatively linked to an ER and/or Golgi leader sequence in one of the following combinations:

(a) human POMGnT1 sequence or catalytic domain sequence thereof operatively linked to a leader sequence which is that of, or derived from that of, a protein selected from: PpSEC12-s; ScMNN9-s; K1GNT1-s; ScMNN2-s; ScMNN2-m; ScPMT5-m; PpPMT1-m or PpBET1-s;
(b) human POMGnT1 sequence or catalytic domain sequence thereof operatively linked to a sequence selected from: SEQ ID NO 9 (or sequence encoding SEQ ID NO 10); SEQ ID NO 13 (or sequence encoding SEQ ID NO 14); SEQ ID NO 39 (or sequence encoding SEQ ID NO 40); SEQ ID NO 41 (or sequence encoding SEQ ID NO 42); SEQ ID NO 43 (or sequence encoding SEQ ID NO 44); SEQ ID NO 73 (or sequence encoding SEQ ID NO 74); SEQ ID NO 87 (or sequence encoding SEQ ID NO 88) or SEQ ID NO 105 (or sequence encoding SEQ ID NO 106);
(c) murine POMGnT1 sequence or catalytic domain sequence thereof operatively linked to a leader sequence which is that of, or derived from that of, a protein selected from: ScMNN9-s; PpKRE2-s; ScKTR2-s; K1GNT1-s; ScMNN2-s; ScMNN2-m; ScMNN5-s; ScMNN6-s; ScPMT5-m; ScPMT6-m; PpPMT1-s; PpPMT 2-s; PpPMT4-s; or PpBET1-s;
(d) murine POMGnT1 sequence or catalytic domain sequence thereof operatively linked to a sequence selected from: SEQ ID NO 13 (or sequence encoding SEQ ID NO 14); SEQ ID NO 33 (or sequence encoding SEQ ID NO 34); SEQ ID NO 37 (or sequence encoding SEQ ID NO 38); SEQ ID NO 39 (or sequence encoding SEQ ID NO 40); SEQ ID NO 41 (or sequence encoding SEQ ID NO 42); SEQ ID NO 43 (or sequence encoding SEQ ID NO 44); SEQ ID NO 45 (or sequence encoding SEQ ID NO 46); SEQ ID NO 51 (or sequence encoding SEQ ID NO 52); SEQ ID NO 73 (or sequence encoding SEQ ID NO: 74); SEQ ID NO 75 (or sequence encoding SEQ ID NO 76); SEQ ID NO 77 (or sequence encoding SEQ ID NO 78); SEQ ID NO 79 (or sequence encoding SEQ ID NO 80); SEQ ID NO 81 (or sequence encoding SEQ ID NO 82); or SEQ ID NO 105 (or sequence encoding SEQ ID NO 106);
(e) frog POMGnT1 sequence or catalytic domain sequence thereof operatively linked to a leader sequence which is that of, or derived from that of, a protein selected from: ScMNS1-s; ScSEC12-m; PpSEC12-s; ScMNN9-s; ScANP1-s; ScHOC1-s; ScMNN10-s; ScMNN11-s; PpKRE2-s; ScKTR2-s; K1GNT1-s; ScMNN2-s; ScMNN2-m; ScMNN1-s; ScMNN6-s; ScPMT5-m; PpPMT1-m; or PpBET1-s; or
(f) frog POMGnT1 sequence or catalytic domain sequence thereof operatively linked to a sequence selected from: SEQ ID NO 3 (or sequence encoding SEQ ID NO 4); SEQ ID NO 7 (or sequence encoding SEQ ID NO 8); SEQ ID NO 9 (or sequence encoding SEQ ID NO 10); SEQ ID NO 13 (or sequence encoding SEQ ID NO 14); SEQ ID NO 17 (or sequence encoding SEQ ID NO 18); SEQ ID NO 19 (or sequence encoding SEQ ID NO 20); SEQ ID NO 21 (or sequence encoding SEQ ID NO 22); SEQ ID NO 23 (or sequence encoding SEQ ID NO 24); SEQ ID NO 33 (or sequence encoding SEQ ID NO 34); SEQ ID NO 37 (or sequence encoding SEQ ID NO 38); SEQ ID NO 39 (or sequence encoding SEQ ID NO 40); SEQ ID NO 41 (or sequence encoding SEQ ID NO 42); SEQ ID NO 43 (or sequence encoding SEQ ID NO 44); SEQ ID NO 49 (or sequence encoding SEQ ID NO 50); SEQ ID NO 51 (or sequence encoding SEQ ID NO 52); SEQ ID NO 73 (or sequence encoding SEQ ID NO 74); SEQ ID NO 87 (or sequence encoding SEQ ID NO 88); or SEQ ID NO 105 (or sequence encoding SEQ ID NO 106).

14. The method of claim 1 wherein nucleic acid sequence encoding the POMGnT1 enzyme from step (a)(ii) is operatively linked to a *Pichia* AOX1, GAP, TEF or PMA promoter.

15. The method of claim 1 wherein nucleic acid sequence encoding the POMGnT1 enzyme from step (a)(ii) is operatively linked to a ScCYC1 transcription termination sequence.

16. The method of claim 1 wherein nucleic acid sequence encoding the POMGnT1 enzyme of step (a)(ii) is operatively linked to promoter and leader sequences; wherein the promoter, leader and POMGnT1 sequences utilized are one of the following promoter-leader-POMGnT1 combinations: AOX1-PpKRE2s-mouse POMGnT1; GAP-K1GNT1s-mouse POMGnT1; AOX1-K1GNT1s-mouse POMGnT1; GAP-K1GNT1s-frog POMGnT1; AOX1-ScMNN2s-mouse POMGnT1; GAP-ScMNN5s-mouse POMGnT1; AOX1-ScMNN5s-mouse POMGnT1; GAP-ScMNN6s-mouse POMGnT1; AOX1-ScPMT5m-mouse POMGnT1 or GAP-ScMNN6s-human POMGNT1.

\* \* \* \* \*